US008551476B2

(12) United States Patent
Mi et al.

(10) Patent No.: US 8,551,476 B2
(45) Date of Patent: *Oct. 8, 2013

(54) SP35 ANTIBODIES AND USES THEREOF

(75) Inventors: Sha Mi, Belmont, MA (US); R. Blake Pepinsky, Arlington, MA (US); Zhaohui Shao, Brookline, MA (US); Christilyn Graff, Cambridge, MA (US)

(73) Assignee: Biogen Idec MA Inc., Cambridge, MA (US)

( * ) Notice: Subject to any disclaimer, the term of this patent is extended or adjusted under 35 U.S.C. 154(b) by 1381 days.

This patent is subject to a terminal disclaimer.

(21) Appl. No.: 11/892,036

(22) Filed: Aug. 17, 2007

(65) Prior Publication Data

US 2009/0017039 A1 Jan. 15, 2009

Related U.S. Application Data

(63) Continuation of application No. PCT/US2006/026271, filed on Jul. 7, 2006.

(60) Provisional application No. 60/697,336, filed on Jul. 8, 2005, provisional application No. 60/771,900, filed on Feb. 10, 2006, provisional application No. 60/814,522, filed on Jun. 19, 2006.

(51) Int. Cl.
*A61K 39/395* (2006.01)
*A61K 39/00* (2006.01)
*A61K 35/30* (2006.01)

(52) U.S. Cl.
USPC ............... 424/130.1; 424/133.1; 424/134.1; 424/135.1; 424/570

(58) Field of Classification Search
None
See application file for complete search history.

(56) References Cited

U.S. PATENT DOCUMENTS

| | | | |
|---|---|---|---|
| 4,399,216 A | 8/1983 | Axel et al. |
| 4,444,887 A | 4/1984 | Hoffman |
| 4,510,245 A | 4/1985 | Cousens et al. |
| 4,634,665 A | 1/1987 | Axel et al. |
| 4,694,778 A | 9/1987 | Learn et al. |
| 4,716,111 A | 12/1987 | Osband et al. |
| 4,816,397 A | 3/1989 | Boss et al. |
| 4,816,567 A | 3/1989 | Cabilly et al. |
| 4,946,778 A | 8/1990 | Ladner et al. |
| 4,968,615 A | 11/1990 | Koszinowski et al. |
| 5,122,464 A | 6/1992 | Wilson et al. |
| 5,168,062 A | 12/1992 | Stinski |
| 5,179,017 A | 1/1993 | Axel et al. |
| 5,223,409 A | 6/1993 | Ladner et al. |
| 5,225,539 A | 7/1993 | Winter |
| 5,252,714 A | 10/1993 | Harris et al. |
| 5,258,498 A | 11/1993 | Huston et al. |
| 5,314,995 A | 5/1994 | Fell, Jr. et al. |
| 5,403,484 A | 4/1995 | Ladner et al. |
| 5,413,923 A | 5/1995 | Kucherlapati et al. |
| 5,427,908 A | 6/1995 | Dower et al. |
| 5,428,130 A | 6/1995 | Capon et al. |
| 5,516,637 A | 5/1996 | Huang et al. |
| 5,530,101 A | 6/1996 | Queen et al. |
| 5,545,806 A | 8/1996 | Lonberg et al. |
| 5,565,332 A | 10/1996 | Hoogenboom et al. |
| 5,565,335 A | 10/1996 | Capon et al. |
| 5,569,825 A | 10/1996 | Lonberg et al. |
| 5,571,698 A | 11/1996 | Ladner et al. |
| 5,574,009 A | 11/1996 | Cohen et al. |
| 5,580,717 A | 12/1996 | Dower et al. |
| 5,585,089 A | 12/1996 | Queen et al. |
| 5,589,369 A | 12/1996 | Seidman et al. |
| 5,625,126 A | 4/1997 | Lonberg et al. |
| 5,633,425 A | 5/1997 | Lonberg et al. |
| 5,658,570 A | 8/1997 | Newman et al. |
| 5,658,727 A | 8/1997 | Barbas et al. |
| 5,661,016 A | 8/1997 | Lonberg et al. |
| 5,693,761 A | 12/1997 | Queen et al. |
| 5,693,762 A | 12/1997 | Queen et al. |
| 5,693,780 A | 12/1997 | Newman et al. |
| 5,698,426 A | 12/1997 | Huse |
| 5,725,859 A | 3/1998 | Omer |
| 5,733,743 A | 3/1998 | Johnson et al. |
| 5,750,753 A | 5/1998 | Kimae et al. |

(Continued)

FOREIGN PATENT DOCUMENTS

| | | |
|---|---|---|
| EP | 0 154 316 B1 | 9/1989 |
| EP | 0 401 384 A1 | 12/1990 |

(Continued)

OTHER PUBLICATIONS

Rudikoff et al PNAS, 79:1979-1983, 1982.*

(Continued)

*Primary Examiner* — Daniel E Kolker
*Assistant Examiner* — Aditi Dutt
(74) *Attorney, Agent, or Firm* — Sterne, Kessler, Goldstein & Fox P.L.L.C.

(57) ABSTRACT

Endogenous Sp35 is a negative regulator for neuronal survival, axon regeneration, oligodendrocyte differentiation and myelination (Negative Regulator). Molecules that block endogenous Sp35 function, such anti-Sp35 antibodies can be used as therapeutics for the treatment of neuron and oligodendrocyte dysfunction. The present invention provides antibodies specific for Sp35, and methods of using such antibodies as antagonists of endogenous Sp35 function. The invention further provides specific hybridoma and phage library-derived monoclonal antibodies, nucleic acids encoding these antibodies, and vectors and host cells comprising these antibodies. The invention further provides methods of promoting oligodendrocyte survival and myelination in a vertebrate, comprising administering to a vertebrate in need of such treatment an effective amount of an anti-Sp35 antibody.

16 Claims, 11 Drawing Sheets

(56) References Cited

U.S. PATENT DOCUMENTS

Figure 1:
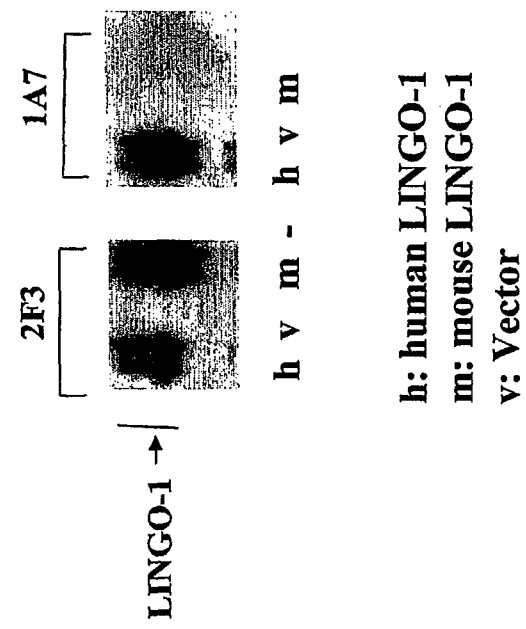

| | | |
|---|---|---|
| 5,756,096 A | 5/1998 | Newman et al. |
| 5,772,997 A | 6/1998 | Hudziak et al. |
| 5,780,225 A | 7/1998 | Wigler et al. |
| 5,807,715 A | 9/1998 | Morrison et al. |
| 5,811,524 A | 9/1998 | Brams et al. |
| 5,814,318 A | 9/1998 | Lonberg et al. |
| 5,821,047 A | 10/1998 | Garrard et al. |
| 5,837,821 A | 11/1998 | Wu |
| 5,892,019 A | 4/1999 | Schlom et al. |
| 5,914,237 A | 6/1999 | Godowski et al. |
| 5,939,598 A | 8/1999 | Kucherlapati et al. |
| 5,969,108 A | 10/1999 | McCafferty et al. |
| 6,025,145 A | 2/2000 | Godowski et al. |
| 6,054,561 A | 4/2000 | Ring |
| 6,075,181 A | 6/2000 | Kucherlapati et al. |
| 6,150,584 A | 11/2000 | Kucherlapati et al. |
| 6,159,730 A | 12/2000 | Reff |
| 6,180,370 B1 | 1/2001 | Queen et al. |
| 6,190,887 B1 | 2/2001 | Boyce et al. |
| 6,280,964 B1 | 8/2001 | Kavanaugh et al. |
| 6,333,169 B1 | 12/2001 | Hudziak et al. |
| 6,338,953 B1 | 1/2002 | Boyce et al. |
| 6,387,371 B1 | 5/2002 | Hudziak et al. |
| 6,399,063 B1 | 6/2002 | Hudziak et al. |
| 6,413,777 B1 | 7/2002 | Reff et al. |
| 6,420,140 B1 | 7/2002 | Hori et al. |
| 6,458,592 B1 | 10/2002 | Jakobovits et al. |
| 6,656,465 B2 | 12/2003 | Clary et al. |
| 6,686,451 B1 | 2/2004 | Desnoyers et al. |
| 6,696,290 B2 | 2/2004 | Fitzpatrick et al. |
| 6,949,245 B2 | 9/2005 | Sliwkowski |
| 6,974,689 B1 | 12/2005 | Ashkenazi et al. |
| 6,987,088 B2 | 1/2006 | Dennis |
| 7,098,302 B2 | 8/2006 | Krag et al. |
| 7,223,558 B2 | 5/2007 | Wu et al. |
| 7,718,776 B2 | 5/2010 | Boyle et al. |
| 7,785,829 B2 | 8/2010 | Mi et al. |
| 8,058,406 B2 | 11/2011 | Mi et al. |
| 8,128,926 B2 | 3/2012 | Mi et al. |
| 8,153,580 B2 | 4/2012 | Mi et al. |
| 2002/0004587 A1 | 1/2002 | Miller et al. |
| 2002/0123057 A1 | 9/2002 | Zauderer et al. |
| 2002/0182671 A1 | 12/2002 | Lal et al. |
| 2003/0195163 A1 | 10/2003 | Wu et al. |
| 2004/0005579 A1 | 1/2004 | Birse et al. |
| 2004/0067490 A1 | 4/2004 | Zhong et al. |
| 2004/0253605 A1 | 12/2004 | McCarthy et al. |
| 2005/0123990 A1 | 6/2005 | Lal et al. |
| 2005/0153396 A1 | 7/2005 | Baker et al. |
| 2005/0214288 A1 | 9/2005 | Bell et al. |
| 2005/0215770 A1 | 9/2005 | Bell et al. |
| 2006/0009288 A1 | 1/2006 | deVos et al. |
| 2006/0009388 A1 | 1/2006 | Mi et al. |
| 2006/0034840 A1 | 2/2006 | Agus et al. |
| 2006/0088523 A1 | 4/2006 | Andya et al. |
| 2007/0059793 A1 | 3/2007 | Mi et al. |
| 2007/0071675 A1 | 3/2007 | Wu et al. |
| 2007/0083334 A1 | 4/2007 | Mintz et al. |
| 2007/0105122 A1 | 5/2007 | Ota et al. |
| 2007/0274918 A1 | 11/2007 | Mosyak et al. |
| 2009/0175872 A1 | 7/2009 | Mi et al. |
| 2009/0246189 A1 | 10/2009 | Mi et al. |
| 2010/0074907 A1 | 3/2010 | Mi et al. |
| 2010/0143362 A1 | 6/2010 | Walmsley et al. |
| 2010/0297121 A1 | 11/2010 | Mi |
| 2011/0311542 A1 | 12/2011 | Mi et al. |
| 2012/0014960 A1 | 1/2012 | Mi et al. |

FOREIGN PATENT DOCUMENTS

| | | |
|---|---|---|
| EP | 0 256 055 B1 | 8/1991 |
| EP | 0 323 997 B1 | 4/1993 |
| EP | 0 396 387 B1 | 12/1993 |
| EP | 0 368 684 B1 | 3/1994 |
| EP | 0 239 400 B1 | 8/1994 |
| EP | 0 338 841 B1 | 3/1995 |
| EP | 0 401 384 B1 | 3/1996 |
| EP | 1 074 617 A2 | 2/2001 |
| EP | 0 058 481 B2 | 5/2003 |
| EP | 0 592 106 B1 | 11/2004 |
| EP | 0 519 596 B1 | 2/2005 |
| EP | 1 574 520 A2 | 9/2005 |
| WO | WO 86/05807 A1 | 10/1986 |
| WO | WO 88/09810 A1 | 12/1988 |
| WO | WO 89/01036 A1 | 2/1989 |
| WO | WO 89/10134 A1 | 11/1989 |
| WO | WO 89/12624 A2 | 12/1989 |
| WO | WO 90/02809 A1 | 3/1990 |
| WO | WO 90/11364 A1 | 10/1990 |
| WO | WO 91/09967 A1 | 7/1991 |
| WO | WO 91/10737 A1 | 7/1991 |
| WO | WO 91/10741 A1 | 7/1991 |
| WO | WO 91/14438 A1 | 10/1991 |
| WO | WO 92/01047 A1 | 1/1992 |
| WO | WO 92/08495 A1 | 5/1992 |
| WO | WO 92/18619 A1 | 10/1992 |
| WO | WO 92/22324 A1 | 12/1992 |
| WO | WO 93/11236 A1 | 6/1993 |
| WO | WO 94/09817 A1 | 5/1994 |
| WO | WO 95/15982 A2 | 6/1995 |
| WO | WO 95/20401 A1 | 8/1995 |
| WO | WO 96/33735 A1 | 10/1996 |
| WO | WO 96/34096 A1 | 10/1996 |
| WO | WO 97/00271 A1 | 1/1997 |
| WO | WO 98/16654 A1 | 4/1998 |
| WO | WO 98/24893 A2 | 6/1998 |
| WO | WO 98/46645 A2 | 10/1998 |
| WO | WO 98/50433 A2 | 11/1998 |
| WO | WO 98/52976 A1 | 11/1998 |
| WO | WO 99/06427 A1 | 2/1999 |
| WO | WO 99/14328 A2 | 3/1999 |
| WO | WO 00/15796 A2 | 3/2000 |
| WO | WO 00/34317 A2 | 6/2000 |
| WO | WO 00/58473 A2 | 10/2000 |
| WO | WO 01/04311 A1 | 1/2001 |
| WO | WO 01/12662 A2 | 2/2001 |
| WO | WO 01/40466 A2 | 6/2001 |
| WO | WO 01/55317 A2 | 8/2001 |
| WO | WO 01/55333 A2 | 8/2001 |
| WO | WO 01/57262 A1 | 8/2001 |
| WO | WO 01/59063 A2 | 8/2001 |
| WO | WO 02/14368 A2 | 2/2002 |
| WO | WO 02/29058 A2 | 4/2002 |
| WO | WO 02/060955 A2 | 8/2002 |
| WO | WO 02/068579 A2 | 9/2002 |
| WO | WO 02/096948 A2 | 12/2002 |
| WO | WO 03/023008 A2 | 3/2003 |
| WO | WO 03/035833 A2 | 5/2003 |
| WO | WO 03/061559 A2 | 7/2003 |
| WO | WO 03/083047 A2 | 10/2003 |
| WO | WO 2004/020404 A2 | 3/2004 |
| WO | WO 2004/050016 A2 | 6/2004 |
| WO | WO 2004/085648 * | 10/2004 |
| WO | WO 2004/085648 A2 | 10/2004 |
| WO | WO 2005/021579 A2 | 3/2005 |
| WO | WO 2005/079566 A2 | 9/2005 |
| WO | WO 2006/002437 * | 1/2006 |
| WO | WO 2006/002437 A2 | 1/2006 |
| WO | WO 2006/119013 A2 | 11/2006 |
| WO | WO 2006/136006 A1 | 12/2006 |
| WO | WO 2007/008547 A2 | 1/2007 |
| WO | WO 2007/098283 * | 8/2007 |
| WO | WO 2008/013782 A2 | 1/2008 |
| WO | WO 2008/058736 A1 | 5/2008 |

OTHER PUBLICATIONS

De Pascalis et al. Jour Immunol, 169: 3076-3084, 2002.*
Wu et al. J. Mol. Biol. 294: 151-162, 1999.*
MacCallum et al. J. Mol. Biol. 262:732-745, 1996.*
Casset et al. BBRC 307: 198-205, 2003.*
Vajdos et al. J. Mol. Biol. 320: 415-428, 2002.*
Holm et al Mol. Immunol. 44: 1075-1084, 2007.*

(56) References Cited

OTHER PUBLICATIONS

Chen et al. J. Mol. Bio. 293, 865-881, 1999.*
Brummell et al. Biochemistry 32:1180-1187, 1993.*
Kobayashi et al. Protein Engineering 12:879-884, 1999.*
Burks et al. PNAS 94:412-417,1997.*
Colman Research in Immunol. 145:33-36,1994.*
Damle, N.K. and Frost, P., "Antibody-targeted chemotherapy with immunoconjugates of calicheamicin," *Curr. Opin. Pharmacol.* 3:386-390, Elsevier Science Ltd. (2003).
Declaration of Robert H. Miller filed in copending U.S. Appl. No. 11/165,576 on May 1, 2008.
Declaration of Robert B. Pepinsky filed in copending U.S. Appl. No. 11/165,576 on Jan. 27, 2009.
Declaration of Sha Mi filed in copending U.S. Appl. No. 11/165,576 on Apr. 28, 2008.
International Search Report and Written Opinion of the International Searching Authority for International Application No. PCT/US06/26271, mailed on Jan. 27, 2009, ISA/US, Virginia, U.S.A.
Battaglia, G., et al., "Protective role of group-II metabotropic glutamate receptors against nigro-striatal degeneration induced by 1-methyl-4-phenyl-1,2,3,6-tetrahydropyridine in mice," *Neuropharmacol.* 45:155-166, Elsevier Science Ltd. (2003).
Baulida, J., et al., "All ErbB Receptors Other Than the Epidermal Growth Factor Receptor are Endocytosis Impaired," *J. Biol. Chem.* 271:5251-5257, The American Society for Biochemistry and Molecular Biology, Inc. (1996).
Baulida, J. and Carpenter, G., "Heregulin Degradation in the Absence of Rapid Receptor-Mediated Internalization," *Exp. Cell Res.* 232:167-172, Academic Press (1997).
Baumann, N., et al., "Biology of Oligodendrocyte and Myelin in the Mammalian Central Nervous System," *J. Physiol. Rev.* 81:871-927, American Physiological Society (2001).
Blum, M., "A null mutation in TGF-α leads to a reduction in midbrain dopaminergic neurons in the substantia nigra," *Nat. Neurosci.* 1:374-377, Nature Publishing Group (1998).
Brittis, P.A., et al., Nogo Domains and a Nogo Receptor: Implications for Axon Regeneration, *Neuron* 30:11-14 Cell Press (2001).
Brundin, P., et al., "The rotating 6-hydroxydopamine-lesioned mouse as a model for assessing functional effects of neuronal grafting,"*Brain Res.* 366:346-349, Elsevier Publishers B.V. (1986).
Carim-Todd, L., et al., "LRRN6A/LERN1 (leucine-rich repeat neuronal protein 1), a novel gene with enriched expression in limbic system and neocortex," *Eur. J. Neurosci.*18 :3167-3182, Federation of European Neuroscience Societies (2003).
Chang, A., et al., "Premyelinating Oligodendrocytes in Chronic Lesions of Multiple Sclerosis," *N. Engl. J. Med.* 346:165-173, Massachusetts Medical Society (2002).
Chen, M.S., et al., "Nogo-A is a Myelin-Associated Neurite Outgrowth Inhibitor and an Antigen for Monoclonal Antibody IN-1," *Nature* 403:434-439, Macmillan Magazines Ltd. (2000).
Chen, Y., et al., "AMIGO and friends: An emerging family of brain-enriched, neuronal growth modulating, type 1 transmembrane proteins with leucine-rich repeats (LRR) and cell adhesion molecule motifs," *Brain Res. Rev.* 51:265-74, Elsevier B.V. (Electronically available Jan. 2006).
Citri, A., et al., "The deaf and the dumb: The biology of ErbB-2 and ErbB-3," *Exp. Cell Res.* 284:54-65, Elsevier Science (2003).
Cohen, S., et al., "Nonchromosomal Antibiotic Resistance in Bacteria: Genetic Transformation of *Escherichia coli* by R-Factor DNA," *Proc. Natl. Acad. Sci. USA* 69:2110-2114 (1972).
Csordás, G., et al,. "Sustained Down-regulation of the Epidermal Growth Factor Receptor by Decorin," *J. Biol. Chem.* 275:32879-32887, The American Society for Biochemistry and Molecular Biology, Inc. (2000).
Domeniconi M., et al., "Myelin-Associated Glycoprotein Interacts with the Nogo66 Receptor to Inhibit Neurite Outgrowth," *Neuron* 35:283-290, Cell Press (2002).
Eby, M.T., et al., "TAJ, a Novel Member of the Tumor Necrosis Factor Receptor Family, Activates the c-Jun N-terminal Kinase Pathway and Mediates Caspase-independent Cell Death," *J. Biol. Chem.* 275:15336-15342, The American Society for Biochemistry and Molecular Biology, Inc. (2000).
Fendly, B.M., et al., "The Extracellular Domain of HER2/neu is a Potential Immunogen for Active Specific Immunotherapy of Breast Cancer," *J. Biol. Resp. Mod.* 9:449-455, Raven Press Ltd. (1990).
Fournier, A.E., et al., "Identification of a Receptor Mediating Nogo-66 Inhibition of Axonal Regeneration," *Nature* 409:341-346, Nature Publishing Group (2001).
Fu, Q.-L., et al., "Blocking LINGO-1 Function Promotes Retinal Ganglion Cell Survival Following Ocular Hypertension and Optic Nerve Transection," *Invest. Ophthal. Vis. Sci.* 49:975-985, Association for Research in Vision and Ophthalmology (Mar. 2008).
Fuxe, K. and Ungerstedt, U., "Antiparkinsonian Drugs and Dopaminergic Neostriatal Mechanisms: Studies in Rats with Unilateral 6-Hydroxydopamine (=6-OH-DA)-Induced Degeneration of the Nigro-Neostriatal DA Pathway and Quantitative Recording of Rotational Behaviour," *Pharmac. Ther.* B:41-47, Pergamon Press (1976).
Ghiglione, C., et al., "The Transmembrane Molecule Kekkon 1 Acts in a Feedback Loop to Negatively Regulate the Activity of the *Drosophila* EGF Receptor during Oogenesis," *Cell* 96:847-856, Cell Press (1999).
Gill, S.S., et al., "Direct brain infusion of glial cell line-derived neurotrophic factor in Parkinson disease," *Nat. Med.* 9:589-595, Nature Publishing Company (2003).
Gill, S.S., et al., "Addendum: Direct brain infusion of glial cell line-derived neurotrophic factor in Parkinson disease," *Nat. Med.* 12:479, Nature Publishing Company (Apr. 2006).
Gille, G., et al., "Oxidative Stress to Dopaminergic Neurons as Models of Parkinson's Disease," *Ann. N.Y. Acad. Sci.* 1018:533-540, New York Academy of Sciences (Jun. 2004).
GrandPré, T., et al., "Identification of the Nogo Inhibitor of Axon Regeneration as a Reticulon Protein," *Nature* 403:439-444, Macmillan Magazines Ltd. (2000).
Grimpe, B., et al., "The Critical Role of Basement Membrane-Independent Laminin γ1 Chain During Axon Regeneration in the CNS," *J. Neurosci.* 22:3144-3160, Society for Neuroscience (2002).
Gur, G., et al., "LRIGI restricts growth factor signaling by enhancing receptor ubiquitylation and degradation," *EMBO J.* 23:3270-3281, Oxford University Press (Aug. 2004).
Ha, H., et al., "Membrane Rafts Play a Crucial Role in Receptor Activator of Nuclear Factor κB Signaling and Osteoclast Function," *J. Biol. Chem.* 278:18573-18580, The American Society for Biochemistry and Molecular Biology, Inc. (2003).
Harwerth, I.-M., et al., "Monoclonal Antibodies against the Extracellular Domain of the erbB-2 Receptor Function as Partial Ligand Agonists," *J. Biol. Chem.* 267:15160-15167, The American Society for Biochemistry and Molecular Biology, Inc. (1992).
Hoet, R.M., et al., "Generation of high-affinity human antibodies by combining donor-derived and synthetic complementarity-determining-region diversity," *Nat. Biotechnol.* 23:344-348, Nature America Publishing (Mar. 2005).
Huang, J., et al., "Glial Membranes at the Node of Ranvier Prevent Neurite Outgrowth," *Science* 310:1813-7, American Association for the Advancement of Science (Dec. 2005).
Isacson, O., "Problems and Solutions for Circuits and Synapses in Parkinson's Disease," *Neuron* 43:165-168, Cell Press (Jul. 2004).
Jones, L.L., et al., "NG2 is a Major Chondroitin Sulfate Proteoglycan Produced after Spinal Cord Injury and Is Expressed by Macrophages and Oligodendrocyte Progenitors," *J. Neurosci.* 22:2792-2803, Society for Neuroscience (2002).
Kasper, C., et al, "Structural Basis of Cell—Cell Adhesion by NCAM," *Nat. Struct. Biol.* 7:389-393, Nature America Inc. (2000).
Kim, J.Y., et al., "The Role of ErbB2 Signaling in the Onset of Terminal Differentiation of Oligodendrocytes In Vivo," *J. Neurosci.* 23:5561-5571, Society of Neuroscience (2003).
Klapper, L.N., et al., "A subclass of tumor-inhibitory monoclonal antibodies to ErbB-2/HER2 blocks crosstalk with growth factor receptors," *Oncogene* 14:2099-2109, Nature Publishing Company (1997).

(56) References Cited

OTHER PUBLICATIONS

Knappik, A., et al., "Fully Synthetic Human Combinatorial Antibody Libraries (HuCAL) Based on Modular Consensus Frameworks and CDRs Randomized with Trinucloetides," *J. Mol. Biol.* 296:57-86, Academic Press (2000).

Kolodny, E.H., "Dysmyelinating and demyelinating conditions in infancy," *Curr. Opin. Neurol. Neurosurg.* 6:379-386, Current Science (1993).

Kornilova, E., et al., "Lysosomal Targeting of Epidermal Growth Factor Receptors via a Kinase-dependent Pathway is Mediated by the Receptor Carboxyl-terminal Residues 1022-1123," *J. Biol. Chem.* 271:30340-30346, The American Society for Biochemistry and Molecular Biology, Inc. (1996).

Laederich, M.B., et al., "The Leucine-rich Repeat Protein LRIG1 is a Negative Regulator of ErbB Family Receptor Tyrosine Kinases," *J. Biol. Chem.* 279:47050-47056, The American Society for Biochemistry and Molecular Biology, Inc. (Nov. 2004).

Laederich, M.B., et al., "The Leucine-rich Repeat Protein LRIG1 is a Negative Regulator of ErbB Family Receptor Tyrosine Kinases," *J. Biol. Chem.* 279:52806, The American Society for Biochemistry and Molecular Biology, Inc. (Dec. 2004).

Li, W., et al., "Neutralization of Myelin-Associated NOGO-A by a NOGO Receptor-FC Fusion Protein," *Society for Neuroscience Abstracts* ABS3332, Society for Neuroscience (2002).

Li, S., et al., "Blockade of Nogo-66, Myelin-Associated Glycoprotein, and Oligodendrocyte Myelin Glycoprotein by Soluble Nogo-66 Receptor Promotes Axonal Sprouting and Recovery after Spinal Injury," *J. Neurosci.* 24:10511-10520, Society of Neuroscience (Nov. 2004).

Lin, L., et al., "Netrin-1 and slit-2 regulate and direct neurite growth of ventral midbrain dopaminergic neurons," *Molec. Cell. Neurosci.* 28:547-555, Elsevier Inc. (Mar. 2005).

Ma, L., et al., "Ligand-Dependent Recruitment of the ErbB4 Signaling Complex into Neuronal Lipid Rafts," *J. Neurosci.* 23:3164-3175, Society of Neuroscience (2003).

McKerracher, L., et al., "Identification of Myelin-Associated Glycoprotein as a Major Myelin-Derived Inhibitor of Neurite Growth," *Neuron* 13:805-811, Cell Press (1994).

Messier, C., et al., "New Techniques in Stereotaxic Surgery and Anesthesia in the Mouse," *Pharmacol. Biochem. Behav.* 63:313-318, Elsevier Science Inc. (1999).

Mi, S., et al., "A Novel CNS-Specific Protein Promotes Axonal Elongation by Modulating RHOA Signaling," *Society for Neuroscience Abstracts*, Abstract No. 891.5, Society for Neuroscience (2003).

Mi, S., et al., "LINGO-1 is a component of the Nogo-66 receptor/p75 signaling complex," *Nat. Neurosci.* 7:221-8, Nature Publishing Group (Mar. 2004).

Mi, S., et al., "LINGO-1 negatively regulates myelination by oligodendrocytes," *Nat. Neurosci.* 8:745-51, Nature Publishing Group (Electronically available May 2005).

Mi, S., et al., "LINGO-1 antagonist promotes spinal cord remyelination and axonal integrity in MOG-induced experimental autoimmune encephalomyelitis," *Nat. Med.* 13:1228-1233, Nature Publishing Group (Oct. 2007).

Mikol D.D. et al., "A Phosphatidylinositol-Linked Peanut Agglutinin-Binding Glycoprotein in Central Nervous System Myelin and on Oligodendrocytes," *J. Cell. Biol.* 106:1273-1279, The Rockefeller University Press (1988).

Morell, P., et al., "Gene Expression in Brain during Cuprizone-Induced Demyelination and Remyelination," *Molec. Cell. Neurosci.* 12:220-227, Academic Press (1998).

Mukhopadhyay, G., et al., "A Novel Role for Myelin-Associated Glycoprotein as an Inhibitor of Axonal Regeneration," *Neuron* 13:757-767, Cell Press (1994).

Nagy, P., et al., "Lipid rafts and the local density of ErbB proteins influence the biological role of homo- and heteroassociations of ErbB2," *J. Cell Sci.* 115:4251-4262, The Company of Biologists Ltd. (2002).

Nagy, Z.A., et al., "Fully human, HLA-DR-specific monoclonal antibodies efficiently induce programmed death of malignant lymphoid cells," *Nat. Med.* 8:801-807, Nature Publishing Group (2002).

Okafuji, T., et al., "Expression pattern of LINGO-1 in the developing nervous system of the chick embryo," *Gene Expr. Patterns* 6:57-62, Elsevier (Electronically available Jul. 2005).

Orlandi, R., et al., "Cloning immunoglobulin variable domains for expression by the polymerase chain reaction," *Proc. Natl. Acad. Sci. USA* 86:3833-3837, National Academy of Sciences (1989).

Park, S.-K., et al., "The erbB2 gene is required for the development of terminally differentiated spinal cord oligodendrocytes," *J. Cell Biol.* 154:1245-1258, The Rockefeller University Press (2001).

Park, J.B., et al., A TNF Receptor Family Member, TROY, is a Coreceptor with Nogo Receptor in Mediating the Inhibitory Activity of Myelin Inhibitors, *Neuron* 3:345-351, Elsevier Inc. (Feb. 2005).

Park, J.B., et al., A TNF Receptor Family Member, TROY, is a Coreceptor with Nogo Receptor in Mediating the Inhibitory Activity of Myelin Inhibitors, Erratum in *Neuron* 3:815, Elsevier Inc. (Mar. 2005).

Pinkas-Kramarski, R., et al., "Neu Differentiation Factor/Neuregulin Isoforms Activate Distinct Receptor Combinations," *J. Biol. Chem.* 271:19029-19032, The American Society for Biochemistry and Molecular Biology, Inc. (1996).

Plant, G.W., et al., "Purified Adult Ensheathing Glia Fail to Myelinate Axons under Culture Conditions that Enable Schwann Cells to Form Myelin," *J. Neurosci.* 22:6083-6091, Society for Neuroscience (2002).

Qiu, X.-B. and Goldberg, A.L., "Nrdp1/FLRF is a ubiquitin ligase promoting ubiquitination and degradation of the epidermal growth factor receptor family member, ErbB3," *Proc. Natl. Acad. Sci. USA* 99:14843-14848, National Academy of Sciences (2002).

Rauchenberger, R., et al., "Human Combinatorial Fab Library Yielding Specific and Functional Antibodies against the Human Fibroblast Growth Factor Receptor 3," *J. Biol. Chem.* 278:38194-38205, The American Society for Biochemistry and Molecular Biology, Inc. (2003).

Rubinson, D.A., et al., "A lentivirus-based system to functionally silence genes in primary mammalian cells, stem cells and transgenic mice by RNA interference," *Nat. Genet.* 33:401-406, Nature Publishing Group (2003).

Rutishauser, U. et al., "Cell Adhesion Molecules in Vertebrate Neural Develeopment," *Physiol. Rev.* 68:819-857, American Physiological Society (1988).

Schrnucker, J., et al., "erbB3 is Dispensable for Oligodendrocyte Development In Vitro and In Vivo," *Glia* 44:67-75, Wiley-Liss, Inc. (2003).

Shah, B.H., et al., "Role of EGF Receptor Transactivation in Phosphoinositide 3-Kinase-Dependent Activation of MAP Kinase by GPCRs," *J. Cell. Physiol.* 206:47-57, Wiley-Liss Inc. (Jan. 2006).

Shao, Z., et al., "TAJ/TROY, an Orphan TNF Receptor Family Member, Binds Nogo-66 Receptor 1 and Regulates Axonal Regeneration," *Neuron* 45:353-9, Elsevier Inc. (Feb. 2005).

Stolt, C.C., et al., "Terminal differentiation of myelin-forming oligodendrocytes depends on the transcription factor Sox10," *Genes & Dev.* 16:165-170, Cold Spring Harbor Laboratory Press (2002).

Sussman, C.R., et al., "The ErbB4 Neurogulin Receptor Mediates Suppression of Oligodendrocyte Maturation," *J. Neurosci.* 25:5757-5762, Society for Neuroscience (Jun. 2005).

Trapp, B.D., et al., "Pathogenesis of tissue injury in MS lesions," *J. Neuroimmunol.* 98:49-56, Elsevier Science B.V. (1999).

Trapp, B.D., et al., "Axonal pathology in multiple sclerosis: relationship to neurologic disability," *Curr. Opin. Neurol.* 12:295-302, Lippincott Williams & Wilkins (1999).

Trifunovski, A. et al. "Neuronal activity-induced regulation of LINGO-1," *Neuroreport* 15:2397-2400, Lippincott, Williams & Wilkins (Oct. 2004).

Tzahar, E., et al., "Bivalence of EGF-like ligands drives the ErbB signaling network," *EMBO J* 16:4938-4950, Oxford University Press (1997).

Vartanian, T., et al., "Failure of spinal cord oligodendrocyte development in mice lacking neuregulin," *Proc. Natl. Acad. Sci. USA* 96:731-735, National Academy of Sciences (1999).

(56) References Cited

OTHER PUBLICATIONS

Wang, K.C., et al., "Oligodendrocyte-Myelin Glycoprotein is a Nogo Receptor Ligand That Inhibits Neurite Outgrowth," *Nature* 417:941-944, Nature Publishing Group (2002).

Williams, E.-J. and Doherty, P., "Evidence for and against a Pivotal Role of PI 3-Kinase in a Neuronal Cell Survival Pathway," *Molec. Cell. Neurosci.* 13:272-280, Academic Press (1999).

Xu, W., et al., "Chaperone-dependent E3 ubiquitin ligase CHIP mediates a degradative pathway for c-ErbB2/Neu," *Proc. Natl. Acad. Sci. USA* 99:12847-12852, National Academy of Sciences (2002).

Yang, L., et al., "A novel azulenyl nitrone antioxidant protects against MPTP and 3-nitropropionic acid neurotoxicities," *Exp. Neurol.* 191:86-93, Elsevier Inc. (Jan. 2005).

Yu, W., et al., "Segregation of Nogo66 receptors into lipid rafts in rat brain and inhibition of Nogo66 signaling by cholesterol depletion," *FEBS Lett.* 577:87-92, Elsevier B.V. (Nov. 2004).

Zhou, P., et al., "ErbB2 Degradation Mediated by the Co-chaperone Protein CHIP," *J. Biol. Chem.* 278:13829-13837, The American Society for Biochemistry and Molecular Biology, Inc. (2003).

NCBI Entrez, Accession No. BC011057, (first available Jul. 30, 2001; last updated Feb. 8, 2007).

NCBI Entrez, Accession No. BC068558, (first available Apr. 6, 2004; last updated Feb. 8, 2007).

NCBI Entrez, Accession No. NM_152570, (first available Sep. 6, 2002; last updated Feb. 11, 2008).

NCBI Entrez, Accession No. NM_032808, (first available May 31, 2001; last updated Feb. 11, 2008).

NCBI Entrez, Accession No. DR000281, (first available May 17, 2005; last updated May 17, 2005).

NCBI Entrez, Accession No. AY324320, (first available May 4, 2004; last updated May 4, 2004).

NCBI Entrez, Accession No. AY324322, (first available May 4, 2004; last updated May 4, 2004).

NCBI Entrez, Accession No. AY324323, (first available May 4, 2004; last updated May 4, 2004).

U.S. Appl. No. 12/092,662, inventors Mi et al., National Phase of PCT/US2006/042990, international filing date of Nov. 3, 2006 (Not Published).

U.S. Appl. No. 12/095,857, inventors Mi et al., National Phase of PCT/US2006/045993, international filing date of Dec. 1, 2006 (Not Published).

Office Action mailed Oct. 1, 2012, in Japanese Patent Application No. 2008-520375 (English language translation included).

Paul, WE, ed. Fundamental Immunology, Third Edition. Raven Press, New York, 1993, pp. 292-295, under the heading "Fv Structure and Diversity in Three Dimensions."

U.S. Appl. No. 13/414,222, inventors Mi et al., filed Mar. 7, 2012.

U.S. Appl. No. 13/356,413, inventors Mi et al., filed Jan. 23, 2012.

Office Action mailed Jun. 24, 2011, in U.S. Appl. No. 12/092,662, Mi, filed Sep. 26, 2008.

Office Action mailed Feb. 9, 2012, in U.S. Appl. No. 12/092,662, Mi, filed Sep. 26, 2008.

Office Action mailed Oct. 25, 2011, in U.S. Appl. No. 13/158,307, Mi, filed Jun. 10, 2011.

Office Action mailed, Aug. 20, 2012 in U.S. Appl. No. 13/158,307.

Office Action mailed, Jul. 24, 2012 in U.S. Appl. No. 11/165,576.

\* cited by examiner

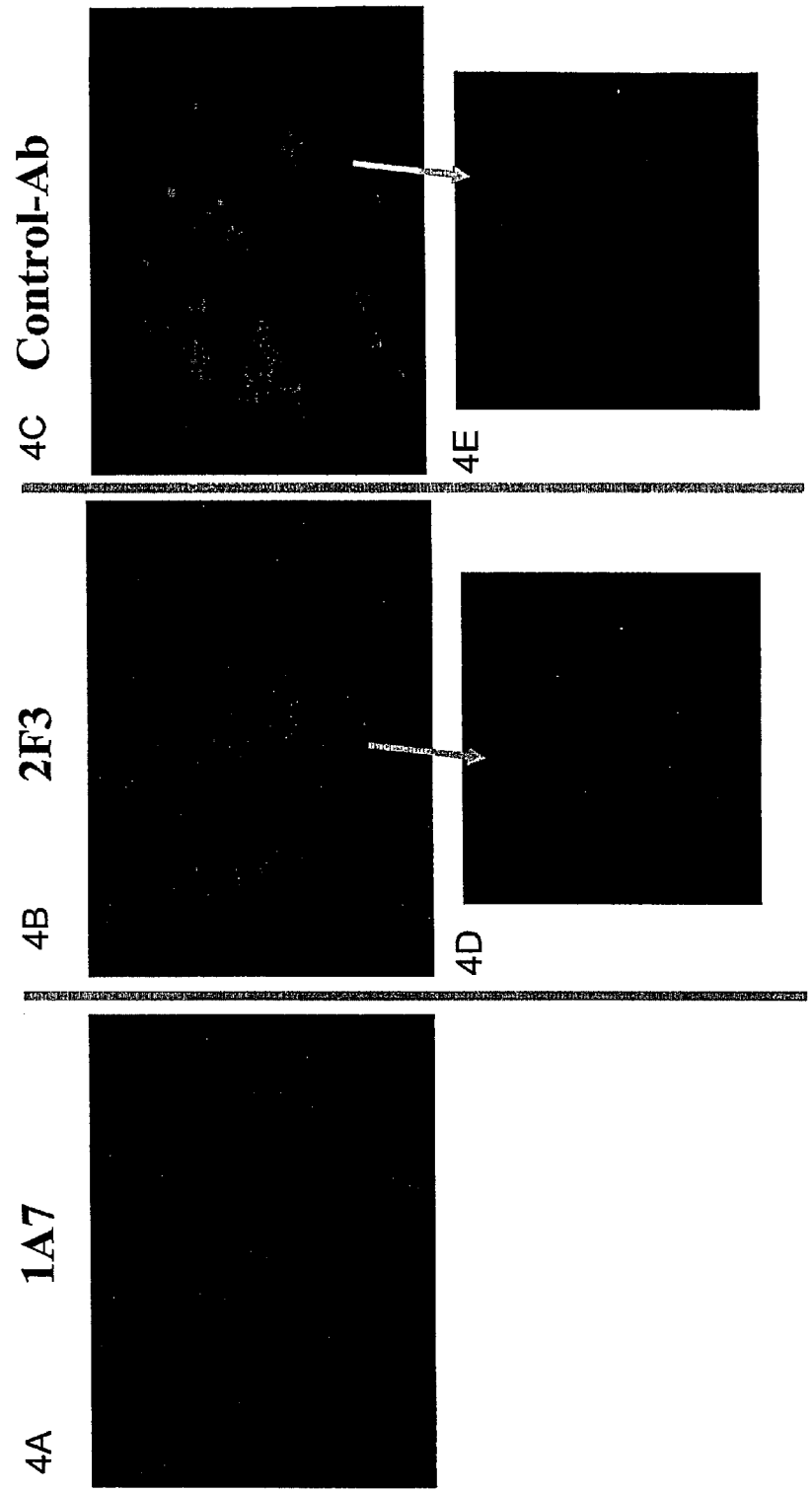

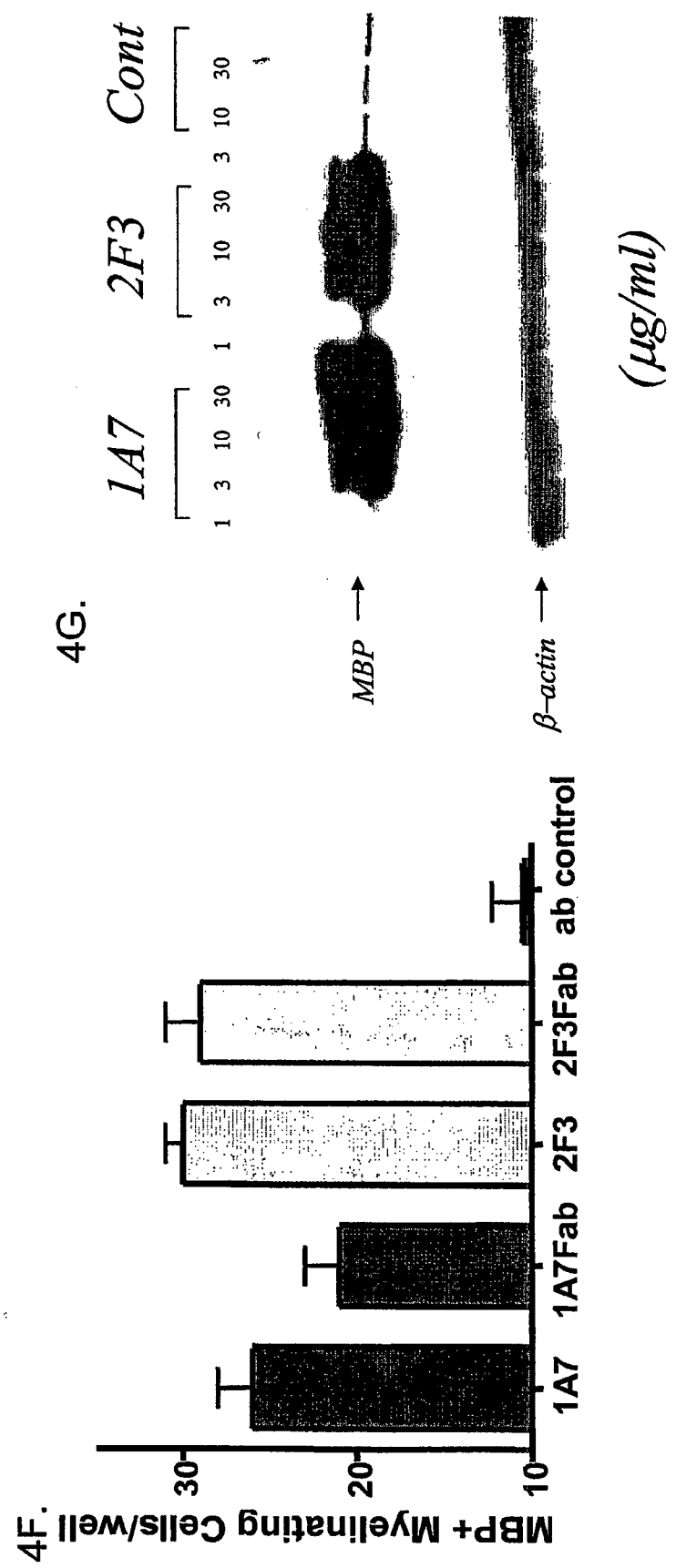
FIG. 4: Anti-LINGO-1 Antibodies Promote Myelination in Co-culture

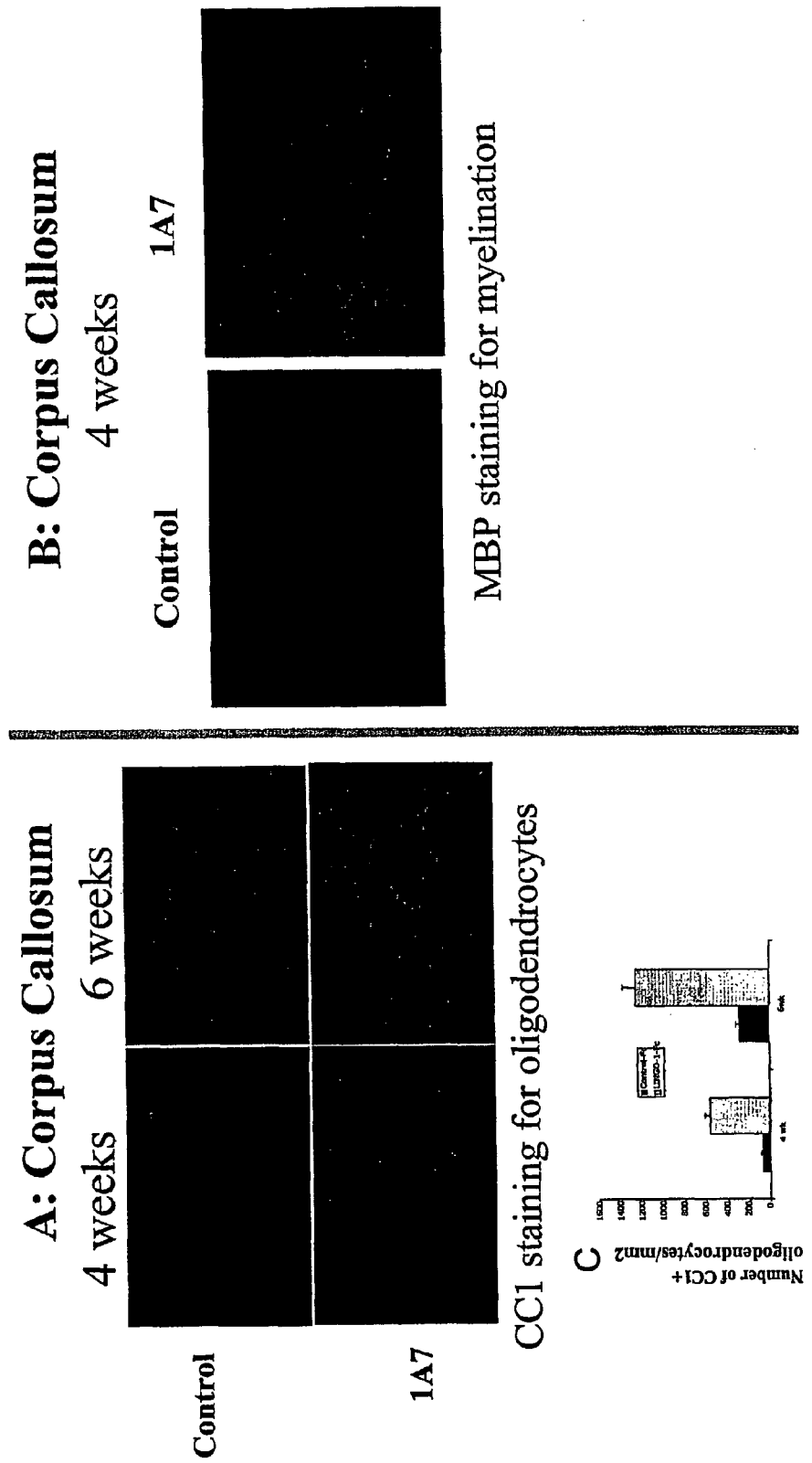
FIG. 5: 1A7 Promotes Oligodendrocyte Survival and Remyelination in Cuprizone Model 1A7 Promotes RGC Neurons Survival

SEQUENCE LISTING

```
<160> NUMBER OF SEQ ID NOS: 409

<210> SEQ ID NO 1
<211> LENGTH: 1845
<212> TYPE: DNA
<213> ORGANISM: Homo sapiens

<400> SEQUENCE: 1
atgctggcgg ggggcgtgag gagcatgccc agccccctcc tggcctgctg gcagcccatc      60
ctcctgctgg tgctgggctc agtgctgtca ggctcggcca cgggctgccc gccccgctgc     120
gagtgctccg cccaggaccg cgctgtgctg tgccaccgca agcgctttgt ggcagtcccc     180
```

```
gagggcatcc ccaccgagac gcgcctgctg gacctaggca agaaccgcat caaaacgctc      240
aaccaggacg agttcgccag cttccgcac ctggaggagc tggagctcaa cgagaacatc       300
gtgagcgccg tggagcccgg cgccttcaac aacctcttca acctccggac gctgggtctc     360
cgcagcaacc gcctgaagct catcccgcta ggcgtcttca ctggcctcag caacctgacc     420
aagctggaca tcagcgagaa caagattgtt atcctgctgg actacatgtt tcaggacctg    480
tacaacctca agtcactgga ggttggcgac aatgacctcg tctacatctc tcaccgcgcc    540
ttcagcggcc tcaacagcct ggagcagctg acgctggaga atgcaacct gacctccatc     600 cccaccgagg cgctgtccca cctgcacggc ctcatcgtcc tgaggctccg gcacctcaac    660
atcaatgcca tccgggacta ctccttcaag aggctctacc gactcaaggt cttggagatc     720
tcccactggc cctacttgga caccatgaca cccaactgcc tctacggcct caacctgacg     780
tccctgtcca tcacacactg caatctgacc gctgtgccct acctggccgt ccgccaccta    840
gtctatctcc gcttcctcaa cctctcctac aaccccatca gcaccattga gggctccatg    900
ttgcatgagc tgctccggct gcaggagatc cagctggtgg gcgggcagct ggccgtggtg    960 gagcccatg ccttccgcgg cctcaactac ctgcgcgtgc tcaatgtctc tggcaaccag     1020
ctgaccacac tggaggaatc agtcttccac tcggtgggca acctggagac actcatcctg   1080
gactccaacc cgctggcctg cgactgtcgg ctcctgtggg tgttccggcg ccgctggcgg    1140
ctcaacttca accggcagca gccacgtgc gccacgcccg agtttgtcca gggcaaggag    1200
ttcaaggact ccctgatgt gctactgccc aactacttca cctgccgccg cgcccgcatc    1260
cgggaccgca aggcccagca ggtgtttgtg gacgagggcc acacggtgca gtttgtgtgc    1320
cgggccgatg gcgacccgcc gccgccatc ctctggctct cacccgaaa gcacctggtc     1380 tcagccaaga gcaatgggcg gctcacagtc ttccctgatg gcacgctgga ggtgcgctac    1440
gcccaggtac aggacaacgg cacgtacctg tgcatcgcgg ccaacgcggg cggcaacgac    1500
tccatgcccg cccacctgca tgtgcgcagc tactcgcccg actggcccca tcagcccaac    1560
aagaccttcg ctttcatctc caaccagccg ggcgagggag aggccaacag cacccgcgcc    1620
actgtgcctt tccccttcga catcaagacc ctcatcatcg ccaccaccat gggcttcatc    1680
tctttcctgg gcgtcgtcct cttctgcctg gtgctgctgt ttctctggag ccggggcaag    1740
ggcaacacaa agcacaacat cgagatcgag tatgtgcccc gaaagtcgga cgcaggcatc    1800
agctccgccg acgcgccccg caagttcaac atgaagatga tatga                     1845
```

<210> SEQ ID NO 2
<211> LENGTH: 614
<212> TYPE: PRT
<213> ORGANISM: Homo sapiens

<400> SEQUENCE: 2

Met Leu Ala Gly Gly Val Arg Ser Met Pro Ser Pro Leu Leu Ala Cys
1               5                   10                  15

Trp Gln Pro Ile Leu Leu Leu Val Leu Gly Ser Val Leu Ser Gly Ser
            20                  25                  30

Ala Thr Gly Cys Pro Pro Arg Cys Glu Cys Ser Ala Gln Asp Arg Ala
        35                  40                  45

Val Leu Cys His Arg Lys Arg Phe Val Ala Val Pro Glu Gly Ile Pro
    50                  55                  60

Thr Glu Thr Arg Leu Leu Asp Leu Gly Lys Asn Arg Ile Lys Thr Leu
65                  70                  75                  80

```
Asn Gln Asp Glu Phe Ala Ser Phe Pro His Leu Glu Leu Glu Leu
                85                  90                  95
Asn Glu Asn Ile Val Ser Ala Val Glu Pro Gly Ala Phe Asn Asn Leu
            100                 105                 110
Phe Asn Leu Arg Thr Leu Gly Leu Arg Ser Asn Arg Leu Lys Leu Ile
            115                 120                 125
Pro Leu Gly Val Phe Thr Gly Leu Ser Asn Leu Thr Lys Leu Asp Ile
    130                 135                 140
Ser Glu Asn Lys Ile Val Ile Leu Leu Asp Tyr Met Phe Gln Asp Leu
145                 150                 155                 160
Tyr Asn Leu Lys Ser Leu Glu Val Gly Asp Asn Asp Leu Val Tyr Ile
                165                 170                 175
Ser His Arg Ala Phe Ser Gly Leu Asn Ser Leu Glu Gln Leu Thr Leu
            180                 185                 190
Glu Lys Cys Asn Leu Thr Ser Ile Pro Thr Glu Ala Leu Ser His Leu
            195                 200                 205
His Gly Leu Ile Val Leu Arg Leu Arg His Leu Asn Ile Asn Ala Ile
    210                 215                 220
Arg Asp Tyr Ser Phe Lys Arg Leu Tyr Arg Leu Lys Val Leu Glu Ile
225                 230                 235                 240
Ser His Trp Pro Tyr Leu Asp Thr Met Thr Pro Asn Cys Leu Tyr Gly
                245                 250                 255
Leu Asn Leu Thr Ser Leu Ser Ile Thr His Cys Asn Leu Thr Ala Val
            260                 265                 270
Pro Tyr Leu Ala Val Arg His Leu Val Tyr Leu Arg Phe Leu Asn Leu
            275                 280                 285
Ser Tyr Asn Pro Ile Ser Thr Ile Glu Gly Ser Met Leu His Glu Leu
    290                 295                 300
Leu Arg Leu Gln Glu Ile Gln Leu Val Gly Gly Gln Leu Ala Val Val
305                 310                 315                 320
Glu Pro Tyr Ala Phe Arg Gly Leu Asn Tyr Leu Arg Val Leu Asn Val
                325                 330                 335
Ser Gly Asn Gln Leu Thr Thr Leu Glu Glu Ser Val Phe His Ser Val
            340                 345                 350
Gly Asn Leu Glu Thr Leu Ile Leu Asp Ser Asn Pro Leu Ala Cys Asp
            355                 360                 365
Cys Arg Leu Leu Trp Val Phe Arg Arg Arg Trp Arg Leu Asn Phe Asn
    370                 375                 380
Arg Gln Gln Pro Thr Cys Ala Thr Pro Glu Phe Val Gln Gly Lys Glu
385                 390                 395                 400
Phe Lys Asp Phe Pro Asp Val Leu Leu Pro Asn Tyr Phe Thr Cys Arg
                405                 410                 415
Arg Ala Arg Ile Arg Asp Arg Lys Ala Gln Gln Val Phe Val Asp Glu
            420                 425                 430
Gly His Thr Val Gln Phe Val Cys Arg Ala Asp Gly Asp Pro Pro Pro
            435                 440                 445
Ala Ile Leu Trp Leu Ser Pro Arg Lys His Leu Val Ser Ala Lys Ser
    450                 455                 460
Asn Gly Arg Leu Thr Val Phe Pro Asp Gly Thr Leu Glu Val Arg Tyr
465                 470                 475                 480
Ala Gln Val Gln Asp Asn Gly Thr Tyr Leu Cys Ile Ala Ala Asn Ala
                485                 490                 495
Gly Gly Asn Asp Ser Met Pro Ala His Leu His Val Arg Ser Tyr Ser
            500                 505                 510
```

```
Pro Asp Trp Pro His Gln Pro Asn Lys Thr Phe Ala Phe Ile Ser Asn
        515                 520                 525

Gln Pro Gly Glu Gly Glu Ala Asn Ser Thr Arg Ala Thr Val Pro Phe
    530                 535                 540

Pro Phe Asp Ile Lys Thr Leu Ile Ile Ala Thr Thr Met Gly Phe Ile
545                 550                 555                 560

Ser Phe Leu Gly Val Val Leu Phe Cys Leu Val Leu Leu Phe Leu Trp
                565                 570                 575

Ser Arg Gly Lys Gly Asn Thr Lys His Asn Ile Glu Ile Glu Tyr Val
            580                 585                 590

Pro Arg Lys Ser Asp Ala Gly Ile Ser Ser Ala Asp Ala Pro Arg Lys
        595                 600                 605

Phe Asn Met Lys Met Ile
        610

<210> SEQ ID NO 3
<211> LENGTH: 6
<212> TYPE: PRT
<213> ORGANISM: Homo sapiens

<400> SEQUENCE: 3

Met Gln Val Ser Lys Arg
1               5

<210> SEQ ID NO 4
<211> LENGTH: 29
<212> TYPE: DNA
<213> ORGANISM: Murinae gen. sp.

<400> SEQUENCE: 4
gcgtctagaa ctggatggtg ggagatgga                                    29

<210> SEQ ID NO 5
<211> LENGTH: 15
<212> TYPE: DNA
<213> ORGANISM: Artificial sequence
<220> FEATURE:
<223> OTHER INFORMATION: VH-CDR1 (Li10)

<400> SEQUENCE: 5
acttacccta tggtt                                                   15

<210> SEQ ID NO 6
<211> LENGTH: 5
<212> TYPE: PRT
<213> ORGANISM: Artificial sequence
<220> FEATURE:
<223> OTHER INFORMATION: VH-CDR1 (Li10)

<400> SEQUENCE: 6

Thr Tyr Pro Met Val
1               5

<210> SEQ ID NO 7
<211> LENGTH: 51
<212> TYPE: DNA
<213> ORGANISM: Artificial sequence
<220> FEATURE:
<223> OTHER INFORMATION: VH-CDR2 (Li10)

<400> SEQUENCE: 7
tggatcggtc cttctggtgg cgttactgct tatgctgact ccgttaaagg t           51
```

```
<210> SEQ ID NO 8
<211> LENGTH: 17
<212> TYPE: PRT
<213> ORGANISM: Artificial sequence
<220> FEATURE:
<223> OTHER INFORMATION: VH-CDR2 (Li10)

<400> SEQUENCE: 8

Trp Ile Gly Pro Ser Gly Gly Val Thr Ala Tyr Ala Asp Ser Val Lys
1               5                   10                  15

Gly

<210> SEQ ID NO 9
<211> LENGTH: 33
<212> TYPE: DNA
<213> ORGANISM: Artificial sequence
<220> FEATURE:
<223> OTHER INFORMATION: VH-CDR3 (Li10)

<400> SEQUENCE: 9
ccctatagca gtggctggtg ggacttcgat ctc                            33

<210> SEQ ID NO 10
<211> LENGTH: 11
<212> TYPE: PRT
<213> ORGANISM: Artificial sequence
<220> FEATURE:
<223> OTHER INFORMATION: VH-CDR3 (Li10)

<400> SEQUENCE: 10

Pro Tyr Ser Ser Gly Trp Trp Asp Phe Asp Leu
1               5                   10

<210> SEQ ID NO 11
<211> LENGTH: 15
<212> TYPE: DNA
<213> ORGANISM: Artificial sequence
<220> FEATURE:
<223> OTHER INFORMATION: VH-CDR1 (Li07)

<400> SEQUENCE: 11
atgtacttta tgggt                                                15

<210> SEQ ID NO 12
<211> LENGTH: 5
<212> TYPE: PRT
<213> ORGANISM: Artificial sequence
<220> FEATURE:
<223> OTHER INFORMATION: VH-CDR1 (Li07)

<400> SEQUENCE: 12

Met Tyr Phe Met Gly
1               5

<210> SEQ ID NO 13
<211> LENGTH: 51
<212> TYPE: DNA
<213> ORGANISM: Artificial sequence
<220> FEATURE:
<223> OTHER INFORMATION: VH-CDR2 (Li07)

<400> SEQUENCE: 13
tctatctctc cttctggtgg ctttacttct tatgctgact ccgttaaagg t        51

<210> SEQ ID NO 14
<211> LENGTH: 17
```

```
<212> TYPE: PRT
<213> ORGANISM: Artificial sequence
<220> FEATURE:
<223> OTHER INFORMATION: VH-CDR2 (Li07)

<400> SEQUENCE: 14

Ser Ile Ser Pro Ser Gly Gly Phe Thr Ser Tyr Ala Asp Ser Val Lys
1               5                   10                  15

Gly

<210> SEQ ID NO 15
<211> LENGTH: 21
<212> TYPE: DNA
<213> ORGANISM: Artificial sequence
<220> FEATURE:
<223> OTHER INFORMATION: VH-CDR3 (Li07)

<400> SEQUENCE: 15
gatcggcatg cttttgatat c                                            21

<210> SEQ ID NO 16
<211> LENGTH: 7
<212> TYPE: PRT
<213> ORGANISM: Artificial sequence
<220> FEATURE:
<223> OTHER INFORMATION: VH-CDR3 (Li07)

<400> SEQUENCE: 16

Asp Arg His Ala Phe Asp Ile
1               5

<210> SEQ ID NO 17
<211> LENGTH: 14
<212> TYPE: DNA
<213> ORGANISM: Artificial sequence
<220> FEATURE:
<223> OTHER INFORMATION: VH-CDR1 (Li05)

<400> SEQUENCE: 17
cttacgctat gggt                                                    14

<210> SEQ ID NO 18
<211> LENGTH: 5
<212> TYPE: PRT
<213> ORGANISM: Artificial sequence
<220> FEATURE:
<223> OTHER INFORMATION: VH-CDR1 (Li05)

<400> SEQUENCE: 18

Ala Tyr Ala Met Gly
1               5

<210> SEQ ID NO 19
<211> LENGTH: 51
<212> TYPE: DNA
<213> ORGANISM: Artificial sequence
<220> FEATURE:
<223> OTHER INFORMATION: VH-CDR2 (Li05)

<400> SEQUENCE: 19
tctatcgttt cttctggtgg ctatactgat tatgctgact ccgttaaagg t            51

<210> SEQ ID NO 20
<211> LENGTH: 17
<212> TYPE: PRT
<213> ORGANISM: Artificial sequence
<220> FEATURE:
```

```
<223> OTHER INFORMATION: VH-CDR2 (Li05)

<400> SEQUENCE: 20

Ser Ile Val Ser Ser Gly Gly Tyr Thr Asp Tyr Ala Asp Ser Val Lys
1               5                   10                  15
Gly

<210> SEQ ID NO 21
<211> LENGTH: 27
<212> TYPE: DNA
<213> ORGANISM: Artificial sequence
<220> FEATURE:
<223> OTHER INFORMATION: VH-CDR3 (Li05)

<400> SEQUENCE: 21
gagggtgacc ataatgcttt tgatatc                                             27

<210> SEQ ID NO 22
<211> LENGTH: 9
<212> TYPE: PRT
<213> ORGANISM: Artificial sequence
<220> FEATURE:
<223> OTHER INFORMATION: VH-CDR3 (Li05)

<400> SEQUENCE: 22

Glu Gly Asp His Asn Ala Phe Asp Ile
1               5

<210> SEQ ID NO 23
<211> LENGTH: 15
<212> TYPE: DNA
<213> ORGANISM: Artificial sequence
<220> FEATURE:
<223> OTHER INFORMATION: VH-CDR1 (Li11)

<400> SEQUENCE: 23
tcttacgcta tgtat                                                          15

<210> SEQ ID NO 24
<211> LENGTH: 5
<212> TYPE: PRT
<213> ORGANISM: Artificial sequence
<220> FEATURE:
<223> OTHER INFORMATION: VH-CDR1 (Li11)

<400> SEQUENCE: 24

Ser Tyr Ala Met Tyr
1               5

<210> SEQ ID NO 25
<211> LENGTH: 51
<212> TYPE: DNA
<213> ORGANISM: Artificial sequence
<220> FEATURE:
<223> OTHER INFORMATION: VH-CDR2 (Li11)

<400> SEQUENCE: 25
tctatctcta cttctggtgg ctatactggt tatgctgact ccgttaaagg t                  51

<210> SEQ ID NO 26
<211> LENGTH: 17
<212> TYPE: PRT
<213> ORGANISM: Artificial sequence
<220> FEATURE:
<223> OTHER INFORMATION: VH-CDR2 (Li11)

<400> SEQUENCE: 26
```

Ser Ile Ser Thr Ser Gly Gly Tyr Thr Gly Tyr Ala Asp Ser Val Lys
1               5                   10                  15
Gly

<210> SEQ ID NO 27
<211> LENGTH: 36
<212> TYPE: DNA
<213> ORGANISM: Artificial sequence
<220> FEATURE:
<223> OTHER INFORMATION: VH-CDR3 (Li11)

<400> SEQUENCE: 27
gataccagcg ataatgacta ctactacatg gacgtc                                    36

<210> SEQ ID NO 28
<211> LENGTH: 12
<212> TYPE: PRT
<213> ORGANISM: Artificial sequence
<220> FEATURE:
<223> OTHER INFORMATION: VH-CDR3 (Li11)

<400> SEQUENCE: 28

Asp Thr Ser Asp Asn Asp Tyr Tyr Tyr Met Asp Val
1               5                   10

<210> SEQ ID NO 29
<211> LENGTH: 15
<212> TYPE: DNA
<213> ORGANISM: Artificial sequence
<220> FEATURE:
<223> OTHER INFORMATION: VH-CDR1 (Li01)

<400> SEQUENCE: 29
aagtaccaga tgact                                                           15

<210> SEQ ID NO 30
<211> LENGTH: 5
<212> TYPE: PRT
<213> ORGANISM: Artificial sequence
<220> FEATURE:
<223> OTHER INFORMATION: VH-CDR1 (Li01)

<400> SEQUENCE: 30

Lys Tyr Gln Met Thr
1               5

<210> SEQ ID NO 31
<211> LENGTH: 51
<212> TYPE: DNA
<213> ORGANISM: Artificial sequence
<220> FEATURE:
<223> OTHER INFORMATION: VH-CDR2 (Li01)

<400> SEQUENCE: 31
tctatctatc cttctggtgg caatactgtt tatgctgact ccgttaaagg t                   51

<210> SEQ ID NO 32
<211> LENGTH: 17
<212> TYPE: PRT
<213> ORGANISM: Artificial sequence
<220> FEATURE:
<223> OTHER INFORMATION: VH-CDR2 (Li01)

<400> SEQUENCE: 32

Ser Ile Tyr Pro Ser Gly Gly Asn Thr Val Tyr Ala Asp Ser Val Lys
1               5                   10                  15

Gly

<210> SEQ ID NO 33
<211> LENGTH: 27
<212> TYPE: DNA
<213> ORGANISM: Artificial sequence
<220> FEATURE:
<223> OTHER INFORMATION: VH-CDR3 (Li01)

<400> SEQUENCE: 33
gggactacag aggcagtctt tgactac                27

<210> SEQ ID NO 34
<211> LENGTH: 9
<212> TYPE: PRT
<213> ORGANISM: Artificial sequence
<220> FEATURE:
<223> OTHER INFORMATION: VH-CDR3 (Li01)

<400> SEQUENCE: 34

Gly Thr Thr Glu Ala Val Phe Asp Tyr
1               5

<210> SEQ ID NO 35
<211> LENGTH: 15
<212> TYPE: DNA
<213> ORGANISM: Artificial sequence
<220> FEATURE:
<223> OTHER INFORMATION: VH-CDR1 (Li12)

<400> SEQUENCE: 35
cagtacaata tgttt                15

<210> SEQ ID NO 36
<211> LENGTH: 5
<212> TYPE: PRT
<213> ORGANISM: Artificial sequence
<220> FEATURE:
<223> OTHER INFORMATION: VH-CDR1 (Li12)

<400> SEQUENCE: 36

Gln Tyr Asn Met Phe
1               5

<210> SEQ ID NO 37
<211> LENGTH: 51
<212> TYPE: DNA
<213> ORGANISM: Artificial sequence
<220> FEATURE:
<223> OTHER INFORMATION: VH-CDR2 (Li12)

<400> SEQUENCE: 37
cgtatctctt cttctggtgg catgactatg tatgctgact ccgttaaagg t                51

<210> SEQ ID NO 38
<211> LENGTH: 17
<212> TYPE: PRT
<213> ORGANISM: Artificial sequence
<220> FEATURE:
<223> OTHER INFORMATION: VH-CDR2 (Li12)

<400> SEQUENCE: 38

Arg Ile Ser Ser Ser Gly Gly Met Thr Met Tyr Ala Asp Ser Val Lys
1               5                   10                  15
Gly

<210> SEQ ID NO 39
<211> LENGTH: 69
<212> TYPE: DNA
<213> ORGANISM: Artificial sequence
<220> FEATURE:
<223> OTHER INFORMATION: VH-CDR3 (Li12)

<400> SEQUENCE: 39
gaagcgttac ggccttattg tagtggtggt agctgctact ccgactacta ctactacggt    60
atggacgtc                                                            69

<210> SEQ ID NO 40
<211> LENGTH: 23
<212> TYPE: PRT
<213> ORGANISM: Artificial sequence
<220> FEATURE:
<223> OTHER INFORMATION: VH-CDR3 (Li12)

<400> SEQUENCE: 40

Glu Ala Leu Arg Pro Tyr Cys Ser Gly Gly Ser Cys Tyr Ser Asp Tyr
1               5                   10                  15

Tyr Tyr Tyr Gly Met Asp Val
            20

<210> SEQ ID NO 41
<211> LENGTH: 15
<212> TYPE: DNA
<213> ORGANISM: Artificial sequence
<220> FEATURE:
<223> OTHER INFORMATION: VH-CDR1 (Li06)

<400> SEQUENCE: 41
gagtacccta tggat                                                     15

<210> SEQ ID NO 42
<211> LENGTH: 5
<212> TYPE: PRT
<213> ORGANISM: Artificial sequence
<220> FEATURE:
<223> OTHER INFORMATION: VH-CDR1 (Li06)

<400> SEQUENCE: 42

Glu Tyr Pro Met Asp
1               5

<210> SEQ ID NO 43
<211> LENGTH: 51
<212> TYPE: DNA
<213> ORGANISM: Artificial sequence
<220> FEATURE:
<223> OTHER INFORMATION: VH-CDR2 (Li06)

<400> SEQUENCE: 43
tctatctatt cttctggtgg ctctactgtt tatgctgact ccattaaagg t              51

<210> SEQ ID NO 44
<211> LENGTH: 17
<212> TYPE: PRT
<213> ORGANISM: Artificial sequence
<220> FEATURE:
<223> OTHER INFORMATION: VH-CDR2 (Li06)

<400> SEQUENCE: 44

Ser Ile Tyr Ser Ser Gly Gly Ser Thr Val Tyr Ala Asp Ser Ile Lys
1               5                   10                  15

Gly

<210> SEQ ID NO 45
<211> LENGTH: 27
<212> TYPE: DNA
<213> ORGANISM: Artificial sequence
<220> FEATURE:
<223> OTHER INFORMATION: VH-CDR3 (Li06)

<400> SEQUENCE: 45
gagggtgact ctgatgcttt tgatatc                                27

<210> SEQ ID NO 46
<211> LENGTH: 9
<212> TYPE: PRT
<213> ORGANISM: Artificial sequence
<220> FEATURE:
<223> OTHER INFORMATION: VH-CDR3 (Li06)

<400> SEQUENCE: 46

Glu Gly Asp Ser Asp Ala Phe Asp Ile
1               5

<210> SEQ ID NO 47
<211> LENGTH: 15
<212> TYPE: DNA
<213> ORGANISM: Artificial sequence
<220> FEATURE:
<223> OTHER INFORMATION: VH-CDR1 (Li08)

<400> SEQUENCE: 47
cattacgaga tggtt                                              15

<210> SEQ ID NO 48
<211> LENGTH: 5
<212> TYPE: PRT
<213> ORGANISM: Artificial sequence
<220> FEATURE:
<223> OTHER INFORMATION: VH-CDR1 (Li08)

<400> SEQUENCE: 48

His Tyr Glu Met Val
1               5

<210> SEQ ID NO 49
<211> LENGTH: 51
<212> TYPE: DNA
<213> ORGANISM: Artificial sequence
<220> FEATURE:
<223> OTHER INFORMATION: VH-CDR2 (Li08)

<400> SEQUENCE: 49
tctatccgtt cttctggtgg cgctactaag tatgctgact ccgttaaagg t        51

<210> SEQ ID NO 50
<211> LENGTH: 17
<212> TYPE: PRT
<213> ORGANISM: Artificial sequence
<220> FEATURE:
<223> OTHER INFORMATION: VH-CDR2 (Li08)

<400> SEQUENCE: 50

Ser Ile Arg Ser Ser Gly Gly Ala Thr Lys Tyr Ala Asp Ser Val Lys
1               5                   10                  15

Gly

```
<210> SEQ ID NO 51
<211> LENGTH: 27
<212> TYPE: DNA
<213> ORGANISM: Artificial sequence
<220> FEATURE:
<223> OTHER INFORMATION: VH-C DR3 (Li08)

<400> SEQUENCE: 51
gagtcgccag acgactactt tgactac                                              27

<210> SEQ ID NO 52
<211> LENGTH: 9
<212> TYPE: PRT
<213> ORGANISM: Artificial sequence
<220> FEATURE:
<223> OTHER INFORMATION: VH-CDR3 (Li08)

<400> SEQUENCE: 52

Glu Ser Pro Asp Asp Tyr Phe Asp Tyr
1               5

<210> SEQ ID NO 53
<211> LENGTH: 15
<212> TYPE: DNA
<213> ORGANISM: Artificial sequence
<220> FEATURE:
<223> OTHER INFORMATION: VH-CDR1 (Li03)

<400> SEQUENCE: 53
cagtacccta tggag                                                           15

<210> SEQ ID NO 54
<211> LENGTH: 5
<212> TYPE: PRT
<213> ORGANISM: Artificial sequence
<220> FEATURE:
<223> OTHER INFORMATION: VH-CDR1 (Li03)

<400> SEQUENCE: 54

Gln Tyr Pro Met Glu
1               5

<210> SEQ ID NO 55
<211> LENGTH: 51
<212> TYPE: DNA
<213> ORGANISM: Artificial sequence
<220> FEATURE:
<223> OTHER INFORMATION: VH-CDR2 (Li03)

<400> SEQUENCE: 55
ggtatctatc cttctggtgg ctctactgtt tatgctgact ccgttaaagg t                   51

<210> SEQ ID NO 56
<211> LENGTH: 17
<212> TYPE: PRT
<213> ORGANISM: Artificial sequence
<220> FEATURE:
<223> OTHER INFORMATION: VH-CDR2 (Li03)

<400> SEQUENCE: 56

Gly Ile Tyr Pro Ser Gly Gly Ser Thr Val Tyr Ala Asp Ser Val Lys
1               5                   10                  15

Gly

<210> SEQ ID NO 57
<211> LENGTH: 30
<212> TYPE: DNA
```

<213> ORGANISM: Artificial sequence
<220> FEATURE:
<223> OTHER INFORMATION: VH-CDR3 (Li03)

<400> SEQUENCE: 57
gcggggcagt ggctgggggga ctttgactac                              30

<210> SEQ ID NO 58
<211> LENGTH: 10
<212> TYPE: PRT
<213> ORGANISM: Artificial sequence
<220> FEATURE:
<223> OTHER INFORMATION: VH-CDR3 (Li03)

<400> SEQUENCE: 58

Ala Gly Gln Trp Leu Gly Asp Phe Asp Tyr
1               5                   10

<210> SEQ ID NO 59
<211> LENGTH: 15
<212> TYPE: DNA
<213> ORGANISM: Artificial sequence
<220> FEATURE:
<223> OTHER INFORMATION: VH-CDR1 (Li09)

<400> SEQUENCE: 59
atgtactcta tggtt                                               15

<210> SEQ ID NO 60
<211> LENGTH: 5
<212> TYPE: PRT
<213> ORGANISM: Artificial sequence
<220> FEATURE:
<223> OTHER INFORMATION: VH-CDR1 (Li09)

<400> SEQUENCE: 60

Met Tyr Ser Met Val
1               5

<210> SEQ ID NO 61
<211> LENGTH: 51
<212> TYPE: DNA
<213> ORGANISM: Artificial sequence
<220> FEATURE:
<223> OTHER INFORMATION: VH-CDR2 (Li09)

<400> SEQUENCE: 61
tatatctctc cttctggtgg caagactatg tatgctgact ccgttaaagg t        51

<210> SEQ ID NO 62
<211> LENGTH: 17
<212> TYPE: PRT
<213> ORGANISM: Artificial sequence
<220> FEATURE:
<223> OTHER INFORMATION: VH-CDR2 (Li09)

<400> SEQUENCE: 62

Tyr Ile Ser Pro Ser Gly Gly Lys Thr Met Tyr Ala Asp Ser Val Lys
1               5                   10                  15
Gly

<210> SEQ ID NO 63
<211> LENGTH: 69
<212> TYPE: DNA
<213> ORGANISM: Artificial sequence
<220> FEATURE:
<223> OTHER INFORMATION: VH-CDR3 (Li09)

```
<400> SEQUENCE: 63
gattcgagac gccggtatta cgattttggg agtggttatc acaactacta ctactactac    60
atggacgtc                                                            69

<210> SEQ ID NO 64
<211> LENGTH: 23
<212> TYPE: PRT
<213> ORGANISM: Artificial sequence
<220> FEATURE:
<223> OTHER INFORMATION: VH-CDR3 (Li09)

<400> SEQUENCE: 64

Asp Ser Arg Arg Arg Tyr Tyr Asp Phe Trp Ser Gly Tyr His Asn Tyr
1               5                   10                  15

Tyr Tyr Tyr Tyr Met Asp Val
            20

<210> SEQ ID NO 65
<211> LENGTH: 15
<212> TYPE: DNA
<213> ORGANISM: Artificial sequence
<220> FEATURE:
<223> OTHER INFORMATION: VH-CDR1 (Li04)

<400> SEQUENCE: 65
cgttacaata tgggt                                                     15

<210> SEQ ID NO 66
<211> LENGTH: 5
<212> TYPE: PRT
<213> ORGANISM: Artificial sequence
<220> FEATURE:
<223> OTHER INFORMATION: VH-CDR1 (Li04)

<400> SEQUENCE: 66

Arg Tyr Asn Met Gly
1               5

<210> SEQ ID NO 67
<211> LENGTH: 51
<212> TYPE: DNA
<213> ORGANISM: Artificial sequence
<220> FEATURE:
<223> OTHER INFORMATION: VH-CDR2 (Li04)

<400> SEQUENCE: 67
gttatctatc cttctggtgg cggtactcat tatgctgact ccgttaaagg t              51

<210> SEQ ID NO 68
<211> LENGTH: 17
<212> TYPE: PRT
<213> ORGANISM: Artificial sequence
<220> FEATURE:
<223> OTHER INFORMATION: VH-CDR2 (Li04)

<400> SEQUENCE: 68

Val Ile Tyr Pro Ser Gly Gly Gly Thr His Tyr Ala Asp Ser Val Lys
1               5                   10                  15

Gly

<210> SEQ ID NO 69
<211> LENGTH: 25
<212> TYPE: DNA
<213> ORGANISM: Artificial sequence
```

```
<220> FEATURE:
<223> OTHER INFORMATION: VH-CDR3 (Li04)

<400> SEQUENCE: 69
tctatagcag atgatgcttt tgata                                          25

<210> SEQ ID NO 70
<211> LENGTH: 9
<212> TYPE: PRT
<213> ORGANISM: Artificial sequence
<220> FEATURE:
<223> OTHER INFORMATION: VH-CDR3 (Li04)

<400> SEQUENCE: 70

Ser Ile Ala Asp Asp Ala Phe Asp Ile
1               5

<210> SEQ ID NO 71
<211> LENGTH: 15
<212> TYPE: DNA
<213> ORGANISM: Artificial sequence
<220> FEATURE:
<223> OTHER INFORMATION: VH-CDR1 (Li02)

<400> SEQUENCE: 71
acttacgaga tgatt                                                     15

<210> SEQ ID NO 72
<211> LENGTH: 5
<212> TYPE: PRT
<213> ORGANISM: Artificial sequence
<220> FEATURE:
<223> OTHER INFORMATION: VH-CDR1 (Li02)

<400> SEQUENCE: 72

Thr Tyr Glu Met Ile
1               5

<210> SEQ ID NO 73
<211> LENGTH: 48
<212> TYPE: DNA
<213> ORGANISM: Artificial sequence
<220> FEATURE:
<223> OTHER INFORMATION: VH-CDR2 (Li73)

<400> SEQUENCE: 73
tctatcggtc cttctggtgg ccttacttgg tatgctgact ccgttaaa                 48

<210> SEQ ID NO 74
<211> LENGTH: 17
<212> TYPE: PRT
<213> ORGANISM: Artificial sequence
<220> FEATURE:
<223> OTHER INFORMATION: VH-CDR2 (Li02)

<400> SEQUENCE: 74

Ser Ile Gly Pro Ser Gly Gly Leu Thr Trp Tyr Ala Asp Ser Val Lys
1               5                   10                  15

Gly

<210> SEQ ID NO 75
<211> LENGTH: 51
<212> TYPE: DNA
<213> ORGANISM: Artificial sequence
<220> FEATURE:
<223> OTHER INFORMATION: VH-CDR3 (Li02)
```

<400> SEQUENCE: 75
atgtattact gtgtacggat tgatgatagt agtggttggg cttttgatat c    51

<210> SEQ ID NO 76
<211> LENGTH: 17
<212> TYPE: PRT
<213> ORGANISM: Artificial sequence
<220> FEATURE:
<223> OTHER INFORMATION: VH-CDR3 (Li02)

<400> SEQUENCE: 76

Met Tyr Tyr Cys Val Arg Ile Asp Asp Ser Ser Gly Trp Ala Phe Asp
1               5                   10                  15
Ile

<210> SEQ ID NO 77
<211> LENGTH: 5
<212> TYPE: PRT
<213> ORGANISM: Murinae gen. sp.

<400> SEQUENCE: 77

Asn Tyr Gly Met Asn
1               5

<210> SEQ ID NO 78
<211> LENGTH: 17
<212> TYPE: PRT
<213> ORGANISM: Murinae gen. sp.

<400> SEQUENCE: 78

Trp Ile Asn Thr Asp Thr Gly Glu Pro Thr Tyr Thr Glu Asp Phe Gln
1               5                   10                  15
Gly

<210> SEQ ID NO 79
<211> LENGTH: 7
<212> TYPE: PRT
<213> ORGANISM: Murinae gen. sp.

<400> SEQUENCE: 79

Glu Gly Val His Phe Asp Tyr
1               5

<210> SEQ ID NO 80
<211> LENGTH: 7
<212> TYPE: PRT
<213> ORGANISM: Murinae gen. sp.

<400> SEQUENCE: 80

Phe Ser Asp Ala Trp Leu Asp
1               5

<210> SEQ ID NO 81
<211> LENGTH: 19
<212> TYPE: PRT
<213> ORGANISM: Murinae gen. sp.

<400> SEQUENCE: 81

Glu Ile Arg Ser Lys Ala Asn Asn His Ala Thr Asn Tyr Ala Glu Ser
1               5                   10                  15
Val Lys Gly

<210> SEQ ID NO 82

```
<211> LENGTH: 4
<212> TYPE: PRT
<213> ORGANISM: Murinae gen. sp.

<400> SEQUENCE: 82

Ser Phe Ala Tyr
1

<210> SEQ ID NO 83
<211> LENGTH: 5
<212> TYPE: PRT
<213> ORGANISM: Murinae gen. sp.

<400> SEQUENCE: 83

Ser Ser Trp Thr Gln
1               5

<210> SEQ ID NO 84
<211> LENGTH: 17
<212> TYPE: PRT
<213> ORGANISM: Murinae gen. sp.

<400> SEQUENCE: 84

Ala Ile Tyr Pro Gly Asp Gly Asp Thr Arg Tyr Thr Gln Lys Phe Lys
1               5                   10                  15

Gly

<210> SEQ ID NO 85
<211> LENGTH: 8
<212> TYPE: PRT
<213> ORGANISM: Murinae gen. sp.

<400> SEQUENCE: 85

His Asn Ser Tyr Gly Met Asp Tyr
1               5

<210> SEQ ID NO 86
<211> LENGTH: 33
<212> TYPE: DNA
<213> ORGANISM: Artificial sequence
<220> FEATURE:
<223> OTHER INFORMATION: VH-CDR1 (Li10)

<400> SEQUENCE: 86
cgggcgagtc agggtattgg caactggtta gcc                                  33

<210> SEQ ID NO 87
<211> LENGTH: 11
<212> TYPE: PRT
<213> ORGANISM: Artificial sequence
<220> FEATURE:
<223> OTHER INFORMATION: VL-CDR1 (Li10)

<400> SEQUENCE: 87

Arg Ala Ser Gln Gly Ile Gly Asn Trp Leu Ala
1               5                   10

<210> SEQ ID NO 88
<211> LENGTH: 21
<212> TYPE: DNA
<213> ORGANISM: Artificial sequence
<220> FEATURE:
<223> OTHER INFORMATION: VL-CDR2 (Li10)

<400> SEQUENCE: 88
gctgcatcca gtttggaaag t                                               21
```

```
<210> SEQ ID NO 89
<211> LENGTH: 7
<212> TYPE: PRT
<213> ORGANISM: Artificial sequence
<220> FEATURE:
<223> OTHER INFORMATION: VL-CDR2 (Li10)

<400> SEQUENCE: 89

Ala Ala Ser Ser Leu Glu Ser
1               5

<210> SEQ ID NO 90
<211> LENGTH: 27
<212> TYPE: DNA
<213> ORGANISM: Artificial sequence
<220> FEATURE:
<223> OTHER INFORMATION: VL-CDR3 (Li10)

<400> SEQUENCE: 90
caacaggctc agactttccc gctcacc                                         27

<210> SEQ ID NO 91
<211> LENGTH: 9
<212> TYPE: PRT
<213> ORGANISM: Artificial sequence
<220> FEATURE:
<223> OTHER INFORMATION: VL-CDR3 (Li10)

<400> SEQUENCE: 91

Gln Gln Ala Gln Thr Phe Pro Leu Thr
1               5

<210> SEQ ID NO 92
<211> LENGTH: 33
<212> TYPE: DNA
<213> ORGANISM: Artificial sequence
<220> FEATURE:
<223> OTHER INFORMATION: VL-CDR1 (Li07)

<400> SEQUENCE: 92
tctggagatc agttgggtga caaacatgtg gct                                  33

<210> SEQ ID NO 93
<211> LENGTH: 11
<212> TYPE: PRT
<213> ORGANISM: Artificial sequence
<220> FEATURE:
<223> OTHER INFORMATION: VL-CDR1 (Li07)

<400> SEQUENCE: 93

Ser Gly Asp Gln Leu Gly Asp Lys His Val Ala
1               5                   10

<210> SEQ ID NO 94
<211> LENGTH: 21
<212> TYPE: DNA
<213> ORGANISM: Artificial sequence
<220> FEATURE:
<223> OTHER INFORMATION: VL-CDR2 (Li07)

<400> SEQUENCE: 94
ctagacatta agaggcccgc a                                               21

<210> SEQ ID NO 95
<211> LENGTH: 7
<212> TYPE: PRT
```

```
<213> ORGANISM: Artificial sequence
<220> FEATURE:
<223> OTHER INFORMATION: VL-CDR2 (Li07)

<400> SEQUENCE: 95

Leu Asp Ile Lys Arg Pro Ala
1               5

<210> SEQ ID NO 96
<211> LENGTH: 24
<212> TYPE: DNA
<213> ORGANISM: Artificial sequence
<220> FEATURE:
<223> OTHER INFORMATION: VL-CDR3 (Li07)

<400> SEQUENCE: 96
caggcgtggg acatcaagac ggtc                                            24

<210> SEQ ID NO 97
<211> LENGTH: 8
<212> TYPE: PRT
<213> ORGANISM: Artificial sequence
<220> FEATURE:
<223> OTHER INFORMATION: VL-CDR3 (Li07)

<400> SEQUENCE: 97

Gln Ala Trp Asp Ile Lys Thr Val
1               5

<210> SEQ ID NO 98
<211> LENGTH: 33
<212> TYPE: DNA
<213> ORGANISM: Artificial sequence
<220> FEATURE:
<223> OTHER INFORMATION: VL-CDR1 (Li05)

<400> SEQUENCE: 98
gggggagaca acattggaag taagagtgtc cac                                  33

<210> SEQ ID NO 99
<211> LENGTH: 11
<212> TYPE: PRT
<213> ORGANISM: Artificial sequence
<220> FEATURE:
<223> OTHER INFORMATION: VL-CDR1 (Li05)

<400> SEQUENCE: 99

Gly Gly Asp Asn Ile Gly Ser Lys Ser Val His
1               5                   10

<210> SEQ ID NO 100
<211> LENGTH: 21
<212> TYPE: DNA
<213> ORGANISM: Artificial sequence
<220> FEATURE:
<223> OTHER INFORMATION: VL-CDR2 (Li05)

<400> SEQUENCE: 100
gatgattatg accggccctc a                                               21

<210> SEQ ID NO 101
<211> LENGTH: 7
<212> TYPE: PRT
<213> ORGANISM: Artificial sequence
<220> FEATURE:
<223> OTHER INFORMATION: VL-CDR2 (Li05)

<400> SEQUENCE: 101
```

Asp Asp Tyr Asp Arg Pro Ser
1               5

<210> SEQ ID NO 102
<211> LENGTH: 33
<212> TYPE: DNA
<213> ORGANISM: Artificial sequence
<220> FEATURE:
<223> OTHER INFORMATION: VL-CDR3 (Li05)

<400> SEQUENCE: 102
caggtgaggg acagccgtac tgaggaacgg gtg         33

<210> SEQ ID NO 103
<211> LENGTH: 11
<212> TYPE: PRT
<213> ORGANISM: Artificial sequence
<220> FEATURE:
<223> OTHER INFORMATION: VL-CDR3 (Li05)

<400> SEQUENCE: 103

Gln Val Arg Asp Ser Arg Thr Glu Glu Arg Val
1               5                   10

<210> SEQ ID NO 104
<211> LENGTH: 33
<212> TYPE: DNA
<213> ORGANISM: Artificial sequence
<220> FEATURE:
<223> OTHER INFORMATION: VL-CDR1 (Li11)

<400> SEQUENCE: 104
cgggcgagtc aggagattgc caactactta gcc         33

<210> SEQ ID NO 105
<211> LENGTH: 11
<212> TYPE: PRT
<213> ORGANISM: Artificial sequence
<220> FEATURE:
<223> OTHER INFORMATION: VL-CDR1 (Li11)

<400> SEQUENCE: 105

Arg Ala Ser Gln Glu Ile Ala Asn Tyr Leu Ala
1               5                   10

<210> SEQ ID NO 106
<211> LENGTH: 21
<212> TYPE: DNA
<213> ORGANISM: Artificial sequence
<220> FEATURE:
<223> OTHER INFORMATION: VL-CDR2 (Li11)

<400> SEQUENCE: 106
gatacataca ctttgcagac t         21

<210> SEQ ID NO 107
<211> LENGTH: 7
<212> TYPE: PRT
<213> ORGANISM: Artificial sequence
<220> FEATURE:
<223> OTHER INFORMATION: VL-CDR2 (Li11)

<400> SEQUENCE: 107

Asp Thr Tyr Thr Leu Gln Thr
1               5

```
<210> SEQ ID NO 108
<211> LENGTH: 27
<212> TYPE: DNA
<213> ORGANISM: Artificial sequence
<220> FEATURE:
<223> OTHER INFORMATION: VL-CDR3 (Li11)

<400> SEQUENCE: 108
caacaggctg acattttccc gctctct                                          27

<210> SEQ ID NO 109
<211> LENGTH: 9
<212> TYPE: PRT
<213> ORGANISM: Artificial sequence
<220> FEATURE:
<223> OTHER INFORMATION: VL-CDR3 (Li11)

<400> SEQUENCE: 109

Gln Gln Ala Asp Ile Phe Pro Leu Ser
1               5

<210> SEQ ID NO 110
<211> LENGTH: 33
<212> TYPE: DNA
<213> ORGANISM: Artificial sequence
<220> FEATURE:
<223> OTHER INFORMATION: VL-CDR1 (Li01)

<400> SEQUENCE: 110
caggcgagtc aggacattag caactattta aat                                   33

<210> SEQ ID NO 111
<211> LENGTH: 11
<212> TYPE: PRT
<213> ORGANISM: Artificial sequence
<220> FEATURE:
<223> OTHER INFORMATION: VL-CDR1 (Li01)

<400> SEQUENCE: 111

Gln Ala Ser Gln Asp Ile Ser Asn Tyr Leu Asn
1               5                   10

<210> SEQ ID NO 112
<211> LENGTH: 21
<212> TYPE: DNA
<213> ORGANISM: Artificial sequence
<220> FEATURE:
<223> OTHER INFORMATION: VL-CDR2 (Li01)

<400> SEQUENCE: 112
gatgcatcca atttggaaac a                                                21

<210> SEQ ID NO 113
<211> LENGTH: 7
<212> TYPE: PRT
<213> ORGANISM: Artificial sequence
<220> FEATURE:
<223> OTHER INFORMATION: VL-CDR2 (Li01)

<400> SEQUENCE: 113

Asp Ala Ser Asn Leu Glu Thr
1               5

<210> SEQ ID NO 114
<211> LENGTH: 30
<212> TYPE: DNA
<213> ORGANISM: Artificial sequence
<220> FEATURE:
```

```
<223> OTHER INFORMATION: VL-CDR3 (Li01)

<400> SEQUENCE: 114
caacaggctg acaggttccc tgcggtcact                                              30

<210> SEQ ID NO 115
<211> LENGTH: 10
<212> TYPE: PRT
<213> ORGANISM: Artificial sequence
<220> FEATURE:
<223> OTHER INFORMATION: VL-CDR3 (Li01)

<400> SEQUENCE: 115

Gln Gln Ala Asp Arg Phe Pro Ala Val Thr
1               5                   10

<210> SEQ ID NO 116
<211> LENGTH: 33
<212> TYPE: DNA
<213> ORGANISM: Artificial sequence
<220> FEATURE:
<223> OTHER INFORMATION: VL-CDR1 (Li06)

<400> SEQUENCE: 116
cgggccagtc agagtattag tagctggttg gcc                                          33

<210> SEQ ID NO 117
<211> LENGTH: 11
<212> TYPE: PRT
<213> ORGANISM: Artificial sequence
<220> FEATURE:
<223> OTHER INFORMATION: VL-CDR1 (Li06)

<400> SEQUENCE: 117

Arg Ala Ser Gln Ser Ile Ser Ser Trp Leu Ala
1               5                   10

<210> SEQ ID NO 118
<211> LENGTH: 21
<212> TYPE: DNA
<213> ORGANISM: Artificial sequence
<220> FEATURE:
<223> OTHER INFORMATION: VL-CDR2 (Li06)

<400> SEQUENCE: 118
gctgcatcca gtttacgaac t                                                       21

<210> SEQ ID NO 119
<211> LENGTH: 7
<212> TYPE: PRT
<213> ORGANISM: Artificial sequence
<220> FEATURE:
<223> OTHER INFORMATION: VL-CDR2 (Li06)

<400> SEQUENCE: 119

Ala Ala Ser Ser Leu Arg Thr
1               5

<210> SEQ ID NO 120
<211> LENGTH: 27
<212> TYPE: DNA
<213> ORGANISM: Artificial sequence
<220> FEATURE:
<223> OTHER INFORMATION: VL-CDR3 (Li06)

<400> SEQUENCE: 120
ctacaagatt acagttaccc tctcact                                                 27
```

<210> SEQ ID NO 121
<211> LENGTH: 9
<212> TYPE: PRT
<213> ORGANISM: Artificial sequence
<220> FEATURE:
<223> OTHER INFORMATION: VL-CDR3 (Li06)

<400> SEQUENCE: 121

Leu Gln Asp Tyr Ser Tyr Pro Leu Thr
1               5

<210> SEQ ID NO 122
<211> LENGTH: 33
<212> TYPE: DNA
<213> ORGANISM: Artificial sequence
<220> FEATURE:
<223> OTHER INFORMATION: VL-CDR1 (Li08)

<400> SEQUENCE: 122
caggcgagtc aggacattag ttactattta aat                                    33

<210> SEQ ID NO 123
<211> LENGTH: 11
<212> TYPE: PRT
<213> ORGANISM: Artificial sequence
<220> FEATURE:
<223> OTHER INFORMATION: VL-CDR1 (Li08)

<400> SEQUENCE: 123

Gln Ala Ser Gln Asp Ile Ser Tyr Tyr Leu Asn
1               5                   10

<210> SEQ ID NO 124
<211> LENGTH: 21
<212> TYPE: DNA
<213> ORGANISM: Artificial sequence
<220> FEATURE:
<223> OTHER INFORMATION: VL-CDR2 (Li08)

<400> SEQUENCE: 124
gatgtatcca atttgcaaac a                                                 21

<210> SEQ ID NO 125
<211> LENGTH: 7
<212> TYPE: PRT
<213> ORGANISM: Artificial sequence
<220> FEATURE:
<223> OTHER INFORMATION: VL-CDR2 (Li08)

<400> SEQUENCE: 125

Asp Val Ser Asn Leu Gln Thr
1               5

<210> SEQ ID NO 126
<211> LENGTH: 27
<212> TYPE: DNA
<213> ORGANISM: Artificial sequence
<220> FEATURE:
<223> OTHER INFORMATION: VL-CDR3 (Li08)

<400> SEQUENCE: 126
caacagtctg ataatctccc tctcact                                           27

<210> SEQ ID NO 127
<211> LENGTH: 9
<212> TYPE: PRT

```
<213> ORGANISM: Artificial sequence
<220> FEATURE:
<223> OTHER INFORMATION: VL-CDR3 (Li08)

<400> SEQUENCE: 127

Gln Gln Ser Asp Asn Leu Pro Leu Thr
1               5

<210> SEQ ID NO 128
<211> LENGTH: 32
<212> TYPE: DNA
<213> ORGANISM: Artificial sequence
<220> FEATURE:
<223> OTHER INFORMATION: VL-CDR1 (Li03)

<400> SEQUENCE: 128
gggcaagtca gagcattagc agctatttaa at                              32

<210> SEQ ID NO 129
<211> LENGTH: 11
<212> TYPE: PRT
<213> ORGANISM: Artificial sequence
<220> FEATURE:
<223> OTHER INFORMATION: VL-CDR1 (Li03)

<400> SEQUENCE: 129

Arg Ala Ser Gln Ser Ile Ser Ser Tyr Leu Asn
1               5                   10

<210> SEQ ID NO 130
<211> LENGTH: 21
<212> TYPE: DNA
<213> ORGANISM: Artificial sequence
<220> FEATURE:
<223> OTHER INFORMATION: VL-CDR2 (Li03)

<400> SEQUENCE: 130
gctgcatcca gtttgcaaag t                                          21

<210> SEQ ID NO 131
<211> LENGTH: 7
<212> TYPE: PRT
<213> ORGANISM: Artificial sequence
<220> FEATURE:
<223> OTHER INFORMATION: VL-CDR2 (Li03)

<400> SEQUENCE: 131

Ala Ala Ser Ser Leu Gln Ser
1               5

<210> SEQ ID NO 132
<211> LENGTH: 27
<212> TYPE: DNA
<213> ORGANISM: Artificial sequence
<220> FEATURE:
<223> OTHER INFORMATION: VL-CDR3 (Li03)

<400> SEQUENCE: 132
caacagagtt acagtacccc gtggacg                                    27

<210> SEQ ID NO 133
<211> LENGTH: 9
<212> TYPE: PRT
<213> ORGANISM: Artificial sequence
<220> FEATURE:
<223> OTHER INFORMATION: VL-CDR3 (Li03)

<400> SEQUENCE: 133
```

Gln Gln Ser Tyr Ser Thr Pro Trp Thr
1               5

<210> SEQ ID NO 134
<211> LENGTH: 33
<212> TYPE: DNA
<213> ORGANISM: Artificial sequence
<220> FEATURE:
<223> OTHER INFORMATION: VL-CDR1 (Li09)

<400> SEQUENCE: 134
cgcgcaagtc agagcatcga cacctattta aat                          33

<210> SEQ ID NO 135
<211> LENGTH: 11
<212> TYPE: PRT
<213> ORGANISM: Artificial sequence
<220> FEATURE:
<223> OTHER INFORMATION: VL-CDR1 (Li09)

<400> SEQUENCE: 135

Arg Ala Ser Gln Ser Ile Asp Thr Tyr Leu Asn
1               5                   10

<210> SEQ ID NO 136
<211> LENGTH: 21
<212> TYPE: DNA
<213> ORGANISM: Artificial sequence
<220> FEATURE:
<223> OTHER INFORMATION: VL-CDR2 (Li09)

<400> SEQUENCE: 136
gctgcatcca agttggaaga c                                       21

<210> SEQ ID NO 137
<211> LENGTH: 7
<212> TYPE: PRT
<213> ORGANISM: Artificial sequence
<220> FEATURE:
<223> OTHER INFORMATION: VL-CDR2 (Li09)

<400> SEQUENCE: 137

Ala Ala Ser Lys Leu Glu Asp
1               5

<210> SEQ ID NO 138
<211> LENGTH: 26
<212> TYPE: DNA
<213> ORGANISM: Artificial sequence
<220> FEATURE:
<223> OTHER INFORMATION: VL-CDR3 (Li09)

<400> SEQUENCE: 138
caacagagtt acagtccccc tctcac                                  26

<210> SEQ ID NO 139
<211> LENGTH: 9
<212> TYPE: PRT
<213> ORGANISM: Artificial sequence
<220> FEATURE:
<223> OTHER INFORMATION: VL-CDR3 (Li09)

<400> SEQUENCE: 139

Gln Gln Ser Tyr Ser Pro Pro Leu Thr
1               5

<210> SEQ ID NO 140
<211> LENGTH: 33
<212> TYPE: DNA
<213> ORGANISM: Artificial sequence
<220> FEATURE:
<223> OTHER INFORMATION: VL-CDR1 (Li02)

<400> SEQUENCE: 140
tctggagata aattggggga taaatttgct tcc                    33

<210> SEQ ID NO 141
<211> LENGTH: 11
<212> TYPE: PRT
<213> ORGANISM: Artificial sequence
<220> FEATURE:
<223> OTHER INFORMATION: VL-CDR1 (Li02)

<400> SEQUENCE: 141

Ser Gly Asp Lys Leu Gly Asp Lys Phe Ala Ser
1               5                   10

<210> SEQ ID NO 142
<211> LENGTH: 21
<212> TYPE: DNA
<213> ORGANISM: Artificial sequence
<220> FEATURE:
<223> OTHER INFORMATION: VL-CDR2 (Li02)

<400> SEQUENCE: 142
caagatagga agcgtctctc a                                 21

<210> SEQ ID NO 143
<211> LENGTH: 7
<212> TYPE: PRT
<213> ORGANISM: Artificial sequence
<220> FEATURE:
<223> OTHER INFORMATION: VL-CDR2 (Li02)

<400> SEQUENCE: 143

Gln Asp Arg Lys Arg Leu Ser
1               5

<210> SEQ ID NO 144
<211> LENGTH: 27
<212> TYPE: DNA
<213> ORGANISM: Artificial sequence
<220> FEATURE:
<223> OTHER INFORMATION: VL-CDR3 (Li02)

<400> SEQUENCE: 144
caggcgtggg acaccaacac tgtggtc                           27

<210> SEQ ID NO 145
<211> LENGTH: 9
<212> TYPE: PRT
<213> ORGANISM: Artificial sequence
<220> FEATURE:
<223> OTHER INFORMATION: VL-CDR3 (Li02)

<400> SEQUENCE: 145

Gln Ala Trp Asp Thr Asn Thr Val Val
1               5

<210> SEQ ID NO 146
<211> LENGTH: 10
<212> TYPE: PRT
<213> ORGANISM: Murinae gen. sp.

```
<400> SEQUENCE: 146

Ser Ala Ser Ser Ser Val Ser Tyr Met His
1               5                   10

<210> SEQ ID NO 147
<211> LENGTH: 7
<212> TYPE: PRT
<213> ORGANISM: Murinae gen. sp.

<400> SEQUENCE: 147

Asp Thr Ser Lys Leu Ala Ser
1               5

<210> SEQ ID NO 148
<211> LENGTH: 9
<212> TYPE: PRT
<213> ORGANISM: Murinae gen. sp.

<400> SEQUENCE: 148

Gln Gln Trp Ser Ser Asn Pro Phe Thr
1               5

<210> SEQ ID NO 149
<211> LENGTH: 11
<212> TYPE: PRT
<213> ORGANISM: Murinae gen. sp.

<400> SEQUENCE: 149

Arg Ala Ser Gly Asn Ile Tyr Asn Tyr Leu Ala
1               5                   10

<210> SEQ ID NO 150
<211> LENGTH: 7
<212> TYPE: PRT
<213> ORGANISM: Murinae gen. sp.

<400> SEQUENCE: 150

Asn Ala Lys Thr Leu Pro Asp
1               5

<210> SEQ ID NO 151
<211> LENGTH: 9
<212> TYPE: PRT
<213> ORGANISM: Murinae gen. sp.

<400> SEQUENCE: 151

Gln His Phe Trp Ala Ile Pro Tyr Thr
1               5

<210> SEQ ID NO 152
<211> LENGTH: 17
<212> TYPE: PRT
<213> ORGANISM: Murinae gen. sp.

<400> SEQUENCE: 152

Lys Ser Ser Gln Ser Leu Leu Asn Ser Gly Asn Gln Lys Asn Tyr Leu
1               5                   10                  15

Thr

<210> SEQ ID NO 153
<211> LENGTH: 7
<212> TYPE: PRT
<213> ORGANISM: Murinae gen. sp.

<400> SEQUENCE: 153
```

```
Trp Ala Ser Thr Arg Glu Ser
1               5

<210> SEQ ID NO 154
<211> LENGTH: 10
<212> TYPE: PRT
<213> ORGANISM: Murinae gen. sp.

<400> SEQUENCE: 154

Gln Asn Asp Tyr Ser Tyr Pro Leu Phe Thr
1               5                   10

<210> SEQ ID NO 155
<211> LENGTH: 17
<212> TYPE: PRT
<213> ORGANISM: Murinae gen. sp.

<400> SEQUENCE: 155

Lys Ser Ser Gln Ser Leu Leu Asn Ser Gly Asn Gln Lys Ser Tyr Leu
1               5                   10                  15

Thr

<210> SEQ ID NO 156
<211> LENGTH: 7
<212> TYPE: PRT
<213> ORGANISM: Murinae gen. sp.

<400> SEQUENCE: 156

Trp Ala Ser Thr Arg Glu Ser
1               5

<210> SEQ ID NO 157
<211> LENGTH: 10
<212> TYPE: PRT
<213> ORGANISM: Murinae gen. sp.

<400> SEQUENCE: 157

Gln Asn Asp Tyr Ser Tyr Pro Leu Phe Thr
1               5                   10

<210> SEQ ID NO 158
<211> LENGTH: 133
<212> TYPE: PRT
<213> ORGANISM: Artificial sequence
<220> FEATURE:
<223> OTHER INFORMATION: VH (Li02)

<400> SEQUENCE: 158

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Glu Met Ile Trp Val Arg Gln Ala Pro Gly Lys Gly Leu Glu Trp Val
        35                  40                  45

Ser Ser Ile Gly Pro Ser Gly Gly Leu Thr Trp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Met Tyr Tyr Cys
                85                  90                  95

Val Arg Ile Asp Asp Ser Ser Gly Trp Ala Phe Asp Ile Trp Gly Gln
            100                 105                 110
```

-continued

```
Gly Thr Thr Val Thr Val Ser Ser Ala Ser Thr Lys Gly Pro Ser Val
        115                 120                 125

Phe Pro Leu Ala Pro
        130

<210> SEQ ID NO 159
<211> LENGTH: 145
<212> TYPE: PRT
<213> ORGANISM: Artificial sequence
<220> FEATURE:
<223> OTHER INFORMATION: VH (Li09)

<400> SEQUENCE: 159

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Met Tyr
            20                  25                  30

Ser Met Val Trp Val Arg Gln Ala Pro Gly Lys Gly Leu Glu Trp Val
        35                  40                  45

Ser Tyr Ile Ser Pro Ser Gly Gly Lys Thr Met Tyr Ala Asp Ser Val
    50                  55                  60

Lys Gly Arg Phe Thr Ile Ser Arg Asp Asn Ser Lys Asn Thr Phe Tyr
65                  70                  75                  80

Leu Gln Met Asn Ser Leu Arg Ala Glu Asp Thr Ala Val Tyr Tyr Cys
                85                  90                  95

Ala Arg Asp Ser Arg Arg Tyr Tyr Asp Phe Trp Ser Gly Tyr His
            100                 105                 110

Asn Tyr Tyr Tyr Tyr Met Asp Val Trp Gly Lys Gly Thr Thr Val
        115                 120                 125

Thr Val Ser Ser Ala Ser Thr Lys Gly Pro Ser Val Phe Pro Leu Ala
    130                 135                 140

Pro
145

<210> SEQ ID NO 160
<211> LENGTH: 131
<212> TYPE: PRT
<213> ORGANISM: Artificial sequence
<220> FEATURE:
<223> OTHER INFORMATION: VH (Li06)

<400> SEQUENCE: 160

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Glu Tyr
            20                  25                  30

Pro Met Asp Trp Val Arg Gln Ala Pro Gly Lys Gly Leu Glu Trp Val
        35                  40                  45

Ser Ser Ile Tyr Ser Ser Gly Gly Ser Thr Val Tyr Ala Asp Ser Ile
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Asp Ser Asp Ala Phe Asp Ile Trp Gly Gln Gly Thr
            100                 105                 110

Met Val Thr Val Ser Ser Ala Ser Thr Lys Gly Pro Ser Val Phe Pro
        115                 120                 125
```

Leu Ala Pro
    130

<210> SEQ ID NO 161
<211> LENGTH: 131
<212> TYPE: PRT
<213> ORGANISM: Artificial sequence
<220> FEATURE:
<223> OTHER INFORMATION: VH (Li05)

<400> SEQUENCE: 161

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
            20                  25                  30

Ala Met Gly Trp Val Arg Gln Ala Pro Gly Lys Gly Leu Glu Trp Val
        35                  40                  45

Ser Ser Ile Val Ser Ser Gly Tyr Thr Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Asp His Asn Ala Phe Asp Ile Trp Gly Gln Gly Thr
            100                 105                 110

Met Val Thr Val Ser Ser Ala Ser Thr Lys Gly Pro Ser Val Phe Pro
        115                 120                 125

Leu Ala Pro
    130

<210> SEQ ID NO 162
<211> LENGTH: 131
<212> TYPE: PRT
<213> ORGANISM: Artificial sequence
<220> FEATURE:
<223> OTHER INFORMATION: VH (Li04)

<400> SEQUENCE: 162

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Asn Met Gly Trp Val Arg Gln Ala Pro Gly Lys Gly Leu Glu Trp Val
        35                  40                  45

Ser Val Ile Tyr Pro Ser Gly Gly Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Ser Ile Ala Asp Asp Ala Phe Asp Ile Trp Gly Gln Gly Thr
            100                 105                 110

Met Val Thr Val Ser Ser Ala Ser Thr Lys Gly Pro Ser Val Phe Pro
        115                 120                 125

Leu Ala Pro
    130

<210> SEQ ID NO 163

```
<211> LENGTH: 131
<212> TYPE: PRT
<213> ORGANISM: Artificial sequence
<220> FEATURE:
<223> OTHER INFORMATION: VH (Li08)

<400> SEQUENCE: 163

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

Glu Met Val Trp Val Arg Gln Ala Pro Gly Lys Gly Leu Glu Trp Val
        35                  40                  45

Ser Ser Ile Arg Ser Ser Gly Gly Ala Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Ser Pro Asp Asp Tyr Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro
    130

<210> SEQ ID NO 164
<211> LENGTH: 134
<212> TYPE: PRT
<213> ORGANISM: Artificial sequence
<220> FEATURE:
<223> OTHER INFORMATION: VH (Li11)

<400> SEQUENCE: 164

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Tyr Trp Val Arg Gln Ala Pro Gly Lys Gly Leu Glu Trp Val
        35                  40                  45

Ser Ser Ile Ser Thr Ser Gly Gly Tyr Thr Gly Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Thr Ser Asp Asn Asp Tyr Tyr Tyr Met Asp Val Trp Gly
            100                 105                 110

Lys Gly Thr Thr Val Thr Val Ser Ser Ala Ser Thr Lys Gly Pro Ser
        115                 120                 125

Val Phe Pro Leu Ala Pro
    130

<210> SEQ ID NO 165
<211> LENGTH: 133
<212> TYPE: PRT
<213> ORGANISM: Artificial sequence
<220> FEATURE:
<223> OTHER INFORMATION: VH (Li10)
```

```
<400> SEQUENCE: 165

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Pro Met Val Trp Val Arg Gln Ala Pro Gly Lys Gly Leu Glu Trp Val
        35                  40                  45

Ser Trp Ile Gly Pro Ser Gly Val Thr Ala Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Pro Tyr Ser Ser Gly Trp Trp Asp Phe Asp Leu Trp Gly Arg
            100                 105                 110

Gly Thr Leu Val Thr Val Ser Ser Ala Ser Thr Lys Gly Pro Ser Val
            115                 120                 125

Phe Pro Leu Ala Pro
    130

<210> SEQ ID NO 166
<211> LENGTH: 131
<212> TYPE: PRT
<213> ORGANISM: Artificial sequence
<220> FEATURE:
<223> OTHER INFORMATION: VH (Li01)

<400> SEQUENCE: 166

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Lys Tyr
            20                  25                  30

Gln Met Thr Trp Val Arg Gln Ala Pro Gly Lys Gly Leu Glu Trp Val
        35                  40                  45

Ser Ser Ile Tyr Pro Ser Gly Asn Thr Val Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Gly Thr Thr Glu Ala Val Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro
    130

<210> SEQ ID NO 167
<211> LENGTH: 129
<212> TYPE: PRT
<213> ORGANISM: Artificial sequence
<220> FEATURE:
<223> OTHER INFORMATION: VH (Li07)

<400> SEQUENCE: 167

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Met Tyr
```

-continued

```
                    20                  25                  30
Phe Met Gly Trp Val Arg Gln Ala Pro Gly Lys Gly Leu Glu Trp Val
            35                  40                  45
Ser Ser Ile Ser Pro Ser Gly Gly Phe Thr Ser Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Asp Arg His Ala Phe Asp Ile Trp Gly Gln Gly Thr Met Val
                100                 105                 110
Thr Val Ser Ser Ala Ser Thr Lys Gly Pro Ser Val Phe Pro Leu Ala
            115                 120                 125
Pro

<210> SEQ ID NO 168
<211> LENGTH: 132
<212> TYPE: PRT
<213> ORGANISM: Artificial sequence
<220> FEATURE:
<223> OTHER INFORMATION: VH (Li03)

<400> SEQUENCE: 168

Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Gln Tyr
                20                  25                  30
Pro Met Glu Trp Val Arg Gln Ala Pro Gly Lys Gly Leu Glu Trp Val
            35                  40                  45
Ser Gly Ile Tyr Pro Ser Gly Ser Thr Val Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Ala Gly Gln Trp Leu Gly Asp Phe Asp Tyr Trp Gly Gln Gly
                100                 105                 110
Thr Leu Val Thr Val Ser Ser Ala Ser Thr Lys Gly Pro Ser Val Phe
            115                 120                 125
Pro Leu Ala Pro
    130

<210> SEQ ID NO 169
<211> LENGTH: 145
<212> TYPE: PRT
<213> ORGANISM: Artificial sequence
<220> FEATURE:
<223> OTHER INFORMATION: VH (Li12)

<400> SEQUENCE: 169

Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Gln Tyr
                20                  25                  30
Asn Met Phe Trp Val Arg Gln Ala Pro Gly Lys Gly Leu Glu Trp Val
            35                  40                  45
Ser Arg Ile Ser Ser Gly Gly Met Thr Met Tyr Ala Asp Ser Val
    50                  55                  60
```

-continued

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Ala Leu Arg Pro Tyr Cys Ser Gly Gly Ser Cys Tyr Ser
            100                 105                 110

Asp Tyr Tyr Tyr Tyr Gly Met Asp Val Trp Gly Gln Gly Thr Thr Val
        115                 120                 125

Thr Val Ser Ser Ala Ser Thr Lys Gly Pro Ser Val Phe Pro Leu Ala
    130                 135                 140

Pro
145

<210> SEQ ID NO 170
<211> LENGTH: 116
<212> TYPE: PRT
<213> ORGANISM: Murinae gen. sp.

<400> SEQUENCE: 170

Gln Val Gln Leu Val Gln Ser Gly Pro Glu Leu Lys Lys Pro Gly Glu
 1               5                  10                  15

Thr Val Lys Ile Ser Cys Lys Ala Ser Gly Tyr Thr Phe Thr Asn Tyr
             20                  25                  30

Gly Met Asn Trp Val Lys Gln Ala Pro Gly Lys Gly Leu Lys Trp Met
         35                  40                  45

Gly Trp Ile Asn Thr Asp Thr Gly Glu Pro Thr Tyr Thr Glu Asp Phe
     50                  55                  60

Gln Gly Arg Phe Ala Phe Ser Leu Glu Thr Ser Ala Ser Thr Val Tyr
 65                  70                  75                  80

Leu Gln Phe Asn Asn Leu Lys Asn Glu Asp Thr Ala Thr Tyr Phe Cys
                 85                  90                  95

Ala Arg Glu Gly Val His Phe Asp Tyr Trp Gly Gln Gly Thr Thr Val
            100                 105                 110

Thr Val Ser Ser
        115

<210> SEQ ID NO 171
<211> LENGTH: 115
<212> TYPE: PRT
<213> ORGANISM: Murinae gen. sp.

<400> SEQUENCE: 171

Glu Val Lys Leu Glu Glu Ser Gly Gly Gly Leu Val Gln Pro Gly Gly
 1               5                  10                  15

Ser Met Lys Leu Ser Cys Ala Ala Ser Gly Phe Thr Phe Ser Asp Ala
             20                  25                  30

Trp Leu Asp Trp Val Arg Gln Ser Pro Glu Lys Gly Leu Glu Trp Val
         35                  40                  45

Ala Glu Ile Arg Ser Lys Ala Asn Asn His Ala Thr Asn Tyr Ala Glu
     50                  55                  60

Ser Val Lys Gly Arg Phe Thr Ile Ser Arg Asp Asp Ser Lys Ser Ser
 65                  70                  75                  80

Val Tyr Leu Gln Met Asn Ser Leu Arg Ala Glu Asp Thr Gly Ile Tyr
                 85                  90                  95

Phe Cys Thr Pro Ser Phe Ala Tyr Trp Gly Gln Gly Thr Thr Val Thr
            100                 105                 110
```

Val Ser Ser
      115

<210> SEQ ID NO 172
<211> LENGTH: 117
<212> TYPE: PRT
<213> ORGANISM: Murinae gen. sp.

<400> SEQUENCE: 172

Gln Val Gln Leu Gln Gln Ser Gly Ala Glu Leu Ala Arg Pro Gly Ala
1               5                   10                  15

Ser Val Lys Leu Ser Cys Arg Ala Ser Gly Tyr Thr Phe Thr Ser Ser
            20                  25                  30

Trp Thr Gln Trp Val Lys Gln Arg Pro Gly Gln Gly Leu Glu Trp Ile
        35                  40                  45

Gly Ala Ile Tyr Pro Gly Asp Gly Asp Thr Arg Tyr Thr Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Ala Ser Glu Asp Ser Ala Val Tyr Tyr Cys
                85                  90                  95

Ala Arg His Asn Ser Tyr Gly Met Asp Tyr Trp Gly Gln Gly Thr Ser
            100                 105                 110

Val Thr Val Ser Ser
        115

<210> SEQ ID NO 173
<211> LENGTH: 399
<212> TYPE: DNA
<213> ORGANISM: Artificial sequence
<220> FEATURE:
<223> OTHER INFORMATION: VH (Li02)

<400> SEQUENCE: 173
gaagttcaat tgttagagtc tggtggcggt cttgttcagc ctggtggttc tttacgtctt      60
tcttgcgctg cttccggatt cactttctct acttacgaga tgatttgggt tcgccaagct     120
cctggtaaag gtttggagtg gtttcttct atcggtcctt ctggtggcct tacttggtat      180
gctgactccg ttaaaggtcg cttcactatc tctagagaca actctaagaa tactctctac     240
ttgcagatga acagcttaag ggctgaggac accgccatgt attactgtgt acggattgat     300
gatagtagtg gttgggcttt tgatatctgg ggccaaggga ccacggtcac cgtctcaagc     360
gcctccacca agggcccatc ggtcttcccg ctagcaccc                            399

<210> SEQ ID NO 174
<211> LENGTH: 435
<212> TYPE: DNA
<213> ORGANISM: Artificial sequence
<220> FEATURE:
<223> OTHER INFORMATION: VH (Li09)

<400> SEQUENCE: 174
gaagttcaat tgttagagtc tggtggcggt cttgttcagc ctggtggttc tttacgtctt      60
tcttgcgctg cttccggatt cactttctct atgtactcta tggtttgggt tcgccaagct     120
cctggtaaag gtttggagtg gtttcttat atctctcctt ctggtggcaa gactatgtat      180
gctgactccg ttaaaggtcg cttcactatc tctagagaca actctaagaa tactttctac     240
ttgcagatga acagcttaag ggctgaggac acggccgtgt attactgtgc gagagattcg     300
agacgccggt attacgatt tggagtggt tatcacaact actactacta ctacatggac      360

```
gtctggggca agggaccac ggtcaccgtc tcaagcgcct ccaccaaggg cccatcggtc    420
ttcccgctag caccc                                                   435

<210> SEQ ID NO 175
<211> LENGTH: 393
<212> TYPE: DNA
<213> ORGANISM: Artificial sequence
<220> FEATURE:
<223> OTHER INFORMATION: VH (Li06)

<400> SEQUENCE: 175
gaagttcaat tgttagagtc tggtggcggt cttgttcagc ctggtggttc tttacgtctt    60
tcttgcgctg cttccggatt cactttctct gagtaccta tggattgggt cgccaagct   120 cctggtaaag gtttggagtg gtttcttct atctattctt ctggtggctc tactgtttat   180
gctgactcca ttaaaggtcg cttcactatc tctagagaca actctaagaa tactctctac   240
ttgcagatga acagcttaag ggctgaggac acggccgtgt attactgtgc cagagagggt   300
gactctgatg cttttgatat ctggggccaa gggacaatgg tcaccgtctc aagcgcctcc   360
accaagggcc catcggtctt cccgctagca ccc                                393

<210> SEQ ID NO 176
<211> LENGTH: 393
<212> TYPE: DNA
<213> ORGANISM: Artificial sequence
<220> FEATURE:
<223> OTHER INFORMATION: VH (Li05)

<400> SEQUENCE: 176
gaagttcaat tgttagagtc tggtggcggt cttgttcagc ctggtggttc tttacgtctt    60
tcttgcgctg cttccggatt cactttctct gcttacgcta tgggttgggt cgccaagct   120 cctggtaaag gtttggagtg gtttcttct atcgtttctt ctggtggcta tactgattat   180
gctgactccg ttaaaggtcg cttcactatc tctagagaca actctaagaa tactctctac   240
ttgcagatga acagcttaag ggctgaggac acggccgtgt attactgtgc cagagagggt   300
gaccataatg cttttgatat ctggggccaa gggacaatgg tcaccgtctc aagcgcctcc   360
accaagggcc catcggtctt cccgctagca ccc                                393

<210> SEQ ID NO 177
<211> LENGTH: 393
<212> TYPE: DNA
<213> ORGANISM: Artificial sequence
<220> FEATURE:
<223> OTHER INFORMATION: VH (Li04)

<400> SEQUENCE: 177
gaagttcaat tgttagagtc tggtggcggt cttgttcagc ctggtggttc tttacgtctt    60
tcttgcgctg cttccggatt cactttctct cgttacaata tgggttgggt cgccaagct   120 cctggtaaag gtttggagtg gtttctgtt atctatcctt ctggtggcgg tactcattat   180
gctgactccg ttaaaggtcg cttcactatc tctagagaca actctaagaa tactctctac   240
ttgcagatga acagcttaag ggctgaggac acggccgtgt attactgtgc gagttctata   300
gcagatgatg cttttgatat ctggggccaa gggacaatgg tcaccgtctc aagcgcctcc   360
accaagggcc catcggtctt cccgctagca ccc                                393

<210> SEQ ID NO 178
<211> LENGTH: 393
```

```
<212> TYPE: DNA
<213> ORGANISM: Artificial sequence
<220> FEATURE:
<223> OTHER INFORMATION: VH (Li08)

<400> SEQUENCE: 178
gaagttcaat tgttagagtc tggtggcggt cttgttcagc ctggtggttc tttacgtctt    60
tcttgcgctg cttccggatt cactttctct cattacgaga tggtttgggt tcgccaagct   120
cctggtaaag gtttggagtg gtttcttct atccgttctt ctggtggcgc tactaagtat   180
gctgactccg ttaaaggtcg cttcactatc tctagagaca actctaagaa tactctctac   240
ttgcagatga acagcttaag ggctgaggac acggccgtgt attactgtgc gaaagagtcg   300
ccagacgact actttgacta ctggggccag ggaaccctgg tcaccgtctc aagcgcctcc   360
accaagggcc catcggtctt cccgctagca ccc                                393

<210> SEQ ID NO 179
<211> LENGTH: 402
<212> TYPE: DNA
<213> ORGANISM: Artificial sequence
<220> FEATURE:
<223> OTHER INFORMATION: VH (Li11)

<400> SEQUENCE: 179
gaagttcaat tgttagagtc tggtggcggt cttgttcagc ctggtggttc tttacgtctt    60
tcttgcgctg cttccggatt cactttctct tcttacgcta tgtattgggt tcgccaagct   120
cctggtaaag gtttggagtg gtttcttct atctctactt ctggtggcta tactggttat   180
gctgactccg ttaaaggtcg cttcactatc tctagagaca actctaagaa tactctctac   240
ttgcagatga acagcttaag ggctgaggac acggccgtgt attactgtgc gagagatacc   300
agcgataatg actactacta catggacgtc tggggcaaag gaccacggt caccgtctca   360 agcgcctcca ccaagggccc atcggtcttc ccgctagcac cc                      402

<210> SEQ ID NO 180
<211> LENGTH: 399
<212> TYPE: DNA
<213> ORGANISM: Artificial sequence
<220> FEATURE:
<223> OTHER INFORMATION: VH (Li10)

<400> SEQUENCE: 180
gaagttcaat tgttagagtc tggtggcggt cttgttcagc ctggtggttc tttacgtctt    60
tcttgcgctg cttccggatt cactttctct acttacccta tggtttgggt tcgccaagct   120
cctggtaaag gtttggagtg gtttcttgg atcggtcctt ctggtggcgt tactgcttat   180
gctgactccg ttaaaggtcg cttcactatc tctagagaca actctaagaa tactctctac   240
ttgcagatga acagcttaag ggctgaggac acggccgtgt attactgtgc gagaccctat   300
agcagtggct ggtgggactt cgatctctgg ggccgtggca ccctggtcac cgtctcaagc   360
gcctccacca agggcccatc ggtcttcccg ctagcaccc                          399

<210> SEQ ID NO 181
<211> LENGTH: 393
<212> TYPE: DNA
<213> ORGANISM: Artificial sequence
<220> FEATURE:
<223> OTHER INFORMATION: VH (Li01)

<400> SEQUENCE: 181
gaagttcaat tgttagagtc tggtggcggt cttgttcagc ctggtggttc tttacgtctt    60
```

```
tcttgcgctg cttccggatt cactttctct aagtaccaga tgacttgggt tcgccaagct    120
cctggtaaag gtttggagtg ggtttcttct atctatcctt ctggtggcaa tactgtttat    180
gctgactccg ttaaaggtcg cttcactatc tctagagaca actctaagaa tactctctac    240
ttgcagatga acagcttaag ggctgaggac acggccgtgt attactgtgc gagtgggact    300
acagaggcag tctttgacta ctggggccag gaaccctggt caccgtctc aagcgcctcc    360 accaagggcc catcggtctt cccgctagca ccc                                 393

<210> SEQ ID NO 182
<211> LENGTH: 387
<212> TYPE: DNA
<213> ORGANISM: Artificial sequence
<220> FEATURE:
<223> OTHER INFORMATION: VH (Li07)

<400> SEQUENCE: 182
gaagttcaat tgttagagtc tggtggcggt cttgttcagc ctggtggttc tttacgtctt    60
tcttgcgctg cttccggatt cactttctct atgtacttta tgggttgggt tcgccaagct    120
cctggtaaag gtttggagtg ggtttcttct atctctcctt ctggtggctt tacttcttat    180
gctgactccg ttaaaggtcg cttcactatc tctagagaca actctaagaa tactctctac    240
ttgcagatga acagcttaag ggctgaggac actgcagtct actattgtgc gagagatcgg    300
catgcttttg atatctgggg ccaagggaca atggtcaccg tctcaagcgc ctccaccaag    360
ggcccatcgg tcttcccgct agcaccc                                        387

<210> SEQ ID NO 183
<211> LENGTH: 396
<212> TYPE: DNA
<213> ORGANISM: Artificial sequence
<220> FEATURE:
<223> OTHER INFORMATION: VH (Li03)

<400> SEQUENCE: 183
gaagttcaat tgttagagtc tggtggcggt cttgttcagc ctggtggttc tttacgtctt    60
tcttgcgctg cttccggatt cactttctct cagtacccta tggagtgggt tcgccaagct    120
cctggtaaag gtttggagtg ggtttctggt atctatcctt ctggtggctc tactgtttat    180
gctgactccg ttaaaggtcg cttcactatc tctagagaca actctaagaa tactctctac    240
ttgcagatga acagcttaag ggctgaggac acggccgtgt attactgtgc gagagcgggg    300
cagtggctgg gggactttga ctactggggc cagggaaccc tggtcaccgt ctcaagcgcc    360
tccaccaagg gcccatcggt cttcccgcta gcaccc                              396

<210> SEQ ID NO 184
<211> LENGTH: 435
<212> TYPE: DNA
<213> ORGANISM: Artificial sequence
<220> FEATURE:
<223> OTHER INFORMATION: VH (Li12)

<400> SEQUENCE: 184
gaagttcaat tgttagagtc tggtggcggt cttgttcagc ctggtggttc tttacgtctt    60
tcttgcgctg cttccggatt cactttctct cagtacaata tgttttgggt tcgccaagct    120
cctggtaaag gtttggagtg ggtttctcgt atctcttctt ctggtggcat gactatgtat    180
gctgactccg ttaaaggtcg cttcactatc tctagagaca actctaagaa tactctctac    240
ttgcagatga acagcttaag ggctgaggac acggctgtgt attactgtgc gagagaagcg    300
```

-continued

```
ttacggcctt attgtagtgg tggtagctgc tactccgact actactacta cggtatggac    360
gtctggggcc aagggaccac ggtcaccgtc tcaagcgcct ccaccaaggg cccatcggtc    420
ttcccgctag caccc                                                     435
```

<210> SEQ ID NO 185
<211> LENGTH: 357
<212> TYPE: DNA
<213> ORGANISM: Artificial sequence
<220> FEATURE:
<223> OTHER INFORMATION: VL (Li02)

<400> SEQUENCE: 185

```
ttctattctc acagtgcaca gtacgaattg actcagccac cctcagtgtc cgtgtcccca    60
ggacagacag ccagcatcac ctgctctgga gataaattgg gggataaatt tgcttcctgg    120
tatcagcaga aggcaggcca gtcccctgtg ctggtcatct ttcaagatag gaagcgtctc    180
tcagggatcc ctgagcgatt ctctggctcc aactctggga cacagccac tctgaccatc     240 agcgggaccc aggctatgga tgaggctgac tattactgtc aggcgtggga caccaacact    300
gtggtcttcg gcggagggac caagctgacc gtcctaggtc agcccaaggc tgccccc      357
```

<210> SEQ ID NO 186
<211> LENGTH: 360
<212> TYPE: DNA
<213> ORGANISM: Artificial sequence
<220> FEATURE:
<223> OTHER INFORMATION: VL (Li09)

<400> SEQUENCE: 186

```
ttctattctc acagtgcaca agacatccag atgacccagt ctccatcctc cctgtctgca    60
tttgtgggag acagagtcgc catcacttgc cgcgcaagtc agagcatcga cacctattta    120
aattggtatc agcagaaacc agggaaagcc cctaaactcc tgatctatgc tgcatccaag    180
ttggaagacg gggtcccatc aagattcagt ggcagtggaa ctgggacaga tttcactctc    240
accatcagaa gtctgcaacc tgaagatttt ggaacttact actgtcaaca gagttacagt    300 cccccctctca ctttcggcgg aaggaccaag gtggagatca aacgaactgt ggctgcacca    360
```

<210> SEQ ID NO 187
<211> LENGTH: 360
<212> TYPE: DNA
<213> ORGANISM: Artificial sequence
<220> FEATURE:
<223> OTHER INFORMATION: VL (Li06)

<400> SEQUENCE: 187

```
ttctattctc acagtgcaca agacatccag atgacccagt ctccttccac cctgtctgca    60
tctgtaggag acagagtcac catcacttgc cgggccagtc agagtattag tagctggttg    120
gcctggtatc agcagaaacc agggaaagcc cctaacctcc tgatctatgc tgcatccagt    180
ttacgaactg gggtcccatc aagattcagg ggcagtggat ctggcacaga tttcactctc    240
accatcagca gcctgcagcc tgaagatttt gcaacgtatt actgtctaca agattacagt    300
taccctctca cttttggcca ggggaccaag ctggagatca aacgaactgt ggctgcacca    360
```

<210> SEQ ID NO 188
<211> LENGTH: 363
<212> TYPE: DNA
<213> ORGANISM: Artificial sequence
<220> FEATURE:
<223> OTHER INFORMATION: VL (Li05)

<400> SEQUENCE: 188

```
ttctattctc acagtgcaca gagcgtcttg actcagccac cctcggtgtc agtggcccca      60
ggccagacgg ccaggatttc ctgtggggga gacaacattg gaagtaagag tgtccactgg     120
taccagcaga ggccaggcca ggcccctgtc ctggtcgtgt atgatgatta tgaccggccc     180
tcagggatcc ctgagcgatt ctctggctcc aactctgggg acacggccat cctgaccatc     240
accagggtcg aagtcgggga tgaggccgac ttttattgtc aggtgaggga cagccgtact     300
gaggaacggg tgttcggcgg agggaccaag gtgaccgtct taggtcagcc aaggctgcc      360
ccc                                                                   363
```

<210> SEQ ID NO 189
<211> LENGTH: 360
<212> TYPE: DNA
<213> ORGANISM: Artificial sequence
<220> FEATURE:
<223> OTHER INFORMATION: VL (Li08)

<400> SEQUENCE: 189

```
ttctattctc acagtgcaca agacatccag atgacccagt ctccatcttc cctgtctgca      60
tctgtaggag acagagtcac catcacttgc caggcgagtc aggacattag ttactattta     120
aattggtatc agcagaagcc agggaaagcc cctaagGtcc tgatctacga tgtatccaat     180
ttgcaaacag ggGtcccatc aaggttcagt ggaagtgcgt ctgcgacaga ttttactctc     240
accatcagca gcctgcagcc tgaagatatt gcgacatatt actgtcaaca gtctgataat     300
ctccctctca ctttcggcgg agggaccaag gtggagatta aacgaactgt ggctgcacca     360
```

<210> SEQ ID NO 190
<211> LENGTH: 360
<212> TYPE: DNA
<213> ORGANISM: Artificial sequence
<220> FEATURE:
<223> OTHER INFORMATION: VL (Li11)

<400> SEQUENCE: 190

```
ttctattctc acagtgcaca agacatccag atgacccagt ctccatcttc tgtgtctgca      60
cctataggag acagagtcac catcacttgt cgggcgagtc aggagattgc caactactta     120
gcctggtatc agcagaaacc agggaaagcc cctaagctcc tgatctatga tacatacact     180
ttgcagactg acgtcccacc gaggttcagc ggcagtggtt cggggacaga tttcactctc     240
actatcagca gcctgcagcc tgaagatact gcaacttact tttgtcaaca ggctgacatt     300
ttcccgctct ctttcggcgg agggaccaag gtggagatca aacgaactgt ggctgcacca     360
```

<210> SEQ ID NO 191
<211> LENGTH: 366
<212> TYPE: DNA
<213> ORGANISM: Artificial sequence
<220> FEATURE:
<223> OTHER INFORMATION: VL (Li10)

<400> SEQUENCE: 191

```
ttctattctc acagtgcaca agacatccag atgacccagt ctccatcttc catgtctgct      60
tctgtagggg acacagtcac catcacttgt cgggcgagtc agggtattgg caactggtta     120
gcctggtatc agcagaaacc agggaaagcc ccaactctcc tgatctatgc tgcatccagt     180
ttggaaagtg ggGtcccatc aaggttcacc ggcagcggca gttcctctgg gatagatttc     240
actctcacca tcagcgacct gcaccctgaa gatttggcaa cttactattg tcaacaggct     300
```

```
cagactttcc cgctcacctt cggcggaggg accagggtgg acctcaagcg aactgtggct    360
gcacca                                                               366

<210> SEQ ID NO 192
<211> LENGTH: 363
<212> TYPE: DNA
<213> ORGANISM: Artificial sequence
<220> FEATURE:
<223> OTHER INFORMATION: VL (Li01)

<400> SEQUENCE: 192
ttctattctc acagtgcaca agacatccag atgacccagt ctccatcctc cctgtctgca    60
tctgtaggag acagagtcac catcacttgc caggcgagtc aggacattag caactattta    120
aattggtatc agcagaaacc agggaaagcc cctaagctcc tgatctacga tgcatccaat    180
ttggaaacag ggtcccatc aaggttcagc ggcagtggat ctgggacaga tttcactctc     240
accatcagca gcctgcagcc tgaagatttt gcaacttact attgtcaaca ggctgacagg    300
ttccctgcgg tcactttcgg cggagggacc aaggtggaga tcaaacgaac tgtggctgca    360
cca                                                                  363

<210> SEQ ID NO 193
<211> LENGTH: 354
<212> TYPE: DNA
<213> ORGANISM: Artificial sequence
<220> FEATURE:
<223> OTHER INFORMATION: VL (Li07)

<400> SEQUENCE: 193
ttctattctc acagtgcaca gagcgaattg actcagccac cctcagtgtc cgtgtcccca    60
ggacagacag ccatcatcac ctgctctgga gatcagttgg gtgacaaaca tgtggcttgg    120
tatcaacaga agccaggcca gtcccctgtg ctggtcatct atctagacat taagaggccc    180
gcagggattt ctgagcgatt ctctggctcc aactctggaa atacagccac tctgaccatc    240
agagggaccc aggctatgga tgaagctgac tattactgtc aggcgtggga catcaagacg    300
gtcttcggcg gggggaccaa gctgaccgtc ctgagtcagc ccaaggctgc cccc          354

<210> SEQ ID NO 194
<211> LENGTH: 360
<212> TYPE: DNA
<213> ORGANISM: Artificial sequence
<220> FEATURE:
<223> OTHER INFORMATION: VL (Li03)

<400> SEQUENCE: 194
ttctattctc acagtgcaca agacatccag atgacccagt ctccatcctc cctgtctgca    60
tctgtaggag acagagtcac catcacttgc cgggcaagtc agagcattag cagctattta    120
aattggtatc agcagaaacc agggaaagcc cctaagctcc tgatctatgc tgcatccagt    180
ttgcaaagtg ggtcccatc aaggttcagt ggcagtggat ctgggacaga tttcactctc     240
accatcagca gtctgcaacc tgaagatttt gcaacttact actgtcaaca gagttacagt    300
accccgtgga cgttcggcca agggaccaag gtggaaatca aacgaactgt ggctgcacca    360

<210> SEQ ID NO 195
<211> LENGTH: 10
<212> TYPE: PRT
<213> ORGANISM: Artificial sequence
<220> FEATURE:
<223> OTHER INFORMATION: VH-CDR1 (L1a.01)
```

<400> SEQUENCE: 195

Gly Tyr Ser Phe Thr Asn Tyr Trp Ile Gly
1               5                   10

<210> SEQ ID NO 196
<211> LENGTH: 17
<212> TYPE: PRT
<213> ORGANISM: Artificial sequence
<220> FEATURE:
<223> OTHER INFORMATION: VH-CDR2 (L1a.01)

<400> SEQUENCE: 196

Ile Ile Asp Pro Asp Asp Ser Tyr Thr Thr Tyr Ser Pro Ser Phe Gln
1               5                   10                  15
Gly

<210> SEQ ID NO 197
<211> LENGTH: 10
<212> TYPE: PRT
<213> ORGANISM: Artificial sequence
<220> FEATURE:
<223> OTHER INFORMATION: VH-CDR3 (L1a.01)

<400> SEQUENCE: 197

Ala Glu Phe Tyr Trp Gly Ala Tyr Asp Gly
1               5                   10

<210> SEQ ID NO 198
<211> LENGTH: 10
<212> TYPE: PRT
<213> ORGANISM: Artificial sequence
<220> FEATURE:
<223> OTHER INFORMATION: VH-CDR1 (L1a.02)

<400> SEQUENCE: 198

Gly Gly Ser Ile Arg Gly Asn Tyr Trp Ser
1               5                   10

<210> SEQ ID NO 199
<211> LENGTH: 14
<212> TYPE: PRT
<213> ORGANISM: Artificial sequence
<220> FEATURE:
<223> OTHER INFORMATION: VH-CDR2 (L1a.02)

<400> SEQUENCE: 199

Ser Ile Asn Tyr Ser Gly Phe Thr Asn Pro Ser Leu Lys Gly
1               5                   10

<210> SEQ ID NO 200
<211> LENGTH: 8
<212> TYPE: PRT
<213> ORGANISM: Artificial sequence
<220> FEATURE:
<223> OTHER INFORMATION: VH-CDR3 (L1a.02)

<400> SEQUENCE: 200

Val Arg His Trp Tyr Phe Asp Val
1               5

<210> SEQ ID NO 201
<211> LENGTH: 10
<212> TYPE: PRT
<213> ORGANISM: Artificial sequence
<220> FEATURE:
<223> OTHER INFORMATION: VH-CDR1 (L1a.03)

<400> SEQUENCE: 201

Gly Tyr Thr Phe Asn Gly Phe Asp Met His
1               5                   10

<210> SEQ ID NO 202
<211> LENGTH: 17
<212> TYPE: PRT
<213> ORGANISM: Artificial sequence
<220> FEATURE:
<223> OTHER INFORMATION: VH-CDR2 (L1a.03)

<400> SEQUENCE: 202

Trp Ile Asp Pro Tyr Asn Gly Ser Thr Thr Tyr Ala Gln Lys Phe Gln
1               5                   10                  15

Gly

<210> SEQ ID NO 203
<211> LENGTH: 13
<212> TYPE: PRT
<213> ORGANISM: Artificial sequence
<220> FEATURE:
<223> OTHER INFORMATION: VH-CDR3 (L1a.03)

<400> SEQUENCE: 203

Asp Phe Tyr Met Asp Gly His Tyr Tyr Ile Phe Asp Val
1               5                   10

<210> SEQ ID NO 204
<211> LENGTH: 10
<212> TYPE: PRT
<213> ORGANISM: Artificial sequence
<220> FEATURE:
<223> OTHER INFORMATION: VH-CDR1 (L1a.04)

<400> SEQUENCE: 204

Gly Tyr Ser Phe Ser Asn Tyr Tyr Ile His
1               5                   10

<210> SEQ ID NO 205
<211> LENGTH: 17
<212> TYPE: PRT
<213> ORGANISM: Artificial sequence
<220> FEATURE:
<223> OTHER INFORMATION: VH-CDR2 (L1a.04)

<400> SEQUENCE: 205

Ile Ile Asp Pro Gly Asp Ser Phe Thr Ser Tyr Ser Pro Ser Phe Gln
1               5                   10                  15

Gly

<210> SEQ ID NO 206
<211> LENGTH: 11
<212> TYPE: PRT
<213> ORGANISM: Artificial sequence
<220> FEATURE:
<223> OTHER INFORMATION: VH-CDR3 (L1a.04)

<400> SEQUENCE: 206

Asp Leu Ala Trp Ile Asp Tyr Gly Phe Asp Tyr
1               5                   10

<210> SEQ ID NO 207
<211> LENGTH: 10
<212> TYPE: PRT
<213> ORGANISM: Artificial sequence

```
<220> FEATURE:
<223> OTHER INFORMATION: VH-CDR1 (L1a.05)

<400> SEQUENCE: 207

Gly Phe Thr Phe Thr Ser His Thr Val Ser
1               5                   10

<210> SEQ ID NO 208
<211> LENGTH: 17
<212> TYPE: PRT
<213> ORGANISM: Artificial sequence
<220> FEATURE:
<223> OTHER INFORMATION: VH-CDR2 (L1a.05)

<400> SEQUENCE: 208

Ser Ile Thr Gly Asn Gly Ser Thr Thr Tyr Tyr Ala Asp Ser Val Lys
1               5                   10                  15

Gly

<210> SEQ ID NO 209
<211> LENGTH: 7
<212> TYPE: PRT
<213> ORGANISM: Artificial sequence
<220> FEATURE:
<223> OTHER INFORMATION: VH-CDR3 (L1a.05)

<400> SEQUENCE: 209

Phe Tyr Gly Asp Phe Asp Ser
1               5

<210> SEQ ID NO 210
<211> LENGTH: 10
<212> TYPE: PRT
<213> ORGANISM: Artificial sequence
<220> FEATURE:
<223> OTHER INFORMATION: VH-CDR1 (L1a.06)

<400> SEQUENCE: 210

Gly Phe Thr Phe Ser Ser Asn Trp Met Ser
1               5                   10

<210> SEQ ID NO 211
<211> LENGTH: 17
<212> TYPE: PRT
<213> ORGANISM: Artificial sequence
<220> FEATURE:
<223> OTHER INFORMATION: VH-CDR2 (L1a.06)

<400> SEQUENCE: 211

Thr Ile Phe Tyr Ser Gly Ser Ser Thr Tyr Tyr Ala Asp Ser Val Lys
1               5                   10                  15

Gly

<210> SEQ ID NO 212
<211> LENGTH: 17
<212> TYPE: PRT
<213> ORGANISM: Artificial sequence
<220> FEATURE:
<223> OTHER INFORMATION: VH-CDR3 (L1a.06)

<400> SEQUENCE: 212

Asp Leu Pro Met Lys Gly Phe Ile Gln Gln Arg Tyr Gly Phe Asp Asp
1               5                   10                  15

Val
```

```
<210> SEQ ID NO 213
<211> LENGTH: 10
<212> TYPE: PRT
<213> ORGANISM: Artificial sequence
<220> FEATURE:
<223> OTHER INFORMATION: VH-CDR1 (L1a.07)

<400> SEQUENCE: 213

Gly Phe Thr Phe Ser Gly Tyr Ala Ile Ser
1               5                   10

<210> SEQ ID NO 214
<211> LENGTH: 17
<212> TYPE: PRT
<213> ORGANISM: Artificial sequence
<220> FEATURE:
<223> OTHER INFORMATION: VH-CDR2 (L1a.07)

<400> SEQUENCE: 214

Thr Ile Trp Gly Ser Gly Ser Thr Thr Tyr Tyr Ala Asp Ser Val Lys
1               5                   10                  15

Gly

<210> SEQ ID NO 215
<211> LENGTH: 11
<212> TYPE: PRT
<213> ORGANISM: Artificial sequence
<220> FEATURE:
<223> OTHER INFORMATION: VH-CDR3 (L1a.07)

<400> SEQUENCE: 215

Glu Tyr Trp Tyr Tyr Asp Gln Phe Thr Ala Val
1               5                   10

<210> SEQ ID NO 216
<211> LENGTH: 12
<212> TYPE: PRT
<213> ORGANISM: Artificial sequence
<220> FEATURE:
<223> OTHER INFORMATION: VH-CDR1 (L1a.08)

<400> SEQUENCE: 216

Gly Asp Ser Val Ser Ser Asn Ser Ala Ala Trp Ser
1               5                   10

<210> SEQ ID NO 217
<211> LENGTH: 18
<212> TYPE: PRT
<213> ORGANISM: Artificial sequence
<220> FEATURE:
<223> OTHER INFORMATION: VH-CDR2 (L1a.08)

<400> SEQUENCE: 217

Arg Ile Tyr Tyr Arg Ser Lys Trp Tyr Asn Asp Tyr Ala Val Ser Val
1               5                   10                  15

Lys Ser

<210> SEQ ID NO 218
<211> LENGTH: 10
<212> TYPE: PRT
<213> ORGANISM: Artificial sequence
<220> FEATURE:
<223> OTHER INFORMATION: VH-CDR3 (L1a.08)

<400> SEQUENCE: 218

Glu Val Tyr Ser Ala Gly Ile Met Asp Tyr
1               5                   10
```

<210> SEQ ID NO 219
<211> LENGTH: 10
<212> TYPE: PRT
<213> ORGANISM: Artificial sequence
<220> FEATURE:
<223> OTHER INFORMATION: VH-CDR1 (L1a.09)

<400> SEQUENCE: 219

Gly Tyr Ser Phe Thr Asn His Trp Ile Gly
1               5                   10

<210> SEQ ID NO 220
<211> LENGTH: 17
<212> TYPE: PRT
<213> ORGANISM: Artificial sequence
<220> FEATURE:
<223> OTHER INFORMATION: VH-CDR2 (L1a.09)

<400> SEQUENCE: 220

Ile Ile Asp Pro Ser Asp Ser Asp Thr Asn Tyr Ser Pro Ser Phe Gln
1               5                   10                  15
Gly

<210> SEQ ID NO 221
<211> LENGTH: 11
<212> TYPE: PRT
<213> ORGANISM: Artificial sequence
<220> FEATURE:
<223> OTHER INFORMATION: VH-CDR3 (L1a.09)

<400> SEQUENCE: 221

Gly Phe Tyr Gly Ile Ala Asp Thr Phe Asp Val
1               5                   10

<210> SEQ ID NO 222
<211> LENGTH: 10
<212> TYPE: PRT
<213> ORGANISM: Artificial sequence
<220> FEATURE:
<223> OTHER INFORMATION: VH-CDR1 (L1a.10)

<400> SEQUENCE: 222

Gly Tyr Ser Phe Thr Asn Tyr Trp Ile Ala
1               5                   10

<210> SEQ ID NO 223
<211> LENGTH: 17
<212> TYPE: PRT
<213> ORGANISM: Artificial sequence
<220> FEATURE:
<223> OTHER INFORMATION: VH-CDR2 (L1a.10)

<400> SEQUENCE: 223

Met Ile Tyr Pro Asp Asp Ser Asn Thr Asn Tyr Ser Pro Ser Phe Gln
1               5                   10                  15
Gly

<210> SEQ ID NO 224
<211> LENGTH: 9
<212> TYPE: PRT
<213> ORGANISM: Artificial sequence
<220> FEATURE:
<223> OTHER INFORMATION: VH-CDR3 (L1a.10)

<400> SEQUENCE: 224

```
Thr Asn Tyr Leu Gly Phe Tyr Asp Ser
1               5
```

<210> SEQ ID NO 225
<211> LENGTH: 10
<212> TYPE: PRT
<213> ORGANISM: Artificial sequence
<220> FEATURE:
<223> OTHER INFORMATION: VH-CDR1 (L1a.11)

<400> SEQUENCE: 225

```
Gly Phe Thr Phe Ser Asp Tyr Gly Ile Ser
1               5                   10
```

<210> SEQ ID NO 226
<211> LENGTH: 17
<212> TYPE: PRT
<213> ORGANISM: Artificial sequence
<220> FEATURE:
<223> OTHER INFORMATION: VH-CDR2 (L1a.11)

<400> SEQUENCE: 226

```
Asn Ile Leu Tyr Asp Gly Ser Glu Thr Tyr Tyr Ala Asp Ser Val Lys
1               5                   10                  15

Gly
```

<210> SEQ ID NO 227
<211> LENGTH: 11
<212> TYPE: PRT
<213> ORGANISM: Artificial sequence
<220> FEATURE:
<223> OTHER INFORMATION: VH-CDR3 (L1a.11)

<400> SEQUENCE: 227

```
Gly Tyr Pro Thr Asp Asp Tyr Ser Phe Asp Ile
1               5                   10
```

<210> SEQ ID NO 228
<211> LENGTH: 12
<212> TYPE: PRT
<213> ORGANISM: Artificial sequence
<220> FEATURE:
<223> OTHER INFORMATION: VH-CDR1 (L1a.12)

<400> SEQUENCE: 228

```
Gly Asp Ser Val Ser Asp Asn Ser Ala Ala Trp Gly
1               5                   10
```

<210> SEQ ID NO 229
<211> LENGTH: 18
<212> TYPE: PRT
<213> ORGANISM: Artificial sequence
<220> FEATURE:
<223> OTHER INFORMATION: VH-CDR2 (L1a.12)

<400> SEQUENCE: 229

```
Arg Ile Tyr Tyr Arg Ser Lys Trp Tyr Asn Asp Tyr Ala Val Ser Val
1               5                   10                  15

Lys Ser
```

<210> SEQ ID NO 230
<211> LENGTH: 16
<212> TYPE: PRT
<213> ORGANISM: Artificial sequence
<220> FEATURE:
<223> OTHER INFORMATION: VH-CDR3 (L1a.12)

-continued

```
<400> SEQUENCE: 230

Gly Arg His Glu Tyr Gly Gly Leu Gly Tyr Ala Glu Ala Met Asp His
1               5                   10                  15

<210> SEQ ID NO 231
<211> LENGTH: 10
<212> TYPE: PRT
<213> ORGANISM: Artificial sequence
<220> FEATURE:
<223> OTHER INFORMATION: VH-CDR1 (L1a.13)

<400> SEQUENCE: 231

Gly Phe Thr Phe Ser Ser Tyr Ala Met Ser
1               5                   10

<210> SEQ ID NO 232
<211> LENGTH: 17
<212> TYPE: PRT
<213> ORGANISM: Artificial sequence
<220> FEATURE:
<223> OTHER INFORMATION: VH-CDR2 (L1a.13)

<400> SEQUENCE: 232

Ala Ile Ser Gly Ser Gly Gly Ser Thr Tyr Tyr Ala Asp Ser Val Lys
1               5                   10                  15

Gly

<210> SEQ ID NO 233
<211> LENGTH: 10
<212> TYPE: PRT
<213> ORGANISM: Artificial sequence
<220> FEATURE:
<223> OTHER INFORMATION: VH-CDR3 (L1a.13)

<400> SEQUENCE: 233

His Tyr Thr Tyr Met His Phe Glu Asp Tyr
1               5                   10

<210> SEQ ID NO 234
<211> LENGTH: 11
<212> TYPE: PRT
<213> ORGANISM: Artificial sequence
<220> FEATURE:
<223> OTHER INFORMATION: VL-CDR1 (L1a.01)

<400> SEQUENCE: 234

Ser Gly Asp Ser Leu Pro Ser Lys Phe Val His
1               5                   10

<210> SEQ ID NO 235
<211> LENGTH: 7
<212> TYPE: PRT
<213> ORGANISM: Artificial sequence
<220> FEATURE:
<223> OTHER INFORMATION: VL-CDR2 (L1a.01)

<400> SEQUENCE: 235

Arg Asp Asn Asn Arg Pro Ser
1               5

<210> SEQ ID NO 236
<211> LENGTH: 8
<212> TYPE: PRT
<213> ORGANISM: Artificial sequence
<220> FEATURE:
<223> OTHER INFORMATION: VL-CDR3 (L1a.01)
```

```
<400> SEQUENCE: 236

Ser Ser Tyr Asp Ala Leu Thr Asp
1               5

<210> SEQ ID NO 237
<211> LENGTH: 12
<212> TYPE: PRT
<213> ORGANISM: Artificial sequence
<220> FEATURE:
<223> OTHER INFORMATION: VL-CDR1 (L1a.02)

<400> SEQUENCE: 237

Arg Ala Ser Gln Ser Ile Thr Asn Ser Tyr Leu Gly
1               5                   10

<210> SEQ ID NO 238
<211> LENGTH: 7
<212> TYPE: PRT
<213> ORGANISM: Artificial sequence
<220> FEATURE:
<223> OTHER INFORMATION: VL-CDR2 (L1a.02)

<400> SEQUENCE: 238

Asp Ala Ser Ser Arg Ala Thr
1               5

<210> SEQ ID NO 239
<211> LENGTH: 8
<212> TYPE: PRT
<213> ORGANISM: Artificial sequence
<220> FEATURE:
<223> OTHER INFORMATION: VL-CDR3 (L1a.02)

<400> SEQUENCE: 239

Gln Gln Ala Ser Asp Ala Pro Glu
1               5

<210> SEQ ID NO 240
<211> LENGTH: 11
<212> TYPE: PRT
<213> ORGANISM: Artificial sequence
<220> FEATURE:
<223> OTHER INFORMATION: VL-CDR1 (L1a.03)

<400> SEQUENCE: 240

Arg Ala Ser Gln Gly Ile Asn Phe Trp Leu Asn
1               5                   10

<210> SEQ ID NO 241
<211> LENGTH: 7
<212> TYPE: PRT
<213> ORGANISM: Artificial sequence
<220> FEATURE:
<223> OTHER INFORMATION: VL-CDR2 (L1a.03)

<400> SEQUENCE: 241

Ala Gly Ser Asn Leu Gln Ser
1               5

<210> SEQ ID NO 242
<211> LENGTH: 8
<212> TYPE: PRT
<213> ORGANISM: Artificial sequence
<220> FEATURE:
<223> OTHER INFORMATION: VL-CDR3 (L1a.03)

<400> SEQUENCE: 242
```

```
Met Gln Asp Ser Asp Phe Pro Phe
1               5

<210> SEQ ID NO 243
<211> LENGTH: 14
<212> TYPE: PRT
<213> ORGANISM: Artificial sequence
<220> FEATURE:
<223> OTHER INFORMATION: VL-CDR1 (L1a.04)

<400> SEQUENCE: 243

Thr Gly Ser Ser Ser Asn Ile Gly Ala Gly Tyr Asp Val Ser
1               5                   10

<210> SEQ ID NO 244
<211> LENGTH: 7
<212> TYPE: PRT
<213> ORGANISM: Artificial sequence
<220> FEATURE:
<223> OTHER INFORMATION: VL-CDR2 (L1a.04)

<400> SEQUENCE: 244

Arg Asn Asn Asn Arg Pro Ser
1               5

<210> SEQ ID NO 245
<211> LENGTH: 8
<212> TYPE: PRT
<213> ORGANISM: Artificial sequence
<220> FEATURE:
<223> OTHER INFORMATION: VL-CDR3 (L1a.04)

<400> SEQUENCE: 245

Gln Thr Tyr Asp Asn Ser Thr Asp
1               5

<210> SEQ ID NO 246
<211> LENGTH: 11
<212> TYPE: PRT
<213> ORGANISM: Artificial sequence
<220> FEATURE:
<223> OTHER INFORMATION: VL-CDR1 (L1a.05)

<400> SEQUENCE: 246

Ser Gly Asp Asn Ile Arg Ser Tyr Tyr Val His
1               5                   10

<210> SEQ ID NO 247
<211> LENGTH: 7
<212> TYPE: PRT
<213> ORGANISM: Artificial sequence
<220> FEATURE:
<223> OTHER INFORMATION: VL-CDR2 (L1a.05)

<400> SEQUENCE: 247

Glu Asp Ser Asn Arg Pro Ser
1               5

<210> SEQ ID NO 248
<211> LENGTH: 10
<212> TYPE: PRT
<213> ORGANISM: Artificial sequence
<220> FEATURE:
<223> OTHER INFORMATION: VL-CDR3 (L1a.05)

<400> SEQUENCE: 248

Gln Ser Tyr Asp Ser Ala Ile Leu Leu His
1               5                   10
```

```
<210> SEQ ID NO 249
<211> LENGTH: 16
<212> TYPE: PRT
<213> ORGANISM: Artificial sequence
<220> FEATURE:
<223> OTHER INFORMATION: VL-CDR1 (L1a.06)

<400> SEQUENCE: 249

Arg Ser Ser Gln Ser Leu Val Leu Arg Thr Gly Tyr Thr Tyr Leu Asn
1               5                   10                  15

<210> SEQ ID NO 250
<211> LENGTH: 7
<212> TYPE: PRT
<213> ORGANISM: Artificial sequence
<220> FEATURE:
<223> OTHER INFORMATION: VL-CDR2 (L1a.06)

<400> SEQUENCE: 250

Leu Val Ser Asn Arg Ala Ser
1               5

<210> SEQ ID NO 251
<211> LENGTH: 8
<212> TYPE: PRT
<213> ORGANISM: Artificial sequence
<220> FEATURE:
<223> OTHER INFORMATION: VL-CDR3 (L1a.06)

<400> SEQUENCE: 251

Gln Gln Tyr Tyr Gly Met Pro Leu
1               5

<210> SEQ ID NO 252
<211> LENGTH: 12
<212> TYPE: PRT
<213> ORGANISM: Artificial sequence
<220> FEATURE:
<223> OTHER INFORMATION: VL-CDR1 (L1a.07)

<400> SEQUENCE: 252

Arg Ala Ser Gln Ser Val Ser Tyr Gln Tyr Leu Ala
1               5                   10

<210> SEQ ID NO 253
<211> LENGTH: 7
<212> TYPE: PRT
<213> ORGANISM: Artificial sequence
<220> FEATURE:
<223> OTHER INFORMATION: VL-CDR2 (L1a.07)

<400> SEQUENCE: 253

Gly Ala Ser Ser Arg Ala Thr
1               5

<210> SEQ ID NO 254
<211> LENGTH: 8
<212> TYPE: PRT
<213> ORGANISM: Artificial sequence
<220> FEATURE:
<223> OTHER INFORMATION: VL-CDR3 (L1a.07)

<400> SEQUENCE: 254

Gln Gln Tyr Gly Ser Val Pro Arg
1               5
```

```
<210> SEQ ID NO 255
<211> LENGTH: 11
<212> TYPE: PRT
<213> ORGANISM: Artificial sequence
<220> FEATURE:
<223> OTHER INFORMATION: VL-CDR1 (L1a.08)

<400> SEQUENCE: 255

Ser Gly Asp Ser Leu Gly Ser Tyr Tyr Val His
1               5                   10

<210> SEQ ID NO 256
<211> LENGTH: 7
<212> TYPE: PRT
<213> ORGANISM: Artificial sequence
<220> FEATURE:
<223> OTHER INFORMATION: VL-CDR2 (L1a.08)

<400> SEQUENCE: 256

Asp Asp Asn Asp Arg Pro Ser
1               5

<210> SEQ ID NO 257
<211> LENGTH: 9
<212> TYPE: PRT
<213> ORGANISM: Artificial sequence
<220> FEATURE:
<223> OTHER INFORMATION: VL-CDR3 (L1a.08)

<400> SEQUENCE: 257

Ser Ala Tyr Asp Tyr Ser Ala Arg Thr
1               5

<210> SEQ ID NO 258
<211> LENGTH: 11
<212> TYPE: PRT
<213> ORGANISM: Artificial sequence
<220> FEATURE:
<223> OTHER INFORMATION: VL-CDR1 (L1a.09)

<400> SEQUENCE: 258

Ser Gly Asp Asn Leu Gly Ser Lys Tyr Val Ser
1               5                   10

<210> SEQ ID NO 259
<211> LENGTH: 7
<212> TYPE: PRT
<213> ORGANISM: Artificial sequence
<220> FEATURE:
<223> OTHER INFORMATION: VL-CDR2 (L1a.09)

<400> SEQUENCE: 259

Asp Asp Asp Asp Arg Pro Ser
1               5

<210> SEQ ID NO 260
<211> LENGTH: 10
<212> TYPE: PRT
<213> ORGANISM: Artificial sequence
<220> FEATURE:
<223> OTHER INFORMATION: VL-CDR3 (L1a.09)

<400> SEQUENCE: 260

Ser Ser Tyr Asp Phe Leu Asn Ile Gly Leu
1               5                   10

<210> SEQ ID NO 261
<211> LENGTH: 11
```

```
<212> TYPE: PRT
<213> ORGANISM: Artificial sequence
<220> FEATURE:
<223> OTHER INFORMATION: VL-CDR1 (L1a.10)

<400> SEQUENCE: 261

Ser Gly Asp Ser Leu Gly Lys Lys Ser Val His
1               5                   10

<210> SEQ ID NO 262
<211> LENGTH: 7
<212> TYPE: PRT
<213> ORGANISM: Artificial sequence
<220> FEATURE:
<223> OTHER INFORMATION: VL-CDR2 (L1a.10)

<400> SEQUENCE: 262

Glu Asp Ser Glu Arg Pro Ser
1               5

<210> SEQ ID NO 263
<211> LENGTH: 8
<212> TYPE: PRT
<213> ORGANISM: Artificial sequence
<220> FEATURE:
<223> OTHER INFORMATION: VL-CDR3 (L1a.10)

<400> SEQUENCE: 263

Ser Ser Tyr Thr Asn Ser Val Asp
1               5

<210> SEQ ID NO 264
<211> LENGTH: 11
<212> TYPE: PRT
<213> ORGANISM: Artificial sequence
<220> FEATURE:
<223> OTHER INFORMATION: VL-CDR1 (L1a.11)

<400> SEQUENCE: 264

Ser Gly Asp Asn Leu Gly Lys Lys Tyr Val Gly
1               5                   10

<210> SEQ ID NO 265
<211> LENGTH: 7
<212> TYPE: PRT
<213> ORGANISM: Artificial sequence
<220> FEATURE:
<223> OTHER INFORMATION: VL-CDR2 (L1a.11)

<400> SEQUENCE: 265

Asp Asp Asp Asn Arg Pro Ser
1               5

<210> SEQ ID NO 266
<211> LENGTH: 8
<212> TYPE: PRT
<213> ORGANISM: Artificial sequence
<220> FEATURE:
<223> OTHER INFORMATION: VL-CDR3 (L1a.11)

<400> SEQUENCE: 266

Gln Ser Tyr Asp Asp Thr Ser Ile
1               5

<210> SEQ ID NO 267
<211> LENGTH: 11
<212> TYPE: PRT
<213> ORGANISM: Artificial sequence
```

```
<220> FEATURE:
<223> OTHER INFORMATION: VL-CDR1 (L1a.12)

<400> SEQUENCE: 267

Ser Gly Asp Ser Leu Gly Asn Lys Tyr Val His
1               5                   10

<210> SEQ ID NO 268
<211> LENGTH: 7
<212> TYPE: PRT
<213> ORGANISM: Artificial sequence
<220> FEATURE:
<223> OTHER INFORMATION: VL-CDR2 (L1a.12)

<400> SEQUENCE: 268

Asp Asp Ser Asp Arg Pro Ser
1               5

<210> SEQ ID NO 269
<211> LENGTH: 8
<212> TYPE: PRT
<213> ORGANISM: Artificial sequence
<220> FEATURE:
<223> OTHER INFORMATION: VL-CDR3 (L1a.12)

<400> SEQUENCE: 269

Gln Thr Trp Asp Tyr Val Gly Tyr
1               5

<210> SEQ ID NO 270
<211> LENGTH: 14
<212> TYPE: PRT
<213> ORGANISM: Artificial sequence
<220> FEATURE:
<223> OTHER INFORMATION: VL-CDR1 (L1a.13)

<400> SEQUENCE: 270

Thr Gly Thr Ser Ser Asp Val Gly Gly Tyr Asn Tyr Val Ser
1               5                   10

<210> SEQ ID NO 271
<211> LENGTH: 7
<212> TYPE: PRT
<213> ORGANISM: Artificial sequence
<220> FEATURE:
<223> OTHER INFORMATION: VL-CDR2 (L1a.13)

<400> SEQUENCE: 271

Asp Val Ser Asn Arg Pro Ser
1               5

<210> SEQ ID NO 272
<211> LENGTH: 10
<212> TYPE: PRT
<213> ORGANISM: Artificial sequence
<220> FEATURE:
<223> OTHER INFORMATION: VL-CDR3 (L1a.13)

<400> SEQUENCE: 272

Gln Ser Tyr Asp Arg Tyr Arg Leu Lys Asn
1               5                   10

<210> SEQ ID NO 273
<211> LENGTH: 119
<212> TYPE: PRT
<213> ORGANISM: Artificial sequence
<220> FEATURE:
<223> OTHER INFORMATION: Li02 (VL)
```

<400> SEQUENCE: 273

Phe Tyr Ser His Ser Ala Gln Tyr Glu Leu Thr Gln Pro Pro Ser Val
1               5                   10                  15

Ser Val Ser Pro Gly Gln Thr Ala Ser Ile Thr Cys Ser Gly Asp Lys
            20                  25                  30

Leu Gly Asp Lys Phe Ala Ser Trp Tyr Gln Gln Lys Ala Gly Gln Ser
        35                  40                  45

Pro Val Leu Val Ile Phe Gln Asp Arg Lys Arg Leu Ser Gly Ile Pro
    50                  55                  60

Glu Arg Phe Ser Gly Ser Asn Ser Gly Asn Thr Ala Thr Leu Thr Ile
65                  70                  75                  80

Ser Gly Thr Gln Ala Met Asp Glu Ala Asp Tyr Tyr Cys Gln Ala Trp
                85                  90                  95

Asp Thr Asn Thr Val Val Phe Gly Gly Gly Thr Lys Leu Thr Val Leu
            100                 105                 110

Gly Gln Pro Lys Ala Ala Pro
        115

<210> SEQ ID NO 274
<211> LENGTH: 120
<212> TYPE: PRT
<213> ORGANISM: Artificial sequence
<220> FEATURE:
<223> OTHER INFORMATION: Li09 (VL)

<400> SEQUENCE: 274

Phe Tyr Ser His Ser Ala Gln Asp Ile Gln Met Thr Gln Ser Pro Ser
1               5                   10                  15

Ser Leu Ser Ala Phe Val Gly Asp Arg Val Ala Ile Thr Cys Arg Ala
            20                  25                  30

Ser Gln Ser Ile Asp Thr Tyr Leu Asn Trp Tyr Gln Gln Lys Pro Gly
        35                  40                  45

Lys Ala Pro Lys Leu Leu Ile Tyr Ala Ala Ser Lys Leu Glu Asp Gly
    50                  55                  60

Val Pro Ser Arg Phe Ser Gly Ser Gly Thr Gly Thr Asp Phe Thr Leu
65                  70                  75                  80

Thr Ile Arg Ser Leu Gln Pro Glu Asp Phe Gly Thr Tyr Tyr Cys Gln
                85                  90                  95

Gln Ser Tyr Ser Pro Pro Leu Thr Phe Gly Gly Gly Thr Lys Val Glu
            100                 105                 110

Ile Lys Arg Thr Val Ala Ala Pro
        115                 120

<210> SEQ ID NO 275
<211> LENGTH: 120
<212> TYPE: PRT
<213> ORGANISM: Artificial sequence
<220> FEATURE:
<223> OTHER INFORMATION: Li06 (VL)

<400> SEQUENCE: 275

Phe Tyr Ser His Ser Ala Gln Asp Ile Gln Met Thr Gln Ser Pro Ser
1               5                   10                  15

Thr Leu Ser Ala Ser Val Gly Asp Arg Val Thr Ile Thr Cys Arg Ala
            20                  25                  30

Ser Gln Ser Ile Ser Ser Trp Leu Ala Trp Tyr Gln Gln Lys Pro Gly
        35                  40                  45

Lys Ala Pro Asn Leu Leu Ile Tyr Ala Ala Ser Ser Leu Arg Thr Gly
            50                  55                  60

Val Pro Ser Arg Phe Arg Gly Ser Gly Ser Gly Thr Asp Phe Thr Leu
 65                  70                  75                  80

Thr Ile Ser Ser Leu Gln Pro Glu Asp Phe Ala Thr Tyr Tyr Cys Leu
                 85                  90                  95

Gln Asp Tyr Ser Tyr Pro Leu Thr Phe Gly Gln Gly Thr Lys Leu Glu
            100                 105                 110

Ile Lys Arg Thr Val Ala Ala Pro
        115                 120

<210> SEQ ID NO 276
<211> LENGTH: 121
<212> TYPE: PRT
<213> ORGANISM: Artificial sequence
<220> FEATURE:
<223> OTHER INFORMATION: Li05 (VL)

<400> SEQUENCE: 276

Phe Tyr Ser His Ser Ala Gln Ser Val Leu Thr Gln Pro Pro Ser Val
 1               5                  10                  15

Ser Val Ala Pro Gly Gln Thr Ala Arg Ile Ser Cys Gly Gly Asp Asn
            20                  25                  30

Ile Gly Ser Lys Ser Val His Trp Tyr Gln Gln Arg Pro Gly Gln Ala
        35                  40                  45

Pro Val Leu Val Val Tyr Asp Asp Tyr Asp Arg Pro Ser Gly Ile Pro
    50                  55                  60

Glu Arg Phe Ser Gly Ser Asn Ser Gly Asp Thr Ala Ile Leu Thr Ile
 65                  70                  75                  80

Thr Arg Val Glu Val Gly Asp Glu Ala Asp Phe Tyr Cys Gln Val Arg
                 85                  90                  95

Asp Ser Arg Thr Glu Glu Arg Val Phe Gly Gly Gly Thr Lys Val Thr
            100                 105                 110

Val Leu Gly Gln Pro Lys Ala Ala Pro
        115                 120

<210> SEQ ID NO 277
<211> LENGTH: 120
<212> TYPE: PRT
<213> ORGANISM: Artificial sequence
<220> FEATURE:
<223> OTHER INFORMATION: Li08 (VL)

<400> SEQUENCE: 277

Phe Tyr Ser His Ser Ala Gln Asp Ile Gln Met Thr Gln Ser Pro Ser
 1               5                  10                  15

Ser Leu Ser Ala Ser Val Gly Asp Arg Val Thr Ile Thr Cys Gln Ala
            20                  25                  30

Ser Gln Asp Ile Ser Tyr Tyr Leu Asn Trp Tyr Gln Gln Lys Pro Gly
        35                  40                  45

Lys Ala Pro Lys Val Leu Ile Tyr Asp Val Ser Asn Leu Gln Thr Gly
    50                  55                  60

Val Pro Ser Arg Phe Ser Gly Ser Ala Ser Thr Asp Phe Thr Leu
 65                  70                  75                  80

Thr Ile Ser Ser Leu Gln Pro Glu Asp Ile Ala Thr Tyr Tyr Cys Gln
                 85                  90                  95

Gln Ser Asp Asn Leu Pro Leu Thr Phe Gly Gly Gly Thr Lys Val Glu
            100                 105                 110

```
Ile Lys Arg Thr Val Ala Ala Pro
        115                 120

<210> SEQ ID NO 278
<211> LENGTH: 120
<212> TYPE: PRT
<213> ORGANISM: Artificial sequence
<220> FEATURE:
<223> OTHER INFORMATION: Li11 (VL)

<400> SEQUENCE: 278

Phe Tyr Ser His Ser Ala Gln Asp Ile Gln Met Thr Gln Ser Pro Ser
1               5                   10                  15

Ser Val Ser Ala Pro Ile Gly Asp Arg Val Thr Ile Thr Cys Arg Ala
            20                  25                  30

Ser Gln Glu Ile Ala Asn Tyr Leu Ala Trp Tyr Gln Gly Lys Pro Gly
        35                  40                  45

Lys Ala Pro Lys Leu Leu Ile Tyr Asp Thr Tyr Thr Leu Gln Thr Asp
    50                  55                  60

Val Pro Pro Arg Phe Ser Gly Ser Gly Ser Gly Thr Asp Phe Thr Leu
65                  70                  75                  80

Thr Ile Ser Ser Leu Gln Pro Glu Asp Thr Ala Thr Tyr Phe Cys Gln
                85                  90                  95

Gln Ala Asp Ile Phe Pro Leu Ser Phe Gly Gly Gly Thr Lys Val Glu
            100                 105                 110

Ile Lys Arg Thr Val Ala Ala Pro
        115                 120

<210> SEQ ID NO 279
<211> LENGTH: 122
<212> TYPE: PRT
<213> ORGANISM: Artificial sequence
<220> FEATURE:
<223> OTHER INFORMATION: Li10 (VL)

<400> SEQUENCE: 279

Phe Tyr Ser His Ser Ala Gln Asp Ile Gln Met Thr Gln Ser Pro Ser
1               5                   10                  15

Ser Met Ser Ala Ser Val Gly Asp Thr Val Thr Ile Thr Cys Arg Ala
            20                  25                  30

Ser Gln Gly Ile Gly Asn Trp Leu Ala Trp Tyr Gln Gln Lys Pro Gly
        35                  40                  45

Lys Ala Pro Thr Leu Leu Ile Tyr Ala Ala Ser Leu Glu Ser Gly
    50                  55                  60

Val Pro Ser Arg Phe Thr Gly Ser Gly Ser Ser Gly Ile Asp Phe
65                  70                  75                  80

Thr Leu Thr Ile Ser Asp Leu His Pro Glu Asp Leu Ala Thr Tyr Tyr
                85                  90                  95

Cys Gln Gln Ala Gln Thr Phe Pro Leu Thr Phe Gly Gly Gly Thr Arg
            100                 105                 110

Val Asp Leu Lys Arg Thr Val Ala Ala Pro
        115                 120

<210> SEQ ID NO 280
<211> LENGTH: 121
<212> TYPE: PRT
<213> ORGANISM: Artificial sequence
<220> FEATURE:
<223> OTHER INFORMATION: Li01 (VL)

<400> SEQUENCE: 280
```

Phe Tyr Ser His Ser Ala Gln Asp Ile Gln Met Thr Gln Ser Pro Ser
1               5                   10                  15

Ser Leu Ser Ala Ser Val Gly Asp Arg Val Thr Ile Thr Cys Gln Ala
                20                  25                  30

Ser Gln Asp Ile Ser Asn Tyr Leu Asn Trp Tyr Gln Gln Lys Pro Gly
            35                  40                  45

Lys Ala Pro Lys Leu Leu Ile Tyr Asp Ala Ser Asn Leu Glu Thr Gly
    50                  55                  60

Val Pro Ser Arg Phe Ser Gly Ser Gly Ser Gly Thr Asp Phe Thr Leu
65                  70                  75                  80

Thr Ile Ser Ser Leu Gln Pro Glu Asp Phe Ala Thr Tyr Tyr Cys Gln
                85                  90                  95

Gln Ala Asp Arg Phe Pro Ala Val Thr Phe Gly Gly Gly Thr Lys Val
            100                 105                 110

Glu Ile Lys Arg Thr Val Ala Ala Pro
            115                 120

<210> SEQ ID NO 281
<211> LENGTH: 118
<212> TYPE: PRT
<213> ORGANISM: Artificial sequence
<220> FEATURE:
<223> OTHER INFORMATION: Li07 (VL)

<400> SEQUENCE: 281

Phe Tyr Ser His Ser Ala Gln Ser Glu Leu Thr Gln Pro Pro Ser Val
1               5                   10                  15

Ser Val Ser Pro Gly Gln Thr Ala Ile Ile Thr Cys Ser Gly Asp Gln
                20                  25                  30

Leu Gly Asp Lys His Val Ala Trp Tyr Gln Gln Lys Pro Gly Gln Ser
            35                  40                  45

Pro Val Leu Val Ile Tyr Leu Asp Ile Lys Arg Pro Ala Gly Ile Ser
    50                  55                  60

Glu Arg Phe Ser Gly Ser Asn Ser Gly Asn Thr Ala Thr Leu Thr Ile
65                  70                  75                  80

Arg Gly Thr Gln Ala Met Asp Glu Ala Asp Tyr Tyr Cys Gln Ala Trp
                85                  90                  95

Asp Ile Lys Thr Val Phe Gly Gly Gly Thr Lys Leu Thr Val Leu Ser
            100                 105                 110

Gln Pro Lys Ala Ala Pro
            115

<210> SEQ ID NO 282
<211> LENGTH: 120
<212> TYPE: PRT
<213> ORGANISM: Artificial sequence
<220> FEATURE:
<223> OTHER INFORMATION: Li03 (VL)

<400> SEQUENCE: 282

Phe Tyr Ser His Ser Ala Gln Asp Ile Gln Met Thr Gln Ser Pro Ser
1               5                   10                  15

Ser Leu Ser Ala Ser Val Gly Asp Arg Val Thr Ile Thr Cys Arg Ala
                20                  25                  30

Ser Gln Ser Ile Ser Ser Tyr Leu Asn Trp Tyr Gln Gln Lys Pro Gly
            35                  40                  45

Lys Ala Pro Lys Leu Leu Ile Tyr Ala Ala Ser Ser Leu Gln Ser Gly
    50                  55                  60

Val Pro Ser Arg Phe Ser Gly Ser Gly Ser Gly Thr Asp Phe Thr Leu
65                  70                  75                  80

Thr Ile Ser Ser Leu Gln Pro Glu Asp Phe Ala Thr Tyr Tyr Cys Gln
                85                  90                  95

Gln Ser Tyr Ser Thr Pro Trp Thr Phe Gly Gln Gly Thr Lys Val Glu
            100                 105                 110

Ile Lys Arg Thr Val Ala Ala Pro
        115                 120

<210> SEQ ID NO 283
<211> LENGTH: 106
<212> TYPE: PRT
<213> ORGANISM: Murinae gen. sp.

<400> SEQUENCE: 283

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Asn Pro Phe Thr
                85                  90                  95

Phe Gly Ser Gly Thr Lys Leu Glu Ile Lys
            100                 105

<210> SEQ ID NO 284
<211> LENGTH: 108
<212> TYPE: PRT
<213> ORGANISM: Murinae gen. sp.

<400> SEQUENCE: 284

Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Asn Ile Tyr Asn Tyr
            20                  25                  30

Leu Ala Trp Phe Gln Gln Lys Gln Gly Lys Ser Pro Gln Leu Leu Val
        35                  40                  45

Tyr Asn Ala Lys Thr Leu Pro Asp Gly Val Pro Ser Arg Phe Ser Gly
    50                  55                  60

Ser Gly Ser Gly Thr Gln Tyr Phe Leu Lys Ile Asn Ser Leu Gln Pro
65                  70                  75                  80

Glu Asp Phe Gly Ser Tyr Tyr Cys Gln His Phe Trp Ala Ile Pro Tyr
                85                  90                  95

Thr Phe Gly Gly Gly Thr Lys Leu Glu Ile Lys Arg
            100                 105

<210> SEQ ID NO 285
<211> LENGTH: 114
<212> TYPE: PRT
<213> ORGANISM: Murinae gen. sp.

<400> SEQUENCE: 285

Asp Ile Val Met Thr Gln Ser Pro Ser Ser Leu Thr Val Thr Ala Gly

```
                1               5                   10                  15
Glu Lys Val Thr Met Ser Cys Lys Ser Ser Gln Ser Leu Leu Asn Ser
                20                  25                  30

Gly Asn Gln Lys Asn Tyr Leu Thr Trp Tyr Gln Gln Lys Pro Gly Gln
                35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Asn Ser Val Gln Ala Glu Asp Leu Ala Val Tyr Tyr Cys Gln Asn
                85                  90                  95

Asp Tyr Ser Tyr Pro Leu Phe Thr Phe Gly Ser Gly Thr Lys Leu Glu
                100                 105                 110

Ile Arg

<210> SEQ ID NO 286
<211> LENGTH: 114
<212> TYPE: PRT
<213> ORGANISM: Murinae gen. sp.

<400> SEQUENCE: 286

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
                20                  25                  30

Gly Asn Gln Lys Ser Tyr Leu Thr Trp Tyr Gln Gln Lys Pro Gly Gln
                35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Asn Ser Val Gln Ala Glu Asp Leu Ala Val Tyr Tyr Cys Gln Asn
                85                  90                  95

Asp Tyr Ser Tyr Pro Leu Phe Thr Phe Gly Ser Gly Thr Lys Leu Glu
                100                 105                 110

Ile Arg

<210> SEQ ID NO 287
<211> LENGTH: 5
<212> TYPE: PRT
<213> ORGANISM: Homo sapiens
<220> FEATURE:
<221> NAME/KEY: MISC_FEATURE
<222> LOCATION: (3)..(5)
<223> OTHER INFORMATION: Xaa is lys, arg, his, glu, or asp.

<400> SEQUENCE: 287

Ile Thr Xaa Xaa Xaa
1               5

<210> SEQ ID NO 288
<211> LENGTH: 5
<212> TYPE: PRT
<213> ORGANISM: Homo sapiens
<220> FEATURE:
<221> NAME/KEY: MISC_FEATURE
<222> LOCATION: (3)..(5)
<223> OTHER INFORMATION: Xaa is lys, arg, his, glu, or asp.

<400> SEQUENCE: 288
```

```
Ala Cys Xaa Xaa Xaa
1               5

<210> SEQ ID NO 289
<211> LENGTH: 5
<212> TYPE: PRT
<213> ORGANISM: Homo sapiens
<220> FEATURE:
<221> NAME/KEY: MISC_FEATURE
<222> LOCATION: (3)..(5)
<223> OTHER INFORMATION: Xaa is lys, arg, his, glu, or asp.

<400> SEQUENCE: 289

Val Cys Xaa Xaa Xaa
1               5

<210> SEQ ID NO 290
<211> LENGTH: 5
<212> TYPE: PRT
<213> ORGANISM: Homo sapiens
<220> FEATURE:
<221> NAME/KEY: MISC_FEATURE
<222> LOCATION: (3)..(5)
<223> OTHER INFORMATION: Xaa is lys, arg, his, glu, or asp.

<400> SEQUENCE: 290

Ser Pro Xaa Xaa Xaa
1               5

<210> SEQ ID NO 291
<211> LENGTH: 5
<212> TYPE: PRT
<213> ORGANISM: Homo sapiens

<400> SEQUENCE: 291

Ser Pro Arg Lys His
1               5

<210> SEQ ID NO 292
<211> LENGTH: 5
<212> TYPE: PRT
<213> ORGANISM: Homo sapiens

<400> SEQUENCE: 292

Ser Pro Arg Lys Lys
1               5

<210> SEQ ID NO 293
<211> LENGTH: 5
<212> TYPE: PRT
<213> ORGANISM: Homo sapiens

<400> SEQUENCE: 293

Ser Pro Arg Lys Arg
1               5

<210> SEQ ID NO 294
<211> LENGTH: 5
<212> TYPE: PRT
<213> ORGANISM: Homo sapiens

<400> SEQUENCE: 294

Ser Pro Lys Lys His
1               5

<210> SEQ ID NO 295
<211> LENGTH: 5
```

```
<212> TYPE: PRT
<213> ORGANISM: Homo sapiens

<400> SEQUENCE: 295

Ser Pro His Lys His
1               5

<210> SEQ ID NO 296
<211> LENGTH: 5
<212> TYPE: PRT
<213> ORGANISM: Homo sapiens

<400> SEQUENCE: 296

Ser Pro Arg Arg His
1               5

<210> SEQ ID NO 297
<211> LENGTH: 5
<212> TYPE: PRT
<213> ORGANISM: Homo sapiens

<400> SEQUENCE: 297

Ser Pro Arg His His
1               5

<210> SEQ ID NO 298
<211> LENGTH: 5
<212> TYPE: PRT
<213> ORGANISM: Homo sapiens

<400> SEQUENCE: 298

Ser Pro Arg Arg Arg
1               5

<210> SEQ ID NO 299
<211> LENGTH: 5
<212> TYPE: PRT
<213> ORGANISM: Homo sapiens

<400> SEQUENCE: 299

Ser Pro His His His
1               5

<210> SEQ ID NO 300
<211> LENGTH: 5
<212> TYPE: PRT
<213> ORGANISM: Homo sapiens

<400> SEQUENCE: 300

Ser Pro Lys Lys Lys
1               5

<210> SEQ ID NO 301
<211> LENGTH: 6
<212> TYPE: PRT
<213> ORGANISM: Homo sapiens

<400> SEQUENCE: 301

Leu Ser Pro Arg Lys His
1               5

<210> SEQ ID NO 302
<211> LENGTH: 6
<212> TYPE: PRT
<213> ORGANISM: Homo sapiens
```

```
<400> SEQUENCE: 302

Leu Ser Pro Arg Lys Lys
1               5

<210> SEQ ID NO 303
<211> LENGTH: 6
<212> TYPE: PRT
<213> ORGANISM: Homo sapiens

<400> SEQUENCE: 303

Leu Ser Pro Arg Lys Arg
1               5

<210> SEQ ID NO 304
<211> LENGTH: 6
<212> TYPE: PRT
<213> ORGANISM: Homo sapiens

<400> SEQUENCE: 304

Leu Ser Pro Lys Lys His
1               5

<210> SEQ ID NO 305
<211> LENGTH: 6
<212> TYPE: PRT
<213> ORGANISM: Homo sapiens

<400> SEQUENCE: 305

Leu Ser Pro His Lys His
1               5

<210> SEQ ID NO 306
<211> LENGTH: 6
<212> TYPE: PRT
<213> ORGANISM: Homo sapiens

<400> SEQUENCE: 306

Leu Ser Pro Arg Arg His
1               5

<210> SEQ ID NO 307
<211> LENGTH: 6
<212> TYPE: PRT
<213> ORGANISM: Homo sapiens

<400> SEQUENCE: 307

Leu Ser Pro Arg His His
1               5

<210> SEQ ID NO 308
<211> LENGTH: 6
<212> TYPE: PRT
<213> ORGANISM: Homo sapiens

<400> SEQUENCE: 308

Leu Ser Pro Arg Arg Arg
1               5

<210> SEQ ID NO 309
<211> LENGTH: 6
<212> TYPE: PRT
<213> ORGANISM: Homo sapiens

<400> SEQUENCE: 309

Leu Ser Pro His His His
```

```
<210> SEQ ID NO 310
<211> LENGTH: 6
<212> TYPE: PRT
<213> ORGANISM: Homo sapiens

<400> SEQUENCE: 310

Leu Ser Pro Lys Lys Lys
1               5

<210> SEQ ID NO 311
<211> LENGTH: 7
<212> TYPE: PRT
<213> ORGANISM: Homo sapiens

<400> SEQUENCE: 311

Trp Leu Ser Pro Arg Lys His
1               5

<210> SEQ ID NO 312
<211> LENGTH: 7
<212> TYPE: PRT
<213> ORGANISM: Homo sapiens

<400> SEQUENCE: 312

Trp Leu Ser Pro Arg Lys Lys
1               5

<210> SEQ ID NO 313
<211> LENGTH: 7
<212> TYPE: PRT
<213> ORGANISM: Homo sapiens

<400> SEQUENCE: 313

Trp Leu Ser Pro Arg Lys Arg
1               5

<210> SEQ ID NO 314
<211> LENGTH: 7
<212> TYPE: PRT
<213> ORGANISM: Homo sapiens

<400> SEQUENCE: 314

Trp Leu Ser Pro Lys Lys His
1               5

<210> SEQ ID NO 315
<211> LENGTH: 7
<212> TYPE: PRT
<213> ORGANISM: Homo sapiens

<400> SEQUENCE: 315

Trp Leu Ser Pro His Lys His
1               5

<210> SEQ ID NO 316
<211> LENGTH: 7
<212> TYPE: PRT
<213> ORGANISM: Homo sapiens

<400> SEQUENCE: 316

Trp Leu Ser Pro Arg Arg His
1               5
```

```
<210> SEQ ID NO 317
<211> LENGTH: 7
<212> TYPE: PRT
<213> ORGANISM: Homo sapiens

<400> SEQUENCE: 317

Trp Leu Ser Pro Arg His His
1               5

<210> SEQ ID NO 318
<211> LENGTH: 7
<212> TYPE: PRT
<213> ORGANISM: Homo sapiens

<400> SEQUENCE: 318

Trp Leu Ser Pro Arg Arg Arg
1               5

<210> SEQ ID NO 319
<211> LENGTH: 7
<212> TYPE: PRT
<213> ORGANISM: Homo sapiens

<400> SEQUENCE: 319

Trp Leu Ser Pro His His His
1               5

<210> SEQ ID NO 320
<211> LENGTH: 7
<212> TYPE: PRT
<213> ORGANISM: Homo sapiens

<400> SEQUENCE: 320

Trp Leu Ser Pro Lys Lys Lys
1               5

<210> SEQ ID NO 321
<211> LENGTH: 6
<212> TYPE: PRT
<213> ORGANISM: Homo sapiens

<400> SEQUENCE: 321

Ile Thr Pro Lys Arg Arg
1               5

<210> SEQ ID NO 322
<211> LENGTH: 5
<212> TYPE: PRT
<213> ORGANISM: Homo sapiens

<400> SEQUENCE: 322

Ala Cys His His Lys
1               5

<210> SEQ ID NO 323
<211> LENGTH: 5
<212> TYPE: PRT
<213> ORGANISM: Homo sapiens

<400> SEQUENCE: 323

Val Cys His His Lys
1               5

<210> SEQ ID NO 324
<211> LENGTH: 5
<212> TYPE: PRT
```

```
<213> ORGANISM: Homo sapiens
<220> FEATURE:
<221> NAME/KEY: MISC_FEATURE
<222> LOCATION: (1)..(2)
<223> OTHER INFORMATION: Xaa is any amino acid.

<400> SEQUENCE: 324

Xaa Xaa Arg Lys His
1               5

<210> SEQ ID NO 325
<211> LENGTH: 5
<212> TYPE: PRT
<213> ORGANISM: Homo sapiens
<220> FEATURE:
<221> NAME/KEY: MISC_FEATURE
<222> LOCATION: (1)..(2)
<223> OTHER INFORMATION: Xaa is any amino acid.

<400> SEQUENCE: 325

Xaa Xaa Arg Arg Arg
1               5

<210> SEQ ID NO 326
<211> LENGTH: 5
<212> TYPE: PRT
<213> ORGANISM: Homo sapiens
<220> FEATURE:
<221> NAME/KEY: MISC_FEATURE
<222> LOCATION: (1)..(2)
<223> OTHER INFORMATION: Xaa is any amino acid.

<400> SEQUENCE: 326

Xaa Xaa Lys Lys Lys
1               5

<210> SEQ ID NO 327
<211> LENGTH: 5
<212> TYPE: PRT
<213> ORGANISM: Homo sapiens
<220> FEATURE:
<221> NAME/KEY: MISC_FEATURE
<222> LOCATION: (1)..(2)
<223> OTHER INFORMATION: Xaa is any amino acid.

<400> SEQUENCE: 327

Xaa Xaa His His His
1               5

<210> SEQ ID NO 328
<211> LENGTH: 5
<212> TYPE: PRT
<213> ORGANISM: Homo sapiens
<220> FEATURE:
<221> NAME/KEY: MISC_FEATURE
<222> LOCATION: (1)..(2)
<223> OTHER INFORMATION: Xaa is any amino acid.

<400> SEQUENCE: 328

Xaa Xaa Arg Lys Lys
1               5

<210> SEQ ID NO 329
<211> LENGTH: 5
<212> TYPE: PRT
<213> ORGANISM: Homo sapiens
<220> FEATURE:
<221> NAME/KEY: MISC_FEATURE
<222> LOCATION: (1)..(2)
<223> OTHER INFORMATION: Xaa is any amino acid.
```

<400> SEQUENCE: 329

Xaa Xaa Arg Lys Arg
1               5

<210> SEQ ID NO 330
<211> LENGTH: 5
<212> TYPE: PRT
<213> ORGANISM: Homo sapiens
<220> FEATURE:
<221> NAME/KEY: MISC_FEATURE
<222> LOCATION: (1)..(2)
<223> OTHER INFORMATION: Xaa is any amino acid.

<400> SEQUENCE: 330

Xaa Xaa Lys Lys His
1               5

<210> SEQ ID NO 331
<211> LENGTH: 5
<212> TYPE: PRT
<213> ORGANISM: Homo sapiens
<220> FEATURE:
<221> NAME/KEY: MISC_FEATURE
<222> LOCATION: (1)..(2)
<223> OTHER INFORMATION: Xaa is any amino acid.

<400> SEQUENCE: 331

Xaa Xaa His Lys His
1               5

<210> SEQ ID NO 332
<211> LENGTH: 5
<212> TYPE: PRT
<213> ORGANISM: Homo sapiens
<220> FEATURE:
<221> NAME/KEY: MISC_FEATURE
<222> LOCATION: (1)..(2)
<223> OTHER INFORMATION: Xaa is any amino acid.

<400> SEQUENCE: 332

Xaa Xaa Arg Arg His
1               5

<210> SEQ ID NO 333
<211> LENGTH: 5
<212> TYPE: PRT
<213> ORGANISM: Homo sapiens
<220> FEATURE:
<221> NAME/KEY: MISC_FEATURE
<222> LOCATION: (1)..(2)
<223> OTHER INFORMATION: Xaa is any amino acid.

<400> SEQUENCE: 333

Xaa Xaa Arg His His
1               5

<210> SEQ ID NO 334
<211> LENGTH: 5
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: Xaa is lys, arg, his, glu, or asp.
<220> FEATURE:
<221> NAME/KEY: MISC_FEATURE
<222> LOCATION: (4)..(4)
<223> OTHER INFORMATION: Xaa is any amino acid.
<220> FEATURE:

```
<221> NAME/KEY: MISC_FEATURE
<222> LOCATION: (5)..(5)
<223> OTHER INFORMATION: Xaa is lys, arg, his, glu, or asp.

<400> SEQUENCE: 334

Ile Thr Xaa Xaa Xaa
1               5

<210> SEQ ID NO 335
<211> LENGTH: 5
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: Xaa is lys, arg, his, glu, or asp.
<220> FEATURE:
<221> NAME/KEY: MISC_FEATURE
<222> LOCATION: (4)..(4)
<223> OTHER INFORMATION: Xaa is any amino acid.
<220> FEATURE:
<221> NAME/KEY: MISC_FEATURE
<222> LOCATION: (5)..(5)
<223> OTHER INFORMATION: Xaa is lys, arg, his, glu, or asp.

<400> SEQUENCE: 335

Ala Cys Xaa Xaa Xaa
1               5

<210> SEQ ID NO 336
<211> LENGTH: 5
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: Xaa is lys, arg, his, glu, or asp.
<220> FEATURE:
<221> NAME/KEY: MISC_FEATURE
<222> LOCATION: (4)..(4)
<223> OTHER INFORMATION: Xaa is any amino acid.
<220> FEATURE:
<221> NAME/KEY: MISC_FEATURE
<222> LOCATION: (5)..(5)
<223> OTHER INFORMATION: Xaa is lys, arg, his, glu, or asp.

<400> SEQUENCE: 336

Val Cys Xaa Xaa Xaa
1               5

<210> SEQ ID NO 337
<211> LENGTH: 5
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: Xaa is lys, arg, his, glu, or asp
<220> FEATURE:
<221> NAME/KEY: MISC_FEATURE
<222> LOCATION: (4)..(4)
<223> OTHER INFORMATION: Xaa is any amino acid.
<220> FEATURE:
<221> NAME/KEY: MISC_FEATURE
<222> LOCATION: (5)..(5)
<223> OTHER INFORMATION: Xaa is lys, arg, his, glu, or asp.

<400> SEQUENCE: 337

Ser Pro Xaa Xaa Xaa
1               5

<210> SEQ ID NO 338
```

```
<211> LENGTH: 5
<212> TYPE: PRT
<213> ORGANISM: Homo sapiens

<400> SEQUENCE: 338

Ser Pro Arg Leu His
1               5

<210> SEQ ID NO 339
<211> LENGTH: 9
<212> TYPE: PRT
<213> ORGANISM: Homo sapiens

<400> SEQUENCE: 339

Arg Arg Ala Arg Ile Arg Asp Arg Lys
1               5

<210> SEQ ID NO 340
<211> LENGTH: 9
<212> TYPE: PRT
<213> ORGANISM: Homo sapiens

<400> SEQUENCE: 340

Lys Lys Val Lys Val Lys Glu Lys Arg
1               5

<210> SEQ ID NO 341
<211> LENGTH: 9
<212> TYPE: PRT
<213> ORGANISM: Homo sapiens

<400> SEQUENCE: 341

Arg Arg Leu Arg Leu Arg Asp Arg Lys
1               5

<210> SEQ ID NO 342
<211> LENGTH: 9
<212> TYPE: PRT
<213> ORGANISM: Homo sapiens

<400> SEQUENCE: 342

Arg Arg Gly Arg Gly Arg Asp Arg Lys
1               5

<210> SEQ ID NO 343
<211> LENGTH: 9
<212> TYPE: PRT
<213> ORGANISM: Homo sapiens

<400> SEQUENCE: 343

Arg Arg Ile Arg Ala Arg Asp Arg Lys
1               5

<210> SEQ ID NO 344
<211> LENGTH: 19
<212> TYPE: DNA
<213> ORGANISM: Artificial sequence
<220> FEATURE:
<223> OTHER INFORMATION: RT-PCR Primer

<400> SEQUENCE: 344
agagacatgc gattggtga                                              19

<210> SEQ ID NO 345
<211> LENGTH: 21
<212> TYPE: DNA
```

```
<213> ORGANISM: Artificial sequence
<220> FEATURE:
<223> OTHER INFORMATION: RT-PCR primer

<400> SEQUENCE: 345
agagatgtag acgaggtcat t                                        21

<210> SEQ ID NO 346
<211> LENGTH: 55
<212> TYPE: DNA
<213> ORGANISM: Artificial sequence
<220> FEATURE:
<223> OTHER INFORMATION: LV1-036 (sense oligo)

<400> SEQUENCE: 346
tgatcgtcat cctgctagac ttcaagagag tctagcagga tgacgatctt ttttc    55

<210> SEQ ID NO 347
<211> LENGTH: 59
<212> TYPE: DNA
<213> ORGANISM: Artificial sequence
<220> FEATURE:
<223> OTHER INFORMATION: LV1-036 (antisense oligo)

<400> SEQUENCE: 347
tcgagaaaaa agatcgtcat cctgctagac tctcttgaag tctagcagga tgacgatca  59

<210> SEQ ID NO 348
<211> LENGTH: 59
<212> TYPE: DNA
<213> ORGANISM: Artificial sequence
<220> FEATURE:
<223> OTHER INFORMATION: Oligonucleotide

<400> SEQUENCE: 348
tgatcctcat ccttctatac ttcaagagag tgtagcagga tgacgatctt ttttctcga  59

<210> SEQ ID NO 349
<211> LENGTH: 59
<212> TYPE: DNA
<213> ORGANISM: Artificial sequence
<220> FEATURE:
<223> OTHER INFORMATION: Oligonucleotide

<400> SEQUENCE: 349
tcgagaaaaa agatcgtcat cctgctagac tctcttgaag tatagaagga tgacgatca  59

<210> SEQ ID NO 350
<211> LENGTH: 41
<212> TYPE: DNA
<213> ORGANISM: Artificial sequence
<220> FEATURE:
<223> OTHER INFORMATION: PCR Primer

<400> SEQUENCE: 350
gaggatctcg acgcggccgc atggagacag acacactcct g                    41

<210> SEQ ID NO 351
<211> LENGTH: 41
<212> TYPE: DNA
<213> ORGANISM: Artificial sequence
<220> FEATURE:
<223> OTHER INFORMATION: PCR Primer

<400> SEQUENCE: 351
ggggcggaat tggatcctca cagatcctct tctgagatga g                    41
```

<210> SEQ ID NO 352
<211> LENGTH: 41
<212> TYPE: DNA
<213> ORGANISM: Artificial sequence
<220> FEATURE:
<223> OTHER INFORMATION: PCR primer

<400> SEQUENCE: 352
gaggatctcg acgcggccgc atggagacag acacactcct g          41

<210> SEQ ID NO 353
<211> LENGTH: 42
<212> TYPE: DNA
<213> ORGANISM: Artificial sequence
<220> FEATURE:
<223> OTHER INFORMATION: PCR primer

<400> SEQUENCE: 353
gatacggatc ctcagccttt gccccggctc catagaaaca gc          42

<210> SEQ ID NO 354
<211> LENGTH: 37
<212> TYPE: DNA
<213> ORGANISM: Artificial sequence
<220> FEATURE:
<223> OTHER INFORMATION: PCR primer

<400> SEQUENCE: 354
cagcaggtcg acgcggccgc atgctggcgg ggggcgt          37

<210> SEQ ID NO 355
<211> LENGTH: 59
<212> TYPE: DNA
<213> ORGANISM: Artificial sequence
<220> FEATURE:
<223> OTHER INFORMATION: PCR primer

<400> SEQUENCE: 355
cagcaggtcg acctcgcccg gctggttggc caaccagccg ggcgaggtcg acctcgagg          59

<210> SEQ ID NO 356
<211> LENGTH: 39
<212> TYPE: DNA
<213> ORGANISM: Artificial sequence
<220> FEATURE:
<223> OTHER INFORMATION: PCR primer

<400> SEQUENCE: 356
ggggatatcc accatggatt ttcaggtgca gattttcag          39

<210> SEQ ID NO 357
<211> LENGTH: 40
<212> TYPE: DNA
<213> ORGANISM: Artificial sequence
<220> FEATURE:
<223> OTHER INFORMATION: PCR primer
<220> FEATURE:
<221> NAME/KEY: misc_feature
<222> LOCATION: (17)..(17)
<223> OTHER INFORMATION: R is A or G.
<220> FEATURE:
<221> NAME/KEY: misc_feature
<222> LOCATION: (25)..(25)
<223> OTHER INFORMATION: K is G or T.
<220> FEATURE:
<221> NAME/KEY: misc_feature
<222> LOCATION: (28)..(28)
<223> OTHER INFORMATION: Y is C or T.
<220> FEATURE:

```
<221> NAME/KEY: misc_feature
<222> LOCATION: (37)..(37)
<223> OTHER INFORMATION: Y is C or T.
<220> FEATURE:
<221> NAME/KEY: misc_feature
<222> LOCATION: (38)..(38)
<223> OTHER INFORMATION: R is A or G.

<400> SEQUENCE: 357 gggatatcc accatgragt cacakacyca ggtcttyrta              40

<210> SEQ ID NO 358
<211> LENGTH: 37
<212> TYPE: DNA
<213> ORGANISM: Artificial sequence
<220> FEATURE:
<223> OTHER INFORMATION: PCR primer

<400> SEQUENCE: 358 gggatatcc accatgaagt tgcctgttag gctgttg                 37

<210> SEQ ID NO 359
<211> LENGTH: 40
<212> TYPE: DNA
<213> ORGANISM: Artificial sequence
<220> FEATURE:
<223> OTHER INFORMATION: PCR primer
<220> FEATURE:
<221> NAME/KEY: misc_feature
<222> LOCATION: (20)..(20)
<223> OTHER INFORMATION: K is G or T.
<220> FEATURE:
<221> NAME/KEY: misc_feature
<222> LOCATION: (25)..(25)
<223> OTHER INFORMATION: W is A or T.
<220> FEATURE:
<221> NAME/KEY: misc_feature
<222> LOCATION: (32)..(32)
<223> OTHER INFORMATION: Y is C or T.
<220> FEATURE:
<221> NAME/KEY: misc_feature
<222> LOCATION: (34)..(34)
<223> OTHER INFORMATION: Y is C or T.
<220> FEATURE:
<221> NAME/KEY: misc_feature
<222> LOCATION: (37)..(37)
<223> OTHER INFORMATION: K is G or T.

<400> SEQUENCE: 359 gggatatcc accatgaggk ccccwgctca gytyctkgga              40

<210> SEQ ID NO 360
<211> LENGTH: 39
<212> TYPE: DNA
<213> ORGANISM: Artificial sequence
<220> FEATURE:
<223> OTHER INFORMATION: PCR primer
<220> FEATURE:
<221> NAME/KEY: misc_feature
<222> LOCATION: (18)..(18)
<223> OTHER INFORMATION: R is A or G.
<220> FEATURE:
<221> NAME/KEY: misc_feature
<222> LOCATION: (28)..(28)
<223> OTHER INFORMATION: K is G or T.
<220> FEATURE:
<221> NAME/KEY: misc_feature
<222> LOCATION: (31)..(31)
<223> OTHER INFORMATION: M is A or C.

<400> SEQUENCE: 360 gggatatcc accatggrat gsagctgkgt matsctctt               39
```

```
<210> SEQ ID NO 361
<211> LENGTH: 39
<212> TYPE: DNA
<213> ORGANISM: Artificial sequence
<220> FEATURE:
<223> OTHER INFORMATION: PCR primer
<220> FEATURE:
<221> NAME/KEY: misc_feature
<222> LOCATION: (17)..(17)
<223> OTHER INFORMATION: R is A or G.
<220> FEATURE:
<221> NAME/KEY: misc_feature
<222> LOCATION: (26)..(26)
<223> OTHER INFORMATION: Y is C or T.
<220> FEATURE:
<221> NAME/KEY: misc_feature
<222> LOCATION: (33)..(33)
<223> OTHER INFORMATION: K is G or T.

<400> SEQUENCE: 361
ggggatatcc accatgract tcgggytgag ctkggtttt                         39

<210> SEQ ID NO 362
<211> LENGTH: 38
<212> TYPE: DNA
<213> ORGANISM: Artificial sequence
<220> FEATURE:
<223> OTHER INFORMATION: PCR primer

<400> SEQUENCE: 362
ggggatatcc accatggctg tcttggggct gctcttct                          38

<210> SEQ ID NO 363
<211> LENGTH: 39
<212> TYPE: DNA
<213> ORGANISM: Artificial sequence
<220> FEATURE:
<223> OTHER INFORMATION: PCR primer
<220> FEATURE:
<221> NAME/KEY: misc_feature
<222> LOCATION: (11)..(11)
<223> OTHER INFORMATION: Y is C or T.
<220> FEATURE:
<221> NAME/KEY: misc_feature
<222> LOCATION: (25)..(26)
<223> OTHER INFORMATION: R is A or G.

<400> SEQUENCE: 363
aggtctagaa yctccacaca caggrrccag tggatagac                         39

<210> SEQ ID NO 364
<211> LENGTH: 22
<212> TYPE: DNA
<213> ORGANISM: Artificial sequence
<220> FEATURE:
<223> OTHER INFORMATION: Primer FR1
<220> FEATURE:
<221> NAME/KEY: misc_feature
<222> LOCATION: (5)..(5)
<223> OTHER INFORMATION: S is C or G.
<220> FEATURE:
<221> NAME/KEY: misc_feature
<222> LOCATION: (6)..(6)
<223> OTHER INFORMATION: M is A or C.
<220> FEATURE:
<221> NAME/KEY: misc_feature
<222> LOCATION: (8)..(8)
<223> OTHER INFORMATION: R is A or G.
<220> FEATURE:
<221> NAME/KEY: misc_feature
<222> LOCATION: (15)..(15)
<223> OTHER INFORMATION: S is C or G.
<220> FEATURE:
```

```
<221> NAME/KEY: misc_feature
<222> LOCATION: (20)..(20)
<223> OTHER INFORMATION: W is A or T.

<400> SEQUENCE: 364
aggtsmarct gcagsagtcw gg                                              22

<210> SEQ ID NO 365
<211> LENGTH: 34
<212> TYPE: DNA
<213> ORGANISM: Artificial sequence
<220> FEATURE:
<223> OTHER INFORMATION: Primer FR4

<400> SEQUENCE: 365
tgaggagacg gtgaccgtgg tcccttggcc ccag                                 34

<210> SEQ ID NO 366
<211> LENGTH: 27
<212> TYPE: DNA
<213> ORGANISM: Artificial sequence
<220> FEATURE:
<223> OTHER INFORMATION: PCR Primer
<220> FEATURE:
<221> NAME/KEY: misc_feature
<222> LOCATION: (6)..(6)
<223> OTHER INFORMATION: R is A or G.
<220> FEATURE:
<221> NAME/KEY: misc_feature
<222> LOCATION: (9)..(9)
<223> OTHER INFORMATION: Y is C or T.
<220> FEATURE:
<221> NAME/KEY: misc_feature
<222> LOCATION: (12)..(12)
<223> OTHER INFORMATION: Y is C or T.
<220> FEATURE:
<221> NAME/KEY: misc_feature
<222> LOCATION: (18)..(18)
<223> OTHER INFORMATION: H is A, C, or T.
<220> FEATURE:
<221> NAME/KEY: misc_feature
<222> LOCATION: (21)..(21)
<223> OTHER INFORMATION: N is A, G, C, or T.
<220> FEATURE:
<221> NAME/KEY: misc_feature
<222> LOCATION: (24)..(24)
<223> OTHER INFORMATION: N is A, G, C, or T.
<220> FEATURE:
<221> NAME/KEY: misc_feature
<222> LOCATION: (27)..(27)
<223> OTHER INFORMATION: Y is C or T.

<400> SEQUENCE: 366
atggartgya aytggathct nccntty                                         27

<210> SEQ ID NO 367
<211> LENGTH: 39
<212> TYPE: DNA
<213> ORGANISM: Artificial sequence
<220> FEATURE:
<223> OTHER INFORMATION: PCR primer
<220> FEATURE:
<221> NAME/KEY: misc_feature
<222> LOCATION: (11)..(11)
<223> OTHER INFORMATION: Y is C or T.
<220> FEATURE:
<221> NAME/KEY: misc_feature
<222> LOCATION: (25)..(26)
<223> OTHER INFORMATION: R is A or G.

<400> SEQUENCE: 367
aggtctagaa yctccacaca caggrrccag tggatagac                            39
```

<210> SEQ ID NO 368
<211> LENGTH: 66
<212> TYPE: DNA
<213> ORGANISM: Artificial sequence
<220> FEATURE:
<223> OTHER INFORMATION: PCR primer

<400> SEQUENCE: 368

```
ggggtatctc tcgagaaaag agagcatcat catcatcatc atatgggaca gttcagagtg    60
ataggg                                                               66
```

<210> SEQ ID NO 369
<211> LENGTH: 40
<212> TYPE: DNA
<213> ORGANISM: Artificial sequence
<220> FEATURE:
<223> OTHER INFORMATION: PCR primer

<400> SEQUENCE: 369

```
ttcgcggccg ctattagcca gggttgatcc agtagaaggg                          40
```

<210> SEQ ID NO 370
<211> LENGTH: 354
<212> TYPE: DNA
<213> ORGANISM: Artificial sequence
<220> FEATURE:
<223> OTHER INFORMATION: Li13 (VH)

<400> SEQUENCE: 370

```
gaagttcaat tgttagagtc tggtggcggt cttgttcagc ctggtggttc tttacgtctt    60
tcttgcgctg cttccggatt cactttctct cattacgaga tgtattgggt tcgccaagct   120
cctggtaaag gtttggagtg ggtttctcgt atcgtttctt ctggtggctt tactaagtat   180
gctgactccg ttaaaggtcg cttcactatc tctagagaca actctaagaa tactctctac   240
ttgcagatga acagcttaag ggctgaggac acggccgtgt attactgtgc aacagagggt   300
gataatgatg cttttgatat ctggggccaa gggaccacgg tcaccgtctc aagc         354
```

<210> SEQ ID NO 371
<211> LENGTH: 324
<212> TYPE: DNA
<213> ORGANISM: Artificial sequence
<220> FEATURE:
<223> OTHER INFORMATION: Li13 (VL)

<400> SEQUENCE: 371

```
gacatccaga tgacccagtc tccagccacc ctgtctttgt ctccagggga aagagccacc    60
ctctcctgca gggccagtca gagtgttagc agctacttag cctggtacca acagaaacct   120
ggccaggctc ccaggctcct catctatgat gcatccaaca gggccactgg catcccagcc   180
aggttcagtg gcagtgggtc tgggacagac ttcactctca ccatcagcag cctagagcct   240
gaagattttg cagtttatta ctgtcagcag cgtagcaact ggccgatgta cacttttggc   300
caggggacca agctggagat caaa                                          324
```

<210> SEQ ID NO 372
<211> LENGTH: 118
<212> TYPE: PRT
<213> ORGANISM: Artificial sequence
<220> FEATURE:
<223> OTHER INFORMATION: Li13 (VH)

<400> SEQUENCE: 372

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

Glu Met Tyr Trp Val Arg Gln Ala Pro Gly Lys Gly Leu Glu Trp Val
        35                  40                  45

Ser Arg Ile Val Ser Ser Gly Gly Phe Thr Lys Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Thr Glu Gly Asp Asn Asp Ala Phe Asp Ile Trp Gly Gln Gly Thr
            100                 105                 110

Thr Val Thr Val Ser Ser
            115

<210> SEQ ID NO 373
<211> LENGTH: 108
<212> TYPE: PRT
<213> ORGANISM: Artificial sequence
<220> FEATURE:
<223> OTHER INFORMATION: Li13 (VL)

<400> SEQUENCE: 373

Asp Ile Gln Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Met
            85                  90                  95

Tyr Thr Phe Gly Gln Gly Thr Lys Leu Glu Ile Lys
            100                 105

<210> SEQ ID NO 374
<211> LENGTH: 354
<212> TYPE: DNA
<213> ORGANISM: Artificial sequence
<220> FEATURE:
<223> OTHER INFORMATION: LI32 (VH)

<400> SEQUENCE: 374
gaagttcaat tgttagagtc tggtggcggt cttgttcagc ctggtggttc tttacgtctt    60
tcttgcgctg cttccggatt cactttctct gcttacatga tgcagtgggt tcgccaagct   120
cctggtaaag gtttggagtg gtttcttcta tctctccttc tggtggcaa tactaagtat   180 gctgactccg ttaaaggtcg cttcactatc tctagagaca actctaagaa tactctctac   240
ttgcagatga acagcttaag ggctgaggac acggccgtgt attactgtgc gagaggagat   300
tatggatact ggttcgaccc ctggggccag ggcaccctgg tcaccgtctc aagc          354

<210> SEQ ID NO 375
<211> LENGTH: 321
```

```
<212> TYPE: DNA
<213> ORGANISM: Artificial sequence
<220> FEATURE:
<223> OTHER INFORMATION: Li32 (VL)

<400> SEQUENCE: 375
gacatccaga tgacccagtc tccagactcc ctgtctgcat ctgttggaga cagagtcacc      60
atcacttgcc aggcgagtca agacattagc tactatttaa attggtatca gcagaaacca    120
gggatggccc ctaaactcct catctacgat gccttcattt tggaaggagg ggccccatca    180
cggttcagtg ggagcggctc tgggacagat ttttctttca ccatcagcaa tctacagcct    240
gaggatattg caacttattt ctgtcaacag tctgatcaac tgcccgtgac cttcggccaa    300
gggaccaagg tggaaatcag a                                              321

<210> SEQ ID NO 376
<211> LENGTH: 118
<212> TYPE: PRT
<213> ORGANISM: Artificial sequence
<220> FEATURE:
<223> OTHER INFORMATION: Li32 (VH)

<400> SEQUENCE: 376

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
            20                  25                  30

Met Met Gln Trp Val Arg Gln Ala Pro Gly Lys Gly Leu Glu Trp Val
        35                  40                  45

Ser Ser Ile Ser Pro Ser Gly Gly Asn Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Asp Tyr Gly Tyr Trp Phe Asp Pro Trp Gly Gln Gly Thr
            100                 105                 110

Leu Val Thr Val Ser Ser
        115

<210> SEQ ID NO 377
<211> LENGTH: 107
<212> TYPE: PRT
<213> ORGANISM: Artificial sequence
<220> FEATURE:
<223> OTHER INFORMATION: Li32 (VL)

<400> SEQUENCE: 377

Asp Ile Gln Met Thr Gln Ser Pro Asp Ser Leu Ser Ala Ser Val Gly
1               5                   10                  15

Asp Arg Val Thr Ile Thr Cys Gln Ala Ser Gln Asp Ile Ser Tyr Tyr
            20                  25                  30

Leu Asn Trp Tyr Gln Gln Lys Pro Gly Met Ala Pro Lys Leu Leu Ile
        35                  40                  45

Tyr Asp Ala Phe Ile Leu Glu Gly Gly Ala Pro Ser Arg Phe Ser Gly
    50                  55                  60

Ser Gly Ser Gly Thr Asp Phe Ser Phe Thr Ile Ser Asn Leu Gln Pro
65                  70                  75                  80

Glu Asp Ile Ala Thr Tyr Phe Cys Gln Gln Ser Asp Gln Leu Pro Val
                85                  90                  95
```

<210> SEQ ID NO 378
<211> LENGTH: 357
<212> TYPE: DNA
<213> ORGANISM: Artificial sequence
<220> FEATURE:
<223> OTHER INFORMATION: Li33 (VH)

<400> SEQUENCE: 378

```
gaagttcaat tgttagagtc tggtggcggt cttgttcagc ctggtggttc tttacgtctt    60
tcttgcgctg cttccggatt cactttctct atttacccta tgttttgggt tcgccaagct   120
cctggtaaag gtttggagtg gtttcttgg atcggtcctt ctggtggcat tactaagtat    180
gctgactccg ttaaaggtcg cttcactatc tctagagaca actctaagaa tactctctac   240
ttgcagatga acagcttaag ggctgaggac acagccacat attactgtgc gagagagggg   300
cataacgact ggtacttcga tctctggggc cgtggcaccc tggtcaccgt ctcaagc      357
```

<210> SEQ ID NO 379
<211> LENGTH: 321
<212> TYPE: DNA
<213> ORGANISM: Artificial sequence
<220> FEATURE:
<223> OTHER INFORMATION: Li33 (VL)

<400> SEQUENCE: 379

```
gacatccaga tgacccagtc tccaggcacc ctgtctttgt ctccagggga agagccacc     60
ctctcctgca gggccagtca gagtgttagc agctacttag cctggtacca acagaaacct   120
ggccaggctc ccaggctcct catctatgat gcatccaaca gggccactgg catcccagcc   180
aggttcagtg gcagtgggtc tgggacagag ttcactctca ccatcagcag cctgcagtct   240
gaggattttg cagtttatta ctgtcagcag tatgataagt ggccgctcac tttcggcgga   300
gggaccaagg tggagatcaa a                                              321
```

<210> SEQ ID NO 380
<211> LENGTH: 119
<212> TYPE: PRT
<213> ORGANISM: Artificial sequence
<220> FEATURE:
<223> OTHER INFORMATION: Li33 (VH)

<400> SEQUENCE: 380

```
Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Ile Tyr
            20                  25                  30
Pro Met Phe Trp Val Arg Gln Ala Pro Gly Lys Gly Leu Glu Trp Val
        35                  40                  45
Ser Trp Ile Gly Pro Ser Gly Gly Ile Thr Lys Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Thr Tyr Tyr Cys
                85                  90                  95
Ala Arg Glu Gly His Asn Asp Trp Tyr Phe Asp Leu Trp Gly Arg Gly
            100                 105                 110
Thr Leu Val Thr Val Ser Ser
        115
```

<210> SEQ ID NO 381
<211> LENGTH: 107
<212> TYPE: PRT
<213> ORGANISM: Artificial sequence
<220> FEATURE:
<223> OTHER INFORMATION: Li33 (VL)

<400> SEQUENCE: 381

Asp Ile Gln Met Thr Gln Ser Pro Gly Thr Leu Ser Leu Ser Pro Gly
1               5                   10                  15
Glu Arg Ala Thr Leu Ser Cys Arg Ala Ser Gln Ser Val Ser Ser Tyr
            20                  25                  30
Leu Ala Trp Tyr Gln Gln Lys Pro Gly Gln Ala Pro Arg Leu Leu Ile
        35                  40                  45
Tyr Asp Ala Ser Asn Arg Ala Thr Gly Ile Pro Ala Arg Phe Ser Gly
    50                  55                  60
Ser Gly Ser Gly Thr Glu Phe Thr Leu Thr Ile Ser Ser Leu Gln Ser
65                  70                  75                  80
Glu Asp Phe Ala Val Tyr Tyr Cys Gln Gln Tyr Asp Lys Trp Pro Leu
                85                  90                  95
Thr Phe Gly Gly Gly Thr Lys Val Glu Ile Lys
            100                 105

<210> SEQ ID NO 382
<211> LENGTH: 357
<212> TYPE: DNA
<213> ORGANISM: Artificial sequence
<220> FEATURE:
<223> OTHER INFORMATION: Li34 (VH)

<400> SEQUENCE: 382
gaagttcaat tgttagagtc tggtggcggt cttgttcagc ctggtggttc tttacgtctt      60
tcttgcgctg cttccggatt cactttctct aattacgaga tgtattgggt tcgccaagct     120
cctggtaaag gtttggagtg gtttctggt atctattctt ctggtggcat tactgtttat      180
gctgactccg ttaaaggtcg cttcactatc tctagagaca actctaagaa tactctctac     240
ttgcagatga acagcttaag ggctgaggac acggccgtgt attactgtgc tagggcagcc     300
atcctcgact ggtacttcga tctctggggc cgtggcaccc tggtcaccgt ctcaagc        357

<210> SEQ ID NO 383
<211> LENGTH: 321
<212> TYPE: DNA
<213> ORGANISM: Artificial sequence
<220> FEATURE:
<223> OTHER INFORMATION: Li34 (VL)

<400> SEQUENCE: 383
gacatccaga tgacccagtc tccatcctcc ctgtctgcat ctgtaggaga cagagtcacc      60
atcacttgcc atgcgagtca ggacattagc aactatttaa gttggtatca gcagaaacca     120
ggtaaagccc ctaaactcct gatctacgat gctttcaatt tggagacagg agtcccatcg     180
aggttcagtg gaagtggatc tggcacagat tttacattca ccatcagcag cctgcagcct     240
gaagattttg caacatatta ctgtcagcac atgataatc tcccattcac tttcggccct     300
gggaccagag tggcgatcag a                                                321

<210> SEQ ID NO 384
<211> LENGTH: 119

```
<212> TYPE: PRT
<213> ORGANISM: Artificial sequence
<220> FEATURE:
<223> OTHER INFORMATION: Li34 (VH)

<400> SEQUENCE: 384

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Glu Met Tyr Trp Val Arg Gln Ala Pro Gly Lys Gly Leu Glu Trp Val
        35                  40                  45

Ser Gly Ile Tyr Ser Ser Gly Gly Ile Thr Val Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Ala Ile Leu Asp Trp Tyr Phe Asp Leu Trp Gly Arg Gly
            100                 105                 110

Thr Leu Val Thr Val Ser Ser
            115

<210> SEQ ID NO 385
<211> LENGTH: 107
<212> TYPE: PRT
<213> ORGANISM: Artificial sequence
<220> FEATURE:
<223> OTHER INFORMATION: Li 34 (VL)

<400> SEQUENCE: 385

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Asn Tyr
            20                  25                  30

Leu Ser Trp Tyr Gln Gln Lys Pro Gly Lys Ala Pro Lys Leu Leu Ile
        35                  40                  45

Tyr Asp Ala Phe Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Gln His Tyr Asp Asn Leu Pro Phe
                85                  90                  95

Thr Phe Gly Pro Gly Thr Arg Val Ala Ile Arg
            100                 105

<210> SEQ ID NO 386
<211> LENGTH: 11
<212> TYPE: PRT
<213> ORGANISM: Artificial sequence
<220> FEATURE:
<223> OTHER INFORMATION: VL-CDR1 (Li13)

<400> SEQUENCE: 386

Arg Ala Ser Gln Ser Val Ser Ser Tyr Leu Ala
1               5                   10

<210> SEQ ID NO 387
<211> LENGTH: 7
<212> TYPE: PRT
<213> ORGANISM: Artificial sequence
```

```
<220> FEATURE:
<223> OTHER INFORMATION: VL-CDR2 (Li13)

<400> SEQUENCE: 387

Asp Ala Ser Asn Arg Ala Thr
1               5

<210> SEQ ID NO 388
<211> LENGTH: 10
<212> TYPE: PRT
<213> ORGANISM: Artificial sequence
<220> FEATURE:
<223> OTHER INFORMATION: VL-CDR3 (Li13)

<400> SEQUENCE: 388

Gln Gln Arg Ser Asn Trp Pro Met Tyr Thr
1               5                   10

<210> SEQ ID NO 389
<211> LENGTH: 5
<212> TYPE: PRT
<213> ORGANISM: Artificial sequence
<220> FEATURE:
<223> OTHER INFORMATION: VH-CDR1 (Li13)

<400> SEQUENCE: 389

His Tyr Glu Met Tyr
1               5

<210> SEQ ID NO 390
<211> LENGTH: 17
<212> TYPE: PRT
<213> ORGANISM: Artificial sequence
<220> FEATURE:
<223> OTHER INFORMATION: VH-CDR2 (Li13)

<400> SEQUENCE: 390

Arg Ile Val Ser Ser Gly Gly Phe Thr Lys Tyr Ala Asp Ser Val Lys
1               5                   10                  15

Gly

<210> SEQ ID NO 391
<211> LENGTH: 9
<212> TYPE: PRT
<213> ORGANISM: Artificial sequence
<220> FEATURE:
<223> OTHER INFORMATION: VH-CDR3 (Li13)

<400> SEQUENCE: 391

Glu Gly Asp Asn Asp Ala Phe Asp Ile
1               5

<210> SEQ ID NO 392
<211> LENGTH: 11
<212> TYPE: PRT
<213> ORGANISM: Artificial sequence
<220> FEATURE:
<223> OTHER INFORMATION: VL-CDR1 (Li32)

<400> SEQUENCE: 392

Gln Ala Ser Gln Asp Ile Ser Tyr Tyr Leu Asn
1               5                   10

<210> SEQ ID NO 393
<211> LENGTH: 7
<212> TYPE: PRT
<213> ORGANISM: Artificial sequence
```

```
<220> FEATURE:
<223> OTHER INFORMATION: VL-CDR2 (Li32)

<400> SEQUENCE: 393

Asp Ala Phe Ile Leu Glu Gly
1               5

<210> SEQ ID NO 394
<211> LENGTH: 9
<212> TYPE: PRT
<213> ORGANISM: Artificial sequence
<220> FEATURE:
<223> OTHER INFORMATION: VL-CDR3 (Li32)

<400> SEQUENCE: 394

Gln Gln Ser Asp Gln Leu Pro Val Thr
1               5

<210> SEQ ID NO 395
<211> LENGTH: 5
<212> TYPE: PRT
<213> ORGANISM: Artificial sequence
<220> FEATURE:
<223> OTHER INFORMATION: VH-CDR1 (Li32)

<400> SEQUENCE: 395

Ala Tyr Met Met Gln
1               5

<210> SEQ ID NO 396
<211> LENGTH: 17
<212> TYPE: PRT
<213> ORGANISM: Artificial sequence
<220> FEATURE:
<223> OTHER INFORMATION: VH-CDR2 (Li32)

<400> SEQUENCE: 396

Ser Ile Ser Pro Ser Gly Gly Asn Thr Lys Tyr Ala Asp Ser Val Lys
1               5                   10                  15

Gly

<210> SEQ ID NO 397
<211> LENGTH: 9
<212> TYPE: PRT
<213> ORGANISM: Artificial sequence
<220> FEATURE:
<223> OTHER INFORMATION: VH-CDR3 (Li32)

<400> SEQUENCE: 397

Gly Asp Tyr Gly Tyr Trp Phe Asp Pro
1               5

<210> SEQ ID NO 398
<211> LENGTH: 11
<212> TYPE: PRT
<213> ORGANISM: Artificial sequence
<220> FEATURE:
<223> OTHER INFORMATION: VL-CDR1 (Li33)

<400> SEQUENCE: 398

Arg Ala Ser Gln Ser Val Ser Ser Tyr Leu Ala
1               5                   10

<210> SEQ ID NO 399
<211> LENGTH: 7
<212> TYPE: PRT
<213> ORGANISM: Artificial sequence
```

```
<220> FEATURE:
<223> OTHER INFORMATION: VL-CDR2 (Li33)

<400> SEQUENCE: 399

Asp Ala Ser Asn Arg Ala Thr
1               5

<210> SEQ ID NO 400
<211> LENGTH: 9
<212> TYPE: PRT
<213> ORGANISM: Artificial sequence
<220> FEATURE:
<223> OTHER INFORMATION: VL-CDR3 (Li33)

<400> SEQUENCE: 400

Gln Gln Tyr Asp Lys Trp Pro Leu Thr
1               5

<210> SEQ ID NO 401
<211> LENGTH: 5
<212> TYPE: PRT
<213> ORGANISM: Artificial sequence
<220> FEATURE:
<223> OTHER INFORMATION: VH-CDR1 (Li33)

<400> SEQUENCE: 401

Ile Tyr Pro Met Phe
1               5

<210> SEQ ID NO 402
<211> LENGTH: 17
<212> TYPE: PRT
<213> ORGANISM: Artificial sequence
<220> FEATURE:
<223> OTHER INFORMATION: VH-CDR2 (Li33)

<400> SEQUENCE: 402

Trp Ile Gly Pro Ser Gly Gly Ile Thr Lys Tyr Ala Asp Ser Val Lys
1               5                   10                  15

Gly

<210> SEQ ID NO 403
<211> LENGTH: 10
<212> TYPE: PRT
<213> ORGANISM: Artificial sequence
<220> FEATURE:
<223> OTHER INFORMATION: VH-CDR3 (Li33)

<400> SEQUENCE: 403

Glu Gly His Asn Asp Trp Tyr Phe Asp Leu
1               5                   10

<210> SEQ ID NO 404
<211> LENGTH: 11
<212> TYPE: PRT
<213> ORGANISM: Artificial sequence
<220> FEATURE:
<223> OTHER INFORMATION: VL-CDR1 (Li34)

<400> SEQUENCE: 404

His Ala Ser Gln Asp Ile Ser Asn Tyr Leu Ser
1               5                   10

<210> SEQ ID NO 405
<211> LENGTH: 7
<212> TYPE: PRT
<213> ORGANISM: Artificial sequence
```

```
<220> FEATURE:
<223> OTHER INFORMATION: VL-CDR2 (Li34)

<400> SEQUENCE: 405

Asp Ala Phe Asn Leu Glu Thr
1               5

<210> SEQ ID NO 406
<211> LENGTH: 9
<212> TYPE: PRT
<213> ORGANISM: Artificial sequence
<220> FEATURE:
<223> OTHER INFORMATION: VL-CDR3 (Li34)

<400> SEQUENCE: 406

Gln His Tyr Asp Asn Leu Pro Phe Thr
1               5

<210> SEQ ID NO 407
<211> LENGTH: 5
<212> TYPE: PRT
<213> ORGANISM: Artificial sequence
<220> FEATURE:
<223> OTHER INFORMATION: VH-CDR1 (Li34)

<400> SEQUENCE: 407

Asn Tyr Glu Met Tyr
1               5

<210> SEQ ID NO 408
<211> LENGTH: 17
<212> TYPE: PRT
<213> ORGANISM: Artificial sequence
<220> FEATURE:
<223> OTHER INFORMATION: VH-CDR2 (Li34)

<400> SEQUENCE: 408

Gly Ile Tyr Ser Ser Gly Gly Ile Thr Val Tyr Ala Asp Ser Val Lys
1               5                   10                  15

Gly

<210> SEQ ID NO 409
<211> LENGTH: 10
<212> TYPE: PRT
<213> ORGANISM: Artificial sequence
<220> FEATURE:
<223> OTHER INFORMATION: VH-CDR3 (Li34)

<400> SEQUENCE: 409

Ala Ala Ile Leu Asp Trp Tyr Phe Asp Leu
1               5                   10
```

SP35 ANTIBODIES AND USES THEREOF

CROSS REFERENCE TO RELATED APPLICATIONS

The present application is a continuation of International Application No. PCT/US2006/026271, filed Jul. 7, 2006, which claims the benefit of U.S. Provisional Application No. 60/814,522, filed Jun. 19, 2006, U.S. Provisional Application No. 60/771,900, filed Feb. 10, 2006 and U.S. Provisional Application No. 60/697,336, filed Jul. 8, 2005, all of which are incorporated herein by reference in their entireties.

BACKGROUND OF THE INVENTION

1. Field of the Invention

This invention relates to neurology, neurobiology and molecular biology. More particularly, this invention relates to molecules and methods for treatment of neurological diseases, disorders and injuries such as spinal cord injury.

2. Background of the Invention

Axons and dendrites extend from neurons. The distal tip of an extending axon or neurite includes a specialized region, known as the growth cone. Growth cones sense the local environment and guide axonal growth toward a neuron's target cell. Growth cones respond to environmental cues, for example, surface adhesiveness, growth factors, neurotransmitters and electric fields. The growth cones generally advance at a rate of one to two millimeters per day. The growth cone explores the area ahead of it and on either side, by means of elongations classified as lamellipodia and filopodia. When an elongation contacts an unfavorable surface, it withdraws. When an elongation contacts a favorable growth surface, it continues to extend and guides the growth cone in that direction. When the growth cone reaches an appropriate target cell a synaptic connection is created.

Nerve cell function is influenced by contact between neurons and other cells in their immediate environment (Rutishauser, et al., 1988, *Physiol. Rev.* 68:819). These cells include specialized glial cells, oligodendrocytes in the central nervous system (CNS), and Schwann cells in the peripheral nervous system (PNS), which sheathe the neuronal axon with myelin (Lemke, 1992, in *An Introduction to Molecular Neurobiology*, Z. Hall, Ed., p. 281, Sinauer).

CNS neurons have the inherent potential to regenerate after injury, but they are inhibited from doing so by inhibitory proteins present in myelin (Brittis et al., 2001, *Neuron* 30:11-14; Jones et al., 2002, *J. Neurosci.* 22:2792-2803; Grimpe et al., 2002, *J. Neurosci.*: 22:3144-3160).

Several myelin inhibitory proteins found on oligodendrocytes have been characterized. Known examples of myelin inhibitory proteins include NogoA (Chen et al., Nature, 2000, 403, 434-439; Grandpre et al., *Nature* 2000, 403, 439-444), myelin associated glycoprotein (MAG) (McKerracher et al., 1994, *Neuron* 13:805-811; Mukhopadhyay et al., 1994, *Neuron* 13:757-767) and oligodendrocyte glycoprotein (OM-gp), Mikol et al., 1988, *J. Cell. Biol.* 106:1273-1279). Each of these proteins has been separately shown to be a ligand for the neuronal Nogo receptor-1 (NgR1 (Wang et al., *Nature* 2002, 417, 941-944; Grandpre et al., *Nature* 2000, 403, 439-444; Chen et al., *Nature*, 2000, 403, 434-439; Domeniconi et al., *Neuron* 2002, published online Jun. 28, 2002).

Nogo receptor-1 (NgR1) is a GPI-anchored membrane protein that contains 8 leucine rich repeats (Fournier et al., 2001, *Nature* 409:341-346). Upon interaction with inhibitory proteins (e.g., NogoA, MAG and OM-gp), the NgR1 complex transduces signals that lead to growth cone collapse and inhibition of neurite outgrowth.

There is an unmet need for molecules and methods for inhibiting NgR1-mediated growth cone collapse and the resulting inhibition of neurite outgrowth. Additionally there is a need for molecules which increase neuronal survival and axon regeneration. Particularly for the treatment of disease, disorders or injuries which involve axonal injury, neuronal or oligodendrocyte cell death, demyelination or dymyelination or generally relate to the nervous system.

Such diseases, disorders or injuries include, but are not limited to, multiple sclerosis (MS), progressive multifocal leukoencephalopathy (PML), encephalomyelitis (EPL), central pontine myelolysis (CPM), adrenoleukodystrophy, Alexander's disease, Pelizaeus Merzbacher disease (PMZ), Globoid cell Leucodystrophy (Krabbe's disease) and Wallerian Degeneration, optic neuritis, transverse myelitis, amylotrophic lateral sclerosis (ALS), Huntington's disease, Alzheimer's disease, Parkinson's disease, spinal cord injury, traumatic brain injury, post radiation injury, neurologic complications of chemotherapy, stroke, acute ischemic optic neuropathy, vitamin E deficiency, isolated vitamin E deficiency syndrome, AR, Bassen-Kornzweig syndrome, Marchiafava-Bignami syndrome, metachromatic leukodystrophy, trigeminal neuralgia, and Bell's palsy. Among these diseases, MS is the most widespread, affecting approximately 2.5 million people worldwide.

MS generally begins with a relapsing-remitting pattern of neurologic involvement, which then progresses to a chronic phase with increasing neurological damage. MS is associated with the destruction of myelin, oligodendrocytes and axons localized to chronic lesions. The demyelination observed in MS is not always permanent and remyelination has been documented in early stages of the disease. Remyelination of neurons requires oligodendrocytes.

Various disease-modifying treatments are available for MS, including the use of corticosteroids and immunomodulators such as interferon beta and Tysabri®. In addition, because of the central role of oligodendrocytes and myelination in MS, there have been efforts to develop therapies to increase oligodendrocyte numbers or enhance myelination. See, e.g., Cohen et al., U.S. Pat. No. 5,574,009; Chang et al., *N. Engl. J. Med.* 346: 165-73 (2002). However, there remains an urgent need to devise additional therapies for MS and other demyelination and dismyelination disorders.

BRIEF SUMMARY OF THE INVENTION

The present invention is based on the discovery that Sp35 (Sp35 is also designated in the literature as LINGO-1 and LRRN6) is expressed in oligodendrocytes and neuronal cells and negatively regulates oligodendrocyte/neuronal differentiation, survival and axon myelination. Furthermore, certain antagonists of Sp35 promote survival, proliferation and differentiation of oligodendrocytes and neuronal cells, as well as myelination of neurons. Based on these discoveries, the invention relates generally to antibodies, antigen binding fragment or derivatives thereof which can be used as an antagonist of Sp35. Additionally, the invention generally relates to methods for treating various disease, disorders or injuries associated with demyelination, dysmyelination, oligodendrocyte/neuronal cell death or axonal injury by the administration of an Sp35 antagonist antibody or antigen binding fragment.

In certain embodiments, the invention includes an isolated antibody or antigen binding fragment thereof which specifically binds to the same Sp35 epitope as a reference monoclonal antibody selected from the group consisting of 201', 3A3, 3A6, 1A7, 1G7, 2B10, 2C11, 2F3, 3P1D10.2C3, 3P1E11.3B7, 3P2C6.3G10.2H7, 3P2C9.2G4, 3P4A6.1D9, 3P4A1.2B9, 3P4C2.2D2, 3P4C5.1D8, 3P4C8.2G9, 30-C12 (Li01), 38-D01 (Li02), 35-E04 (Li03), 36-C09 (Li04), 30-A11 (Li05), 34-F02 (Li06), 29-E07 (Li07), 34-G04 (Li08), 36-A12 (Li09), 28-D02 (Li10), 30-B01 (Li11), 34-B03 (Li12), Li13, Li32, Li33, Li34, 3383 (L1a.1), 3495 (L1a.2), 3563 (L1a.3), 3564 (L1a.4), 3565 (L1a.5), 3566 (L1a.6), 3567 (L1a.7), 3568 (L1a.8), 3569 (L1a.9), 3570 (L1a.10), 3571 (L1a.11), 3582 (L1a.12), and 1968 (L1a.13).

Certain embodiments of the invention include an isolated polypeptide comprising an immunoglobulin heavy chain variable region (VH) wherein the CDR1, CDR2 and CDR3 regions are selected from the polypeptide sequences shown in Table 4 or at least 80%, 85%, 90 or 95% identical to the polypeptide sequences shown in Table 4.

Certain embodiments of the invention include an isolated polypeptide comprising an immunoglobulin light chain variable region (VL) wherein the CDR1, CDR2 and CDR3 regions are selected from the polypeptide sequences shown in Table 5 or at least 80%, 85%, 90% or 95% identical to the polypeptide sequences shown in Table 5.

Certain embodiments of the invention include an isolated polypeptide comprising an immunoglobulin heavy chain variable region (VH) selected from the group consisting of SEQ ID NOs: 158 to 172, 372, 376, 380 and 384, as shown in Table 6, or at least 80%, 85%, 90% or 95% identical to said SEQ ID NOs: 158 to 172, 372, 376, 380 and 384 as shown in Table 6.

Certain embodiments of the invention include an isolated polypeptide comprising an immunoglobulin light chain variable region (VL) selected from the group consisting of SEQ ID NOs: 273 to 286, 373, 377, 381 and 385, as shown in Table 8, or at least 80%, 85%, 90% or 95% identical to said SEQ ID NOs: 273 to 286, 373, 377, 381 and 385, as shown in Table 8.

In additional embodiments, the invention includes an isolated polynucleotide comprising a nucleic acid encoding an immunoglobulin heavy chain variable region (VH) wherein the CDR1, CDR2 and CDR3 regions are selected from the group selected from the polynucleotide sequences shown in Table 4 or at least 80%, 85%, 90 or 95% identical to the polynucleotide sequences shown in Table 4.

In other embodiments, the invention includes an isolated polynucleotide comprising a nucleic acid encoding an immunoglobulin light chain variable region (VL) wherein the CDR1, CDR2 and CDR3 regions are selected from the polynucleotide sequences shown in Table 5 or at least 80%, 85%, 90% or 95% identical to the polynucleotide sequences shown in Table 5.

Other embodiments of the invention include, an isolated polynucleotide comprising a nucleic acid encoding an immunoglobulin heavy chain variable region (VH) selected from the group consisting of SEQ ID NOs: 173 to 184, 370, 374, 378 and 382, as shown in Table 7, or at least 80%, 85%, 90% or 95% identical to said SEQ ID NOs: 173 to 184, 370, 374, 378 and 382, as shown in Table 7.

Other embodiments of the invention include, an isolated polynucleotide comprising a nucleic acid encoding an immunoglobulin light chain variable region (VL) selected from the group consisting of SEQ ID NOs: 185 to 194, 371, 375, 379 and 383, as shown in Table 9, or at least 80%, 85%, 90% or 95% identical to said SEQ ID NOs: 185 to 194, 371, 375, 379 and 383, as shown in Table 9.

In certain embodiments, the invention includes compositions comprising the antibodies or antigen binding fragments described herein.

In additional embodiments, the invention includes methods for treating CNS injury, ALS, Huntington's disease, Alzheimer's disease, Parkinson's disease, diabetic neuropathy and stroke comprising administering to an animal in need of said treatment an effective amount of an agent selected from the group consisting of an isolated Sp35 antibody or fragment thereof or compositions comprising said antibody or fragment thereof.

In other embodiments, the invention includes methods for treating disease or disorders associated with inhibition of oligodendrocyte growth or differentiation; demyelination or dysmyelination of CNS neurons including multiple sclerosis (MS), progressive multifocal leukoencephalopathy (PML), encephalomyelitis (EPL), central pontine myelolysis (CPM), Wallerian Degeneration, adrenoleukodystrophy, Alexander's disease, and Pelizaeus Merzbacher disease (PMZ) by administering to an animal in need of said treatment an effective amount of an agent selected from the group consisting of an isolated Sp35 antibody or fragment thereof or compositions comprising said antibody or fragment thereof.

Other embodiments of the present invention include a method of inhibiting signal transduction by Nogo receptor 1 (NgR1), comprising contacting the NgR1 with an effective amount of an agent selected from the group consisting of the isolated Sp35 antibody or fragment thereof or compositions comprising said antibody or fragment thereof.

Additional embodiments of the present invention include a method of decreasing inhibition of axonal growth of a central nervous system (CNS) neuron, comprising contacting the neuron with an effective amount of an agent selected from the group consisting of the isolated Sp35 antibody or fragment thereof of or compositions comprising said antibody or fragment thereof.

Other embodiments of the present invention include a method of inhibiting growth cone collapse of a CNS neuron, comprising contacting the neuron with an effective amount of an agent selected from the group consisting of the isolated Sp35 antibody or fragment thereof or compositions comprising said antibody or fragment thereof.

BRIEF DESCRIPTION OF THE DRAWINGS/FIGURES

FIG. 1: SDS-PAGE gel showing immunoprecipitation of Sp35 by monoclonal antibodies 1A7 and 2F3.

Figure 2:
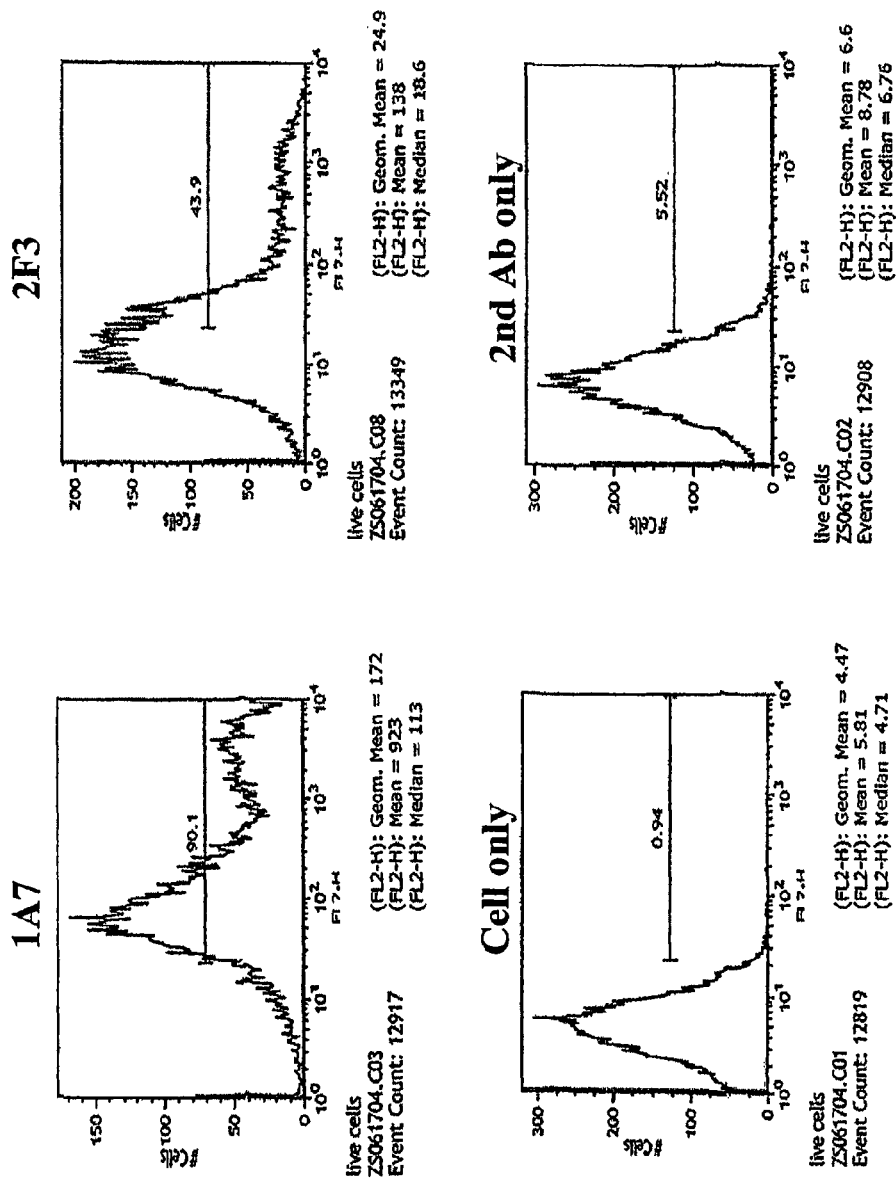

FIG. 2: FACS result showing that MAbs 1A7 and 2F3 bound to COS-7 or 293 cells expressing Sp35, but not to control cells with no Sp35 expression.

Figure 3:
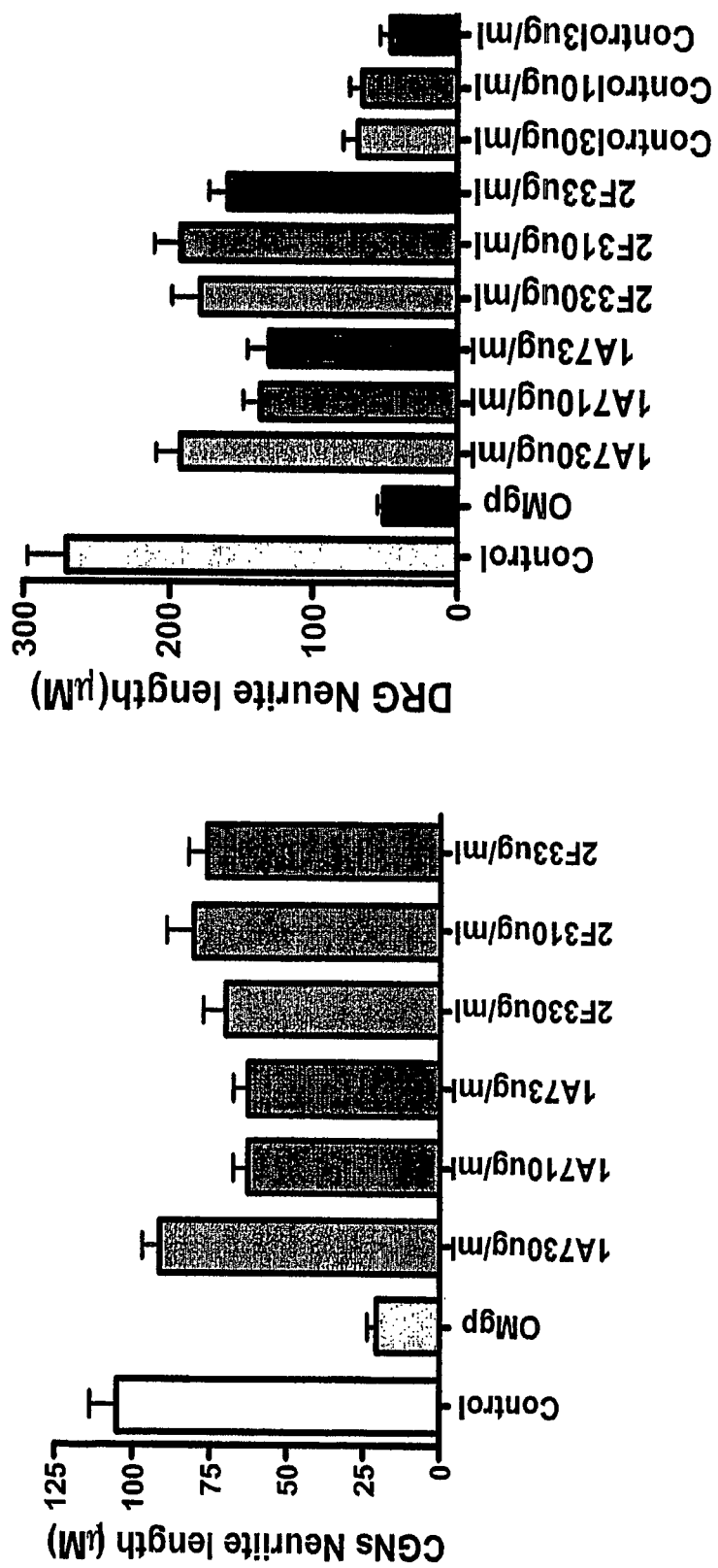

FIG. 3: MAbs 1A7 and 2F3 protected DRG neurons from myelin-mediated inhibition of neurite outgrowth.

FIG. 4A-G: Immunohistochemical staining ("IHC") of cocultures of DRG neurons and oligodendrocytes treated with monoclonal antibodies 1A7 and 2F3, or control antibody. Panels D and E are enlargements of panels B and C, respectively. Staining with anti-βIII-tubulin antibody to identify axons, or anti-MBP antibody to identify oligodendrocytes. F: Quantitation of MBP+ myelinating cells upon treatment of cocultures with 1A7 or 2F3. G: Western blot analysis to quantify the MBP produced from cocultures of DRG neurons and oligodendrocytes treated with monoclonal antibodies 1A7 and 2F3.

FIG. 5A-C: A: CC1 antibody staining of mouse oligodendrocytes in cuprizone model. B. Anti-MBP protein antibody or luxol fast blue staining of mouse neurons in cuprizone model. C: Quantitation of CC1 antibody-positive oligodendrocytes at four weeks and 6 weeks.

Figure 6:
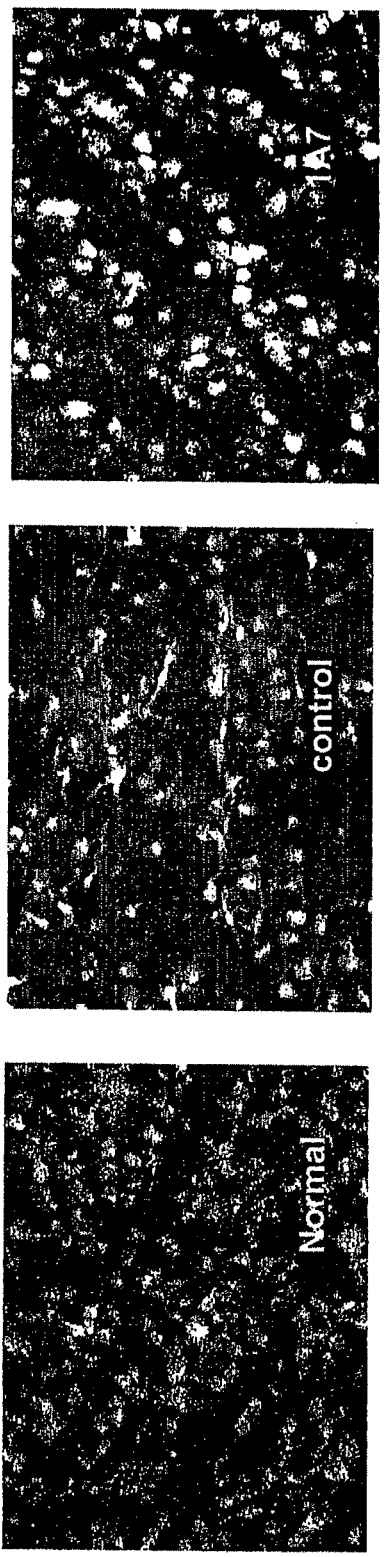

FIG. 6: Surviving RGCs. Treatment with monoclonal antibody 1A7 Anti-Sp35 antibody 1A7 treated animals showed significant neuronal survival (80%) when compared to control-antibody or PBS treated animals, which each only showed approximately 50% neuronal survival.

Figure 7:
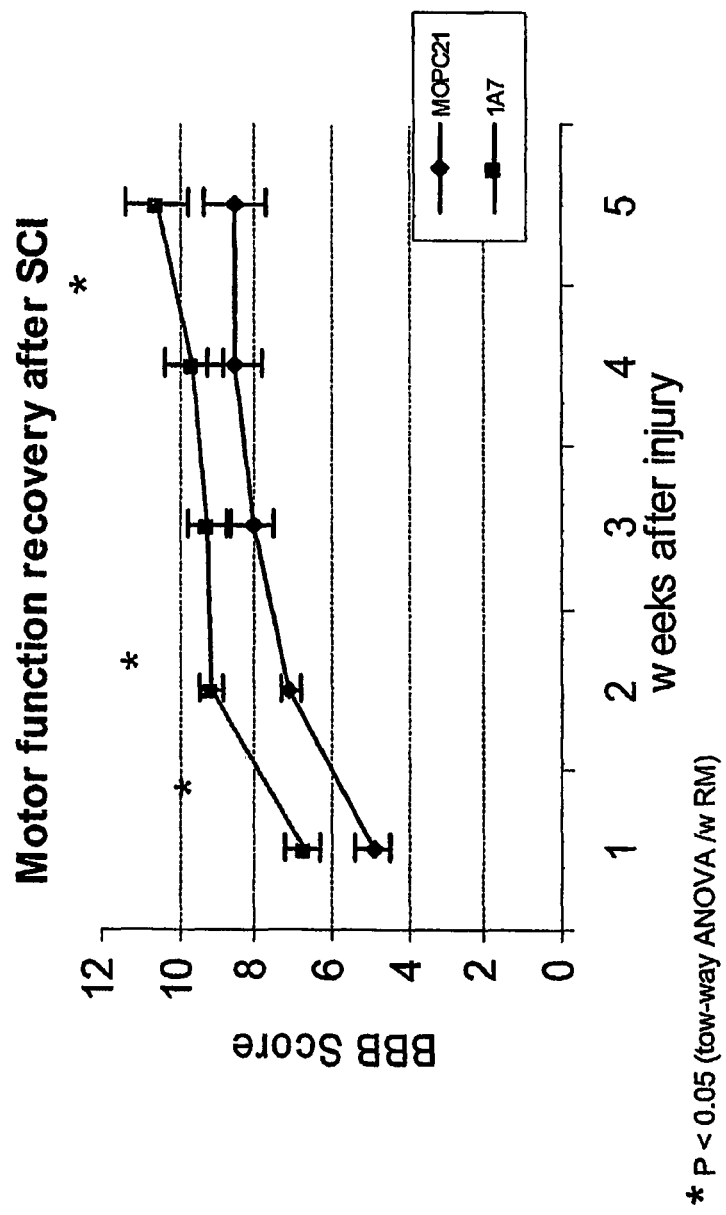

FIG. 7. BBB scores of mice receiving anti-Sp35 antibody 1A7 after spinal cord injury as described in Example 8.

Figure 8:
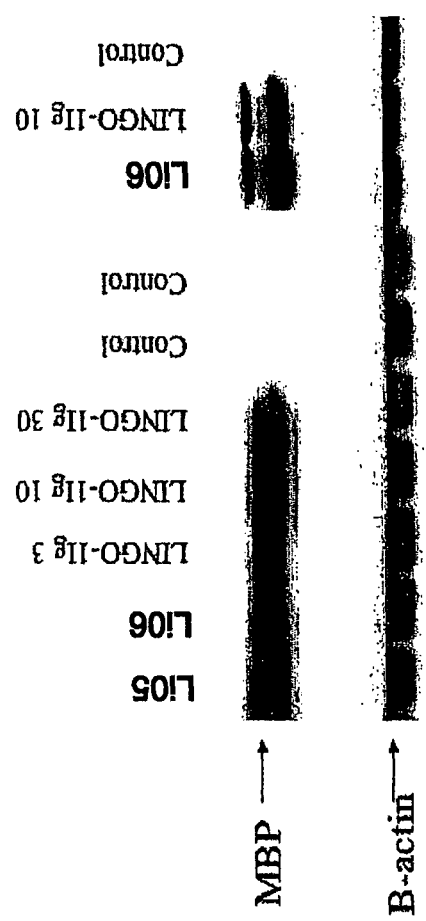

FIG. 8. Western blot of co-cultured oligodendrocytes and DRGs after incubation with anti-Sp35 antibodies Li05, Li06 and 3, 10 and 30 mg of Sp35-Fc (LINGO-1-Ig) as described in Example 9.

Figure 9:
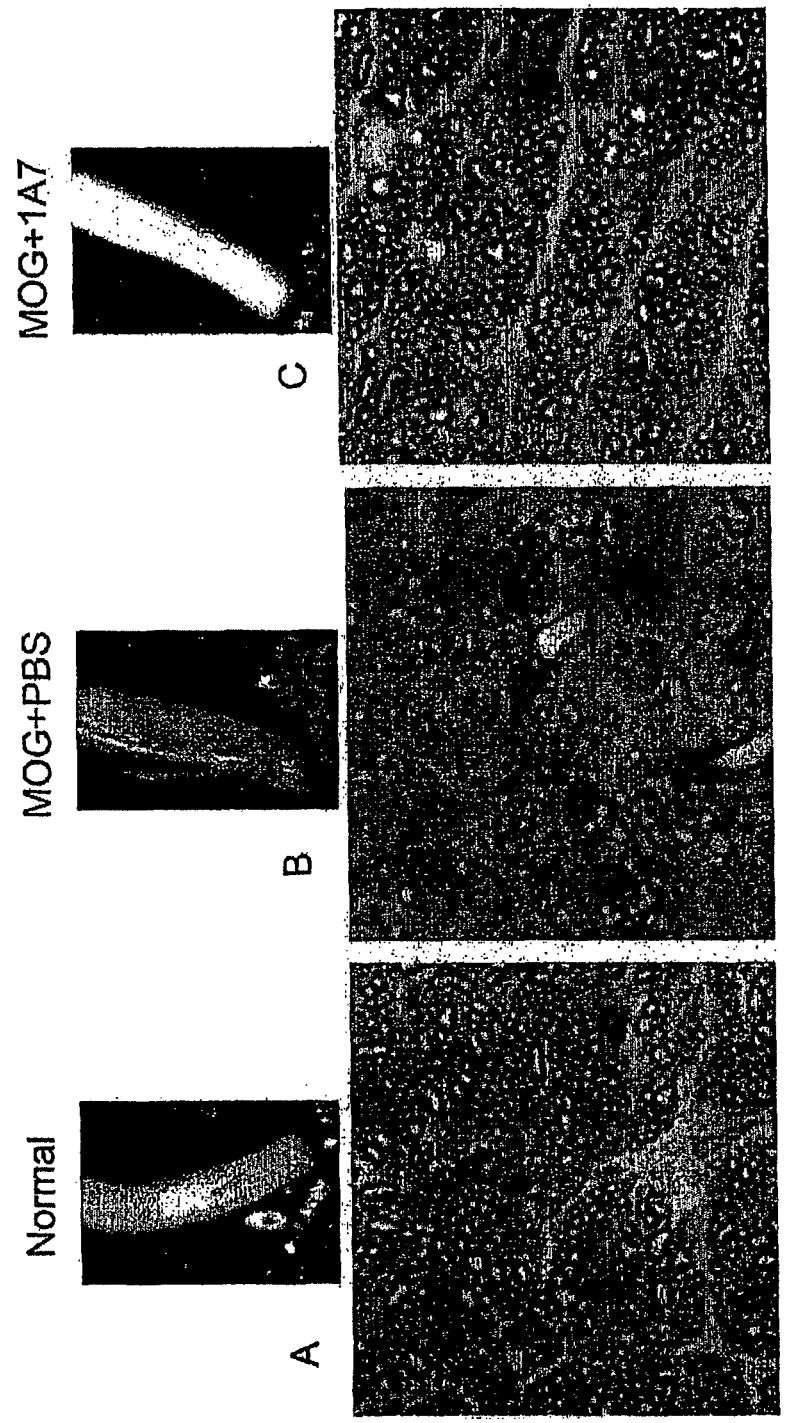

FIG. 9. Photographs of the optic nerves of A) Normal Rats; B) Myelin Oligodendrocyte Glycoprotein (MOG) induced Experimental Autoimmune Encephalomyelitis (EAE) rats; and C) Myelin Oligodendrocyte Glycoprotein (MOG) induced Experimental Autoimmune Encephalomyelitis (EAE) rats treated with the Sp35 antibody 1A7. Electron micrographs of each optic nerve are shown below each photograph of the optic nerve.

Figure 10:
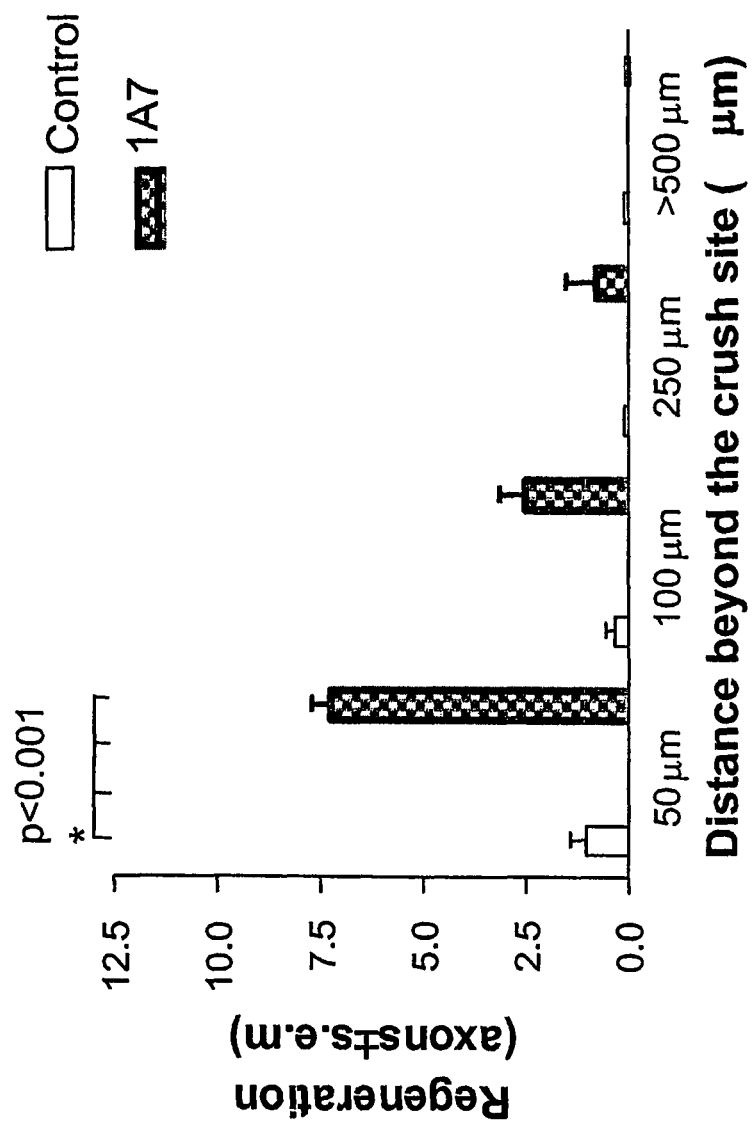

FIG. 10. Graph of the number of regenerative neuronal fibers per section counted in animals receiving an intravitreal injection of the Sp35 antibody 1A7 after optic nerve crush.

DETAILED DESCRIPTION OF THE INVENTION

I. Definitions

It is to be noted that the term "a" or "an" entity refers to one or more of that entity; for example, "an Sp35 antibody," is understood to represent one or more Sp35 antibodies. As such, the terms "a" (or "an"), "one or more," and "at least one" can be used interchangeably herein.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" may be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis.

A polypeptide of the invention may be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides may have a defined three-dimensional structure, although they do not necessarily have such structure. Polypeptides with a defined three-dimensional structure are referred to as folded, and polypeptides which do not possess a defined three-dimensional structure, but rather can adopt a large number of different conformations, and are referred to as unfolded. As used herein, the term glycoprotein refers to a protein coupled to at least one carbohydrate moiety that is attached to the protein via an oxygen-containing or a nitrogen-containing side chain of an amino acid residue, e.g., a serine residue or an asparagine residue.

By an "isolated" polypeptide or a fragment, variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated for purposed of the invention, as are native or recombinant polypeptides which have been separated, fractionated, or partially or substantially purified by any suitable technique.

Also included as polypeptides of the present invention are fragments, derivatives, analogs, or variants of the foregoing polypeptides, and any combination thereof. The terms "fragment," "variant," "derivative" and "analog" when referring to Sp35 antibodies or antibody polypeptides of the present invention include any polypeptides which retain at least some of the antigen-binding properties of the corresponding native antibody or polypeptide. Fragments of polypeptides of the present invention include proteolytic fragments, as well as deletion fragments, in addition to specific antibody fragments discussed elsewhere herein. Variants of Sp35 antibodies and antibody polypeptides of the present invention include fragments as described above, and also polypeptides with altered amino acid sequences due to amino acid substitutions, deletions, or insertions. Variants may occur naturally or be non-naturally occurring Non-naturally occurring variants may be produced using art-known mutagenesis techniques. Variant polypeptides may comprise conservative or non-conservative amino acid substitutions, deletions or additions. Derivatives of Sp35 antibodies and antibody polypeptides of the present invention, are polypeptides which have been altered so as to exhibit additional features not found on the native polypeptide. Examples include fusion proteins. Variant polypeptides may also be referred to herein as "polypeptide analogs." As used herein a "derivative" of an Sp35 antibody or antibody polypeptide refers to a subject polypeptide having one or more residues chemically derivatized by reaction of a functional side group. Also included as "derivatives" are those peptides which contain one or more naturally occurring amino acid derivatives of the twenty standard amino acids. For example, 4-hydroxyproline may be substituted for proline; 5-hydroxylysine may be substituted for lysine; 3-methylhistidine may be substituted for histidine; homoserine may be substituted for serine; and ornithine may be substituted for lysine.

The term "polynucleotide" is intended to encompass a singular nucleic acid as well as plural nucleic acids, and refers to an isolated nucleic acid molecule or construct, e.g., messenger RNA (mRNA) or plasmid DNA (pDNA). A polynucleotide may comprise a conventional phosphodiester bond or a non-conventional bond (e.g., an amide bond, such as found in peptide nucleic acids (PNA)). The term "nucleic acid" refer to any one or more nucleic acid segments, e.g., DNA or RNA fragments, present in a polynucleotide. By "isolated" nucleic acid or polynucleotide is intended a nucleic acid molecule, DNA or RNA, which has been removed from its native environment. For example, a recombinant polynucleotide encoding an Sp35 antibody contained in a vector is considered isolated for the purposes of the present invention. Further examples of an isolated polynucleotide include recombinant polynucleotides maintained in heterologous host cells or purified (partially or substantially) polynucleotides in solution. Isolated RNA molecules include in vivo or in vitro RNA transcripts of polynucleotides of the present invention. Isolated polynucleotides or nucleic acids according to the present invention further include such molecules produced synthetically. In addition, polynucleotide or a nucleic acid may be or may include a regulatory element such as a promoter, ribosome binding site, or a transcription terminator.

As used herein, a "coding region" is a portion of nucleic acid which consists of codons translated into amino acids. Although a "stop codon" (TAG, TGA, or TAA) is not translated into an amino acid, it may be considered to be part of a coding region, but any flanking sequences, for example promoters, ribosome binding sites, transcriptional terminators, introns, and the like, are not part of a coding region. Two or more coding regions of the present invention can be present in a single polynucleotide construct, e.g., on a single vector, or in separate polynucleotide constructs, e.g., on separate (different) vectors. Furthermore, any vector may contain a single coding region, or may comprise two or more coding regions, e.g., a single vector may separately encode an immunoglobulin heavy chain variable region and an immunoglobulin light chain variable region. In addition, a vector, polynucleotide, or nucleic acid of the invention may encode heterologous coding regions, either fused or unfused to a nucleic acid encoding an Sp35 antibody or fragment, variant, or derivative thereof. Heterologous coding regions include without limitation specialized elements or motifs, such as a secretory signal peptide or a heterologous functional domain.

In certain embodiments, the polynucleotide or nucleic acid is DNA. In the case of DNA, a polynucleotide comprising a nucleic acid which encodes a polypeptide normally may include a promoter and/or other transcription or translation control elements operably associated with one or more coding regions. An operable association is when a coding region for a gene product, e.g., a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter may be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription. Suitable promoters and other transcription control regions are disclosed herein.

A variety of transcription control regions are known to those skilled in the art. These include, without limitation, transcription control regions which function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit β-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Similarly, a variety of translation control elements are known to those of ordinary skill in the art. These include, but are not limited to ribosome binding sites, translation initiation and termination codons, and elements derived from picornaviruses (particularly an internal ribosome entry site, or IRES, also referred to as a CITE sequence).

In other embodiments, a polynucleotide of the present invention is RNA, for example, in the form of messenger RNA (mRNA).

Polynucleotide and nucleic acid coding regions of the present invention may be associated with additional coding regions which encode secretory or signal peptides, which direct the secretion of a polypeptide encoded by a polynucleotide of the present invention. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the complete or "full length" polypeptide to produce a secreted or "mature" form of the polypeptide. In certain embodiments, the native signal peptide, e.g., an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, may be used. For example, the wild-type leader sequence may be substituted with the leader sequence of human tissue plasminogen activator (TPA) or mouse β-glucuronidase.

The present invention is directed to certain Sp35 antibodies, or antigen-binding fragments, variants, or derivatives thereof. Unless specifically referring to full-sized antibodies such as naturally-occurring antibodies, the term "Sp35 antibodies" encompasses full-sized antibodies as well as antigen-binding fragments, variants, analogs, or derivatives of such antibodies, e.g., naturally occurring antibody or immunoglobulin molecules or engineered antibody molecules or fragments that bind antigen in a manner similar to antibody molecules.

The terms "antibody" and "immunoglobulin" are used interchangeably herein. An antibody or immunoglobulin comprises at least the variable domain of a heavy chain, and normally comprises at least the variable domains of a heavy chain and a light chain. Basic immunoglobulin structures in vertebrate systems are relatively well understood. See, e.g., Harlow et al., Antibodies: A Laboratory Manual, (Cold Spring Harbor Laboratory Press, 2nd ed. 1988).

As will be discussed in more detail below, the term "immunoglobulin" comprises various broad classes of polypeptides that can be distinguished biochemically. Those skilled in the art will appreciate that heavy chains are classified as gamma, mu, alpha, delta, or epsilon, ($\gamma$, $\mu$, $\alpha$, $\delta$, $\epsilon$) with some subclasses among them (e.g., $\gamma 1$-$\gamma 4$). It is the nature of this chain that determines the "class" of the antibody as IgG, IgM, IgA IgG, or IgE, respectively. The immunoglobulin subclasses (isotypes) e.g., $IgG_1$, $IgG_2$, $IgG_3$, $IgG_4$, $IgA_1$, etc. are well characterized and are known to confer functional specialization. Modified versions of each of these classes and isotypes are readily discernable to the skilled artisan in view of the instant disclosure and, accordingly, are within the scope of the instant invention. All immunoglobulin classes are clearly within the scope of the present invention, the following discussion will generally be directed to the IgG class of immunoglobulin molecules. With regard to IgG, a standard immunoglobulin molecule comprises two identical light chain polypeptides of molecular weight approximately 23,000 Daltons, and two identical heavy chain polypeptides of molecular weight 53,000-70,000. The four chains are typically joined by disulfide bonds in a "Y" configuration wherein the light chains bracket the heavy chains starting at the mouth of the "Y" and continuing through the variable region.

Light chains are classified as either kappa or lambda (κ, λ). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain.

Both the light and heavy chains are divided into regions of structural and functional homology. The terms "constant" and "variable" are used functionally. In this regard, it will be appreciated that the variable domains of both the light ($V_L$) and heavy ($V_H$) chain portions determine antigen recognition and specificity. Conversely, the constant domains of the light chain ($C_L$) and the heavy chain ($C_H 1$, $C_H 2$ or $C_H 3$) confer important biological properties such as secretion, transplacental mobility, Fc receptor binding, complement binding, and the like. By convention the numbering of the constant region domains increases as they become more distal from the antigen binding site or amino-terminus of the antibody. The N-terminal portion is a variable region and at the C-terminal portion is a constant region; the $C_H 3$ and $C_L$ domains actually comprise the carboxy-terminus of the heavy and light chain, respectively.

As indicated above, the variable region allows the antibody to selectively recognize and specifically bind epitopes on antigens. That is, the $V_L$ domain and $V_H$ domain, or subset of the complementarity determining regions (CDRs), of an antibody combine to form the variable region that defines a three dimensional antigen binding site. This quaternary antibody structure forms the antigen binding site present at the end of each arm of the Y. More specifically, the antigen binding site is defined by three CDRs on each of the $V_H$ and $V_L$ chains. In some instances, e.g., certain immunoglobulin molecules derived from camelid species or engineered based on camelid immunoglobulins, a complete immunoglobulin molecule may consist of heavy chains only, with no light chains. See, e.g., Hamers-Casterman et al., Nature 363:446-448 (1993).

In naturally occurring antibodies, the six "complementarity determining regions" or "CDRs" present in each antigen binding domain are short, non-contiguous sequences of amino acids that are specifically positioned to form the antigen binding domain as the antibody assumes its three dimensional configuration in an aqueous environment. The remainder of the amino acids in the antigen binding domains, referred to as "framework" regions, show less inter-molecular variability. The framework regions largely adopt a β-sheet conformation and the CDRs form loops which connect, and in some cases form part of, the β-sheet structure. Thus, framework regions act to form a scaffold that provides for positioning the CDRs in correct orientation by inter-chain, non-covalent interactions. The antigen binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable region by one of ordinary skill in the art, since they have been precisely defined (see, "Sequences of Proteins of Immunological Interest," Kabat, E., et al., U.S. Department of Health and Human Services, (1983); and Chothia and Lesk, J. Mol. Biol., 196: 901-917 (1987), which are incorporated herein by reference in their entireties).

In the case where there are two or more definitions of a term which is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. This particular region has been described by Kabat et al., U.S. Dept. of Health and Human Services, "Sequences of Proteins of Immunological Interest" (1983) and by Chothia et al., J. Mol. Biol. 196:901-917 (1987), which are incorporated herein by reference, where the definitions include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth below in Table 1 as a comparison. The exact residue numbers which encompass a particular CDR will vary depending on the sequence and size of the CDR. Those skilled in the art can routinely determine which residues comprise a particular CDR given the variable region amino acid sequence of the antibody.

TABLE 1

| CDR Definitions[1] | | |
|---|---|---|
| | Kabat | Chothia |
| $V_H$ CDR1 | 31-35 | 26-32 |
| $V_H$ CDR2 | 50-65 | 52-58 |
| $V_H$ CDR3 | 95-102 | 95-102 |
| $V_L$ CDR1 | 24-34 | 26-32 |
| $V_L$ CDR2 | 50-56 | 50-52 |
| $V_L$ CDR3 | 89-97 | 91-96 |

[1]Numbering of all CDR definitions in Table 1 is according to the numbering conventions set forth by Kabat et al. (see below).

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983). Unless otherwise specified, references to the numbering of specific amino acid residue positions in an Sp35 antibody or antigen-binding fragment, variant, or derivative thereof of the present invention are according to the Kabat numbering system.

In camelid species, the heavy chain variable region, referred to as $V_H H$, forms the entire antigen-binding domain. The main differences between camelid $V_H H$ variable regions and those derived from conventional antibodies ($V_H$) include (a) more hydrophobic amino acids in the light chain contact surface of $V_H$ as compared to the corresponding region in $V_HH$, (b) a longer CDR3 in $V_HH$, and (c) the frequent occurrence of a disulfide bond between CDR1 and CDR3 in $V_HH$.

Antibodies or antigen-binding fragments, variants, or derivatives thereof of the invention include, but are not limited to, polyclonal, monoclonal, multispecific, human, humanized, primatized, or chimeric antibodies, single chain antibodies, epitope-binding fragments, e.g., Fab, Fab' and F(ab')$_2$, Fd, Fvs, single-chain Fvs (scFv), single-chain antibodies, disulfide-linked Fvs (sdFv), fragments comprising either a $V_L$ or $V_H$ domain, fragments produced by a Fab expression library, and anti-idiotypic (anti-Id) antibodies (including, e.g., anti-Id antibodies to Sp35 antibodies disclosed herein). ScFv molecules are known in the art and are described, e.g., in U.S. Pat. No. 5,892,019. Immunoglobulin or antibody molecules of the invention can be of any type (e.g., IgG, IgE, IgM, IgD, IgA, and IgY), class (e.g., IgG1, IgG2, IgG3, IgG4, IgA1 and IgA2) or subclass of immunoglobulin molecule.

Antibody fragments, including single-chain antibodies, may comprise the variable region(s) alone or in combination with the entirety or a portion of the following: hinge region, $C_H1$, $C_H2$, and $C_H3$ domains. Also included in the invention are antigen-binding fragments also comprising any combination of variable region(s) with a hinge region, $C_H1$, $C_H2$, and $C_H3$ domains. Antibodies or immunospecific fragments thereof for use in the diagnostic and therapeutic methods disclosed herein may be from any animal origin including birds and mammals. Preferably, the antibodies are human, murine, donkey, rabbit, goat, guinea pig, camel, llama, horse, or chicken antibodies. In another embodiment, the variable region may be condricthoid in origin (e.g., from sharks). As used herein, "human" antibodies include antibodies having the amino acid sequence of a human immunoglobulin and include antibodies isolated from human immunoglobulin libraries or from animals transgenic for one or more human immunoglobulins and that do not express endogenous immunoglobulins, as described infra and, for example in, U.S. Pat. No. 5,939,598 by Kucherlapati et al.

As used herein, the term "heavy chain portion" includes amino acid sequences derived from an immunoglobulin heavy chain. A polypeptide comprising a heavy chain portion comprises at least one of: a $C_H1$ domain, a hinge (e.g., upper, middle, and/or lower hinge region) domain, a $C_H2$ domain, a $C_H3$ domain, or a variant or fragment thereof. For example, a binding polypeptide for use in the invention may comprise a polypeptide chain comprising a $C_H1$ domain; a polypeptide chain comprising a $C_H1$ domain, at least a portion of a hinge domain, and a $C_H2$ domain; a polypeptide chain comprising a $C_H1$ domain and a $C_H3$ domain; a polypeptide chain comprising a $C_H1$ domain, at least a portion of a hinge domain, and a $C_H3$ domain, or a polypeptide chain comprising a $C_H1$ domain, at least a portion of a hinge domain, a $C_H2$ domain, and a $C_H3$ domain. In another embodiment, a polypeptide of the invention comprises a polypeptide chain comprising a $C_H3$ domain. Further, a binding polypeptide for use in the invention may lack at least a portion of a $C_H2$ domain (e.g., all or part of a $C_H2$ domain). As set forth above, it will be understood by one of ordinary skill in the art that these domains (e.g., the heavy chain portions) may be modified such that they vary in amino acid sequence from the naturally occurring immunoglobulin molecule.

In certain Sp35 antibodies, or antigen-binding fragments, variants, or derivatives thereof disclosed herein, the heavy chain portions of one polypeptide chain of a multimer are identical to those on a second polypeptide chain of the multimer. Alternatively, heavy chain portion-containing monomers of the invention are not identical. For example, each monomer may comprise a different target binding site, forming, for example, a bispecific antibody.

The heavy chain portions of a binding polypeptide for use in the diagnostic and treatment methods disclosed herein may be derived from different immunoglobulin molecules. For example, a heavy chain portion of a polypeptide may comprise a $C_H1$ domain derived from an IgG1 molecule and a hinge region derived from an IgG3 molecule. In another example, a heavy chain portion can comprise a hinge region derived, in part, from an IgG1 molecule and, in part, from an IgG3 molecule. In another example, a heavy chain portion can comprise a chimeric hinge derived, in part, from an IgG1 molecule and, in part, from an IgG4 molecule.

As used herein, the term "light chain portion" includes amino acid sequences derived from an immunoglobulin light chain. Preferably, the light chain portion comprises at least one of a $V_L$ or $C_L$ domain.

Sp35 antibodies, or antigen-binding fragments, variants, or derivatives thereof disclosed herein may be described or specified in terms of the epitope(s) or portion(s) of an antigen, e.g., a target polypeptide (Sp35) that they recognize or specifically bind. The portion of a target polypeptide which specifically interacts with the antigen binding domain of an antibody is an "epitope," or an "antigenic determinant." A target polypeptide may comprise a single epitope, but typically comprises at least two epitopes, and can include any number of epitopes, depending on the size, conformation, and type of antigen. Furthermore, it should be noted that an "epitope" on a target polypeptide may be or include non-polypeptide elements, e.g., an "epitope may include a carbohydrate side chain.

The minimum size of a peptide or polypeptide epitope for an antibody is thought to be about four to five amino acids. Peptide or polypeptide epitopes preferably contain at least seven, more preferably at least nine and most preferably between at least about 15 to about 30 amino acids. Since a CDR can recognize an antigenic peptide or polypeptide in its tertiary form, the amino acids comprising an epitope need not be contiguous, and in some cases, may not even be on the same peptide chain. In the present invention, peptide or polypeptide epitope recognized by Sp35 antibodies of the present invention contains a sequence of at least 4, at least 5, at least 6, at least 7, more preferably at least 8, at least 9, at least 10, at least 15, at least 20, at least 25, or between about 15 to about 30 contiguous or non-contiguous amino acids of Sp35.

By "specifically binds," it is generally meant that an antibody binds to an epitope via its antigen binding domain, and that the binding entails some complementarity between the antigen binding domain and the epitope. According to this definition, an antibody is said to "specifically bind" to an epitope when it binds to that epitope, via its antigen binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D."

By "preferentially binds," it is meant that the antibody specifically binds to an epitope more readily than it would bind to a related, similar, homologous, or analogous epitope. Thus, an antibody which "preferentially binds" to a given epitope would more likely bind to that epitope than to a related epitope, even though such an antibody may cross-react with the related epitope.

By way of non-limiting example, an antibody may be considered to bind a first epitope preferentially if it binds said first epitope with a dissociation constant ($K_D$) that is less than the antibody's $K_D$ for the second epitope. In another non-limiting example, an antibody may be considered to bind a first antigen preferentially if it binds the first epitope with an affinity that is at least one order of magnitude less than the antibody's $K_D$ for the second epitope. In another non-limiting example, an antibody may be considered to bind a first epitope preferentially if it binds the first epitope with an affinity that is at least two orders of magnitude less than the antibody's $K_D$ for the second epitope.

In another non-limiting example, an antibody may be considered to bind a first epitope preferentially if it binds the first epitope with an off rate (k(off)) that is less than the antibody's k(off) for the second epitope. In another non-limiting example, an antibody may be considered to bind a first epitope preferentially if it binds the first epitope with an affinity that is at least one order of magnitude less than the antibody's k(off) for the second epitope. In another non-limiting example, an antibody may be considered to bind a first epitope preferentially if it binds the first epitope with an affinity that is at least two orders of magnitude less than the antibody's k(off) for the second epitope.

An antibody or antigen-binding fragment, variant, or derivative disclosed herein may be said to bind a target polypeptide disclosed herein or a fragment or variant thereof with an off rate (k(off)) of less than or equal to $5 \times 10^{-2}$ sec$^{-1}$, $10^{-2}$ sec$^{-1}$, $5 \times 10^{-3}$ sec$^{-1}$ or $10^{-3}$ sec$^{-1}$. More preferably, an antibody of the invention may be said to bind a target polypeptide disclosed herein or a fragment or variant thereof with an off rate (k(off)) less than or equal to $5 \times 10^{-4}$ sec$^{-1}$, $10^{-4}$ sec$^{-1}$, $5 \times 10^{-5}$ sec$^{-1}$, or $10^{-5}$ sec$^{-1}$ $5 \times 10^{-6}$ sec$^{-1}$, $10^{-6}$ sec$^{-1}$, $5 \times 10^{-7}$ sec$^{-1}$ or $10^{-7}$ sec$^{-1}$.

An antibody or antigen-binding fragment, variant, or derivative disclosed herein may be said to bind a target polypeptide disclosed herein or a fragment or variant thereof with an on rate (k(on)) of greater than or equal to $10^3$ M$^{-1}$ sec$^{-1}$, $5 \times 10^3$ M$^{-1}$ sec$^{-1}$, $10^4$ M$^{-1}$ sec$^1$ or $5 \times 10^4$ M$^{-1}$ sec$^{-1}$. More preferably, an antibody of the invention may be said to bind a target polypeptide disclosed herein or a fragment or variant thereof with an on rate (k(on)) greater than or equal to $10^5$ M$^{-1}$ sec$^{-1}$, $5 \times 10^5$ M$^{-1}$ sec$^{-1}$ $10^6$ M$^{-1}$ sec$^{-1}$, or $5 \times 10^6$ M$^{-1}$ sec$^{-1}$ or $10^7$ M$^{-1}$ sec$^{-1}$.

An antibody is said to competitively inhibit binding of a reference antibody to a given epitope if it preferentially binds to that epitope to the extent that it blocks, to some degree, binding of the reference antibody to the epitope. Competitive inhibition may be determined by any method known in the art, for example, competition ELISA assays. An antibody may be said to competitively inhibit binding of the reference antibody to a given epitope by at least 90%, at least 80%, at least 70%, at least 60%, or at least 50%.

As used herein, the term "affinity" refers to a measure of the strength of the binding of an individual epitope with the CDR of an immunoglobulin molecule. See, e.g., Harlow et al., Antibodies: A Laboratory Manual, (Cold Spring Harbor Laboratory Press, 2nd ed. 1988) at pages 27-28. As used herein, the term "avidity" refers to the overall stability of the complex between a population of immunoglobulins and an antigen, that is, the functional combining strength of an immunoglobulin mixture with the antigen. See, e.g., Harlow at pages 29-34. Avidity is related to both the affinity of individual immunoglobulin molecules in the population with specific epitopes, and also the valencies of the immunoglobulins and the antigen. For example, the interaction between a bivalent monoclonal antibody and an antigen with a highly repeating epitope structure, such as a polymer, would be one of high avidity.

Sp35 antibodies or antigen-binding fragments, variants or derivatives thereof of the invention may also be described or specified in terms of their cross-reactivity. As used herein, the term "cross-reactivity" refers to the ability of an antibody, specific for one antigen, to react with a second antigen; a measure of relatedness between two different antigenic substances. Thus, an antibody is cross reactive if it binds to an epitope other than the one that induced its formation. The cross reactive epitope generally contains many of the same complementary structural features as the inducing epitope, and in some cases, may actually fit better than the original.

For example, certain antibodies have some degree of cross-reactivity, in that they bind related, but non-identical epitopes, e.g., epitopes with at least 95%, at least 90%, at least 85%, at least 80%, at least 75%, at least 70%, at least 65%, at least 60%, at least 55%, and at least 50% identity (as calculated using methods known in the art and described herein) to a reference epitope. An antibody may be said to have little or no cross-reactivity if it does not bind epitopes with less than 95%, less than 90%, less than 85%, less than 80%, less than 75%, less than 70%, less than 65%, less than 60%, less than 55%, and less than 50% identity (as calculated using methods known in the art and described herein) to a reference epitope. An antibody may be deemed "highly specific" for a certain epitope, if it does not bind any other analog, ortholog, or homolog of that epitope.

Sp35 antibodies or antigen-binding fragments, variants or derivatives thereof of the invention may also be described or specified in terms of their binding affinity to a polypeptide of the invention. Preferred binding affinities include those with a dissociation constant or Kd less than $5 \times 10^{-2}$ M, $10^{-2}$M, $5 \times 10^{-3}$ M, $10^{-3}$M, $5 \times 10^{-4}$M, $10^{-4}$M, $5 \times 10^{-5}$M, $10^{-5}$ M, $5 \times 10^{-6}$M, $10^{-6}$M, $5 \times 10^{-7}$M, $10^{-7}$ M, $5 \times 10^{-8}$M, $10^{-8}$M, $5 \times 10^{-9}$M, $10^{-9}$M, $5 \times 10^{-10}$M, $10^{-10}$M, $5 \times 10^{-11}$M, $10^{-11}$M, $5 \times 10^{-12}$M, $10^{-12}$M, $5 \times 10^{-13}$M, $10^{-13}$ M, $5 \times 10^{-14}$M, $10^{-14}$ M, $5 \times 10^{-15}$M, or $10^{-15}$M.

Sp35 antibodies or antigen-binding fragments, variants or derivatives thereof of the invention may be "multispecific," e.g., bispecific, trispecific or of greater multispecificity, meaning that it recognizes and binds to two or more different epitopes present on one or more different antigens (e.g., proteins) at the same time. Thus, whether an Sp35 antibody is "monospecfic" or "multispecific," e.g., "bispecific," refers to the number of different epitopes with which a binding polypeptide reacts. Multispecific antibodies may be specific for different epitopes of a target polypeptide described herein or may be specific for a target polypeptide as well as for a heterologous epitope, such as a heterologous polypeptide or solid support material.

As used herein the term "valency" refers to the number of potential binding domains, e.g., antigen binding domains, present in an Sp35 antibody, binding polypeptide or antibody. Each binding domain specifically binds one epitope. When an Sp35 antibody, binding polypeptide or antibody comprises more than one binding domain, each binding domain may specifically bind the same epitope, for an antibody with two binding domains, termed "bivalent monospecific," or to different epitopes, for an antibody with two binding domains, termed "bivalent bispecific." An antibody may also be bispecific and bivalent for each specificity (termed "bispecific tetravalent antibodies"). In another embodiment, tetravalent minibodies or domain deleted antibodies can be made.

Bispecific bivalent antibodies, and methods of making them, are described, for instance in U.S. Pat. Nos. 5,731,168;

5,807,706; 5,821,333; and U.S. Appl. Publ. Nos. 2003/020734 and 2002/0155537, the disclosures of all of which are incorporated by reference herein. Bispecific tetravalent antibodies, and methods of making them are described, for instance, in WO 02/096948 and WO 00/44788, the disclosures of both of which are incorporated by reference herein. See generally, PCT publications WO 93/17715; WO 92/08802; WO 91/00360; WO 92/05793; Tutt et al., J. Immunol. 147:60-69 (1991); U.S. Pat. Nos. 4,474,893; 4,714,681; 4,925,648; 5,573,920; 5,601,819; Kostelny et al., J. Immunol. 148:1547-1553 (1992).

As previously indicated, the subunit structures and three dimensional configuration of the constant regions of the various immunoglobulin classes are well known. As used herein, the term "$V_H$ domain" includes the amino terminal variable domain of an immunoglobulin heavy chain and the term "$C_H1$ domain" includes the first (most amino terminal) constant region domain of an immunoglobulin heavy chain. The $C_H1$ domain is adjacent to the $V_H$ domain and is amino terminal to the hinge region of an immunoglobulin heavy chain molecule.

As used herein the term "$C_H2$ domain" includes the portion of a heavy chain molecule that extends, e.g., from about residue 244 to residue 360 of an antibody using conventional numbering schemes (residues 244 to 360, Kabat numbering system; and residues 231-340, EU numbering system; see Kabat E A et al. op. cit. The $C_H2$ domain is unique in that it is not closely paired with another domain. Rather, two N-linked branched carbohydrate chains are interposed between the two $C_H2$ domains of an intact native IgG molecule. It is also well documented that the $C_H3$ domain extends from the $C_H2$ domain to the C-terminal of the IgG molecule and comprises approximately 108 residues.

As used herein, the term "hinge region" includes the portion of a heavy chain molecule that joins the $C_H1$ domain to the $C_H2$ domain. This hinge region comprises approximately 25 residues and is flexible, thus allowing the two N-terminal antigen binding regions to move independently. Hinge regions can be subdivided into three distinct domains: upper, middle, and lower hinge domains (Roux et al., J. Immunol. 161:4083 (1998)).

As used herein the term "disulfide bond" includes the covalent bond formed between two sulfur atoms. The amino acid cysteine comprises a thiol group that can form a disulfide bond or bridge with a second thiol group. In most naturally occurring IgG molecules, the $C_H1$ and $C_L$ regions are linked by a disulfide bond and the two heavy chains are linked by two disulfide bonds at positions corresponding to 239 and 242 using the Kabat numbering system (position 226 or 229, EU numbering system).

As used herein, the term "chimeric antibody" will be held to mean any antibody wherein the immunoreactive region or site is obtained or derived from a first species and the constant region (which may be intact, partial or modified in accordance with the instant invention) is obtained from a second species. In preferred embodiments the target binding region or site will be from a non-human source (e.g. mouse or primate) and the constant region is human.

As used herein, the term "engineered antibody" refers to an antibody in which the variable domain in either the heavy and light chain or both is altered by at least partial replacement of one or more CDRs from an antibody of known specificity and, if necessary, by partial framework region replacement and sequence changing. Although the CDRs may be derived from an antibody of the same class or even subclass as the antibody from which the framework regions are derived, it is envisaged that the CDRs will be derived from an antibody of different class and preferably from an antibody from a different species. An engineered antibody in which one or more "donor" CDRs from a non-human antibody of known specificity is grafted into a human heavy or light chain framework region is referred to herein as a "humanized antibody." It may not be necessary to replace all of the CDRs with the complete CDRs from the donor variable region to transfer the antigen binding capacity of one variable domain to another. Rather, it may only be necessary to transfer those residues that are necessary to maintain the activity of the target binding site. Given the explanations set forth in, e.g., U.S. Pat. Nos. 5,585,089, 5,693,761, 5,693,762, and 6,180,370, it will be well within the competence of those skilled in the art, either by carrying out routine experimentation or by trial and error testing to obtain a functional engineered or humanized antibody.

As used herein the term "properly folded polypeptide" includes polypeptides (e.g., Sp35 antibodies) in which all of the functional domains comprising the polypeptide are distinctly active. As used herein, the term "improperly folded polypeptide" includes polypeptides in which at least one of the functional domains of the polypeptide is not active. In one embodiment, a properly folded polypeptide comprises polypeptide chains linked by at least one disulfide bond and, conversely, an improperly folded polypeptide comprises polypeptide chains not linked by at least one disulfide bond.

As used herein the term "engineered" includes manipulation of nucleic acid or polypeptide molecules by synthetic means (e.g. by recombinant techniques, in vitro peptide synthesis, by enzymatic or chemical coupling of peptides or some combination of these techniques).

As used herein, the terms "linked," "fused" or "fusion" are used interchangeably. These terms refer to the joining together of two more elements or components, by whatever means including chemical conjugation or recombinant means. An "in-frame fusion" refers to the joining of two or more polynucleotide open reading frames (ORFs) to form a continuous longer ORF, in a manner that maintains the correct translational reading frame of the original ORFs. Thus, a recombinant fusion protein is a single protein containing two ore more segments that correspond to polypeptides encoded by the original ORFs (which segments are not normally so joined in nature.) Although the reading frame is thus made continuous throughout the fused segments, the segments may be physically or spatially separated by, for example, in-frame linker sequence. For example, polynucleotides encoding the CDRs of an immunoglobulin variable region may be fused, in-frame, but be separated by a polynucleotide encoding at least one immunoglobulin framework region or additional CDR regions, as long as the "fused" CDRs are co-translated as part of a continuous polypeptide.

In the context of polypeptides, a "linear sequence" or a "sequence" is an order of amino acids in a polypeptide in an amino to carboxyl terminal direction in which residues that neighbor each other in the sequence are contiguous in the primary structure of the polypeptide.

The term "expression" as used herein refers to a process by which a gene produces a biochemical, for example, an RNA or polypeptide. The process includes any manifestation of the functional presence of the gene within the cell including, without limitation, gene knockdown as well as both transient expression and stable expression. It includes without limitation transcription of the gene into messenger RNA (mRNA), transfer RNA (tRNA), small hairpin RNA (shRNA), small interfering RNA (siRNA) or any other RNA product, and the translation of such mRNA into polypeptide(s). If the final desired product is a biochemical, expression includes the creation of that biochemical and any precursors. Expression of a gene produces a "gene product." As used herein, a gene product can be either a nucleic acid, e.g., a messenger RNA produced by transcription of a gene, or a polypeptide which is translated from a transcript. Gene products described herein further include nucleic acids with post transcriptional modifications, e.g., polyadenylation, or polypeptides with post translational modifications, e.g., methylation, glycosylation, the addition of lipids, association with other protein subunits, proteolytic cleavage, and the like.

As used herein, the terms "treat" or "treatment" refer to both therapeutic treatment and prophylactic or preventative measures, wherein the object is to prevent or slow down (lessen) an undesired physiological change or disorder, such as the progression of multiple sclerosis. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, and zoo, sports, or pet animals such as dogs, cats, guinea pigs, rabbits, rats, mice, horses, cattle, cows, and so on.

As used herein, phrases such as "a subject that would benefit from administration of an Sp35 antibody" and "an animal in need of treatment" includes subjects, such as mammalian subjects, that would benefit from administration of an Sp35 antibody used, e.g., for detection of an Sp35 polypeptide (e.g., for a diagnostic procedure) and/or from treatment, i.e., palliation or prevention of a disease such as MS, with an Sp35 antibody. As described in more detail herein, the Sp35 antibody can be used in unconjugated form or can be conjugated, e.g., to a drug, prodrug, or an isotope.

II. Sp35

Naturally occurring human Sp35 (Sp35) is a glycosylated central nervous system-specific protein which is predicted to have 614 amino acids (SEQ ID NO: 2), including a 33 amino acid signal sequence. Sp 35 is also known in the art by the names LINGO-1, LRRN6, LRRN6A, FLJ14594, LERN1, MGC17422 and UNQ201. The human, full-length wild-type Sp35 polypeptide contains an LRR domain consisting of 14 leucine-rich repeats (including N- and C-terminal caps), an Ig domain, a transmembrane region, and a cytoplasmic domain. The cytoplasmic domain contains a canonical tyrosine phosphorylation site. In addition, the naturally occurring Sp35 protein contains a signal sequence, a short basic region between the LRRCT and Ig domain, and a transmembrane region between the Ig domain and the cytoplasmic domain. The human Sp35 gene (SEQ ID NO:1) contains alternative translation start codons, so that six additional amino acids, i.e., MQVSKR (SEQ ID NO: 3) may or may not be present at the N-terminus of the Sp35 signal sequence. Table 2 lists the Sp35 domains and other regions, according to amino acid residue number, based on the Sp35 amino acid sequence presented herein as SEQ ID NO: 2. The Sp35 polypeptide is characterized in more detail in PCT Publication No. WO 2004/085648, which is incorporated herein by reference in its entirety.

TABLE 2

Sp35 Domains

| Domain or Region | Beginning Residue | Ending Residue |
| --- | --- | --- |
| Signal Sequence | 1 | 33 or 35 |
| LRRNT | 34 or 36 | 64 |
| LRR | 66 | 89 |
| LRR | 90 | 113 |
| LRR | 114 | 137 |
| LRR | 138 | 161 |
| LRR | 162 | 185 |
| LRR | 186 | 209 |
| LRR | 210 | 233 |
| LRR | 234 | 257 |
| LRR | 258 | 281 |
| LRR | 282 | 305 |
| LRR | 306 | 329 |
| LRR | 330 | 353 |
| LRRCT | 363 | 414 or 416 |
| Basic | 415 or 417 | 424 |
| Ig | 419 | 493 |
| Connecting sequence | 494 | 551 |
| Transmembrane | 552 | 576 |
| Cytoplasmic | 577 | 614 |

Tissue distribution and developmental expression of Sp35 has been studied in humans and rats. Sp35 biology has been studied in an experimental animal (rat) model. Expression of rat Sp35 is localized to neurons and oligodendrocytes, as determined by northern blot and immuno-histochemical staining. Rat Sp35 mRNA expression level is regulated developmentally, peaking shortly after birth, i.e., ca. postnatal day one. In a rat spinal cord transection injury model, Sp35 is up-regulated at the injury site, as determined by RT-PCR. See Mi et al. *Nature Neurosci.* 7:221-228 (2004).

In the context of the amino acids comprising the various structural and functional domains of an Sp35 polypeptide, the term "about" includes the particularly recited value and values larger or smaller by several (e.g., 10, 9, 8, 7, 6, 5, 4, 3, 2, or 1) amino acids. Since the location of these domains as listed in Table 1 have been predicted by computer graphics, one of ordinary skill would appreciate that the amino acid residues constituting the domains may vary slightly (e.g., by about 1 to 15 residues) depending on the criteria used to define the domain.

The inventors have discovered that full-length, wild-type Sp35 binds to NgR1. See PCT Publication No. WO 2004/085648. The inventors have also discovered that Sp35 is expressed in oligodendrocytes and that the Sp35 protein is involved in the regulation of oligodendrocyte-mediated myelination of axons. See U.S Patent Publication No. 2006/0009388 A1, which is incorporated herein by reference in its entirety.

The nucleotide sequence for the full-length Sp35 molecule is as follows:

ATGCTGGCGGGGGGCGTGAGGAGCATGCCCAGCCCCCTCCTGGCCTGCTGGCAGCCCATCCTCCTGCTGG (SEQ ID NO: 1)

TGCTGGGCTCAGTGCTGTCAGGCTCGGCCACGGGCTGCCCGCCCCGCTGCGAGTGCTCCGCCCAGGACCG

-continued
```
CGCTGTGCTGTGCCACCGCAAGCGCTTTGTGGCAGTCCCCGAGGGCATCCCCACCGAGACGCGCCTGCTG

GACCTAGGCAAGAACCGCATCAAAACGCTCAACCAGGACGAGTTCGCCAGCTTCCCGCACCTGGAGGAGC

TGGAGCTCAACGAGAACATCGTGAGCGCCGTGGAGCCCGGCGCCTTCAACAACCTCTTCAACCTCCGGAC

GCTGGGTCTCCGCAGCAACCGCCTGAAGCTCATCCCGCTAGGCGTCTTCACTGGCCTCAGCAACCTGACC

AAGCTGGACATCAGCGAGAACAAGATTGTTATCCTGCTGGACTACATGTTTCAGGACCTGTACAACCTCA

AGTCACTGGAGGTTGGCGACAATGACCTCGTCTACATCTCTCACCGCGCCTTCAGCGGCCTCAACAGCCT

GGAGCAGCTGACGCTGGAGAAATGCAACCTGACCTCCATCCCCACCGAGGCGCTGTCCCACCTGCACGGC

CTCATCGTCCTGAGGCTCCGGCACCTCAACATCAATGCCATCCGGGACTACTCCTTCAAGAGGCTCTACC

GACTCAAGGTCTTGGAGATCTCCCACTGGCCCTACTTGGACACCATGACACCCAACTGCCTCTACGGCCT

CAACCTGACGTCCCTGTCCATCACACACTGCAATCTGACCGCTGTGCCCTACCTGGCCGTCCGCCACCTA

GTCTATCTCCGCTTCCTCAACCTCTCCTACAACCCCATCAGCACCATTGAGGGCTCCATGTTGCATGAGC

TGCTCCGGCTGCAGGAGATCCAGCTGGTGGGCGGGCAGCTGGCCGTGGTGGAGCCCTATGCCTTCCGCGG

CCTCAACTACCTGCGCGTGCTCAATGTCTCTGGCAACCAGCTGACCACACTGGAGGAATCAGTCTTCCAC

TCGGTGGGCAACCTGGAGACACTCATCCTGGACTCCAACCCGCTGGCCTGCGACTGTCGGCTCCTGTGGG

TGTTCCGGCGCCGCTGGCGGCTCAACTTCAACCGGCAGCAGCCCACGTGCGCCACGCCCGAGTTTGTCCA

GGGCAAGGAGTTCAAGGACTTCCCTGATGTGCTACTGCCCAACTACTTCACCTGCCGCCGCGCCCGCATC

CGGGACCGCAAGGCCCAGCAGGTGTTTGTGGACGAGGGCCACACGGTGCAGTTTGTGTGCCGGGCCGATG

GCGACCCGCCGCCCGCCATCCTCTGGCTCTCACCCCGAAAGCACCTGGTCTCAGCCAAGAGCAATGGGCG

GCTCACAGTCTTCCCTGATGGCACGCTGGAGGTGCGCTACGCCCAGGTACAGGACAACGGCACGTACCTG

TGCATCGCGGCCAACGCGGGCGGCAACGACTCCATGCCCGCCCACCTGCATGTGCGCAGCTACTCGCCCG

ACTGGCCCCATCAGCCCAACAAGACCTTCGCTTTCATCTCCAACCAGCCGGGCGAGGGAGAGGCCAACAG

CACCCGCGCCACTGTGCCTTTCCCCTTCGACATCAAGACCCTCATCATCGCCACCACCATGGGCTTCATC

TCTTTCCTGGGCGTCGTCCTCTTCTGCCTGGTGCTGCTGTTTCTCTGGAGCCGGGGCAAGGGCAACACAA

AGCACAACATCGAGATCGAGTATGTGCCCCGAAAGTCGGACGCAGGCATCAGCTCCGCCGACGCGCCCCG

CAAGTTCAACATGAAGATGATATGA.
```

The polypeptide sequence for the full-length Sp35 polypeptide is as follows:

```
MLAGGVRSMPSPLLACWQPILLLVLGSVLSGSATGCPPRCECSAQDRAVLCHRKRFVAVPEGIPTETRL    (SEQ ID NO: 2)

LDLGKNRIKTLNQDEFASFPHLEELELNENIVSAVEPGAFNNLFNLRTLGLRSNRLKLIPLGVFTGLSN

LTKLDISENKIVILLDYMFQDLYNLKSLEVGDNDLVYISHAAFSGLNSLEQLTLEKCNLTSIPTEALSH

LHGLIVLRLRHLNINAIRDYSFKRLYRLKVLEISHWPYLDTMTPNCLYGLNLTSLSITHCNLTAVPYLA

VRHLVYLRFLNLSYNPISTIEGSMLHELLRLQEIQLVGGQLAVVEPYAFRGLNYLRVLNVSGNQLTTLE

ESVFHSVGNLETLILDSNPLACDCRLLWVFRRRWRLNFNRQQPTCATPEFVQGKEFAAFPDVLLPNYFT

CRRARIRDRKAQQVFVDEGHTVQFVCRADGDPPPAILWLSPRKHLVSAKSNGRLTVFPDGTLEVRYAQV

QDNGTYLCIAANAGGNDSMPAHLHVRSYSPDWPHQPNKTFAFISNQPGEGEANSTRATVPFPFDIKTLI

IATTMGFISFLGVVLFCLVLLFLWSRGKGNTKHIEIEYVPRKSDAGISSADAPRKNMKMI.
```

III. Sp35 Antibodies

In one embodiment, the present invention is directed to Sp35 antibodies, or antigen-binding fragments, variants, or derivatives thereof. For example, the present invention includes at least the antigen-binding domains of certain monoclonal antibodies, and fragments, variants, and derivatives thereof shown in Tables 3A and 3B.

Table 3A describes the regions of the Sp35 polypeptide that are bound by certain full-length phage library derived antibodies. These antibodies have the same variable regions as the Fab fragments derived from Phage Display Library-1, as indicated in Table 3B (e.g. D05 in Table 3A has the same variable region as Li05 in Table 3B, D06 in Table 3A has the same variable region as Li06 in Table 3B, etc.). The antibodies were tested for binding Sp35 fragments as defined in Table 3A, using methods well known in the art.

Table 3B describes the ability of the named monoclonal antibodies or Fab fragments to detect Sp35 in various assays such as: Fluorescent Activated Cell Sorting (FACS), Immunoprecipitation (IP), Western blot analysis, Immunohistochemistry (IHC) and Enzyme Linked Immunosorbent Assay (ELISA). Detailed protocols for performing these assays are described herein or are well known and understood by those of ordinary skill in the art. Hybridoma-derived monoclonal antibodies listed in Table 3B were produced by injection of soluble Sp35 into mice and then isolated using hybridoma technology which is well known in the art and described herein. Monoclonal antibodies and antibody Fab fragments listed in Table 3B were isolated from two different phage display libraries using techniques known in the art.

TABLE 3A

| Sp35 Fragment | D03 (Li03 Variable Region) | D05 (Li05 Variable Region) | D06 (Li06 Variable Region) | D08 (Li08 Variable Region) | D11 (Li03 Variable Region) | D13 (Li13 Variable Region) | D33 (Li33 Variable Region) |
|---|---|---|---|---|---|---|---|
| 1-432 rat Fc | + | + | + | − | + | − | + |
| 417-493 rat Fc | − | +/− | +/− | − | − | − | − |
| AP-Sp35 (1-419) | N/D | + | −/+ | −/+ | N/D | N/D | N/D |
| AP-Sp35 (418-498) | N/D | − | − | − | N/D | N/D | N/D |
| 417-498 human Fc | − | − | − | − | − | − | − |
| 417-503 human Fc | − | − | − | − | − | − | − |
| 363-498 human Fc | − | − | − | − | − | − | − |
| 244-498 human Fc | − | − | − | − | − | − | − |

TABLE 3B

SP35 MONOCLONAL ANTIBODIES

| | FACs | | Immunoprecipitation | | | Western | | IHC on Transfected Cells | | IHC on Tissues | | ELISA | | | | |
|---|---|---|---|---|---|---|---|---|---|---|---|---|---|---|---|---|
| | huSp35 | mSp35 | sp35Fc | huSp35 | mSp35 | mouse/ rat sp35 | huSp35 | huSp35 | mSp35 | WT (parafin) | KO (parafin) | 34-417 | 417-493 | 419-495 | 1-532 | 34-532 |
| 201' | | | | yes | | No (mouse and rat) | N/A | N/A | N/A | yes | yes | | | | | |
| 3A3 | – | – | + | – | – | No (mouse and rat) | no | no | no | | | | | | | |
| 3A6 | ++ | +/– | ++ | +++ | –/+ | No (mouse and rat) | yes w background | yes w background | no | | | yes | | +/– | yes | yes |
| 1A7 | ++ | – | ++ | +++ | –/+ | No (mouse and rat) | yes w background | yes w background | no | | | | | | | |
| 1G7 | ++ | +/– | + | +++ | + | No (mouse and rat) | yes w background | yes w background | no | | | | | | | |
| 2B10 | ++ | +/– | – | +++ | –/+ | No (mouse and rat) | no | no | no | | | yes | | | yes | |
| 2C11 | – | – | – | – | – | No (mouse and rat) | no | no | no | | | | | | | |
| 2F3 | +/– | +/– | – | +++ | +++ | yes with over-expressed mSp35 | yes | yes | yes | yes | yes | yes | | | yes | |

HYBRIDOMA-DERIVED MONOCLONAL ANTIBODIES

| | FACs | | Immunoprecipitation | | | Western | | IHC on Transfected Cells | | IHC on Tissues | | ELISA | | | | |
|---|---|---|---|---|---|---|---|---|---|---|---|---|---|---|---|---|
| | huSp35 | mSp35 | sp35Fc | huSp35 | mSp35 | mouse/ rat sp35 | huSp35 | huSp35 | mSp35 | WT (parafin) | KO (parafin) | 34-417 | 417-493 | 419-495 | 1-532 | 34-532 |
| 3P1B1.1F9 | | | | +++ | – | | | | | | | | | +/– | yes | yes |
| 3P1D10.2C3 | | | | +++ | – | | | | | | | | | +/– | yes | yes |
| 3P1E11.3B7 | | | | +++ | – | | | | | | | | | | | |
| 3P2C6. | | | | +++ | – | | | | | | | | | | | |
| 3G10.2H7 | | | | +++ | – | | | | | | | | | +/– | yes | yes |
| 3P2C9.2G4 | | | | +++ | – | | | | | | | | | +/– | yes | yes |
| 3P4A6.1D9 | | | | +++ | – | | | | | | | | | +/– | yes | yes |
| 3P4A1.2B9 | | | | +++ | +++ | | | | | | | | | | | |
| 3P4C2.2D2 | | | | +++ | – | | | | | | yes | | | | yes | yes |
| 3P4C5.1D8 | | | | +++ | +++ | | | | | | | | | +/– | yes | yes |
| 3P4C8.2G9 | | | | +++ | +++ | | | | | | yes | | | | yes | yes |
| 7P1D5.1G9 | + | + | | +++ | +++ (lower band) | Yes (mouse) | yes | | | | | | | | | |
| 1B6.4 | +++ | +++ | | +++ (upper band) | +++ (lower band) | No (mouse) | no | | | | | | | | | |
| 2C7.2 | +++ | +++ | | +++ (upper band) | +++ (lower band) | No (mouse) | no | | | | | | | | | |
| 2D6.1 | ++ (binds to 293 cells) | ++ (binds to 293 cells) | | – | – | No (mouse) | no | | | | | | | | | |
| 2F7.3 | ++ | ++ | | +++ | +++ | Yes | yes | | | | | | | | | |

TABLE 3B-continued

SP35 MONOCLONAL ANTIBODIES

| | FACs | | Immunoprecipitation | | | Western | | IHC on Transfected Cells | | IHC on Tissues | | ELISA | | | | | |
|---|---|---|---|---|---|---|---|---|---|---|---|---|---|---|---|---|---|
| | huSp35 | mSp35 | sp35Fc | huSp35 | mSp35 | huSp35 | mouse/ rat sp35 | huSp35 | mSp35 | WT (parafin) | KO (parafin) | 34-417 | 417-493 | 419-495 | 1-532 | 34-532 |
| 2H3.2 | ++ | ++ | | (lower band) | (lower band) | yes | Yes (mouse) | | | | | | | | | |
| 3C11.1 | ++ | ++ | | +++ (lower band) | +++ (lower band) | yes | Yes (mouse) | | | | | | | | | |
| 3E3.1 | +++ | +++ | | +++ (upper band) | +++ (lower band) | no | No (mouse) | | | | | | | | | |
| 3H11.2 | ++ | ++ | | +++ (lower band) | +++ (lower band) | yes | Yes (mouse) | | | | | | | | | |
| 3G8.1 | + | + | | +++ (upper band) | +++ | no | No (mouse) | | | | | | | | | |
| 2B8.1 | ++ | ++ | | +++ (upper band) | + (lower band) | no | No (mouse) | | | | | | | | | |
| 3B5.2 | +++ | +++ | | +++ (upper band) | +++ (lower band) | no | No (mouse) | | | | | | | | | |

PHAGE DISPLAY LIBRARY-1 DERIVED MONOCLONAL Fab FRAGMENTS

| | FACs | | Immunoprecipitation | | | | | | | | | | | | | |
|---|---|---|---|---|---|---|---|---|---|---|---|---|---|---|---|---|
| | huSp35 | mSp35 | sp35Fc | huSp35 | mSp35 | | | | | | | | | | | |
| 30-C12 (Li01) | + | | | ++ | ++ | | | | | | | | | | | |
| 38-D01 (Li02) | + | | | −/+ | −/+ | | | | | | | | | | | |
| 35-E04 (Li03) | + | | | ++ | +++ | | | | | | | | | | | |
| 36-C09 (Li04) | + | | | −/+ | −/+ | | | | | | | | | | | |
| 34-A11 (Li05) | + | | ++ | ++ | ++ | | | | | | | | | | | |
| 34-F02 (Li06) | + | | | ++ | ++ | | | | | | | | | | | |
| 29-E07 (Li07) | + | | | ++ | ++ | | | | | | | | | | | |
| 34-G04 (Li08) | +/− | | + | − | − | | | | | | | | | | | |
| 36-A12 (Li09) | | | | −/+ | +/− | | | | | | | | | | | |
| 28-D02 (Li10) | | | | ++ | + | | | | | | | | | | | |
| 30-B01 (Li11) | ++ | | | ++ | ++ | | | | | | | | | | | |
| 34-B03 (Li12) | | | | + | + | | | | | | | | | | | |

PHAGE DISPLAY LIBRARY-2 DERIVED MONOCLONAL Fab FRAGMENTS

| | FACs | | | | | Western huSp35 | | IHC on Transfected Cells huSp35 mSp35 | | IHC on Tissues WT (parafin) KO (parafin) | | ELISA 34-417 | 417-493 | 419-495 | 1-532 | 34-532 |
|---|---|---|---|---|---|---|---|---|---|---|---|---|---|---|---|---|
| 3383 (1) | + | − | | | | N/A | | N/A | N/A | yes | yes | | | | yes | yes |
| 3495 (2) | + | − | | | | faint | | no | no | yes | yes | | | +/− | yes | yes |
| 3563 (3) | + | | | | | no | | no | no | | | yes | yes | | yes | yes |
| 3564 (4) | + | | | | | no | | no | no | | | yes | yes | | yes | yes |
| 3565 (5) | + | | | | | no | | no | no | yes | yes | | | +/− | yes | yes |
| 3566 (6) | + | | | | | yes | | yes | very faint | | | yes | yes | | yes | yes |

TABLE 3B-continued

SP35 MONOCLONAL ANTIBODIES

| | FACs | | Immunoprecipitation | | Western mouse/ | | IHC on Transfected Cells | | IHC on Tissues | | ELISA | | | | | |
|---|---|---|---|---|---|---|---|---|---|---|---|---|---|---|---|---|
| | huSp35 | mSp35 | sp35Fc | huSp35 | mSp35 | huSp35 | rat sp35 | huSp35 | mSp35 | WT (parafin) | KO (parafin) | 34-417 | 417-493 | 419-495 | 1-532 | 34-532 |
| 3567 (7) | + | | | | | | | yes | no | yes | yes | | | +/- | yes | yes |
| 3568 (8) | + | | | | | | | no | no | | | yes | | | yes | |
| 3569 (9) | + | | | | | | | no | no | | | yes | | | yes | |
| 3570 (10) | + | | | | | | | no | no | | | yes | | | yes | |
| 3571 (11) | + | | | | | | | no | no | | | | | | yes | |
| 3582 (12) | +/- | | | | | | | no | no | | | | | | yes | |
| 1968 (13) | +/- | - | | ++ | | weak | no | very faint | yes w bg | yes | yes | yes | | +/- | yes | yes |
| 3011 | - | | | +/- | | | | only stain very few cells | faint | | | | | | | |
| 3012 | - | | | - | | | | no | no | | | | | | | |
| 3013 | sticky | | | + | | | | yes w high bg | yes | | | | | | | |
| 3418 | sticky | | | | | | | yes w high bg | yes | | | | | | | |
| 3422 | - | | | | | | | very faint | yes w high bg | | | | | | | |
| 3562 | sticky | | | | | | | no | no | | | | | | | |

PHAGE DISPLAY LIBRARY-1 DERIVED COMPLETE MONOCLONAL ANTIBODIES

| D05 | ++ |
| D07 | +++ |
| D08 | ++ |
| D10 | +++ |
| D11 | +++ |

Key:
huSp35 = human Sp35 protein
mSp35 = mouse Sp35 protein
WT = wild-type
KO = knock-out
IHC = immunohistochemistry
FACS = Fluorescent Activated Cell Sorting As used herein, the term "antigen binding domain" includes a site that specifically binds an epitope on an antigen (e.g., an epitope of Sp35). The antigen binding domain of an antibody typically includes at least a portion of an immunoglobulin heavy chain variable region and at least a portion of an immunoglobulin light chain variable region. The binding site formed by these variable regions determines the specificity of the antibody.

The present invention is more specifically directed to an Sp35 antibody, or antigen-binding fragment, variant or derivatives thereof, where the Sp35 antibody binds to the same epitope as a monoclonal antibody selected from the group consisting of 201', 3A3, 3A6, 1A7, 1G7, 2B10, 2C11, 2F3, 3P1D10.2C3, 3P1E11.3B7, 3P2C6.3G10.2H7, 3P2C9.2G4, 3P4A6.1D9, 3P4A1.2B9, 3P4C2.2D2, 3P4C5.1D8, 3P4C8.2G9, 30-C12 (Li01), 38-D01 (Li02), 35-E04 (Li03), 36-C09 (Li04), 30-A11 (Li05), 34-F02 (Li06), 29-E07 (Li07), 34-G04 (Li08), 36-A 12 (Li09), 28-D02 (Li10), 30-B01 (Li11), 34-B03 (Li12), Li13, Li32, Li33, Li34, 3383 (L1a.1), 3495 (L1a.2), 3563 (L1a.3), 3564 (L1a.4), 3565 (L1a.5), 3566 (L1a.6), 3567 (L1a.7), 3568 (L1a.8), 3569 (L1a.9), 3570 (L1a.10), 3571 (L1a.11), 3582 (L1a.12), and 1968 (L1a.13).

The invention is further drawn to an Sp35 antibody, or antigen-binding fragment, variant or derivatives thereof, where the Sp35 antibody competitively inhibits a monoclonal antibody selected from the group consisting of 201', 3A3, 3A6, 1A7, 1G7, 2B10, 2C11, 2F3, 3P1D10.2C3, 3P1E11.3B7, 3P2C6.3G10.2H7, 3P2C9.2G4, 3P4A6.1D9, 3P4A1.2B9, 3P4C2.2D2, 3P4C5.1D8, 3P4C8.2G9, 30-C12 (L100), 38-D01 (Li02), 35-E04 (Li03), 36-C09 (Li04), 30-A11 (Li05), 34-F02 (Li06), 29-E07 (Li07), 34-G04 (Li08), 36-A12 (Li09), 28-D02 (Li10), 30-B01 (Li11), 34-B03 (Li12), Li13, Li32, Li33, Li34, 3383 (L1a.1), 3495 (L1a.2), 3563 (L1a.3), 3564 (L1a.4), 3565 (L1a.5), 3566 (L1a.6), 3567 (L1a.7), 3568 (L1a.8), 3569 (L1a.9), 3570 (L1a.10), 3571 (L1a.11), 3582 (L1a.12), and 1968 (L1a.13) from binding to Sp35.

The invention is also drawn to an Sp35 antibody, or antigen-binding fragment, variant or derivatives thereof, where the Sp35 antibody comprises at least the antigen binding region of a monoclonal antibody selected from the group consisting of 201', 3A3, 3A6, 1A7, 1G7, 2B10, 2C11, 2F3, 3P1D10.2C3, 3P1E11.3B7, 3P2C6.3G10.2H7, 3P2C9.2G4, 3P4A6.1D9, 3P4A1.2B9, 3P4C2.2D2, 3P4C5.1D8, 3P4C8.2G9, 30-C12 (L100), 38-D01 (Li02), 35-E04 (Li03), 36-C09 (Li04), 30-A11 (Li05), 34-F02 (Li06), 29-E07 (Li07), 34-G04 (Li08), 36-A12 (Li09), 28-D02 (Li10), 30-B01 (Li11), 34-B03 (Li12), Li13, Li32, Li33, Li34, 3383 (L1a.1), 3495 (L1a.2), 3563 (L1a.3), 3564 (L1a.4), 3565 (L1a.5), 3566 (L1a.6), 3567 (L1a.7), 3568 (L1a.8), 3569 (L1a.9), 3570 (L1a.10), 3571 (L1a.11), 3582 (L1a.12), and 1968 (L1a.13).

In certain embodiments, the present invention is directed to an antibody, or antigen-binding fragment, variant, or derivative thereof which specifically or preferentially binds to a particular Sp35 polypeptide fragment or domain. Such Sp35 polypeptide fragments include, but are not limited to, an Sp35 polypeptide comprising, consisting essentially of, or consisting of amino acids 34 to 532; 34 to 417; 34 to 425; 34 to 493; 66 to 532; 66 to 417; 66 to 426; 66 to 493; 66 to 532; 417 to 532; 417 to 425 (the Sp35 basic region); 417 to 493; 417 to 532; 419 to 493 (the Sp351 g region); or 425 to 532 of SEQ ID NO:2; or an Sp35 variant polypeptide at least 70%, 75%, 80%, 85%, 90%, or 95% identical to amino acids 34 to 532; 34 to 417; 34 to 425; 34 to 493; 66 to 532; 66 to 417; 66 to 426; 66 to 493; 66 to 532; 417 to 532; 417 to 425 (the Sp35 basic region); 417 to 493; 417 to 532; 419 to 493 (the Sp351 g region); or 425 to 532 of SEQ ID NO:2.

Additional Sp35 peptide fragments to which certain antibodies, or antigen-binding fragments, variants, or derivatives thereof of the present invention bind include, but are not limited to those fragments comprising, consisting essentially of, or consisting of one or more leucine-rich-repeats (LRR) of Sp35. Such fragments, include, for example, fragments comprising, consisting essentially of, or consisting of amino acids 66 to 89; 66 to 113; 66 to 137; 90 to 113; 114 to 137; 138 to 161; 162 to 185; 186 to 209; 210 to 233; 234 to 257; 258 to 281; 282 to 305; 306 to 329; or 330 to 353 of SEQ ID NO:2. Corresponding fragments of a variant Sp35 polypeptide at least 70%, 75%, 80%, 85%, 90%, or 95% identical to amino acids 66 to 89; 66 to 113; 90 to 113; 114 to 137; 138 to 161; 162 to 185; 186 to 209; 210 to 233; 234 to 257; 258 to 281; 282 to 305; 306 to 329; or 330 to 353 of SEQ ID NO:2 are also contemplated.

Additional Sp35 peptide fragments to which certain antibodies, or antigen-binding fragments, variants, or derivatives thereof of the present invention bind include, but are not limited to those fragments comprising, consisting essentially of, or consisting of one or more cysteine rich regions flanking the LRR of Sp35. Such fragments, include, for example, a fragment comprising, consisting essentially of, or consisting of amino acids 34 to 64 of SEQ ID NO:2 (the N-terminal LRR flanking region (LRRNT)), or a fragment comprising, consisting essentially of, or consisting of amino acids 363 to 416 of SEQ ID NO:2 (the C-terminal LRR flanking region (LRRCT)), amino acids Corresponding fragments of a variant Sp35 polypeptide at least 70%, 75%, 80%, 85%, 90%, or 95% identical to amino acids 34 to 64 and 363 to 416 of SEQ ID NO:2 are also contemplated.

As known in the art, "sequence identity" between two polypeptides is determined by comparing the amino acid sequence of one polypeptide to the sequence of a second polypeptide. When discussed herein, whether any particular polypeptide is at least about 70%, 75%, 80%, 85%, 90% or 95% identical to another polypeptide can be determined using methods and computer programs/software known in the art such as, but not limited to, the BESTFIT program (Wisconsin Sequence Analysis Package, Version 8 for Unix, Genetics Computer Group, University Research Park, 575 Science Drive, Madison, Wis. 53711). BESTFIT uses the local homology algorithm of Smith and Waterman, *Advances in Applied Mathematics* 2:482-489 (1981), to find the best segment of homology between two sequences. When using BESTFIT or any other sequence alignment program to determine whether a particular sequence is, for example, 95% identical to a reference sequence according to the present invention, the parameters are set, of course, such that the percentage of identity is calculated over the full length of the reference polypeptide sequence and that gaps in homology of up to 5% of the total number of amino acids in the reference sequence are allowed.

Additional Sp35 peptide fragments to which certain antibodies, or antigen-binding fragments, variants, or derivatives thereof of the present invention bind include, but are not limited to those fragments comprising, consisting essentially of, or consisting of amino acids 41 to 525 of SEQ ID NO:2; 40 to 526 of SEQ ID NO:2; 39 to 527 of SEQ ID NO:2; 38 to 528 of SEQ ID NO:2; 37 to 529 of SEQ ID NO:2; 36 to 530 of SEQ ID NO:2; 35 to 531 of SEQ ID NO:2; 34 to 531 of SEQ ID NO:2; 46 to 520 of SEQ ID NO:2; 45 to 521 of SEQ ID NO:2; 44 to 522 of SEQ ID NO:2; 43 to 523 of SEQ ID NO:2; and 42 to 524 of SEQ ID NO:2.

Still additional Sp35 peptide fragments to which certain antibodies, or antigen-binding fragments, variants, or derivatives thereof of the present invention bind include, but are not limited to those fragments comprising, consisting essentially of, or consisting of amino acids 1 to 33 of SEQ ID NO:2; 1 to 35 of SEQ ID NO:2; 34 to 64 of SEQ ID NO:2; 36 to 64 of SEQ ID NO:2; 66 to 89 of SEQ ID NO:2; 90 to 113 of SEQ ID NO:2; 114 to 137 of SEQ ID NO:2; 138 to 161 of SEQ ID NO:2; 162 to 185 of SEQ ID NO:2; 186 to 209 of SEQ ID NO:2; 210 to 233 of SEQ ID NO:2; 234 to 257 of SEQ ID NO:2; 258 to 281 of SEQ ID NO:2; 282 to 305 of SEQ ID NO:2; 306 to 329 of SEQ ID NO:2; 330 to 353 of SEQ ID NO:2; 363 to 416 of SEQ ID NO:2; 417 to 424 of SEQ ID NO:2; 419 to 493 of SEQ ID NO:2; and 494 to 551 of SEQ ID NO:2.

Further still, Sp35 peptide fragments to which certain antibodies, or antigen-binding fragments, variants, or derivatives thereof of the present invention bind include, but are not limited to those fragments comprising, consisting essentially of, or consisting of amino acids 1 to 33 of SEQ ID NO:2; 1 to 35 of SEQ ID NO:2; 1 to 64 of SEQ ID NO:2; 1 to 89 of SEQ ID NO:2; 1 to 113 of SEQ ID NO:2; 1 to 137 of SEQ ID NO:2; 1 to 161 of SEQ ID NO:2; 1 to 185 of SEQ ID NO:2; 1 to 209 of SEQ ID NO:2; 1 to 233 of SEQ ID NO:2; 1 to 257 of SEQ ID NO:2; 1 to 281 of SEQ ID NO:2; 1 to 305 of SEQ ID NO:2; 1 to 329 of SEQ ID NO:2; 1 to 353 of SEQ ID NO:2; 1 to 416 of SEQ ID NO:2; 1 to 424 of SEQ ID NO:2; 1 to 493 of SEQ ID NO:2; 1 to 551 of SEQ ID NO:2; 1 to 531 of SEQ ID NO:2 and 1 to 532 of SEQ ID NO:2.

Additional Sp35 peptide fragments to which certain antibodies, or antigen-binding fragments, variants, or derivatives thereof of the present invention bind include, but are not limited to those fragments comprising, consisting essentially of, or consisting of amino acids 34 to 64 of SEQ ID NO:2; 34 to 89 of SEQ ID NO:2; 34 to 113 of SEQ ID NO:2; 34 to 137 of SEQ ID NO:2; 34 to 161 of SEQ ID NO:2; 34 to 185 of SEQ ID NO:2; 34 to 209 of SEQ ID NO:2; 34 to 233 of SEQ ID NO:2; 34 to 257 of SEQ ID NO:2; 34 to 281 of SEQ ID NO:2; 34 to 305 of SEQ ID NO:2; 34 to 329 of SEQ ID NO:2; 34 to 353 of SEQ ID NO:2; 34 to 416 of SEQ ID NO:2; 34 to 424 of SEQ ID NO:2; 34 to 493 of SEQ ID NO:2; and 34 to 551 of SEQ ID NO:2.

More additional Sp35 peptide fragments to which certain antibodies, or antigen-binding fragments, variants, or derivatives thereof of the present invention bind include, but are not limited to those fragments comprising, consisting essentially of, or consisting of amino acids 34 to 530 of SEQ ID NO:2; 34 to 531 of SEQ ID NO:2; 34 to 532 of SEQ ID NO:2; 34 to 533 of SEQ ID NO:2; 34 to 534 of SEQ ID NO:2; 34 to 535 of SEQ ID NO:2; 34 to 536 of SEQ ID NO:2; 34 to 537 of SEQ ID NO:2; 34 to 538 of SEQ ID NO:2; 34 to 539 of SEQ ID NO:2; 30 to 532 of SEQ ID NO:2; 31 to 532 of SEQ ID NO:2; 32 to 532 of SEQ ID NO:2; 33 to 532 of SEQ ID NO:2; 34 to 532 of SEQ ID NO:2; 35 to 532 of SEQ ID NO:2; 36 to 532 of SEQ ID NO:2; 30 to 531 of SEQ ID NO:2; 31 to 531 of SEQ ID NO:2; 32 to 531 of SEQ ID NO:2; 33 to 531 of SEQ ID NO:2; 34 to 531 of SEQ ID NO:2; 35 to 531 of SEQ ID NO:2; and 36 to 531 of SEQ ID NO:2.

Further still, Sp35 peptide fragments to which certain antibodies, or antigen-binding fragments, variants, or derivatives thereof of the present invention bind include, but are not limited to those fragments comprising, consisting essentially of, or consisting of amino acids 36 to 64 of SEQ ID NO:2; 36 to 89 of SEQ ID NO:2; 36 to 113 of SEQ ID NO:2; 36 to 137 of SEQ ID NO:2; 36 to 161 of SEQ ID NO:2; 36 to 185 of SEQ ID NO:2; 36 to 209 of SEQ ID NO:2; 36 to 233 of SEQ ID NO:2; 36 to 257 of SEQ ID NO:2; 36 to 281 of SEQ ID NO:2; 36 to 305 of SEQ ID NO:2; 36 to 329 of SEQ ID NO:2; 36 to 353 of SEQ ID NO:2; 36 to 416 of SEQ ID NO:2; 36 to 424 of SEQ ID NO:2; 36 to 493 of SEQ ID NO:2; and 36 to 551 of SEQ ID NO:2.

Additional Sp35 peptide fragments to which certain antibodies, or antigen-binding fragments, variants, or derivatives thereof of the present invention bind include, but are not limited to those fragments comprising, consisting essentially of, or consisting of amino acids 36 to 530 of SEQ ID NO:2; 36 to 531 of SEQ ID NO:2; 36 to 532 of SEQ ID NO:2; 36 to 533 of SEQ ID NO:2; 36 to 534 of SEQ ID NO:2; 36 to 535 of SEQ ID NO:2; 36 to 536 of SEQ ID NO:2; 36 to 537 of SEQ ID NO:2; 36 to 538 of SEQ ID NO:2; and 36 to 539 of SEQ ID NO:2.

More Sp35 peptide fragments to which certain antibodies, or antigen-binding fragments, variants, or derivatives thereof of the present invention bind include, but are not limited to those fragments comprising, consisting essentially of, or consisting of amino acids 417 to 493 of SEQ ID NO:2; 417 to 494 of SEQ ID NO:2; 417 to 495 of SEQ ID NO:2; 417 to 496 of SEQ ID NO:2; 417 to 497 of SEQ ID NO:2; 417 to 498 of SEQ ID NO:2; 417 to 499 of SEQ ID NO:2; 417 to 500 of SEQ ID NO:2; 417 to 492 of SEQ ID NO:2; 417 to 491 of SEQ ID NO:2; 412 to 493 of SEQ ID NO:2; 413 to 493 of SEQ ID NO:2; 414 to 493 of SEQ ID NO:2; 415 to 493 of SEQ ID NO:2; 416 to 493 of SEQ ID NO:2; 411 to 493 of SEQ ID NO:2; 410 to 493 of SEQ ID NO:2; 410 to 494 of SEQ ID NO:2; 411 to 494 of SEQ ID NO:2; 412 to 494 of SEQ ID NO:2; 413 to 494 of SEQ ID NO:2; 414 to 494 of SEQ ID NO:2; 415 to 494 of SEQ ID NO:2; 416 to 494 of SEQ ID NO:2; 417 to 494 of SEQ ID NO:2; and 418 to 494 of SEQ ID NO:2.

In an additional embodiment Sp35 peptide fragments to which certain antibodies, or antigen-binding fragments, variants, or derivatives thereof of the present invention bind include, an Sp35 polypeptide comprising, consisting essentially of, or consisting of peptides of the Ig domain of Sp35 or fragments, variants, or derivatives of such polypeptides. Specifically, polypeptides comprising, consisting essentially of, or consisting of the following polypeptide sequences: $ITX_1X_2X_3$ (SEQ ID NO:287), $ACX_1X_2X_3$ (SEQ ID NO:288), $VCX_1X_2X_3$ (SEQ ID NO:289) and $SPX_1X_2X_3$ (SEQ ID NO:290) where $X_1$ is lysine, arginine, histidine, glutamine, or asparagine, $X_2$ is lysine, arginine, histidine, glutamine, or asparagine and $X_3$ is lysine, arginine, histidine, glutamine, or asparagine. For example, Sp35 peptide fragments to which certain antibodies, or antigen-binding fragments, variants, or derivatives thereof of the present invention bind include, those fragments comprising, consisting essentially of, or consisting of the following polypeptide sequences: SPRKH (SEQ ID NO:291), SPRKK (SEQ ID NO:292), SPRKR (SEQ ID NO:293), SPKKH (SEQ ID NO:294), SPHKH (SEQ ID NO:295), SPRRH (SEQ ID NO:296), SPRHH (SEQ ID NO:297), SPRRR (SEQ ID NO:298), SPHHH (SEQ ID NO:299) SPKKK (SEQ ID NO:300), LSPRKH (SEQ ID NO:301), LSPRKK (SEQ ID NO:302), LSPRKR (SEQ ID NO:303), LSPKKH (SEQ ID NO:304), LSPHKH (SEQ ID NO:305), LSPRRH (SEQ ID NO:306), LSPRHH (SEQ ID NO:307), LSPRRR (SEQ ID NO:308), LSPHHH (SEQ ID NO:309) LSPKKK (SEQ ID NO:310), WLSPRKH (SEQ ID NO:311), WLSPRKK (SEQ ID NO:312), WLSPRKR (SEQ ID NO:313), WLSPKKH (SEQ ID NO:314), WLSPHKH (SEQ ID NO:315), WLSPRRH (SEQ ID NO:316), WLSPRHH (SEQ ID NO:317), WLSPRRR (SEQ ID NO:318), WLSPHHH (SEQ ID NO:319) WLSPKKK (SEQ ID NO:320). These Sp35 polypeptides include the basic "RKH loop" (Arginine- Lysine-Histidine amino acids 456-458) in the Ig domain of Sp35. Additional Sp35 peptides which include a basic tripeptide are ITPKRR (SEQ ID NO:321), ACHHK (SEQ ID NO:322) and VCHHK (SEQ ID NO:323).

Additional Sp35 peptide fragments to which certain antibodies, or antigen-binding fragments, variants, or derivatives thereof of the present invention bind include, an Sp35 polypeptide comprising, consisting essentially of, or consisting of peptides of the Ig domain of Sp35 or fragments, variants, or derivatives of such polypeptides. Specifically, peptides comprising, consisting essentially of, or consisting of the following polypeptide sequences: $X_4X_5RKH$ (SEQ ID NO:324), $X_4X_5RRR$ (SEQ ID NO:325), $X_4X_5KKK$ (SEQ ID NO:326), $X_4X_5HHH$ (SEQ ID NO:327), $X_4X_5RKK$ (SEQ ID NO:328), $X_4X_5RKR$ (SEQ ID NO:329), $X_4X_5KKH$ (SEQ ID NO:330), $X_4X_5HKH$ (SEQ ID NO:331), $X_4X_5RRH$ (SEQ ID NO:332) and $X_4X_5RHH$ (SEQ ID NO:333) where $X_4$ is any amino acid and $X_5$ is any amino acid.

In other embodiments Sp35 peptide fragments to which certain antibodies, or antigen-binding fragments, variants, or derivatives thereof of the present invention bind include, an Sp35 polypeptide comprising, consisting essentially of, or consisting of peptides of the Ig domain of Sp35 or fragments, variants, or derivatives of such polypeptides. Specifically, polypeptides comprising, consisting essentially of, or consisting of the following polypeptide sequences: $ITX_6X_7X_8$ (SEQ ID NO:334), $ACX_6X_7X_8$ (SEQ ID NO:335), $VCX_6X_7X_8$ (SEQ ID NO:336) and $SPX_6X_7X_8$ (SEQ ID NO:337) where $X_6$ is lysine, arginine, histidine, glutamine, or asparagine, $X_7$ is any amino acid and $X_8$ is lysine, arginine, histidine, glutamine, or asparagine. For example, a polypeptide comprising, consisting essentially of, or consisting of the following polypeptide sequence: SPRLH (SEQ ID NO:338).

Sp35 peptide fragments to which certain antibodies, or antigen-binding fragments, variants, or derivatives thereof of the present invention bind include, an Sp35 polypeptide comprising, consisting essentially of, or consisting of peptides which contain amino acids 452-458 in the Ig domain of Sp35, or derivatives thereof, wherein amino acid 452 is a tryptophan or phenylalanine residue.

Additional Sp35 peptide fragments to which certain antibodies, or antigen-binding fragments, variants, or derivatives thereof of the present invention bind include, an Sp35 polypeptide comprising, consisting essentially of, or consisting of peptides of the basic domain of Sp35. Specifically, peptides comprising, consisting essentially of, or consisting of the following polypeptide sequences: RRARIRDRK (SEQ ID NO:339), KKVKVKEKR (SEQ ID NO:340), RRLRLRDRK (SEQ ID NO:341), RRGRGRDRK (SEQ ID NO:342) and RRIRARDRK (SEQ ID NO:343).

Additional exemplary soluble Sp35 polypeptides and methods and materials for obtaining these molecules for producing antibodies or antibody fragments of the present invention may be found, e.g., in International Patent Application No. PCT/US2004/008323, incorporated herein by reference in its entirety.

Methods of making antibodies are well known in the art and described herein. Once antibodies to various fragments of, or to the full-length Sp35 without the signal sequence, have been produced, determining which amino acids, or epitope, of Sp35 to which the antibody or antigen binding fragment binds can be determined by eptiope mapping protocols as described herein as well as methods known in the art (e.g. double antibody-sandwich ELISA as described in "Chapter 11—Immunology," *Current Protocols in Molecular Biology*, Ed. Ausubel et al., v.2, John Wiley & Sons, Inc. (1996)). Additional epitope mapping protocols may be found in Morris, G. *Epitope Mapping Protocols*, New Jersey: Humana Press (1996), which are both incorporated herein by reference in their entireties. Epitope mapping can also be performed by commercially available means (i.e. Proto-PROBE, Inc. (Milwaukee, Wis.)).

Additionally, antibodies produced which bind to any portion of Sp35 can then be screened for their ability to act as an antagonist of Sp35 and thus promote neurite outgrowth, neuronal and oligodendrocyte survival, proliferation and differentiation as well as promote myelination. Antibodies can be screened for oligodendrocyte/neuronal survival by using the method as described in Examples 10 and 11. Additionally, antibodies can be screened for their ability to promote myelination by using the method of Example 9. Finally, antibodies can be screened for their ability to promote oligodendrocyte proliferation and differentiation, as well as neurite outgrowth by using the method as described in Example 7. Other antagonist functions of antibodies of the present invention can be tested using other assays as described in the Examples herein.

In other embodiments, the present invention includes an antibody, or antigen-binding fragment, variant, or derivative thereof which specifically or preferentially binds to at least one epitope of Sp35, where the epitope comprises, consists essentially of, or consists of at least about four to five amino acids of SEQ ID NO:2, at least seven, at least nine, or between at least about 15 to about 30 amino acids of SEQ ID NO:2. The amino acids of a given epitope of SEQ ID NO:2 as described may be, but need not be contiguous or linear. In certain embodiments, the at least one epitope of Sp35 comprises, consists essentially of, or consists of a non-linear epitope formed by the extracellular domain of Sp35 as expressed on the surface of a cell or as a soluble fragment, e.g., fused to an IgG Fc region. Thus, in certain embodiments the at least one epitope of Sp35 comprises, consists essentially of, or consists of at least 4, at least 5, at least 6, at least 7, at least 8, at least 9, at least 10, at least 15, at least 20, at least 25, between about 15 to about 30, or at least 10, 15, 20, 25, 30, 35, 40, 45, 50, 55, 60, 65, 70, 75, 80, 85, 90, 95, or 100 contiguous or non-contiguous amino acids of SEQ ID NO:2, where the non-contiguous amino acids form an epitope through protein folding.

In other embodiments, the present invention includes an antibody, or antigen-binding fragment, variant, or derivative thereof which specifically or preferentially binds to at least one epitope of Sp35, where the epitope comprises, consists essentially of, or consists of, in addition to one, two, three, four, five, six or more contiguous or non-contiguous amino acids of SEQ ID NO:2 as described above, and an additional moiety which modifies the protein, e.g., a carbohydrate moiety may be included such that the Sp35 antibody binds with higher affinity to modified target protein than it does to an unmodified version of the protein. Alternatively, the Sp35 antibody does not bind the unmodified version of the target protein at all.

In certain aspects, the present invention is directed to an antibody, or antigen-binding fragment, variant, or derivative thereof which specifically binds to a Sp35 polypeptide or fragment thereof, or an Sp35 variant polypeptide, with an affinity characterized by a dissociation constant ($K_D$) which is less than the $K_D$ for said reference monoclonal antibody.

In certain embodiments, an antibody, or antigen-binding fragment, variant, or derivative thereof of the invention binds specifically to at least one epitope of Sp35 or fragment or variant described above, i.e., binds to such an epitope more readily than it would bind to an unrelated, or random epitope; binds preferentially to at least one epitope of Sp35 or fragment or variant described above, i.e., binds to such an epitope more readily than it would bind to a related, similar, homologous, or analogous epitope; competitively inhibits binding of a reference antibody which itself binds specifically or preferentially to a certain epitope of Sp35 or fragment or variant described above; or binds to at least one epitope of Sp35 or fragment or variant described above with an affinity characterized by a dissociation constant $K_D$ of less than about $5\times10^{-2}$ M, about $10^{-2}$ M, about $5\times10^{-3}$ M, about $10^{-3}$ M, about $5\times10^{-4}$ M, about $10^{-4}$ M, about $5\times10^{-5}$ M, about $10^{-5}$ M, about $5\times10^{-6}$ M, about $10^{-6}$ M, about $5\times10^{-7}$ M, about $10^{-7}$ M, about $5\times10^{-8}$ M, about $10^{-8}$ M, about $5\times10^{-9}$ M, about $10^{-9}$ M, about $5\times10^{-10}$ M, about $10^{-10}$ M, about $5\times10^{-11}$ M, about $10^{-11}$ M, about $5\times10^{-12}$ M, about $10^{-12}$ M, about $5\times10^{-13}$ M, about $10^{-13}$ M, about $5\times10^{-14}$ M, about $10^{-14}$ M, about $5\times10^{-15}$ M, or about $10^{-15}$ M. In a particular aspect, the antibody or fragment thereof preferentially binds to a human Sp35 polypeptide or fragment thereof, relative to a murine Sp35 polypeptide or fragment thereof.

As used in the context of antibody binding dissociation constants, the term "about" allows for the degree of variation inherent in the methods utilized for measuring antibody affinity. For example, depending on the level of precision of the instrumentation used, standard error based on the number of samples measured, and rounding error, the term "about $10^{-2}$ M" might include, for example, from 0.05 M to 0.005 M.

In specific embodiments, an antibody, or antigen-binding fragment, variant, or derivative thereof of the invention binds Sp35 polypeptides or fragments or variants thereof with an off rate (k(off)) of less than or equal to $5\times10^{-2}$ sec$^{-1}$, $10^{-2}$ sec$^{-1}$, $5\times10^{-3}$ sec$^{-1}$ or $10^{-3}$ sec$^{-1}$. Alternatively, an antibody, or antigen-binding fragment, variant, or derivative thereof of the invention binds Sp35 polypeptides or fragments or variants thereof with an off rate (k(off)) of less than or equal to $5\times10^{-4}$ sec$^{-1}$, $10^{-4}$ sec$^{-1}$, $5\times10^{-5}$ sec$^{-1}$, or $10^{-5}$ sec$^{-1}$ $5\times10^{-6}$ sec$^{-1}$, $10^{-6}$ sec$^{-1}$, $5\times10^{-7}$ sec$^{-1}$ or $10^{-7}$ sec$^{-1}$.

In other embodiments, an antibody, or antigen-binding fragment, variant, or derivative thereof of the invention binds Sp35 polypeptides or fragments or variants thereof with an on rate (k(on)) of greater than or equal to $10^3$ M$^{-1}$ sec$^{-1}$, $5\times10^3$ M$^{-1}$ sec$^{-1}$, $10^4$ M$^{-1}$ sec$^{-1}$ or $5\times10^4$ M$^{-1}$ sec$^{-1}$. Alternatively, an antibody, or antigen-binding fragment, variant, or derivative thereof of the invention binds Sp35 polypeptides or fragments or variants thereof with an on rate (k(on)) greater than or equal to $10^5$ M$^{-1}$ sec$^{-1}$, $5\times10^5$ M$^{-1}$ sec$^{-1}$, $10^6$ M$^{-1}$ sec$^{-1}$, or $5\times106$ M$^{-1}$ sec$^{-1}$ or $10^7$ M$^{-1}$ sec$^{-1}$.

In various embodiments, an Sp35 antibody, or antigen-binding fragment, variant, or derivative thereof as described herein is an antagonist of Sp35 activity. In certain embodiments, for example, binding of an antagonist Sp35 antibody to Sp35, as expressed on neurons, blocks myelin-associated neurite outgrowth inhibition or neuronal cell death. In other embodiments, binding of the Sp35 antibody to Sp35, as expressed on oligodendrocytes, blocks inhibition of oligodendrocyte growth or differentiation, or blocks demyelination or dysmyelination of CNS neurons.

Unless it is specifically noted, as used herein a "fragment thereof" in reference to an antibody refers to an antigen-binding fragment, i.e., a portion of the antibody which specifically binds to the antigen. In one embodiment, an Sp35 antibody, e.g., an antibody of the invention is a bispecific Sp35 antibody, binding polypeptide, or antibody, e.g., a bispecific antibody, minibody, domain deleted antibody, or fusion protein having binding specificity for more than one epitope, e.g., more than one antigen or more than one epitope on the same antigen. In one embodiment, a bispecific Sp35 antibody, binding polypeptide, or antibody has at least one binding domain specific for at least one epitope on a target polypeptide disclosed herein, e.g., Sp35. In another embodiment, a bispecific Sp35 antibody, binding polypeptide, or antibody has at least one binding domain specific for an epitope on a target polypeptide and at least one target binding domain specific for a drug or toxin. In yet another embodiment, a bispecific Sp35 antibody, binding polypeptide, or antibody has at least one binding domain specific for an epitope on a target polypeptide disclosed herein, and at least one binding domain specific for a prodrug. A bispecific Sp35 antibody, binding polypeptide, or antibody may be a tetravalent antibody that has two target binding domains specific for an epitope of a target polypeptide disclosed herein and two target binding domains specific for a second target. Thus, a tetravalent bispecific Sp35 antibody, binding polypeptide, or antibody may be bivalent for each specificity.

Sp35 antibodies, or antigen-binding fragments, variants, or derivatives thereof of the invention, as known by those of ordinary skill in the art, can comprise a constant region which mediates one or more effector functions. For example, binding of the C1 component of complement to an antibody constant region may activate the complement system. Activation of complement is important in the opsonisation and lysis of cell pathogens. The activation of complement also stimulates the inflammatory response and may also be involved in autoimmune hypersensitivity. Further, antibodies bind to receptors on various cells via the Fc region, with a Fc receptor binding site on the antibody Fc region binding to a Fc receptor (FcR) on a cell. There are a number of Fc receptors which are specific for different classes of antibody, including IgG (gamma receptors), IgE (epsilon receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell-mediated cytotoxicity, or ADCC), release of inflammatory mediators, placental transfer and control of immunoglobulin production.

Accordingly, certain embodiments of the invention include an Sp35 antibody, or antigen-binding fragment, variant, or derivative thereof, in which at least a fraction of one or more of the constant region domains has been deleted or otherwise altered so as to provide desired biochemical characteristics such as reduced effector functions, the ability to non-covalently dimerize, increased ability to localize at the site of a tumor, reduced serum half-life, or increased serum half-life when compared with a whole, unaltered antibody of approximately the same immunogenicity. For example, certain antibodies for use in the diagnostic and treatment methods described herein are domain deleted antibodies which comprise a polypeptide chain similar to an immunoglobulin heavy chain, but which lack at least a portion of one or more heavy chain domains. For instance, in certain antibodies, one entire domain of the constant region of the modified antibody will be deleted, for example, all or part of the $C_H2$ domain will be deleted.

In certain Sp35 antibodies, or antigen-binding fragments, variants, or derivatives thereof described herein, the Fc portion may be mutated to decrease effector function using techniques known in the art. For example, the deletion or inactivation (through point mutations or other means) of a constant region domain may reduce Fc receptor binding of the circulating modified antibody thereby increasing tumor localization. In other cases it may be that constant region modifications consistent with the instant invention moderate complement binding and thus reduce the serum half life and nonspecific association of a conjugated cytotoxin. Yet other modifications of the constant region may be used to modify disulfide linkages or oligosaccharide moieties that allow for enhanced localization due to increased antigen specificity or antibody flexibility. The resulting physiological profile, bioavailability and other biochemical effects of the modifications, such as tumor localization, biodistribution and serum half-life, may easily be measured and quantified using well know immunological techniques without undue experimentation.

Modified forms of Sp35 antibodies, or antigen-binding fragments, variants, or derivatives thereof of the invention can be made from whole precursor or parent antibodies using techniques known in the art. Exemplary techniques are discussed in more detail herein.

In certain embodiments both the variable and constant regions of Sp35 antibodies, or antigen-binding fragments, variants, or derivatives thereof are fully human. Fully human antibodies can be made using techniques that are known in the art and as described herein. For example, fully human antibodies against a specific antigen can be prepared by administering the antigen to a transgenic animal which has been modified to produce such antibodies in response to antigenic challenge, but whose endogenous loci have been disabled. Exemplary techniques that can be used to make such antibodies are described in U.S. Pat. Nos. 6,150,584; 6,458,592; 6,420,140 which are incorporated by reference in their entireties. Other techniques are known in the art. Fully human antibodies can likewise be produced by various display technologies, e.g., phage display or other viral display systems, as described in more detail elsewhere herein.

Sp35 antibodies, or antigen-binding fragments, variants, or derivatives thereof of the invention can be made or manufactured using techniques that are known in the art. In certain embodiments, antibody molecules or fragments thereof are "recombinantly produced," i.e., are produced using recombinant DNA technology. Exemplary techniques for making antibody molecules or fragments thereof are discussed in more detail elsewhere herein.

Sp35 antibodies, or antigen-binding fragments, variants, or derivatives thereof of the invention also include derivatives that are modified, e.g., by the covalent attachment of any type of molecule to the antibody such that covalent attachment does not prevent the antibody from specifically binding to its cognate epitope. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

In certain embodiments, Sp35 antibodies, or antigen-binding fragments, variants, or derivatives thereof of the invention will not elicit a deleterious immune response in the animal to be treated, e.g., in a human. In one embodiment, Sp35 antibodies, or antigen-binding fragments, variants, or derivatives thereof of the invention are modified to reduce their immunogenicity using art-recognized techniques. For example, antibodies can be humanized, primatized, deimmunized, or chimeric antibodies can be made. These types of antibodies are derived from a non-human antibody, typically a murine or primate antibody, that retains or substantially retains the antigen-binding properties of the parent antibody, but which is less immunogenic in humans. This may be achieved by various methods, including (a) grafting the entire non-human variable domains onto human constant regions to generate chimeric antibodies; (b) grafting at least a part of one or more of the non-human complementarity determining regions (CDRs) into a human framework and constant regions with or without retention of critical framework residues; or (c) transplanting the entire non-human variable domains, but "cloaking" them with a human-like section by replacement of surface residues. Such methods are disclosed in Morrison et al., *Proc. Natl. Acad. Sci.* 81:6851-6855 (1984); Morrison et al., *Adv. Immunol.* 44:65-92 (1988); Verhoeyen et al., *Science* 239:1534-1536 (1988); Padlan, *Molec. Immun.* 28:489-498 (1991); Padlan, *Molec. Immun.* 31:169-217 (1994), and U.S. Pat. Nos. 5,585,089, 5,693,761, 5,693,762, and 6,190,370, all of which are hereby incorporated by reference in their entirety.

De-immunization can also be used to decrease the immunogenicity of an antibody. As used herein, the term "de-immunization" includes alteration of an antibody to modify T cell epitopes (see, e.g., WO9852976A1, WO0034317A2). For example, $V_H$ and $V_L$ sequences from the starting antibody are analyzed and a human T cell epitope "map" from each V region showing the location of epitopes in relation to complementarity-determining regions (CDRs) and other key residues within the sequence. Individual T cell epitopes from the T cell epitope map are analyzed in order to identify alternative amino acid substitutions with a low risk of altering activity of the final antibody. A range of alternative $V_H$ and $V_L$ sequences are designed comprising combinations of amino acid substitutions and these sequences are subsequently incorporated into a range of binding polypeptides, e.g., Sp35-specific antibodies or immunospecific fragments thereof for use in the diagnostic and treatment methods disclosed herein, which are then tested for function. Typically, between 12 and 24 variant antibodies are generated and tested. Complete heavy and light chain genes comprising modified V and human C regions are then cloned into expression vectors and the subsequent plasmids introduced into cell lines for the production of whole antibody. The antibodies are then compared in appropriate biochemical and biological assays, and the optimal variant is identified.

Sp35 antibodies, or antigen-binding fragments, variants, or derivatives thereof of the invention may be generated by any suitable method known in the art. Polyclonal antibodies to an antigen of interest can be produced by various procedures well known in the art. For example, an Sp35 antibody, e.g., a binding polypeptide, e.g., an Sp35-specific antibody or immunospecific fragment thereof can be administered to various host animals including, but not limited to, rabbits, mice, rats, chickens, hamsters, goats, donkeys, etc., to induce the production of sera containing polyclonal antibodies specific for the antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al.,

*Antibodies: A Laboratory Manual*, Cold Spring Harbor Laboratory Press, 2nd ed. (1988); Hammerling et al., in: *Monoclonal Antibodies and T-Cell Hybridomas* Elsevier, N.Y., 563-681 (1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced. Thus, the term "monoclonal antibody" is not limited to antibodies produced through hybridoma technology. Monoclonal antibodies can be prepared using Sp35 knockout mice to increase the regions of epitope recognition. Monoclonal antibodies can be prepared using a wide variety of techniques known in the art including the use of hybridoma and recombinant and phage display technology as described elsewhere herein.

Using art recognized protocols, in one example, antibodies are raised in mammals by multiple subcutaneous or intraperitoneal injections of the relevant antigen (e.g., purified tumor associated antigens such as Sp35 or cells or cellular extracts comprising such antigens) and an adjuvant. This immunization typically elicits an immune response that comprises production of antigen-reactive antibodies from activated splenocytes or lymphocytes. While the resulting antibodies may be harvested from the serum of the animal to provide polyclonal preparations, it is often desirable to isolate individual lymphocytes from the spleen, lymph nodes or peripheral blood to provide homogenous preparations of monoclonal antibodies (MAbs). Preferably, the lymphocytes are obtained from the spleen.

In this well known process (Kohler et al., *Nature* 256:495 (1975)) the relatively short-lived, or mortal, lymphocytes from a mammal which has been injected with antigen are fused with an immortal tumor cell line (e.g. a myeloma cell line), thus, producing hybrid cells or "hybridomas" which are both immortal and capable of producing the genetically coded antibody of the B cell. The resulting hybrids are segregated into single genetic strains by selection, dilution, and regrowth with each individual strain comprising specific genes for the formation of a single antibody. They produce antibodies which are homogeneous against a desired antigen and, in reference to their pure genetic parentage, are termed "monoclonal."

Hybridoma cells thus prepared are seeded and grown in a suitable culture medium that preferably contains one or more substances that inhibit the growth or survival of the unfused, parental myeloma cells. Those skilled in the art will appreciate that reagents, cell lines and media for the formation, selection and growth of hybridomas are commercially available from a number of sources and standardized protocols are well established. Generally, culture medium in which the hybridoma cells are growing is assayed for production of monoclonal antibodies against the desired antigen. Preferably, the binding specificity of the monoclonal antibodies produced by hybridoma cells is determined by in vitro assays such as immunoprecipitation, radioimmunoassay (RIA) or enzyme-linked immunoabsorbent assay (ELISA). After hybridoma cells are identified that produce antibodies of the desired specificity, affinity and/or activity, the clones may be subcloned by limiting dilution procedures and grown by standard methods (Goding, *Monoclonal Antibodies: Principles and Practice*, Academic Press, pp 59-103 (1986)). It will further be appreciated that the monoclonal antibodies secreted by the subclones may be separated from culture medium, ascites fluid or serum by conventional purification procedures such as, for example, protein-A, hydroxylapatite chromatography, gel electrophoresis, dialysis or affinity chromatography.

Antibody fragments that recognize specific epitopes may be generated by known techniques. For example, Fab and F(ab')$_2$ fragments may be produced by proteolytic cleavage of immunoglobulin molecules, using enzymes such as papain (to produce Fab fragments) or pepsin (to produce F(ab')$_2$ fragments). F(ab')$_2$ fragments contain the variable region, the light chain constant region and the $C_H1$ domain of the heavy chain.

Those skilled in the art will also appreciate that DNA encoding antibodies or antibody fragments (e.g., antigen binding sites) may also be derived from antibody libraries, such as phage display libraries. In a particular, such phage can be utilized to display antigen-binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv OE DAB (individual Fv region from light or heavy chains) or disulfide stabilized Fv antibody domains recombinantly fused to either the phage gene III or gene VIII protein. Exemplary methods are set forth, for example, in EP 368 684 B1; U.S. Pat. No. 5,969,108, Hoogenboom, H. R. and Chames, *Immunol. Today* 21:371 (2000); Nagy et al. *Nat. Med.* 8:801 (2002); Huie et al., *Proc. Natl. Acad. Sci. USA* 98:2682 (2001); Lui et al., *J. Mol. Biol.* 315:1063 (2002), each of which is incorporated herein by reference. Several publications (e.g., Marks et al., *Bio/Technology* 10:779-783 (1992)) have described the production of high affinity human antibodies by chain shuffling, as well as combinatorial infection and in vivo recombination as a strategy for constructing large phage libraries. In another embodiment, Ribosomal display can be used to replace bacteriophage as the display platform (see, e.g., Hanes et al., *Nat. Biotechnol.* 18:1287 (2000); Wilson et al., *Proc. Natl. Acad. Sci. USA* 98:3750 (2001); or Irving et al., *J. Immunol. Methods* 248:31 (2001)). In yet another embodiment, cell surface libraries can be screened for antibodies (Boder et al., *Proc. Natl. Acad. Sci. USA* 97:10701 (2000); Daugherty et al., *J. Immunol. Methods* 243:211 (2000)). Such procedures provide alternatives to traditional hybridoma techniques for the isolation and subsequent cloning of monoclonal antibodies.

In phage display methods, functional antibody domains are displayed on the surface of phage particles which carry the polynucleotide sequences encoding them. For example, DNA sequences encoding $V_H$ and $V_L$ regions are amplified from animal cDNA libraries (e.g., human or murine cDNA libraries of lymphoid tissues) or synthetic cDNA libraries. In certain embodiments, the DNA encoding the $V_H$ and $V_L$ regions are joined together by an scFv linker by PCR and cloned into a phagemid vector (e.g., p CANTAB 6 or pComb 3 HSS). The vector is electroporated in *E. coli* and the *E. coli* is infected with helper phage. Phage used in these methods are typically filamentous phage including fd and M13 and the $V_H$ or $V_L$ regions are usually recombinantly fused to either the phage gene III or gene VIII. Phage expressing an antigen binding domain that binds to an antigen of interest (i.e., an Sp35 polypeptide or a fragment thereof) can be selected or identified with antigen, e.g., using labeled antigen or antigen bound or captured to a solid surface or bead.

Additional examples of phage display methods that can be used to make the antibodies include those disclosed in Brinkman et al., *J. Immunol. Methods* 182:41-50 (1995); Ames et al., *J. Immunol. Methods* 184:177-186 (1995); Kettleborough et al., *Eur. J. Immunol.* 24:952-958 (1994); Persic et al., *Gene* 187:9-18 (1997); Burton et al., *Advances in Immunology* 57:191-280 (1994); PCT Application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria. For example, techniques to recombinantly produce Fab, Fab' and F(ab')$_2$ fragments can also be employed using methods known in the art such as those disclosed in PCT publication WO 92/22324; Mullinax et al., *BioTechniques* 12(6):864-869 (1992); and Sawai et al., *AJRI* 34:26-34 (1995); and Better et al., *Science* 240:1041-1043 (1988) (said references incorporated by reference in their entireties).

Examples of techniques which can be used to produce single-chain Fvs and antibodies include those described in U.S. Pat. Nos. 4,946,778 and 5,258,498; Huston et al., *Methods in Enzymology* 203:46-88 (1991); Shu et al., *PNAS* 90:7995-7999 (1993); and Skerra et al., *Science* 240:1038-1040 (1988). For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See, e.g., Morrison, *Science* 229:1202 (1985); Oi et al., *BioTechniques* 4:214 (1986); Gillies et al., *J. Immunol. Methods* 125:191-202 (1989); U.S. Pat. Nos. 5,807,715; 4,816,567; and 4,816397, which are incorporated herein by reference in their entireties. Humanized antibodies are antibody molecules derived from a non-human species antibody that bind the desired antigen having one or more complementarity determining regions (CDRs) from the non-human species and framework regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., *Nature* 332:323 (1988), which are incorporated herein by reference in their entireties.) Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, *Molecular Immunology* 28(4/5):489-498 (1991); Studnicka et al., *Protein Engineering* 7(6):805-814 (1994); Roguska. et al., *PNAS* 91:969-973 (1994)), and chain shuffling (U.S. Pat. No. 5,565,332, which is incorporated by reference in its entirety).

Completely human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered nonfunctional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring that express human antibodies. The transgenic mice are immunized in the normal fashion with a selected antigen, e.g., all or a portion of a desired target polypeptide. Monoclonal antibodies directed against the antigen can be obtained from the immunized, transgenic mice using conventional hybridoma technology. The human immunoglobulin transgenes harbored by the transgenic mice rearrange during B-cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar *Int. Rev. Immunol.* 13:65-93 (1995). For a detailed discussion of this technology for producing human antibodies and human monoclonal antibodies and protocols for producing such antibodies, see, e.g., PCT publications WO 98/24893; WO 96/34096; WO 96/33735; U.S. Pat. Nos. 5,413,923; 5,625,126; 5,633,425; 5,569,825; 5,661,016; 5,545,806; 5,814,318; and 5,939,598, which are incorporated by reference herein in their entirety. In addition, companies such as Abgenix, Inc. (Freemont, Calif.) and GenPharm (San Jose, Calif.) can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., *Bio/Technology* 12:899-903 (1988). See also, U.S. Pat. No. 5,565,332, which is incorporated by reference in its entirety.)

Further, antibodies to target polypeptides of the invention can, in turn, be utilized to generate anti-idiotype antibodies that "mimic" target polypeptides using techniques well known to those skilled in the art. (See, e.g., Greenspan & Bona, *FASEB J.* 7(5):437-444 (1989) and Nissinoff, *J. Immunol.* 147(8):2429-2438 (1991)). For example, antibodies which bind to and competitively inhibit polypeptide multimerization and/or binding of a polypeptide of the invention to a ligand can be used to generate anti-idiotypes that "mimic" the polypeptide multimerization and/or binding domain and, as a consequence, bind to and neutralize polypeptide and/or its ligand. Such neutralizing anti-idiotypes or Fab fragments of such anti-idiotypes can be used in therapeutic regimens to neutralize polypeptide ligand. For example, such anti-idiotypic antibodies can be used to bind a desired target polypeptide and/or to bind its ligands/receptors, and thereby block its biological activity.

In another embodiment, DNA encoding desired monoclonal antibodies may be readily isolated and sequenced using conventional procedures (e.g., by using oligonucleotide probes that are capable of binding specifically to genes encoding the heavy and light chains of murine antibodies). The isolated and subcloned hybridoma cells serve as a preferred source of such DNA. Once isolated, the DNA may be placed into expression vectors, which are then transfected into prokaryotic or eukaryotic host cells such as E. coli cells, simian COS cells, Chinese Hamster Ovary (CHO) cells or myeloma cells that do not otherwise produce immunoglobulins. More particularly, the isolated DNA (which may be synthetic as described herein) may be used to clone constant and variable region sequences for the manufacture antibodies as described in Newman et al., U.S. Pat. No. 5,658,570, filed Jan. 25, 1995, which is incorporated by reference herein. Essentially, this entails extraction of RNA from the selected cells, conversion to cDNA, and amplification by PCR using Ig specific primers. Suitable primers for this purpose are also described in U.S. Pat. No. 5,658,570. As will be discussed in more detail below, transformed cells expressing the desired antibody may be grown up in relatively large quantities to provide clinical and commercial supplies of the immunoglobulin.

In one embodiment, an Sp35 antibody of the invention comprises at least one heavy or light chain CDR of an antibody molecule. In another embodiment, an Sp35 antibody of the invention comprises at least two CDRs from one or more antibody molecules. In another embodiment, an Sp35 antibody of the invention comprises at least three CDRs from one or more antibody molecules. In another embodiment, an Sp35 antibody of the invention comprises at least four CDRs from one or more antibody molecules. In another embodiment, an Sp35 antibody of the invention comprises at least five CDRs from one or more antibody molecules. In another embodiment, an Sp35 antibody of the invention comprises at least six CDRs from one or more antibody molecules. Exemplary antibody molecules comprising at least one CDR that can be included in the subject Sp35 antibodies are described herein.

In a specific embodiment, the amino acid sequence of the heavy and/or light chain variable domains may be inspected to identify the sequences of the complementarity determining regions (CDRs) by methods that are well know in the art, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody. The framework regions may be naturally occurring or consensus framework regions, and preferably human framework regions (see, e.g., Chothia et al., *J. Mol. Biol.* 278:457-479 (1998) for a listing of human framework regions). Preferably, the polynucleotide generated by the combination of the framework regions and CDRs encodes an antibody that specifically binds to at least one epitope of a desired polypeptide, e.g., Sp35. Preferably, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

In addition, techniques developed for the production of "chimeric antibodies" (Morrison et al., *Proc. Natl. Acad. Sci.* 81:851-855 (1984); Neuberger et al., *Nature* 312:604-608 (1984); Takeda et al., *Nature* 314:452-454 (1985)) by splicing genes from a mouse antibody molecule of appropriate antigen specificity together with genes from a human antibody molecule of appropriate biological activity can be used. As used herein, a chimeric antibody is a molecule in which different portions are derived from different animal species, such as those having a variable region derived from a murine monoclonal antibody and a human immunoglobulin constant region, e.g., humanized antibodies.

Alternatively, techniques described for the production of single chain antibodies (U.S. Pat. No. 4,694,778; Bird, *Science* 242:423-442 (1988); Huston et al., *Proc. Natl. Acad. Sci. USA* 85:5879-5883 (1988); and Ward et al., *Nature* 334:544-554 (1989)) can be adapted to produce single chain antibodies. Single chain antibodies are formed by linking the heavy and light chain fragments of the Fv region via an amino acid bridge, resulting in a single chain antibody. Techniques for the assembly of functional Fv fragments in *E. coli* may also be used (Skerra et al., *Science* 242:1038-1041 (1988)).

Yet other embodiments of the present invention comprise the generation of human or substantially human antibodies in transgenic animals (e.g., mice) that are incapable of endogenous immunoglobulin production (see e.g., U.S. Pat. Nos. 6,075,181, 5,939,598, 5,591,669 and 5,589,369 each of which is incorporated herein by reference). For example, it has been described that the homozygous deletion of the antibody heavy-chain joining region in chimeric and germ-line mutant mice results in complete inhibition of endogenous antibody production. Transfer of a human immunoglobulin gene array to such germ line mutant mice will result in the production of human antibodies upon antigen challenge. Another preferred means of generating human antibodies using SCID mice is disclosed in U.S. Pat. No. 5,811,524 which is incorporated herein by reference. It will be appreciated that the genetic material associated with these human antibodies may also be isolated and manipulated as described herein.

Yet another highly efficient means for generating recombinant antibodies is disclosed by Newman, *Biotechnology* 10: 1455-1460 (1992). Specifically, this technique results in the generation of primatized antibodies that contain monkey variable domains and human constant sequences. This reference is incorporated by reference in its entirety herein. Moreover, this technique is also described in commonly assigned U.S. Pat. Nos. 5,658,570, 5,693,780 and 5,756,096 each of which is incorporated herein by reference.

In another embodiment, lymphocytes can be selected by micromanipulation and the variable genes isolated. For example, peripheral blood mononuclear cells can be isolated from an immunized mammal and cultured for about 7 days in vitro. The cultures can be screened for specific IgGs that meet the screening criteria. Cells from positive wells can be isolated. Individual Ig-producing B cells can be isolated by FACS or by identifying them in a complement-mediated hemolytic plaque assay. Ig-producing B cells can be micromanipulated into a tube and the $V_H$ and $V_L$ genes can be amplified using, e.g., RT-PCR. The $V_H$ and $V_L$ genes can be cloned into an antibody expression vector and transfected into cells (e.g., eukaryotic or prokaryotic cells) for expression.

Alternatively, antibody-producing cell lines may be selected and cultured using techniques well known to the skilled artisan. Such techniques are described in a variety of laboratory manuals and primary publications. In this respect, techniques suitable for use in the invention as described below are described in *Current Protocols in Immunology*, Coligan et al., Eds., Green Publishing Associates and Wiley-Interscience, John Wiley and Sons, New York (1991) which is herein incorporated by reference in its entirety, including supplements.

Antibodies for use in the diagnostic and therapeutic methods disclosed herein can be produced by any method known in the art for the synthesis of antibodies, in particular, by chemical synthesis or preferably, by recombinant expression techniques as described herein.

In one embodiment, an Sp35 antibody, or antigen-binding fragment, variant, or derivative thereof of the invention comprises a synthetic constant region wherein one or more domains are partially or entirely deleted ("domain-deleted antibodies"). In certain embodiments compatible modified antibodies will comprise domain deleted constructs or variants wherein the entire $C_H2$ domain has been removed ($\Delta C_H2$ constructs). For other embodiments a short connecting peptide may be substituted for the deleted domain to provide flexibility and freedom of movement for the variable region. Those skilled in the art will appreciate that such constructs are particularly preferred due to the regulatory properties of the $C_H2$ domain on the catabolic rate of the antibody. Domain deleted constructs can be derived using a vector (e.g., from Biogen IDEC Incorporated) encoding an $IgG_1$ human constant domain (see, e.g., WO 02/060955A2 and WO02/096948A2, which are incorporated by reference in their entireties). This exemplary vector was engineered to delete the $C_H2$ domain and provide a synthetic vector expressing a domain deleted $IgG_1$ constant region.

In certain embodiments, Sp35 antibodies, or antigen-binding fragments, variants, or derivatives thereof of the invention are minibodies. Minibodies can be made using methods described in the art (see, e.g., see e.g., U.S. Pat. No. 5,837,821 or WO 94/09817A1, which are incorporated by reference in their entireties).

In one embodiment, an Sp35 antibody, or antigen-binding fragment, variant, or derivative thereof of the invention comprises an immunoglobulin heavy chain having deletion or substitution of a few or even a single amino acid as long as it permits association between the monomeric subunits. For example, the mutation of a single amino acid in selected areas of the $C_H2$ domain may be enough to substantially reduce Fc binding and thereby increase tumor localization. Similarly, it may be desirable to simply delete that part of one or more constant region domains that control the effector function (e.g. complement binding) to be modulated. Such partial deletions of the constant regions may improve selected characteristics of the antibody (serum half-life) while leaving other desirable functions associated with the subject constant region domain intact. Moreover, as alluded to above, the constant regions of the disclosed antibodies may be synthetic through the mutation or substitution of one or more amino acids that enhances the profile of the resulting construct. In this respect it may be possible to disrupt the activity provided by a conserved binding site (e.g. Fc binding) while substantially maintaining the configuration and immunogenic profile of the modified antibody. Yet other embodiments comprise the addition of one or more amino acids to the constant region to enhance desirable characteristics such as effector function or provide for more cytotoxin or carbohydrate attachment. In such embodiments it may be desirable to insert or replicate specific sequences derived from selected constant region domains.

The present invention also provides antibodies that comprise, consist essentially of, or consist of, variants (including derivatives) of antibody molecules (e.g., the $V_H$ regions and/or $V_L$ regions) described herein, which antibodies or fragments thereof immunospecifically bind to an Sp35 polypeptide or fragment or variant thereof. Standard techniques known to those of skill in the art can be used to introduce mutations in the nucleotide sequence encoding an Sp35 antibody, including, but not limited to, site-directed mutagenesis and PCR-mediated mutagenesis which result in amino acid substitutions. Preferably, the variants (including derivatives) encode less than 50 amino acid substitutions, less than 40 amino acid substitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the reference $V_H$ region, $V_H$CDR1, $V_H$CDR2, $V_H$CDR3, $V_L$ region, $V_L$CDR1, $V_L$CDR2, or $V_L$CDR3. A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity (e.g., the ability to bind an Sp35 polypeptide).

For example, it is possible to introduce mutations only in framework regions or only in CDR regions of an antibody molecule. Introduced mutations may be silent or neutral missense mutations, i.e., have no, or little, effect on an antibody's ability to bind antigen. These types of mutations may be useful to optimize codon usage, or improve a hybridoma's antibody production. Alternatively, non-neutral missense mutations may alter an antibody's ability to bind antigen. The location of most silent and neutral missense mutations is likely to be in the framework regions, while the location of most non-neutral missense mutations is likely to be in CDR, though this is not an absolute requirement. One of skill in the art would be able to design and test mutant molecules with desired properties such as no alteration in antigen binding activity or alteration in binding activity (e.g., improvements in antigen binding activity or change in antibody specificity). Following mutagenesis, the encoded protein may routinely be expressed and the functional and/or biological activity of the encoded protein, (e.g., ability to immunospecifically bind at least one epitope of an Sp35 polypeptide) can be determined using techniques described herein or by routinely modifying techniques known in the art.

IV. Polynucleotides Encoding Sp35 Antibodies

The present invention also provides for nucleic acid molecules encoding Sp35 antibodies, or antigen-binding fragments, variants, or derivatives thereof of the invention.

In one embodiment, the present invention provides an isolated polynucleotide comprising, consisting essentially of, or consisting of a nucleic acid encoding an immunoglobulin heavy chain variable region ($V_H$), where at least one of the CDRs of the heavy chain variable region or at least two of the CDRs of the heavy chain variable region are at least 80%, 85%, 90% or 95% identical to reference heavy chain CDR1, CDR2, or CDR3 amino acid sequences from monoclonal Sp35 antibodies disclosed herein. Alternatively, the CDR1, CDR2, and CDR3 regions of the $V_H$ are at least 80%, 85%, 90% or 95% identical to reference heavy chain CDR1, CDR2, and CDR3 amino acid sequences from monoclonal Sp35 antibodies disclosed herein. Thus, according to this embodiment a heavy chain variable region of the invention has CDR1, CDR2, or CDR3 polypeptide sequences related to the polypeptide sequences shown in Table 4:

TABLE 4

Reference VH CDR1, CDR2, and CDR3 amino acid sequences*

| Antibody Name | VH-CDR1 | VH-CDR2 | VH-CDR3 |
| --- | --- | --- | --- |
| Li10 | P = TYPMV (SEQ ID NO: 6) N = ACTTACCCTATGGTT (SEQ ID NO: 5) | P = WIGPSGGVTAYADSVKG (SEQ ID NO: 8) N = TGGATCGGTCCTTCT GGTGGCGTTACTGCTTA TGCTGACTCCGTTAAAGGT (SEQ ID NO: 7) | P = PYSSGWWDFDL (SEQ ID NO: 10) N = CCCTATAGCAGTGGCT GGTGGGACTTCGATCTC (SEQ ID NO: 9) |
| Li07 | P = MYFMG (SEQ ID NO: 12) N = ATGTACTTTATGGGT (SEQ ID NO: 11) | P = SISPSGGFTSYADSVKG (SEQ ID NO: 14) N = TCTATCTCTCCTTCTGGTGGCTTTAC TTCTTATGCTGACTCCGTTAAAGGT (SEQ ID NO: 13) | P = DRHAFDI (SEQ ID NO: 16) N = GATCGGCATGCTTTTGATATC (SEQ ID NO: 15) |
| Li05 | P = AYAMG (SEQ ID NO: 18) N = CTTACGCTATGGGT (SEQ ID NO: 17) | P = SIVSSGGYTDYADSVKG (SEQ ID NO: 20) N = TCTATCGTTTCTTCTGGTGGCT ATACTGATTATGCTGACTCCGTTAAAGGT (SEQ ID NO: 19) | P = EGDHNAFDI (SEQ ID NO: 22) N = GAGGGTGACCATAATGCTTTT GATATC (SEQ ID NO: 21) |
| Li11 | P = SYAMY (SEQ ID NO: 24) N = TCTTACGCTATGTAT (SEQ ID NO: 23) | P = SISTSGGYTGYADSVKG (SEQ ID NO: 26) N = TCTATCTCTACTTCTGGTGGCTA TACTGGTTATGCTGACTCCGTTAAAGGT (SEQ ID NO: 25) | P = DTSDNDYYYMDV (SEQ ID NO: 28) N = GATACCAGCGATAATGAC TACTACTACATGGACGTC (SEQ ID NO: 27) |
| Li01 | P = KYQMT (SEQ ID NO: 30) N == AAGTACCAGATGAC (SEQ ID NO: 29) | P = SIYPSGGNTVYADSVKG (SEQ ID NO: 32) N = TCTATCTATCCTTCTGGTGGCAA TACTGTTTATGCTGACTCCGTTAAAGGT (SEQ ID NO: 31) | P = GTTEAVFDY (SEQ ID NO: 34) N = GGGACTACAGAGGCAGTCTT TGACTAC (SEQ ID NO: 33) |
| Li12 | P = QYNMF (SEQ ID NO: 36) N = CAGTACAATATGTTT (SEQ ID NO: 35) | P = RISSSGGMTMYADSVKG (SEQ ID NO: 38) N = CGTATCTCTTCTTCTGGTGGCAT GACTATGTATGCTGACTCCGTTAAAGGT (SEQ ID NO: 37) | P = EALRPYCSGGSCYSDYYYGMDV (SEQ ID NO: 40) N = GAAGCGTTACGGCCTTATTG TAGTGGTGGTAGCTGCTACTCCG ACTACTACTACTACGGTATGGAC GTC (SEQ ID NO: 39) |
| Li06 | P = EYPMD (SEQ ID NO: 42) N = GAGTACCCTATGGAT (SEQ ID NO: 41) | P = SIYSSGGSTVYADSIKG (SEQ ID NO: 44) N = TCTATCTATTCTTCTGGTGGCTC TACTGTTTATGCTGACTCCATTAAAGGT (SEQ ID NO: 43) | P = EGDSDAFDI (SEQ ID NO: 46) N = GAGGGTGACTCTGATGCTTTT GATATC (SEQ ID NO: 45) |
| Li08 | P = HYEMV (SEQ ID NO: 48) N = CATTACGAGATGGTT (SEQ ID NO: 47) | P = SIRSSGGATKYADSVKG (SEQ ID NO: 50) N = TCTATCCGTTCTTCTGGTGGCGCTAC TAAGTATGCTGACTCCGTTAAAGGT (SEQ ID NO: 49) | P = ESPDDYFDY (SEQ ID NO: 52) N = GAGTCGCCAGACGACTACTTT GACTAC (SEQ ID NO: 51) |
| Li03 | P = QYPME (SEQ ID NO: 54) N = CAGTACCCTATGGAG (SEQ ID NO: 53) | P = GIYPSGGSTVYADSVKG (SEQ ID NO: 56) N = GGTATCTATCCTTCTGGTGGCTCTA CTGTTTATGCTGACTCCGTTAAAGGT (SEQ ID NO: 55) | P = AGQWLGDFDY (SEQ ID NO: 58) N = GCGGGGCAGTGGCTGGGGGAC TTTGACTAC (SEQ ID NO: 57) |

TABLE 4-continued

Reference VH CDR1, CDR2, and CDR3 amino acid sequences*

| Antibody Name | VH-CDR1 | VH-CDR2 | VH-CDR3 |
|---|---|---|---|
| Li09 | P = MYSMV (SEQ ID NO: 60)<br>N = ATGTACTCTATGGTT (SEQ ID NO: 59) | P = YISPSGGKTMYADSVKG (SEQ ID NO: 62)<br>N = TATATCTCTCCTTCTGGTGGCAAG ACTATGTATGCTGACTCCGTTAAAGGT (SEQ ID NO: 61) | P = DSRRYYDFWSGYHNYYYYMDV (SEQ ID NO: 64)<br>N = GATTCGAGACGCCGGTATTACGA TTTTTGGAGTGGTTATCACAACTACT ACTACTACATGGACGTC (SEQ ID NO: 63) |
| Li04 | P = RYNMG (SEQ ID NO: 66)<br>N = CGTTACAATATGGGT (SEQ ID NO: 65) | P = VIYPSGGGTHYADSVKG (SEQ ID NO: 68)<br>N = GTTATCTATCCTTCTGGTGGCGGT ACTCATTATGCTGACTCCGTTAAAGGT (SEQ ID NO: 67) | P = SIADDAFDI (SEQ ID NO: 70)<br>N = TCTATAGCAGATGATGCTTTTGATATC (SEQ ID NO: 69) |
| Li02 | P = TYEMI (SEQ ID NO: 72)<br>N = ACTTACGAGATGATT (SEQ ID NO: 71) | P = SIGPSGGLTWYADSVKG (SEQ ID NO: 74)<br>N = TCTATCGGTCCTTCTGGTGGCC TTACTTGGTATGCTGACTCCGTTAAA (SEQ ID NO: 73) | P = MYYCVRIDDSSGWAFDI (SEQ ID NO: 76)<br>N = ATGTATTACTGTGTACGGATTGATGA TAGTAGTGGTTGGGCTTTTGATATC (SEQ ID NO: 75) |
| Li13 | P = HYEMY (SEQ ID NO: 389) | P = RIVSSGGFTKYADSVKG (SEQ ID NO: 390) | P = EGDNDAFDI (SEQ ID NO: 391) |
| Li32 | P = AYMMQ (SEQ ID NO: 395) | P = SISPSGGNTKYADSVKG (SEQ ID NO: 396) | P = GDYGYWFDP (SEQ ID NO: 397) |
| Li33 | P = IYPMF (SEQ ID NO: 401) | P = WIGPSGGITKYADSVKG (SEQ ID NO: 402) | P = EGHNDWYFDL (SEQ ID NO: 403) |
| Li34 | P = NYEMY (SEQ ID NO: 407) | P = GIYSSGGITVYADSVKG (SEQ ID NO: 408) | P = AAILDWYFDL (SEQ ID NO: 409) |
| 1A47 | P = NYGMN (SEQ ID NO: 77) | P = WINTDTGEPTYTEDFQG (SEQ ID NO: 78) | P = EGVHFDY (SEQ ID NO: 79) |
| 2F3 | P = FSDAWLD (SEQ ID NO: 80) | P = EIRSKANNHATNYAESVKG (SEQ ID NO: 81) | P = SFAY (SEQ ID NO: 82) |
| 3P1D10.2C3 and 3P1E11.3B7 | P = SSWTQ (SEQ ID NO: 83) | P = AIYPGDGDTRYTQKFKG (SEQ ID NO: 84) | P = HNSYGMDY (SEQ ID NO: 85) |
| L1a.01 | P = GYSFTNYWIG (SEQ ID NO: 195) | P = IIDPDDSYTTYSPSFQG (SEQ ID NO: 196) | P = AEFYWGAYDG (SEQ ID NO: 197) |
| L1a.02 | P = GGSIRGNYWS (SEQ ID NO: 198) | P = SINYSGFTNPSLKG (SEQ ID NO: 199) | P = VRHWYFDV (SEQ ID NO: 200) |
| L1a.03 | P = GYTFNGFDMH (SEQ ID NO: 201) | P = WIDPYNGSTFYAQKFQG (SEQ ID NO: 202) | P = DFYMDGHYYIFDV (SEQ ID NO: 203) |
| L1a.04 | P = GYSFSNYYIH (SEQ ID NO: 204) | P = IIDPGDSFTSYSPSFQG (SEQ ID NO: 205) | P = DLAWIDYGFDY (SEQ ID NO: 206) |
| L1a.05 | P = GFTFTSHITVS (SEQ ID NO: 207) | P = SITGNGSTTYYADSVKG (SEQ ID NO: 208) | P = FYGDFDS (SEQ ID NO: 209) |
| L1a.06 | P = GFTFSSNWMS (SEQ ID NO: 210) | P = TIFYSGSSTYYADSVKG (SEQ ID NO: 211) | P = DLPMKGFIQQRYGFDDV (SEQ ID NO: 212) |
| L1a.07 | P = GFTFSGYAIS (SEQ ID NO: 213) | P = TIWGSGSTTYYADSVKG (SEQ ID NO: 214) | P = EYWYYDQFTAV (SEQ ID NO: 215) |
| L1a.08 | P = GDSVSSNSAAWS (SEQ ID NO: 216) | P = RIYYRSKWYNDYAVSVKS (SEQ ID NO: 217) | P = EVYSAGIMDY (SEQ ID NO: 218) |
| L1a.09 | P = GYSFTNHWIG (SEQ ID NO: 219) | P = IIDPSDSDTNYSPSFQG (SEQ ID NO: 220) | P = GFYGIADTFDV (SEQ ID NO: 221) |
| L1a.10 | P = GYSFTNYWIA (SEQ ID NO: 222) | P = MIYPDDSNTNYSPSFQG (SEQ ID NO: 223) | P = TNYLGFYDS (SEQ ID NO: 224) |
| L1a.11 | P = GFTFSDYGIS (SEQ ID NO: 225) | P = NILYDGSETYYADSVKG (SEQ ID NO: 226) | P = GYPTDDYSFDI (SEQ ID NO: 227) |

TABLE 4-continued

Reference VH CDR1, CDR2, and CDR3 amino acid sequences*

| Antibody Name | VH-CDR1 | VH-CDR2 | VH-CDR3 |
|---|---|---|---|
| L1a.12 | P = GDSVSDNSAAWG (SEQ ID NO: 228) | P = RIYYRSKWYNDYAVSVKS (SEQ ID NO: 229) | P = GRHEYGGLGYAEAMDH (SEQ ID NO: 230) |
| L1a.13 | P = GFTFSSYAMS (SEQ ID NO: 231) | P = AISGSGGSTYYADSVKG (SEQ ID NO: 232) | P = HYTYMHFEDY (SEQ ID NO: 233) |

*Determined by the Kabat system (see supra).
N = nucleotide sequence, P = polypeptide sequence.

In certain embodiments, an antibody or antigen-binding fragment comprising the VH encoded by the polynucleotide specifically or preferentially binds to Sp35.

In another embodiment, the present invention provides an isolated polynucleotide comprising, consisting essentially of, or consisting of a nucleic acid encoding an immunoglobulin heavy chain variable region (VH) in which the CDR1, CDR2, and CDR3 regions have polypeptide sequences which are identical to the CDR1, CDR2, and CDR3 groups shown in Table 4. In certain embodiments, an antibody or antigen-binding fragment comprising the VH encoded by the polynucleotide specifically or preferentially binds to Sp35.

In a further aspect, the present invention provides an isolated polynucleotide comprising, consisting essentially of, or consisting of a nucleic acid encoding an immunoglobulin heavy chain variable region (VH) in which the CDR1, CDR2, and CDR3 regions are encoded by nucleotide sequences which are identical to the nucleotide sequences which encode the CDR1, CDR2, and CDR3 groups shown in Table 4. In certain embodiments, an antibody or antigen-binding fragment comprising the VH encoded by the polynucleotide specifically or preferentially binds to Sp35.

In certain embodiments, an antibody or antigen-binding fragment thereof comprising, consisting essentially of, or consisting of a VH encoded by one or more of the polynucleotides described above specifically or preferentially binds to the same epitope as a monoclonal antibody selected from the group consisting of: 201', 3A3, 3A6, 1A7, 1G7, 2B10, 2C11, 2F3, 3P1D10.2C3, 3P1E11.3B7, 3P2C6.3G10.2H7, 3P2C9.2G4, 3P4A6.1D9, 3P4A1.2B9, 3P4C2.2D2, 3P4C5.1D8, 3P4C8.2G9, 30-C12 (L100), 38-D01 (Li022), 35-E04 (Li033), 36-C09 (Li04), 30-A11 (Li05), 34-F02 (Li06), 29-E07 (Li07), 34-G04 (Li08), 36-A12 (Li09), 28-D02 (Li10), 30-B01 (Li11), 34-B03 (L12), Li13, Li32, Li33, Li34, 3383 (L1a.1), 3495 (L1a.2), 3563 (L1a.3), 3564 (L1a.4), 3565 (L1a.5), 3566 (L1a.6), 3567 (L1a.7), 3568 (L1a.8), 3569 (L1a.9), 3570 (L1a.10), 3571 (L1a.11), 3582 (L1a.12), and 1968 (L1a.13), or will competitively inhibit such a monoclonal antibody from binding to Sp35.

In certain embodiments, an antibody or antigen-binding fragment thereof comprising, consisting essentially of, or consisting of a VH encoded by one or more of the polynucleotides described above specifically or preferentially binds to an Sp35 polypeptide or fragment thereof, or a Sp35 variant polypeptide, with an affinity characterized by a dissociation constant ($K_D$) no greater than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M.

In another embodiment, the present invention provides an isolated polynucleotide comprising, consisting essentially of, or consisting of a nucleic acid encoding an immunoglobulin light chain variable region (VL), where at least one of the CDRs of the light chain variable region or at least two of the CDRs of the light chain variable region are at least 80%, 85%, 90% or 95% identical to reference light chain CDR1, CDR2, or CDR3 amino acid sequences from monoclonal Sp35 antibodies disclosed herein. Alternatively, the CDR1, CDR2, and CDR3 regions of the VL are at least 80%, 85%, 90% or 95% identical to reference light chain CDR1, CDR2, and CDR3 amino acid sequences from monoclonal Sp35 antibodies disclosed herein. Thus, according to this embodiment a light chain variable region of the invention has CDR1, CDR2, or CDR3 polypeptide sequences related to the polypeptide sequences shown in Table 5:

TABLE 5

Reference VL CDR1, CDR2, and CDR3 amino acid sequences*

| Antibody Name | VL-CDR1 | VL-CDR2 | VL-CDR3 |
|---|---|---|---|
| Li10 | P = RASQGIGNWLA (SEQ ID NO: 87) N = CGGGCGAGTCAGGG TATTGGCAACTGGTTAGCC (SEQ ID NO: 86) | P = AASSLES (SEQ ID NO: 89) N = GCTGCATCCAGTTTGGAAAGT (SEQ ID NO: 88) | P = QQAQTFPLT (SEQ ID NO: 91) N = CAACAGGCTCAGAC TTTCCCGCTCACC (SEQ ID NO: 90) |
| Li07 | P = SGDQLGDKHVA (SEQ ID NO: 93) N = TCTGGAGATCAGTTG GGTGACAAACATGTGGCT (SEQ ID NO: 92) | P = LDIKRPA (SEQ ID NO: 95) N = CTAGACATTAAGAGGCCCGCA (SEQ ID NO: 94) | P = QAWDIKTV (SEQ ID NO: 97) N = CAGGCGTGGGACATC AAGACGGTC (SEQ ID NO: 96) |

TABLE 5-continued

Reference VL CDR1, CDR2, and CDR3 amino acid sequences*

| Antibody Name | VL-CDR1 | VL-CDR2 | VL-CDR3 |
|---|---|---|---|
| Li05 | P = GGDNIGSKSVH (SEQ ID NO: 99) N = GGGGGAGACAACAT TGGAAGTAAGAGTGTCCAC (SEQ ID NO: 98) | P = DDYDRPS (SEQ ID NO: 101) N = GATGATTATGACCGGCCCTCA (SEQ ID NO: 100) | P = QVRDSRTEERV (SEQ ID NO: 103) N = CAGGTGAGGGACAGCCG TACTGAGGAACGGGTG (SEQ ID NO: 102) |
| Li11 | P = RASQEIANYLA (SEQ ID NO: 105) N = CGGGCGAGTCAGGAG ATTGCCAACTACTTAGCC (SEQ ID NO: 104) | P = DTYTLQT (SEQ ID NO: 107) N = GATACATACACTTTGCAGACT (SEQ ID NO: 106) | P = QQADIFPLS (SEQ ID NO: 109) N = CAACAGGCTGACATTTT CCCGCTCTCT (SEQ ID NO: 108) |
| Li01 | P = QASQDISNYLN (SEQ ID NO: 111) N = CAGGCGAGTCAGGA CATTAGCAACTATTTAAAT (SEQ ID NO: 110) | P = DASNLET (SEQ ID NO: 113) N = GATGCATCCAATTTGGAAACA (SEQ ID NO: 112) | P = QQADRFPAVT (SEQ ID NO: 115) N = CAACAGGCTGACAGGTTC CCTGCGGTCACT (SEQ ID NO: 114) |
| Li06 | P = RASQSISSWLA (SEQ ID NO: 117) N = CGGGCCAGTCAGAGTA TTAGTAGCTGGTTGGCC (SEQ ID NO: 116) | P = AASSLRT (SEQ ID NO: 119) N = GCTGCATCCAGTTTACGAACT (SEQ ID NO: 118) | P = LQDYSYPLT (SEQ ID NO: 121) N = CTACAAGATTACAGTTAC CCTCTCACT (SEQ ID NO: 120) |
| Li08 | P = QASQDISYYLN (SEQ ID NO: 123) N = CAGGCGAGTCAGGAC ATTAGTTACTATTTAAAT (SEQ ID NO: 122) | P = DVSNLQT (SEQ ID NO: 125) N = GATGTATCCAATTTGCAAACA (SEQ ID NO: 124) | P = QQSDNLPLT (SEQ ID NO: 127) N = CAACAGTCTGATA ATCTCCCTCTCACT (SEQ ID NO: 126) |
| Li03 | P = RASQSISSYLN (SEQ ID NO: 129) N = GGGCAAGTCAGAGC ATTAGCAGCTATTTAAAT (SEQ ID NO: 128) | P = AASSLQS (SEQ ID NO: 131) N = GCTGCATCCAGTTTGCAAAGT (SEQ ID NO: 130) | P = QQSYSTPWT (SEQ ID NO: 133) N = CAACAGAGTTACA GTACCCCGTGGACG (SEQ ID NO: 132) |
| Li09 | P = RASQSIDTYLN (SEQ ID NO: 135) N = CGCGCAAGTCAGAGC ATCGACACCTATTTAAAT (SEQ ID NO: 134) | P = AASKLED (SEQ ID NO: 137) N = GCTGCATCCAAGTTGGAAGAC (SEQ ID NO: 136) | P = QQSYSPPLT (SEQ ID NO: 139) N = CAACAGAGTTACAG TCCCCCTCTCAC (SEQ ID NO: 138) |
| Li02 | P = SGDKLGDKFAS (SEQ ID NO: 141) N = TCTGGAGATAAATTGG GGGATAAATTTGCTTCC (SEQ ID NO: 140) | P = QDRKRLS (SEQ ID NO: 143) N = CAAGATAGGAAGCGTCTCTCA (SEQ ID NO: 142) | P = QAWDTNTVV (SEQ ID NO: 145) N = CAGGCGTGGGACA CCAACACTGTGGTC (SEQ ID NO: 144) |
| Li13 | P = RASQSVSSYLA (SEQ ID NO: 386) | P = DASNRAT (SEQ ID NO: 387) | P = QQRSNWPMYT (SEQ ID NO: 388) |
| Li32 | P = QASQDISYYLN (SEQ ID NO: 392) | P = DAFILEG (SEQ ID NO: 393) | P = QQSDQLPVT (SEQ ID NO: 394) |
| Li33 | P = RASQSVSSYLA (SEQ ID NO: 398) | P = DASNRAT (SEQ ID NO: 399) | P = QQYDKWPLT (SEQ ID NO: 400) |
| Li34 | P = HASQDISNYLS (SEQ ID NO: 404) | P = DAFNLET (SEQ ID NO: 405) | P = PQHYDNLPFT (SEQ ID NO: 406) |
| 1A47 | P = SASSSVSYMH (SEQ ID NO: 146) | P = DTSKLAS (SEQ ID NO: 147) | P = QQWSSNPFT (SEQ ID NO: 148) |
| 2F3 | P = RASGNIYNYLA (SEQ ID NO: 149) | P = NAKTLPD (SEQ ID NO: 150) | P = QHFWAIPYT (SEQ ID NO: 151) |
| 3P1D10.2C3 | P = KSSQSLLNSGNQKNYLT (SEQ ID NO: 152) | P = WASTRES (SEQ ID NO: 153) | P = QNDYSYPLFT (SEQ ID NO: 154) |
| 3P1E11.3B7 | P = KSSQSLLNSGNQKSYLT (SEQ ID NO: 155) | P = WASTRES (SEQ ID NO: 156) | P = QNDYSYPLFT (SEQ ID NO: 157) |
| L1a.01 | P = SGDSLPSKFVH (SEQ ID NO: 234) | P = RDNNRPS (SEQ ID NO: 235) | P = SSYDALTD (SEQ ID NO: 236) |

TABLE 5-continued

Reference VL CDR1, CDR2, and CDR3 amino acid sequences*

| Antibody Name | VL-CDR1 | VL-CDR2 | VL-CDR3 |
|---|---|---|---|
| L1a.02 | P = RASQSITNSYLG (SEQ ID NO: 237) | P = DASSRAT (SEQ ID NO: 238) | P = QQASDAPE (SEQ ID NO: 239) |
| L1a.03 | P = RASQGINFWLN (SEQ ID NO: 240) | P = AGSNLQS (SEQ ID NO: 241) | P = MQDSDFPF (SEQ ID NO: 242) |
| L1a.04 | P = TGSSSNIGAGYDVS (SEQ ID NO: 243) | P = RNNNRPS (SEQ ID NO: 244) | P = QTYDNSTD (SEQ ID NO: 245) |
| L1a.05 | P = SGDNIRSYYVH (SEQ ID NO: 246) | P = EDSNRPS (SEQ ID NO: 247) | P = QSYDSAILLH (SEQ ID NO: 248) |
| L1a.06 | P = RSSQSLVLRTGYTYLN (SEQ ID NO: 249) | P = LVSNRAS (SEQ ID NO: 250) | P = QQYYGMPL (SEQ ID NO: 251) |
| L1a.07 | P = RASQSVSYQYLA (SEQ ID NO: 252) | P = GASSRAT (SEQ ID NO: 253) | P = QQYGSVPR (SEQ ID NO: 254) |
| L1a.08 | P = SGDSLGSYYVH (SEQ ID NO: 255) | P = DDNDRPS (SEQ ID NO: 256) | P = SAYDYSART (SEQ ID NO: 257) |
| L1a.09 | P = SGDNLGSKYVS (SEQ ID NO: 258) | P = DDDDRPS (SEQ ID NO: 259) | P = SSYDFLNIGL (SEQ ID NO: 260) |
| L1a.10 | P = SGDSLGKKSVH (SEQ ID NO: 261) | P = EDSERPS (SEQ ID NO: 262) | P = SSYTNSVD (SEQ ID NO: 263) |
| L1a.11 | P = SGDNLGKKYVG (SEQ ID NO: 264) | P = DDDNRPS (SEQ ID NO: 265) | P = QSYDDTSI (SEQ ID NO: 266) |
| L1a.12 | P = SGDSLGNKYVH (SEQ ID NO: 267) | P = DDSDRPS (SEQ ID NO: 268) | P = QTWDYVGY (SEQ ID NO: 269) |
| L1a.13 | P = TGTSSDVGGYNYVS (SEQ ID NO: 270) | P = DVSNRPS (SEQ ID NO: 271) | P = QSYDRYRLKN (SEQ ID NO: 272) |

*Determined by the Kabat system (see supra).
N = nucleotide sequence, P = polypeptide sequence.

In certain embodiments, an antibody or antigen-binding fragment comprising the VL encoded by the polynucleotide specifically or preferentially binds to Sp35.

In another embodiment, the present invention provides an isolated polynucleotide comprising, consisting essentially of, or consisting of a nucleic acid encoding an immunoglobulin light chain variable region (VL) in which the CDR1, CDR2, and CDR3 regions have polypeptide sequences which are identical to the CDR1, CDR2, and CDR3 groups shown in Table 5. In certain embodiments, an antibody or antigen-binding fragment comprising the VL encoded by the polynucleotide specifically or preferentially binds to Sp35.

In a further aspect, the present invention provides an isolated polynucleotide comprising, consisting essentially of, or consisting of a nucleic acid encoding an immunoglobulin light chain variable region (VL) in which the CDR1, CDR2, and CDR3 regions are encoded by nucleotide sequences which are identical to the nucleotide sequences which encode the CDR1, CDR2, and CDR3 groups shown in Table 5. In certain embodiments, an antibody or antigen-binding fragment comprising the VL encoded by the polynucleotide specifically or preferentially binds to Sp35.

In certain embodiments, an antibody or antigen-binding fragment thereof comprising, consisting essentially of, or consisting of a VL encoded by one or more of the polynucleotides described above specifically or preferentially binds to the same epitope as a monoclonal antibody selected from the group consisting of 201', 3A3, 3A6, 1A7, 1G7, 2B10, 2C11, 2F3, 3P1D10.2C3, 3P1E11.3B7, 3P2C6.3G10.2H7, 3P2C9.2G4, 3P4A6.1D9, 3P4A1.2B9, 3P4C2.2D2, 3P4C5.1D8, 3P4C8.2G9, 30-C12 (L100), 38-D01 (Li02), 35-E04 (Li03), 36-C09 (Li04), 30-A11 (Li05), 34-F02 (Li06), 29-E07 (Li07), 34-G04 (Li08), 36-A12 (Li09), 28-D02 (Li10), 30-B01 (Li11), 34-B03 (Li12), Li13, Li32, Li33, Li34, 3383 (L1a.1), 3495 (L1a.2), 3563 (L1a.3), 3564 (L1a.4), 3565 (L1a.5), 3566 (L1a.6), 3567 (L1a.7), 3568 (L1a.8), 3569 (L1a.9), 3570 (L1a.10), 3571 (L1a.11), 3582 (L1a.12), and 1968 (L1a.13), or will competitively inhibit such a monoclonal antibody from binding to Sp35.

In certain embodiments, an antibody or antigen-binding fragment thereof comprising, consisting essentially of, or consisting of a VL encoded by one or more of the polynucleotides described above specifically or preferentially binds to an Sp35 polypeptide or fragment thereof, or a Sp35 variant polypeptide, with an affinity characterized by a dissociation constant ($K_D$) no greater than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M.

In a further embodiment, the present invention includes an isolated polynucleotide comprising, consisting essentially of, or consisting of a nucleic acid encoding a VH at least 80%, 85%, 90% or 95% identical to a reference VH polypeptide sequence selected from the group consisting of SEQ ID NOs: 158 to 172, 372, 376, 380, and 384 shown in Table 6. In certain embodiments, an antibody or antigen-binding fragment comprising the VH encoded by the polynucleotide specifically or preferentially binds to Sp35.

In another aspect, the present invention includes an isolated polynucleotide comprising, consisting essentially of, or consisting of a nucleic acid sequence encoding a VH having a polypeptide sequence selected from the group consisting of SEQ ID NOs: 158 to 172, 372, 376, 380 and 384 shown in Table 6. In certain embodiments, an antibody or antigen-binding fragment comprising the VH encoded by the polynucleotide specifically or preferentially binds to Sp35.

TABLE 6

VH Polypeptide Sequences

| VH | Sequence | SEQ ID NO: |
|---|---|---|
| Li02 | EVQLLESGGGLVQPGGSLRLSCAASGFTFSTYEMIWVRQAPGKGLEWVSSIGP SGGLTWYADSVKGRFTISRDNSKNTLYLQMNSLRAEDTAMYYCVRIDDSSGW AFDIWGQGTTVTVSSASTKGPSVFPLAP | 158 |
| Li09 | EVQLLESGGGLVQPGGSLRLSCAASGFTFSMYSMVWVRQAPGKGLEWVSYIS PSGGKTMYADSVKGRFTISRDNSKNTFYLQMNSLRAEDTAVYYCARDSRRRY YDFWSGYHNYYYYYMDVWGKGTTVTVSSASTKGPSVFPLAP | 159 |
| Li06 | EVQLLESGGGLVQPGGSLRLSCAASGFTFSEYPMDWVRQAPGKGLEWVSSIY SSGGSTVYADSIKGRFTISRDNSKNTLYLQMNSLRAEDTAVYYCAREGDSDAF DIWGQGTMVTVSSASTKGPSVFPLAP | 160 |
| Li05 | EVQLLESGGGLVQPGGSLRLSCAASGFTFSAYAMGWVRQAPGKGLEWVSSIV SSGGYTDYADSVKGRFTISRDNSKNTLYLQMNSLRAEDTAVYYCAREGDHNA FDIWGQGTMVTVSSASTKGPSVFPLAP | 161 |
| Li04 | EVQLLESGGGLVQPGGSLRLSCAASGFTFSRYNMGWVRQAPGKGLEWVSVIY PSGGGTHYADSVKGRFTISRDNSKNTLYLQMNSLRAEDTAVYYCASSIADDAF DIWGQGTMVTVSSASTKGPSVFPLAP | 162 |
| Li08 | EVQLLESGGGLVQPGGSLRLSCAASGFTFSHYEMVWVRQAPGKGLEWVSSIRS SGGATKYADSVKGRFTISRDNSKNTLYLQMNSLRAEDTAVYYCAKESPDDYF DYWGQGTLVTVSSASTKGPSVFPLAP | 163 |
| Li11 | EVQLLESGGGLVQPGGSLRLSCAASGFTFSSYAMYWVRQAPGKGLEWVSSIST SGGYTGYADSVKGRFTISRDNSKNTLYLQMNSLRAEDTAVYYCARDTSDNDY YYMDVWGKGTTVTVSSASTKGPSVFPLAP | 164 |
| Li10 | EVQLLESGGGLVQPGGSLRLSCAASGFTFSTYPMVWVRQAPGKGLEWVSWIG PSGGVTAYADSVKGRFTISRDNSKNTLYLQMNSLRAEDTAVYYCARPYSSGW WDFDLWGRGTLVTVSSASTKGPSVFPLAP | 165 |
| Li01 | EVQLLESGGGLVQPGGSLRLSCAASGFTFSKYQMTWVRQAPGKGLEWVSSIY PSGGNTVYADSVKGRFTISRDNSKNTLYLQMNSLRAEDTAVYYCASGTTEAV FDYWGQGTLVTVSSASTKGPSVFPLAP | 166 |
| Li07 | EVQLLESGGGLVQPGGSLRLSCAASGFTFSMYFMGWVRQAPGKGLEWVSSIS PSGGFTSYADSVKGRFTISRDNSKNTLYLQMNSLAAEDTAVYYCARDRHAFD IWGQGTMVTVSSASTKGPSVFPLAP | 167 |
| Li03 | EVQLLESGGGLVQPGGSLRLSCAASGFTFSQYPMEWVRQAPGKGLEWVSGIY PSGGSTVYADSVKGRFTISRDNSKNTLYLQMNSLRAEDTAVYYCARAGQWL GDFDYWGQGTLVTVSSASTKGPSVFPLAP | 168 |
| Li12 | EVQLLESGGGLVQPGGSLRLSCAASGFTFSQYNMFWVRQAPGKGLEWVSRISS SGGMTMYADSVKGRFTISRDNSKNTLYLQMNSLRAEDTAVYYCAREALRPY CSGGSCYSDYYYGMDVWGQGTTVTVSSASTKGPSVFPLAP | 169 |
| 1A7 | QVQLVQSGPELKKPGETVKISCKASGYTFTNYGMNWVKQAPGKGLKWMGW INTDTGEPTYTEDFQGRFAFSLETSASTVYLQFNNLKNEDTATYFCAREGVHF DYWGQGTTVTVSS | 170 |
| 2F3 | EVKLEESGGGLVQPGGSMKLSCAASGFTFSDAWLDWVRQSPEKGLEWVAEIR SKANNHATNYAESVKGRFTISRDDSKSSVYLQMNSLRAEDTGIYFCTPSFAYW GQGTTVTVSS | 171 |
| 3P1D 102C 3 and 3P1E 11.3B 7 | QVQLQQSGAELARPGASVKLSCRASGYTFTSSWTQWVKQRPGQGLEWIGAIY PGDGDTRYTQKFKGKATLTADKSSSTAYMQLSSLASEDSAVYYCARHNSYG MDYWGQGTSVTVSS | 172 |
| Li13 | EVQLLESGGGLVQPGGSLRLSCAASGFTFSHYEMYWVRQAPGKGLEWVSRIV SSGGFTKYADSVKGRFTISRDNSKNTLYLQMNSLRAEDTAVYYCATEGDNDA FDIWGQGTTVTVSS | 372 |

TABLE 6-continued

VH Polypeptide Sequences

| VH | Sequence | SEQ ID NO: |
|---|---|---|
| Li32 | EVQLLESGGGLVQPGGSLRLSCAASGFTFSAYMMQWVRQAPGKGLEWVSSIS PSGGNTKYADSVKGRFTISRDNSKNTLYLQMNSLRAEDTAVYYCARGDYGY WFDPWGQGTLVTVSS | 376 |
| Li33 | EVQLLESGGGLVQPGGSLRLSCAASGFTFSIYPMFWVRQAPGKGLEWVSWIGP SGGITKYADSVKGRFTISRDNSKNTLYLQMNSLRAEDTATYYCAREGHNDWY FDLWGRGTLVTVSS | 380 |
| Li34 | EVQLLESGGGLVQPGGSLRLSCAASGFTFSNYEMYWVRQAPGKGLEWVSGIY SSGGITVYADSVKGRFTISRDNSKNTLYLQMNSLRAEDTAVYYCARAAILDW YFDLWGRGTLVTVSS | 384 |

In a further embodiment, the present invention includes an isolated polynucleotide comprising, consisting essentially of, or consisting of a nucleic acid encoding a VH at least 80%, 85%, 90% or 95% identical to a reference VH polypeptide sequence selected from the group consisting of SEQ ID NOs: 158-172, 372, 376, 380, and 384. In certain embodiments, an antibody or antigen-binding fragment comprising the VH encoded by the polynucleotide specifically or preferentially binds to Sp35.

In another aspect, the present invention includes an isolated polynucleotide comprising, consisting essentially of, or consisting of a nucleic acid sequence encoding a VH of the invention, selected from the group consisting of SEQ ID NOs: 158-172, 372, 376, 380, and 384. In certain embodiments, an antibody or antigen-binding fragment comprising the VH encoded by the polynucleotide specifically or preferentially binds to Sp35.

In certain embodiments, an antibody or antigen-binding fragment thereof comprising, consisting essentially of, or consisting of a VH encoded by one or more of the polynucleotides described above specifically or preferentially binds to the same epitope as a monoclonal antibody selected from the group consisting of, (201') 3A3, 3A6, 1A7, 1G7, 2B10, 2C11, 2F3, 3P1D10.2C3, 3P1E11.3B7, 3P2C6.3G10.2H7, 3P2C9.2G4, 3P4A6.1D9, 3P4A1.2B9, 3P4C2.2D2, 3P4C5.1D8, 3P4C8.2G9, 30-C12 (L100), 38-D01 (Li02), 35-E04 (Li03), 36-C09 (Li04), 30-A11 (Li05), 34-F02 (Li06), 29-E07 (Li07), 34-G04 (Li08), 36-A12 (Li09), 28-D02 (Li10), 30-B01 (Li11), 34-B03 (Li12), Li13, Li32, Li33, Li34, 3383 (L1a.1), 3495 (L1a.2), 3563 (L1a.3), 3564 (L1a.4), 3565 (L1a.5), 3566 (L1a.6), 3567 (L1a.7), 3568 (L1a.8), 3569 (L1a.9), 3570 (L1a.10), 3571 (L1a.11), 3582 (L1a.12), and 1968 (L1a.13), or will competitively inhibit such a monoclonal antibody from binding to Sp35.

In certain embodiments, an antibody or antigen-binding fragment thereof comprising, consisting essentially of, or consisting of a VH encoded by one or more of the polynucleotides described above specifically or preferentially binds to an Sp35 polypeptide or fragment thereof, or a Sp35 variant polypeptide, with an affinity characterized by a dissociation constant ($K_D$) no greater than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M.

In additional embodiments, the present invention includes an isolated polynucleotide which encodes a heavy chain variable region ($V_H$), where the polynucleotide comprises a $V_H$ nucleic acid sequence selected from the group consisting of SEQ ID NOs 173 to 184, 370, 374, 378 and 382, as shown in Table 7. In certain embodiments, an antibody or antigen-binding fragment comprising the VH encoded by the polynucleotide specifically or preferentially binds to Sp35.

TABLE 7

VH Polynucleotide Sequences

| VH | Sequence | SEQ ID NO: |
|---|---|---|
| Li02 | GAAGTTCAATTGTTAGAGTCTGGTGGCGGTCTTGTTCAGCCTGGTGGTTCTTTAC GTCTTTCTTGCGCTGCTTCCGGATTCACTTTCTCTACTTACGAGATGATTTGGGT TCGCCAAGCTCCTGGTAAAGGTTTGGAGTGGGTTTCTTCTATCGGTCCTTCTGGT GGCCTTACTTGGTATGCTGACTCCGTTAAAGGTCGCTTCACTATCTCTAGAGACA ACTCTAAGAATACTCTCTACTTGCAGATGAACAGCTTAAGGGCTGAGGACACCGC CATGTATTACTGTGTACGGATTGATGATAGTAGTGGTTGGGCTTTTGATATCTGG GGCCAAGGGACCACGGTCACCGTCTCAAGCGCCTCCACCAAGGGCCCATCGGTCT TCCCGCTAGCACCC | 173 |
| Li09 | GAAGTTCAATTGTTAGAGTCTGGTGGCGGTCTTGTTCAGCCTGGTGGTTCTTTAC GTCTTTCTTGCGCTGCTTCCGGATTCACTTTCTCTATGTACTCTATGGTTTGGGT TCGCCAAGCTCCTGGTAAAGGTTTGGAGTGGGTTTCTTATATCTCTCCTTCTGGT GGCAAGACATATGTATGCTGACTCCGTTAAAGGTCGCTTCACTATCTCTAGAGACA ACTCTAAGAATACTTTCTACTTGCAGATGAACAGCTTAAGGGCTGAGGACACGGC CGTGTATTACTGTGCGAGAGATTCGAGACGCCGGTATTACGATTTTTGGAGTGGT TATCACAACTACTACTACTACTACATGGACGTCTGGGGCAAAGGGACCACGGTCA CCGTCTCAAGCGCCTCCACCAAGGGCCCATCGGTCTTCCCGCTAGCACCC | 174 |

TABLE 7-continued

VH Polynucleotide Sequences

| VH | Sequence | SEQ ID NO: |
|---|---|---|
| Li06 | GAAGTTCAATTGTTAGAGTCTGGTGGCGGTCTTGTTCAGCCTGGTGGTTCTTTAC GTCTTTCTTGCGCTGCTTCCGGATTCACTTTCTCTGAGTACCCTATGGATTGGGT TCGCCAAGCTCCTGGTAAAGGTTTGGAGTGGGTTTCTTCTATCTATTCTTCTGGT GGCTCTACTGTTTATGCTGACTCCATTAAAGGTCGCTTCACTATCTCTAGAGACA ACTCTAAGAATACTCTCTACTTGCAGATGAACAGCTTAAGGGCTGAGGACACGGC CGTGTATTACTGTGCCAGAGAGGGTGACTCTGATGCTTTTGATATCTGGGGCCAA GGGACAATGGTCACCGTCTCAAGCGCCTCCACCAAGGGCCCATCGGTCTTCCCGC TAGCACCC | 175 |
| Li05 | GAAGTTCAATTGTTAGAGTCTGGTGGCGGTCTTGTTCAGCCTGGTGGTTCTTTAC GTCTTTCTTGCGCTGCTTCCGGATTCACTTTCTCTGCTTACGCTATGGGTTGGGT TCGCCAAGCTCCTGGTAAAGGTTTGGAGTGGGTTTCTTCTATCGTTTCTTCTGGT GGCTATACTGATTATGCTGACTCCGTTAAAGGTCGCTTCACTATCTCTAGAGACA ACTCTAAGAATACTCTCTACTTGCAGATGAACAGCTTAAGGGCTGAGGACACGGC CGTGTATTACTGTGCCAGAGAGGGTGACCATAATGCTTTTGATATCTGGGGCCAA GGGACAATGGTCACCGTCTCAAGCGCCTCCACCAAGGGCCCATCGGTCTTCCCGC TAGCACCC | 176 |
| Li04 | GAAGTTCAATTGTTAGAGTCTGGTGGCGGTCTTGTTCAGCCTGGTGGTTCTTTAC GTCTTTCTTGCGCTGCTTCCGGATTCACTTTCTCTCGTTACAATATGGGTTGGGT TCGCCAAGCTCCTGGTAAAGGTTTGGAGTGGGTTTCTGTTATCTATCCTTCTGGT GGCGGTACTCATTATGCTGACTCCGTTAAAGGTCGCTTCACTATCTCTAGAGACA ACTCTAAGAATACTCTCTACTTGCAGATGAACAGCTTAAGGGCTGAGGAACACGGC CGTGTATTACTGTGCGAGTTCTATAGCAGATGATGCTTTTGATATCTGGGGCCAA GGGACAATGGTCACCGTCTCAAGCGCCTCCACCAAGGGCCCATCGGTCTTCCCGC TAGCACCC | 177 |
| Li08 | GAAGTTCAATTGTTAGAGTCTGGTGGCGGTCTTGTTCAGCCTGGTGGTTCTTTAC GTCTTTCTTGCGCTGCTTCCGGATTCACTTTCTCTCATTACGAGATGGTTTGGGT TCGCCAAGCTCCTGGTAAAGGTTTGGAGTGGGTTTCTTCTATCCGTTCTTCTGGT GGCGCTACTAAGTATGCTGACTCCGTTAAAGGTCGCTTCACTATCTCTAGAGAAA ACTCTAAGAATACTCTCTACTTGCAGATGAACAGCTTAAGGGCTGAGGACACGGC CGTGTATTACTGTGCGAAAGAGTCGCCAGACGACTACTTTGACTACTGGGGCCAG GGAACCCTGGTCACCGTCTCAAGCGCCTCCACCAAGGGCCCATCGGTCTTCCCGC TAGCACCC | 178 |
| Li11 | GAAGTTCAATTGTTAGAGTCTGGTGGCGGTCTTGTTCAGCCTGGTGGTTCTTTAC GTCTTTCTTGCGCTGCTTCCGGATTCACTTTCTCTTCTTACGCTATGTATTGGGT TCGCCAAGCTCCTGGTAAAGGTTTGGAGTGGGTTTCTTCTATCTCTACTTCTGGT GGCTATACTGGTTATGCTGACTCCGTTAAAGGTCGCTTCACTATCTCTAGAGACA ACTCTAAGAATACTCTCTACTTGCAGATGAACAGCTTAAGGGCTGAGGACACGGC CGTGTATTACTGTGCGAGAGATACCAGCGATAATGACTACTACTAAATGGACGTC TGGGGCAAAGGGACCACGGTCACCGTCTCAAGCGCCTCCACCAAGGGCCCATCGG TCTTCCCGCTAGCACCC | 179 |
| Li10 | GAAGTTCAATTGTTAGAGTCTGGTGGCGGTCTTGTTCAGCCTGGTGGTTCTTTAC GTCTTTCTTGCGCTGCTTCCGGATTCACTTTCTCTACTTACCCTATGGTTTGGGT TCGCCAAGCTCCTGGTAAAGGTTTGGAGTGGGTTTCTTGGATCGGTCCTTCTGGT GGCGTTACTGCTTATGCTGACTCCGTTAAAGGTCGCTTCACTATCTCTAGAGACA ACTCTAAGAATACTCTCTACTTGCAGATGAACAGCTTAAGGGCTGAGGACACGGC CGTGTATTACTGTGCGAGACCCTATAGCAGTGGCTGGTGGGACTTCGATCTCTGG GGCCGTGGCACCCTGGTCACCGTCTCAAGCGCCTCCACCAAGGGCCCATCGGTCT TCCCGCTAGCACCC | 180 |
| Li01 | GAAGTTCAATTGTTAGAGTCTGGTGGCGGTCTTGTTCAGCCTGGTGGTTCTTTAC GTCTTTCTTGCGCTGCTTCCGGATTCACTTTCTCTAAGTACAAGATGACTTGGGT TCGCCAAGCTCCTGGTAAAGGTTTGGAGTGGGTTTCTTCTATCTATCCTTCTGGT GGCAATACTGTTTATGCTGACTCCGTTAAAGGTCGCTTCACTATCTCTAGAGACA ACTCTAAGAATACTCTCTACTTGCAGATGAACAGCTTAAGGGCTGAGGACACGGC CGTGTATTACTGTGCGAGTGGGACTACAGAGGCAGTCTTTGACTACTGGGGCCAG GGAACCCTGGTCACCGTCTCAAGCGCCTCCACCAAGGGCCCATCGGTCTTCCCGC TAGCACCC | 181 |
| Li07 | GAAGTTCAATTGTTAGAGTCTGGTGGCGGTCTTGTTCAGCCTGGTGGTTCTTTAC GTCTTTCTTGCGCTGCTTCCGGATTCACTTTCTCTATGTACTTTATGGGTTGGGT TCGCCAAGCTCCTGGTAAAGGTTTGGAGTGGGTTTCTTCTATCTCTCCTTCTGGT GGCTTTACTTCTTATGCTGACTCCGTTAAAGGTCGCTTCACTATCTCTAGAGACA ACTCTAAGAATACTCTCTACTTGCAGATGAACAGCTTAAGGGCTGAGGACACTGC AGTCTACTATTGTGCGAGAGATCGGCATGCTTTTGATATCTGGGGCCAAGGGACA ATGGTCACCGTCTCAAGCGCCTCCACCAAGGGCCCATCGGTCTTCCCGCTAGCAC CC | 182 |

TABLE 7-continued

VH Polynucleotide Sequences

| VH | Sequence | SEQ ID NO: |
|---|---|---|
| Li03 | GAAGTTCAATTGTTAGAGTCTGGTGGCGGTCTTGTTCAGCCTGGTGGTTCTTTAC GTCTTTCTTGCGCTGCTTCCGGATTCACTTTCTCTCAGTACCCTATGGAGTGGGT TCGCCAAGCTCCTGGTAAAGGTTTGGAGTGGGTTTCTGGTATCTATCCTTCTGGT GGCTCTACTGTTTATGCTGACTCCGTTAAAGGTCGCTTCACTATCTCTAGAGACA ACTCTAAGAATACTCTCTACTTGCAGATGAACAGCTTAAGGGCTGAGGACACGGC CGTGTATTACTGTGCGAGAGCGGGGCAGTGGCTGGGGGACTTTGACTACTGGGGC CAGGGAACCCTGGTCACCGTCTCAAGCGCCTCCACCAAGGGCCCATCGGTCTTCC CGCTAGCACCC | 183 |
| Li12 | GAAGTTCAATTGTTAGAGTCTGGTGGCGGTCTTGTTCAGCCTGGTGGTTCTTTAC GTCTTTCTTGCGCTGCTTCCGGATTCACTTTCTCTCAGTACAATATGTTTTGGGT TCGCCAAGCTCCTGGTAAAGGTTTGGAGTGGGTTTCTCGTATCTCTTCTTCTGGT GGCATGACTATGTATGCTGACTCCGTTAAAGGTCGCTTCACTATCTCTAGAGACA ACTCTAAGAATACTCTCTACTTGCAGATGAACAGCTTAAGGGCTGAGGACACGGC TGTGTATTACTGTGCGAGAGAAGCGTTACGGCCTTATTGTAGTGGTGGTAGCTGC TACTCCGACTACTACTACGGTATGGACGTCTGGGGCCAAGGGACCACGGTCA CCGTCTCAAGCGCCTCCACCAAGGGCCCATCGGTCTTCCCGCTAGCACCC | 184 |
| Li13 | GAAGTTCAATTGTTAGAGTCTGGTGGCGGTCTTGTTCAGCCTGGTGGTTCTTTA CGTCTTTCTTGCGCTGCTTCCGGATTCACTTTCTCTCATTACGAGATGTATTGG GTTCGCCAAGCTCCTGGTAAAGGTTTGGAGTGGGTTTCTCGTATCGTTTCTTCT GGTGGCTTTACTAAGTATGCTGACTCCGTTAAAGGTCGCTTCACTATCTCTAGA GACAACTCTAAGAATACTCTCTACTTGCAGATGAACAGCTTAAGGGCTGAGGAC ACGGCCGTGTATTACTGTGCAACAGAGGGTGATAATGATGCTTTTGATATCTGG GGCCAAGGGACCACGGTCACCGTCTCAAGC | 370 |
| Li32 | GAAGTTCAATTGTTAGAGTCTGGTGGCGGTCTTGTTCAGCCTGGTGGTTCTTTA CGTCTTTCTTGCGCTGCTTCCGGATTCACTTTCTCTGCTTACATGATGCAGTGG GTTCCCCAAGCTCCTGGTAAAGGTTTGGAGTGGGTTTCTTCTATCTCTCCTTCT GGTGGCAATACTAAGTATGCTGACTCCGTTAAAGGTCGCTTCACTATCTCTAGA GACAACTCTAAGAATACTCTCTACTTGCAGATGAACAGCTTAAGGGCTGAGGAC ACGGCCGTGTATTACTGTGCGAGAGGAGATTATGGATACTGGTTCGACCCCTGG GGCCAGGGCACCCTGGTCACCGTCTCAAGC | 374 |
| Li33 | GAAGTTCAATTGTTAGAGTCTGGTGGCGGTCTTGTTCAGCCTGGTGGTTCTTTA CGTCTTTCTTGCGCTGCTTCCGGATTCACTTTCTCTATTTACCCTATGTTTTGG GTTCGCCAAGCTCCTGGTAAAGGTTTGGAGTGGGTTTCTTGGATCGGTCCTTCT GGTGGCATTACTAAGTATGCTGACTCCGTTAAAGGTCGCTTCACTATCTCTAGA GACAACTCTAAGAATACTCTCTACTTGCAQATGAACAGCTTAAGGGCTGAGGAC ACAGCCACATATTACTGTGCGAGAGAGGGGCATAACGACTGGTACTTCGATCTC TGGGGCCGTGGCACCCTGGTCACCGTCTCAAGC | 378 |
| Li34 | GAAGTTCAATTGTTAGAGTCTGGTGGCGGTCTTGTTCAGCCTGGTGGTTCTTTA CGTCTTTCTTGCGCTGCTTCCGGATTCACTTTCTCTAATTACGAGATGTATTGG GTTCGCCAAGCTCCTGGTAAAGGTTTGGAGTGGGTTTCTGGTATCTATTCTTCT GGTGGCATTACTGTTTATGCTGACTCCGTTAAAGGTCGCTTCACTATCTCTAGA GACAACTCTAAGAATACTCTCTACTTGCAGATGAACAGCTTAAGGGCTGAGGAC ACGGCCGTGTATTACTGTGCTAGGGCAGCCATCCTCGACTGGTACTTCGATCTC TGGGGCCGTGGCACCCTGGTCACCGTCTCAAGC | 382 |

In a further embodiment, the present invention includes an isolated polynucleotide comprising, consisting essentially of, or consisting of a VH-encoding nucleic acid at least 80%, 85%, 90% or 95% identical to a reference nucleic acid sequence selected from the group consisting of SEQ ID NOs: 173-184, 370, 374, 378 and 382 of Table 7. In certain embodiments, the polynucleotide encodes a VH polypeptide which specifically or preferentially binds to Sp35.

In certain embodiments, an antibody or antigen-binding fragment thereof comprising, consisting essentially of, or consisting of a VH encoded by one or more of the polynucleotides described above specifically or preferentially binds to the same epitope as a monoclonal antibody selected from the group consisting of, (201') 3A3, 3A6, 1A7, 1G7, 2B10, 2C11, 2F3, 3P1D10.2C3, 3P1E11.3B7, 3P2C6.3G10.2H7, 3P2C9.2G4, 3P4A6.1D9, 3P4A1.2B9, 3P4C2.2D2, 3P4C5.1D8, 3P4C8.2G9, 30-C12 (L100), 38-D01 (Li02), 35-E04 (Li03), 36-C09 (Li04), 30-A11 (Li05), 34-F02 (Li06), 29-E07 (Li07), 34-G04 (Li08), 36-A12 (Li09), 28-D02 (Li10), 30-B01 (Li11), 34-B03 (Li12), Li13, Li32, Li33, Li34, 3383 (L1a.1), 3495 (L1a.2), 3563 (L1a.3), 3564 (L1a.4), 3565 (L1a.5), 3566 (L1a.6), 3567 (L1a.7), 3568 (L1a.8), 3569 (L1a.9), 3570 (L1a.10), 3571 (L1a.11), 3582 (L1a.12), and 1968 (L1a.13), or will competitively inhibit such a monoclonal antibody from binding to Sp35.

In certain embodiments, an antibody or antigen-binding fragment thereof comprising, consisting essentially of, or consisting of a VH encoded by one or more of the polynucleotides described above specifically or preferentially binds to an Sp35 polypeptide or fragment thereof, or a Sp35 variant polypeptide, with an affinity characterized by a dissociation constant ($K_D$) no greater than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M.

In a further embodiment, the present invention includes an isolated polynucleotide comprising, consisting essentially of, or consisting of a nucleic acid encoding a VL at least 80%, 85%, 90% or 95% identical to a reference VL polypeptide sequence selected from the group consisting of SEQ ID NOs: 273 to 286, 373, 377, 381 and 385, shown in Table 8. In certain embodiments, an antibody or antigen-binding fragment comprising the VL encoded by the polynucleotide specifically or preferentially binds to Sp35.

In another aspect, the present invention includes an isolated polynucleotide comprising, consisting essentially of, or consisting of a nucleic acid sequence encoding a VL having a polypeptide sequence selected from the group consisting of SEQ ID NOs: 273 to 286, 373, 377, 381 and 385, shown in Table 8. In certain embodiments, an antibody or antigen-binding fragment comprising the VL encoded by the polynucleotide specifically or preferentially binds to Sp35.

TABLE 8

VL Polypeptide Sequences

| VL | Sequence | SEQ ID NO: |
|---|---|---|
| Li02 | FYSHSAQYELTQPPSVSVSPGQTASITCSGDKLGDKFASWYQQKAGQSPVLV IFQDRKRLSGIPERFSGSNSGNTATLTISGTQAMDEADYYCQAWDTNTVVFG GGTKLTVLGQPKAAP | 273 |
| Li09 | FYSHSAQDIQMTQSPSSLSAFVGDRVAITCRASQSIDTYLNWYQQKPGKAPK LLIYAASKLEDGVPSRFSGSGTGTDFTLTIRSLQPEDFGTYYCQQSYSPPLTFG GGTKVEIKRTVAAP | 274 |
| Li06 | FYSHSAQDIQMTQSPSTLSASVGDRVTITCRASQSISSWLAWYQQKPGKAPN LLIYAASSLRTGVPSRFRGSGSGTDFTLTISSLQPEDFATYYCLQDYSYPLTFG QGTKLEIKRTVAAP | 275 |
| Li05 | FYSHSAQSVLTQPPSVSVAPGQTARISCGGDNIGSKSVHWYQQRPGQAPVLV VYDDYDRPSGIPERFSGSNSGDTAILTITRVEVGDEADFYCQVRDSRTEERVF GGGTKVTVLGQPKAAP | 276 |
| Li08 | FYSHSAQDIQMTQSPSSLSASVGDRVTITCQASQDISYYLNWYQQKPGKAPK VLIYDVSNLQTGVPSRFSGSASATDFTLTISSLQPEDIATYYCQQSDNLPLTFG GGTKVEIKRTVAAP | 277 |
| Li11 | FYSHSAQDIQMTQSPSSVSAPIGDRVTITCRASQEIANYLAWYQQKPGKAPK LLIYDTYTLQTDVPPRFSGSGSGTDFTLTISSLQPEDTATYFCQQADIFPLSFG GGTKVEIKRTVAAP | 278 |
| Li10 | FYSHSAQDIQMTQSPSSMSASVGDTVTITCRASQGIGNWLAWYQQKPGKAP TLLIYAASSLESGVPSRFTGSGSSSGIDFTLTISDLHPEDLATYYCQQAQTFPLT FGGGTRVDLKRTVAAP | 279 |
| Li01 | FYSHSAQDIQMTQSPSSLSASVGDRVTITCQASQDISNYLNWYQQKPGKAPK LLIYDASNLETGVPSRFSGSGSGTDFTLTISSLQPEDFATYYCQQADRFPAVTF GGGTKVEIKRTVAAP | 280 |
| Li07 | FYSHSAQSELTQPPSVSVSPGQTAIITCSGDQLGDKHVAWYQQKPGQSPVLVI YLDIKRPAGISERFSGSNSGNTATLTIRGTQAMDEADYYCQAWDIKTVFGGG TKLTVLSQPKAAP | 281 |
| Li03 | FYSHSAQDIQMTQSPSSLSASVGDRVTITCRASQSISSYLNWYQQKPGKAPKL LIYAASSLQSGVPSRFSGSGSGTDFTLTISSLQPEDFATYYCQQSYSTPWTFGQ GTKVEIKRTVAAP | 282 |
| 1A7 | QIVLTQSPAIMSASPGEKVTMTCSASSSVSYMHWYQQKSGTSPKRWIYDTSK LASGVPARFSGSGSGTSYSLTISSMEAEDAATYYCQQWSSNPFTFGSGTKLEI K | 283 |
| 2F3 | DIQMTQSPASLSASVGETVTITCRASGNIYNYLAWFQQKQGKSPQLLVYNAK TLPDGVPSRFSGSGSGTQYFLKINSLQPEDFGSYYCQHFWAIPYTFGGGTKLE IKR | 284 |
| 3P1D 10.2C 3 | DIVMTQSPSSLTVTAGEKVTMSCKSSQSLLNSGNQKNYLTWYQQKPGQPPK LLIYWASTRESGVPDRFTGSGSGTDFTLTINSVQAEDLAVYYCQNDYSYPLFT FGSGTKLEIR | 285 |
| 3P1E1 1.3B7 | DIVMTQSPSSLTVTAGEKVTMSCKSSQSLLNSGNQKSYLTWYQQKPGQPPK LLIYWASTRESGVPDRFTGSGSGTDFTLTINSVQAEDLAVYYCQNDYSYPLF TFGSGTKLEIR | 286 |
| Li13 | DIQMTQSPATLSLSPGERATLSCRASQSVSSYLAWYQQKPGQAPRLLIYDAS NRATGIPARFSGSGSGTDFTLTISSLEPEDFAVYYCQQRSNWPMYTFGQGTK LEIK | 373 |

TABLE 8-continued

VL Polypeptide Sequences

| VL | Sequence | SEQ ID NO: |
|---|---|---|
| Li32 | DIQMTQSPDSLSASVGDRVTITCQASQDISYYLNWYQQKPGMAPKLLIYDA FILEGGAPSRFSGSGSGTDFSFTISNLQPEDIATYFCQQSDQLPVTFGQGTKVE IR | 377 |
| Li33 | DIQMTQSPGTLSLSPGERATLSCRASQSVSSYLAWYQQKPGQAPRLLIYDAS NRATGIPARFSGSGSGTEFTLTISSLQSEDFAVYYCQQYDKWPLTFGGGTKV ELK | 381 |
| Li34 | DIQMTQSPSSLSASVGDRVTITCHASQDISNYLSWYQQKPGKAPKLLIYDAF NLETGVPSRFSGSGSGTDFTFTISSLQPEDFATYYCQHYDNLPFTFGPGTRVA IR | 385 |

In a further embodiment, the present invention includes an isolated polynucleotide comprising, consisting essentially of, or consisting of a nucleic acid encoding a VL at least 80%, 85%, 90% or 95% identical to a reference VL polypeptide sequence selected from the group consisting of SEQ ID NOs: 273 to 286, 373, 377, 381 and 385. In certain embodiments, an antibody or antigen-binding fragment comprising the VL encoded by the polynucleotide specifically or preferentially binds to Sp35.

In another aspect, the present invention includes an isolated polynucleotide comprising, consisting essentially of, or consisting of a nucleic acid sequence encoding a VL of the invention, selected from the group consisting of SEQ ID NOs: 273 to 286, 373, 377, 381 and 385. In certain embodiments, an antibody or antigen-binding fragment comprising the VL encoded by the polynucleotide specifically or preferentially binds to Sp35.

In certain embodiments, an antibody or antigen-binding fragment thereof comprising, consisting essentially of, or consisting of a VL encoded by one or more of the polynucleotides described above specifically or preferentially binds to the same epitope as a monoclonal antibody selected from the group consisting of 201', 3A3, 3A6, 1A7, 1G7, 2B10, 2C11, 2F3, 3P1D10.2C3, 3P1E11.3B7, 3P2C6.3G10.2H7, 3P2C9.2G4, 3P4A6.1D9, 3P4A1.2B9, 3P4C2.2D2, 3P4C5.1D8, 3P4C8.2G9, 30-C12 (L100), 38-D01 (Li02), 35-E04 (Li03), 36-C09 (Li04), 30-A11 (Li05), 34-F02 (Li06), 29-E07 (Li07), 34-G04 (Li08), 36-A12 (Li09), 28-D02 (Li10), 30-B01 (Li11), 34-B03 (Li12), Li13, Li32, Li33, Li34, 3383 (L1a.1), 3495 (L1a.2), 3563 (L1a.3), 3564 (L1a.4), 3565 (L1a.5), 3566 (L1a.6), 3567 (L1a.7), 3568 (L1a.8), 3569 (L1a.9), 3570 (L1a.10), 3571 (L1a.11), 3582 (L1a.12), and 1968 (L1a.13), or will competitively inhibit such a monoclonal antibody from binding to Sp35.

In certain embodiments, an antibody or antigen-binding fragment thereof comprising, consisting essentially of, or consisting of a VL encoded by one or more of the polynucleotides described above specifically or preferentially binds to an Sp35 polypeptide or fragment thereof, or a Sp35 variant polypeptide, with an affinity characterized by a dissociation constant ($K_D$) no greater than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M.

In additional embodiments, the present invention includes an isolated polynucleotide which encodes a light chain variable region ($V_L$), where the polynucleotide comprises a $V_L$ nucleic acid sequence selected from the group consisting of SEQ ID NOs 185 to 194, 371, 375, 379 and 383, as shown in Table 9. In certain embodiments, an antibody or antigen-binding fragment comprising the VL encoded by the polynucleotide specifically or preferentially binds to Sp35.

TABLE 9

VL Polynucleotide Sequences

| VL | Sequence | SEQ ID NO: |
|---|---|---|
| Li02 | TTCTATTCTCACAGTGCACAGTACGAATTGACTCAGCCACCCTCAGTGTCCGTGTC CCCAGGACAGACAGCCAGCATCACCTGCTCTGGAGATAAATTGGGGGATAAATTTG CTTCCTGGTATCAGCAGAAGGCAGGCCAGTCCCCTGTGCTGGTCATCTTTCAAGAT AGGAAGCGTCTCTCAGGGATCCCTGAGCGATTCTCTCGCTCCAACTCTGGGAACAC AGCCACTCTGACCATCAGCGGGACCCAGGCTATGGATGAGGCTGACTATTACTGTC AGGCGTGGGACACCAACACTGTGGTCTTCGGCGGAGGGACCAAGCTGACCGTCCTA GGTCAGCCCAAGGCTGCCCCC | 185 |
| Li09 | TTCTATTCTCACAGTGCACAAGACATCCAGATGACCCAGTCTCCATCCTCCCTGTC TGCATTTGTGGGAGACAGAGTCGCCATCACTTGCCGCGCAAGTCAGAGCATCGACA CCTATTTAAATTGGTATCAGCAGAAACCAGGGAAAGCCCCTAAACTCCTGATCTAT GCTGCATCCAAGTTGGAAGACGGGGTCCCATCAAGATTCAGTGGCAGTGGAACTGG GACAGATTTCACTCTCACCATCAGAAGTCTGCAACCTGAAGATTTTGGAACTTACT ACTGTCAACAGAGTTACAGTCCCCCTCTCACTTTCGGCGGAGGGACCAAGGTGGAG ATCAAACGAACTGTGGCTGCACCA | 186 |

TABLE 9-continued

VL Polynucleotide Sequences

| VL | Sequence | SEQ ID NO: |
|---|---|---|
| Li06 | TTCTATTCTCACAGTGCACAAGACATCCAGATGACCCAGTCTCCTTCCACCCTGTC<br>TGCATCTGTAGGAGACAGAGTCACCATCACTTGCCGGGCCAGTCAGAGTATTAGTA<br>GCTGGTTGGCCTGGTATCAGCAGAAACCAGGGAAAGCCCCTAACCTCCTGATCTAT<br>GCTGCATCCAGTTTACGAACTGGGGTCCCATCAAGATTCAGGGGCAGTGGATCTGG<br>CACAGATTTCACTCTCACCATCAGCAGCCTGCAGCCTGAAGATTTTGCAACGTATT<br>ACTGTCTACAAGATTACAGTTACCCTCTCACTTTTGGCCAGGGGACCAAGCTGGAG<br>ATCAAACGAACTGTGGCTGCACCA | 187 |
| Li05 | TTCTATTCTCACAGTGCACAGAGCGTCTTGACTCAGCCACCCTCGGTGTCAGTGGC<br>CCCAGGCCAGACGGCCAGGATTTCCTGTGGGGGAGACAACATTGGAAGTAAGAGTG<br>TCCACTGGTACCACCAGAGGCCAGGCCAGGCCCCTGTCCTGGTCGTGTATGATGAT<br>TATGACCGGCCCTCAGGGATCCCTGAGCGATTCTCTGGCTCCAACTCTGGGGACAC<br>GGCCATCCTGACCATCACCAGGGTCGAAGTCGGGGATGAGGCCGACTTTTATTGTC<br>AGGTGAGGGACAGCCGTACTGAGGAACGGGTGTTCGGCGGAGGGACCAAGGTGACC<br>GTCTTAGGTCAGCCCAAGGCTGCCCCC | 188 |
| Li08 | TTCTATTCTCACAGTGCACAAGACATCCAGATGACCCAGTCTCCATCTTCCCTGTC<br>TGCATCTGTAGGAGACAGAGTCACCATCACTTGCCAGGCGAGTCAGGACATTAGTT<br>ACTATTTAAATTGGTATCAGCAGAAGCCAGGGAAAGCCCCTAAGGTCCTGATCTAC<br>GATGTATCCAATTTGCAAACAGGGGTCCCATCAAGGTTCAGTGGAAGTGCGTCTGC<br>GACAGATTTTACTCTCACCATCAGCAGCCTGCAGCCTGAAGATATTGCGACATATT<br>ACTGTCAACAGTCTGATAATCTCCCTCTCACTTTCGGCGGAGGGACCAAGGTGGAG<br>ATTAAACGAACTGTGGCTGCACCA | 189 |
| Li11 | TTCTATTCTCACAGTGCACAAGACATCCAGATGACCCAGTCTCCATCTTCTGTGTC<br>TGCACCTATAGGAGACAGAGTCACCATCACTTGTCGGGCGAGTCAGGAGATTGCCA<br>ACTACTTAGCCTGGTATCAGCAGAAACCAGGGAAAGCCCCTAAGCTCCTGATCTAT<br>GATACATACACTTTGCAGACTGACGTCCCACCGAGGTTCAGCGGCAGTGGTTCGGG<br>GACAGATTTCACTCTCACTATCAGCAGCCTGCAGCCTGAAGATACTGCAACTTACT<br>TTTGTCAACAGGCTGACATTTTCCCGCTCTCTTTCGGCGGAGGGACCAAGGTGGAG<br>ATCAAACGAACTGTGGCTGCACCA | 190 |
| Li10 | TTCTATTCTCACAGTGCACAAGACATCCAGATGACCCAGTCTCCATCTTCCATGTC<br>TGCTTCTGTAGGGGACACAGTCACCATCACTTGTCGGGCGAGTCAGGGTATTGGCA<br>ACTGGTTAGCCTGGTATCAGCAGAAACCAGGGAAAGCCCCAACTCTCCTGATCTAT<br>GCTGCATCCAGTTTGGAAAGTGGGGTCCCATCAAGGTTCACCGGCAGCGGCAGTTC<br>CTCTGGGATAGATTTCACTCTCACCATCAGCGACCTGCACCCTGAAGATTTGGCAA<br>CTTACTATTGTCAACAGGCTCAGACTTTCCCGCTCACCTTCGGCGGAGGGACCAGG<br>GTGGACCTCAAGCGAACTGTGGCTGCACCA | 191 |
| Li01 | TTCTATTCTCACAGTGCACAAGACATCCAGATGACCCAGTCTCCATCCTCCCTGTC<br>TGCATCTGTAGGAGACAGAGTCACCATCACTTGCCAGGCGAGTCAGGACATTAGCA<br>ACTATTTAAATTGGTATCAGCAGAAACCAGGGAAAQCCCCTAAGCTCCTGATCTAC<br>GATGCATCCAATTTGGAAACAGGGGTCCCATCAAGGTTCAGCGGCAGTGGATCTGG<br>GACAGATTTCACTCTCACCATCAGCAGCCTGCAGCCTGAAGATTTTGCAACTTACT<br>ATTGTCAACAGGCTGACAGGTTCCCTGCGGTCACTTTCGGCGGAGGGACCAAGGTG<br>GAGATCAAACGAACTGTGGCTGCACCA | 192 |
| Li07 | TTCTATTCTCACAGTGCACAGAGCGAATTGACTCAGCCACCCTCAGTGTCCGTGTC<br>CCCAGGACAGACAGCCATCATCACCTGCTCTGGAGATCTGTTGGGTGCAAACATG<br>TGGCTTGGTATCAACAGAAGCCAGGCCAGTCCCCTGTGCTGGTCATCTATCTAGAC<br>ATTAAGAGGCCCGCAGGGATTTCTGAGCGATTCTCTGGCTCCAACTCTGGAAATAC<br>AGCCACTCTGACCATCAGAGGGACCCAGGCTATGGATGAAGCTGACTATTACTGTC<br>AGGCGTGGGACATCAAGACGGTCTTCGGCGGGGGGACCAAGCTGACCGTCCTGAGT<br>CAGCCCAAGCCTGCCCCC | 193 |
| Li03 | TTCTATTCTCACAGTGCACAAGACATCCAGATGACCCAGTCTCCATCCTCCCTGTC<br>TGCATCTGTAGGAGACAGAGTCACCATCACTTGCCGGGCAAGTCAGAGCATTAGCA<br>GCTATTTAAATTGGTATCAGCAGAAACCAGGGAAAGCCCCTAAGCTCCTGATCTAT<br>GCTGCATCCAGTTTGCAAAGTGGGGTCCCATCAAGGTTCAGTGGCAGTGGATCTGG<br>GACAGATTTCACTCTCACCATCAGCAGTCTGCAACCTGAAGATTTTGCAACTTACT<br>ACTGTCAACAGAGTTACAGTACCCCGTGGACGTTCGGCCAAGGGACCAAGGTGGAA<br>ATCAAACGAACTGTGGCTGCACCA | 194 |
| Li13 | GACATCCAGATGACCCAGTCTCCAGCCACCCTGTCTTTGTCTCCAGGGGAAAGAG<br>CCACCCTCTCCTGCAGGGCCAGTCAGAGTGTTAGCAGCTACTTAGCCTGGTACCA<br>ACAGAAACCTGGCCAGGCTCCCAGGCTCCTCATCTATGATGCATCCAACAGGGCC<br>ACTGGCATCCCAGCCAGGTTCAGTGGCAGTGGGTCTGGGACAGACTTCACTCTCA<br>CCATCAGCAGCCTAGAGCCTGAAGATTTTGCAGTTTATTACTGTCAGCAGCGTAG<br>CAACTGGCCGATGTACACTTTTGGCCAGGGGACCAAGCTGGAGATCAAA | 371 |

TABLE 9-continued

VL Polynucleotide Sequences

| VL | Sequence | SEQ ID NO: |
|---|---|---|
| Li32 | GACATCCAGATGACCCAGTCTCCAGACTCCCTGTCTGCATCTGTTGGAGACAGAG<br>TCACCATCACTTGCCAGGCGAGTCAAGACATTAGCTACTATTTAAATTGGTATCA<br>GCAGAAACCAGGGATGGCCCCTAAACTCCTCATCTACGATGCCTTCATTTTGGAA<br>GGAGGGGCCCCATCACGGTTCAGTGGGAGCGGCTCTGGGACAGATTTTTCTTTCA<br>CCATCAGCAATCTACAGCCTGAGGATATTGCAACTTATTTCTGTCAACAGTCTGA<br>TCAACTGCCCGTGACCTTCGGCCAAGGGACCAAGGTGQAAATCAGA | 375 |
| Li33 | GACATCCAGATGACCCAGTCTCCAGGCACCCTGTCTTTGTCTCCAGGGGAAAGAG<br>CCACCCTCTCCTGCAGGGCCAGTCAGAGTGTTAGCAGCTACTTAGCCTGGTACCA<br>ACAGAAACCTGGCCAGGCTCCCAGGCTCCTCATCTATGATGCATCCAACAGGGCC<br>ACTGGCATCCCAGCCAGGTTCAGTGGCAGTGGGTCTGGGACAGAGTTCACTCTCA<br>CCATCAGCAGCCTGCAGTCTGAGGATTTTGCAGTTTATTACTGTCAGCAGTATGA<br>TAAGTGGCCGCTCACTTTCGGCGGAGGGACCAAGGTGGAGATCAAA | 379 |
| Li34 | GACATCCAGATGACCCAGTCTCCATCCTCCCTCTCTGCATCTGTAGGAGACAGAG<br>TCACCATCACTTGCCATGCGAGTCAGGACATTAGCAACTATTTAAGTTGGTATCA<br>GCAGAAACCAGGTAAAGCCCCTAAACTCCTGATCTACGATGCTTTCAATTTGGAG<br>ACAGGAGTCCCATCGAGGTTCAGTGGAAGTGGATCTQGCACAGATTTTACATTCA<br>CCATCAGCAGCCTGCAGCCTGAAGATTTTGCAACATATTACTGTCAGCACTATCA<br>TAATCTCCCATTCACTTTCGGCCCTGGGACCAGAGTGGCGATCAGA | 383 |

In a further embodiment, the present invention includes an isolated polynucleotide comprising, consisting essentially of, or consisting of a nucleic acid encoding a VL at least 80%, 85%, 90%, or 95% identical to a VL polynucleotide selected from the group consisting of SEQ ID NOs: 185-194, 371, 375, 379 and 383 of Table 9. In certain embodiments, the polynucleotide encodes a VL polypeptide which specifically or preferentially binds to Sp35.

In certain embodiments, an antibody or antigen-binding fragment thereof comprising, consisting essentially of, or consisting of a VL encoded by one or more of the polynucleotides described above specifically or preferentially binds to the same epitope as a monoclonal antibody selected from the group consisting of 201', 3A3, 3A6, 1A7, 1G7, 2B10, 2C11, 2F3, 3P1D10.2C3, 3P1E11.3B7, 3P2C6.3G10.2H7, 3P2C9.2G4, 3P4A6.1D9, 3P4A1.2B9, 3P4C2.2D2, 3P4C5.1D8, 3P4C8.2G9, 30-C12 (Li00), 38-D01 (Li02), 35-E04 (Li03), 36-C09 (Li04), 30-A11 (Li05), 34-F02 (Li06), 29-E07 (Li07), 34-G04 (Li08), 36-A12 (Li09), 28-D02 (Li10), 30-B01 (Li11), 34-B03 (Li12), Li13, Li32, Li33, Li34, 3383 (L1a.1), 3495 (L1a.2), 3563 (L1a.3), 3564 (L1a.4), 3565 (L1a.5), 3566 (L1a.6), 3567 (L1a.7), 3568 (L1a.8), 3569 (L1a.9), 3570 (L1a.10), 3571 (L1a.11), 3582 (L1a.12), and 1968 (L1a.13), or will competitively inhibit such a monoclonal antibody from binding to Sp35.

In certain embodiments, an antibody or antigen-binding fragment thereof comprising, consisting essentially of, or consisting of a VL encoded by one or more of the polynucleotides described above specifically or preferentially binds to an Sp35 polypeptide or fragment thereof, or a Sp35 variant polypeptide, with an affinity characterized by a dissociation constant ($K_D$) no greater than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M.

Any of the polynucleotides described above may further include additional nucleic acids, encoding, e.g., a signal peptide to direct secretion of the encoded polypeptide, antibody constant regions as described herein, or other heterologous polypeptides as described herein.

Also, as described in more detail elsewhere herein, the present invention includes compositions comprising the polynucleotides comprising one or more of the polynucleotides described above. In one embodiment, the invention includes compositions comprising a first polynucleotide and second polynucleotide wherein said first polynucleotide encodes a VH polypeptide as described herein and wherein said second polynucleotide encodes a VL polypeptide as described herein. Specifically a composition which comprises, consists essentially of, or consists of a VH polynucleotide, as show in Table 7, and a VL polynucleotide, as shown in Table 9, wherein said VH polynucleotide and said VL polynucleotide are selected from the group consisting of:
  i) SEQ ID NO:173 and SEQ ID NO:185;
  ii) SEQ ID NO:174 and SEQ ID NO:186;
  iii) SEQ ID NO:175 and SEQ ID NO:187;
  iv) SEQ ID NO:176 and SEQ ID NO:188;
  v) SEQ ID NO:178 and SEQ ID NO:189;
  vi) SEQ ID NO:179 and SEQ ID NO:190;
  vii) SEQ ID NO:180 and SEQ ID NO:191;
  viii) SEQ ID NO:181 and SEQ ID NO:192;
  ix) SEQ ID NO:182 and SEQ ID NO:193;
  x) SEQ ID NO:183 and SEQ ID NO:194;
  xi) SEQ ID NO:370 and SEQ ID NO:371;
  xii) SEQ ID NO:374 and SEQ ID NO:375;
  xiii) SEQ ID NO:378 and SEQ ID NO:379; and
  xiv) SEQ ID NO:382 and SEQ ID NO:385.

The present invention also includes fragments of the polynucleotides of the invention, as described elsewhere. Additionally polynucleotides which encode fusion polynucleotides, Fab fragments, and other derivatives, as described herein, are also contemplated by the invention.

The polynucleotides may be produced or manufactured by any method known in the art. For example, if the nucleotide sequence of the antibody is known, a polynucleotide encoding the antibody may be assembled from chemically synthesized oligonucleotides (e.g., as described in Kutmeier et al., *BioTechniques* 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an Sp35 antibody, or antigen-binding fragment, variant, or derivative thereof may be generated from nucleic acid from a suitable source. If a clone containing a nucleic acid encoding a particular antibody is not available, but the sequence of the antibody molecule is known, a nucleic acid encoding the antibody may be chemically synthesized or obtained from a suitable source (e.g., an antibody cDNA library, or a cDNA library generated from, or nucleic acid, preferably poly A+RNA, isolated from, any tissue or cells expressing the antibody or other Sp35 antibody, such as hybridoma cells selected to express an antibody) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody or other Sp35 antibody. Amplified nucleic acids generated by PCR may then be cloned into replicable cloning vectors using any method well known in the art.

Once the nucleotide sequence and corresponding amino acid sequence of the Sp35 antibody, or antigen-binding fragment, variant, or derivative thereof is determined, its nucleotide sequence may be manipulated using methods well known in the art for the manipulation of nucleotide sequences, e.g., recombinant DNA techniques, site directed mutagenesis, PCR, etc. (see, for example, the techniques described in Sambrook et al., *Molecular Cloning, A Laboratory Manual,* 2d Ed., Cold Spring Harbor Laboratory, Cold Spring Harbor, N.Y. (1990) and Ausubel et al., eds., *Current Protocols in Molecular Biology,* John Wiley & Sons, NY (1998), which are both incorporated by reference herein in their entireties), to generate antibodies having a different amino acid sequence, for example to create amino acid substitutions, deletions, and/or insertions.

A polynucleotide encoding an Sp35 antibody, or antigen-binding fragment, variant, or derivative thereof can be composed of any polyribonucleotide or polydeoxyribonucleotide, which may be unmodified RNA or DNA or modified RNA or DNA. For example, a polynucleotide encoding Sp35 antibody, or antigen-binding fragment, variant, or derivative thereof can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, a polynucleotide encoding an Sp35 antibody, or antigen-binding fragment, variant, or derivative thereof can be composed of triple-stranded regions comprising RNA or DNA or both RNA and DNA. A polynucleotide encoding an Sp35 antibody, or antigen-binding fragment, variant, or derivative thereof may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

An isolated polynucleotide encoding a non-natural variant of a polypeptide derived from an immunoglobulin (e.g., an immunoglobulin heavy chain portion or light chain portion) can be created by introducing one or more nucleotide substitutions, additions or deletions into the nucleotide sequence of the immunoglobulin such that one or more amino acid substitutions, additions or deletions are introduced into the encoded protein. Mutations may be introduced by standard techniques, such as site-directed mutagenesis and PCR-mediated mutagenesis. Preferably, conservative amino acid substitutions are made at one or more non-essential amino acid residues.

V. Sp35 Antibody Polypeptides

The present invention is further directed to isolated polypeptides which make up Sp35 antibodies, antigen binding fragments, variants or derivatives thereof. Sp35 antibodies of the present invention comprise polypeptides, e.g., amino acid sequences encoding Sp35-specific antigen binding regions derived from immunoglobulin molecules. A polypeptide or amino acid sequence "derived from" a designated protein refers to the origin of the polypeptide. In certain cases, the polypeptide or amino acid sequence which is derived from a particular starting polypeptide or amino acid sequence has an amino acid sequence that is essentially identical to that of the starting sequence, or a portion thereof, wherein the portion consists of at least 10-20 amino acids, at least 20-30 amino acids, at least 30-50 amino acids, or which is otherwise identifiable to one of ordinary skill in the art as having its origin in the starting sequence.

In one embodiment, the present invention provides an isolated polypeptide comprising, consisting essentially of, or consisting of an immunoglobulin heavy chain variable region (VH), where at least one of CDRs of the heavy chain variable region or at least two of the CDRs of the heavy chain variable region are at least 80%, 85%, 90% or 95% identical to reference heavy chain CDR1, CDR2 or CDR3 amino acid sequences from monoclonal Sp35 antibodies disclosed herein. Alternatively, the CDR1, CDR2 and CDR3 regions of the VH are at least 80%, 85%, 90% or 95% identical to reference heavy chain CDR1, CDR2 and CDR3 amino acid sequences from monoclonal Sp35 antibodies disclosed herein. Thus, according to this embodiment a heavy chain variable region of the invention has CDR1, CDR2, and CDR3 polypeptide sequences related to the groups shown in Table 4, supra. In certain embodiments, an antibody or antigen-binding fragment comprising the VH polypeptide specifically or preferentially binds to Sp35.

In another embodiment, the present invention provides an isolated polypeptide comprising, consisting essentially of, or consisting of an immunoglobulin heavy chain variable region (VH) in which the CDR1, CDR2, and CDR3 regions have polypeptide sequences which are identical to the CDR1, CDR2, and CDR3 groups shown in Table 4. In certain embodiments, an antibody or antigen-binding fragment comprising the VH polypeptide specifically or preferentially binds to Sp35.

In a further embodiment, the present invention includes an isolated polypeptide comprising, consisting essentially of, or consisting of a VH polypeptide at least 80%, 85%, 90% 95% or 100% identical to a reference VH polypeptide sequence selected from the group consisting of SEQ ID NOs:158 to 172, 372, 376, 380 and 384 as shown in Table 6. In certain embodiments, an antibody or antigen-binding fragment comprising the VH polypeptide specifically or preferentially binds to Sp35.

In another aspect, the present invention includes an isolated polypeptide comprising, consisting essentially of, or consisting of a VH polypeptide selected from the group consisting of SEQ ID NOs: 158 to 172, 372, 376, 380 and 384 as shown in Table 6. In certain embodiments, an antibody or antigen-binding fragment comprising the VH polypeptide specifically or preferentially binds to Sp35.

In certain embodiments, an antibody or antigen-binding fragment thereof comprising, consisting essentially of, or consisting of a one or more of the VH polypeptides described above specifically or preferentially binds to the same epitope as a monoclonal antibody selected from the group consisting of 201', 3A3, 3A6, 1A7, 1G7, 2B10, 2C11, 2F3, 3P1D10.2C3, 3P1E11.3B7, 3P2C6.3G10.2H7, 3P2C9.2G4, 3P4A6.1D9, 3P4A1.2B9, 3P4C2.2D2, 3P4C5.1D8, 3P4C8.2G9, 30-C12 (L100), 38-D01 (Li02), 35-E04 (Li03), 36-C09 (Li04), 30-A11 (Li05), 34-F02 (Li06), 29-E07 (Li07), 34-G04 (Li08), 36-A12 (Li09), 28-D02 (Li10), 30-B01 (Li11), 34-B03 (Li12), Li13, Li32, Li33, Li34, 3383 (L1a.1), 3495 (L1a.2), 3563 (L1a.3), 3564 (L1a.4), 3565 (L1a.5), 3566 (L1a.6), 3567 (L1a.7), 3568 (L1a.8), 3569 (L1a.9), 3570 (L1a.10), 3571 (L1a.11), 3582 (L1a.12), and 1968 (L1a.13), or will competitively inhibit such a monoclonal antibody from binding to Sp35.

In certain embodiments, an antibody or antigen-binding fragment thereof comprising, consisting essentially of, or consisting of one or more of the VH polypeptides described above specifically or preferentially binds to an Sp35 polypeptide or fragment thereof, or a Sp35 variant polypeptide, with an affinity characterized by a dissociation constant ($K_D$) no greater than $5\times10^{-2}$ M, $10^{-2}$ M, $5\times10^{-3}$ M, $10^{-3}$ M, $5\times10^{-4}$ M, $10^{-4}$ M, $5\times10^{-5}$ M, $10^{-5}$ M, $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, or $10^{-15}$ M.

In another embodiment, the present invention provides an isolated polypeptide comprising, consisting essentially of, or consisting of an immunoglobulin light chain variable region (VL), where at least one of the CDRs of the light chain variable region or at least two of the CDRs of the light chain variable region are at least 80%, 85%, 90% or 95% identical to reference heavy chain CDR1, CDR2, or CDR3 amino acid sequences from monoclonal Sp35 antibodies disclosed herein. Alternatively, the CDR1, CDR2 and CDR3 regions of the VL are at least 80%, 85%, 90% or 95% identical to reference light chain CDR1, CDR2, and CDR3 amino acid sequences from monoclonal Sp35 antibodies disclosed herein. Thus, according to this embodiment a light chain variable region of the invention has CDR1, CDR2, and CDR3 polypeptide sequences related to the polypeptides shown in Table 5, supra. In certain embodiments, an antibody or antigen-binding fragment comprising the VL polypeptide specifically or preferentially binds to Sp35.

In another embodiment, the present invention provides an isolated polypeptide comprising, consisting essentially of, or consisting of an immunoglobulin light chain variable region (VL) in which the CDR1, CDR2, and CDR3 regions have polypeptide sequences which are identical to the CDR1, CDR2, and CDR3 groups shown in Table 5. In certain embodiments, an antibody or antigen-binding fragment comprising the VL polypeptide specifically or preferentially binds to Sp35.

In a further embodiment, the present invention includes an isolated polypeptide comprising, consisting essentially of, or consisting of a VL polypeptide at least 80%, 85%, 90% or 95% identical to a reference VL polypeptide sequence selected from the group consisting of SEQ ID NOs:273 to 286, 373, 377, 381 and 385, shown in Table 8. In certain embodiments, an antibody or antigen-binding fragment comprising the VL polypeptide specifically or preferentially binds to Sp35.

In another aspect, the present invention includes an isolated polypeptide comprising, consisting essentially of, or consisting of a VL polypeptide selected from the group consisting of SEQ ID NOs: 273 to 286, 373, 377, 381 and 385, shown in Table 8. In certain embodiments, an antibody or antigen-binding fragment comprising the VL polypeptide specifically or preferentially binds to Sp35.

In certain embodiments, an antibody or antigen-binding fragment thereof comprising, consisting essentially of, one or more of the VL polypeptides described above specifically or preferentially binds to the same epitope as a monoclonal antibody selected from the group consisting of 201', 3A3, 3A6, 1A7, 1G7, 2B10, 2C11, 2F3, 3P1D10.2C3, 3P1E11.3B7, 3P2C6.3G10.2H7, 3P2C9.2G4, 3P4A6.1D9, 3P4A1.2B9, 3P4C2.2D2, 3P4C5.1D8, 3P4C8.2G9, 30-C12 (L100), 38-D01 (Li02), 35-E04 (Li03), 36-C09 (Li04), 30-A11 (Li05), 34-F02 (Li06), 29-E07 (Li07), 34-G04 (Li08), 36-A12 (Li09), 28-D02 (Li10), 30-B01 (Li11), 34-B03 (Li12), Li13, Li32, Li33, Li34, 3383 (L1a.1), 3495 (L1a.2), 3563 (L1a.3), 3564 (L1a.4), 3565 (L1a.5), 3566 (L1a.6), 3567 (L1a.7), 3568 (L1a.8), 3569 (L1a.9), 3570 (L1a.10), 3571 (L1a.11), 3582 (L1a.12), and 1968 (L1a.13), or will competitively inhibit such a monoclonal antibody from binding to Sp35.

In certain embodiments, an antibody or antigen-binding fragment thereof comprising, consisting essentially of, or consisting of a one or more of the VL polypeptides described above specifically or preferentially binds to an Sp35 polypeptide or fragment thereof, or a Sp35 variant polypeptide, with an affinity characterized by a dissociation constant ($K_D$) no greater than $5\times10^{-2}$ M, $10^{-2}$ M, $5\times10^{-3}$ M, $10^{-3}$ M, $5\times10^{-4}$ M, $10^{-4}$ M, $5\times10^{-5}$ M, $10^{-5}$ M, $5\times10^{-6}$ M, $10^{-6}$ M, $5\times10^{-7}$ M, $10^{-7}$ M, $5\times10^{-8}$ M, $10^{-8}$M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, or $10^{-15}$ M.

In other embodiments, an antibody or antigen-binding fragment thereof comprises, consists essentially of or consists of a VH polypeptide, as shown in Table 6, and a VL polypeptide, as shown in Table 8, selected from the group consisting of:
  i) SEQ ID NO:170 and SEQ ID NO:283;
  ii) SEQ ID NO:171 and SEQ ID NO:284;
  iii) SEQ ID NO:172 and SEQ ID NO:285;
  iv) SEQ ID NO:172 and SEQ ID NO:286;
  v) SEQ ID NO:158 and SEQ ID NO:273;
  vi) SEQ ID NO:159 and SEQ ID NO:274;
  vii) SEQ ID NO:160 and SEQ ID NO:275;
  viii) SEQ ID NO:161 and SEQ ID NO:276;
  ix) SEQ ID NO:163 and SEQ ID NO:277;
  x) SEQ ID NO:164 and SEQ ID NO:278;
  xi) SEQ ID NO:165 and SEQ ID NO:279;
  xii) SEQ ID NO:166 and SEQ ID NO:280;
  xiii) SEQ ID NO:167 and SEQ ID NO:281;
  xiv) SEQ ID NO:168 and SEQ ID NO:282;
  xv) SEQ ID NO:372 and SEQ ID NO:373;
  xvi) SEQ ID NO:376 and SEQ ID NO:377;
  xvii) SEQ ID NO:380 and SEQ ID NO:381; and
  xviii) SEQ ID NO:384 and SEQ ID NO:385.

Any of the polypeptides described above may further include additional polypeptides, e.g., a signal peptide to direct secretion of the encoded polypeptide, antibody constant regions as described herein, or other heterologous polypeptides as described herein. Additionally, polypeptides of the invention include polypeptide fragments as described elsewhere. Additionally polypeptides of the invention include fusion polypeptide, Fab fragments, and other derivatives, as described herein.

Also, as described in more detail elsewhere herein, the present invention includes compositions comprising the polypeptides described above.

It will also be understood by one of ordinary skill in the art that Sp35 antibody polypeptides as disclosed herein may be modified such that they vary in amino acid sequence from the naturally occurring binding polypeptide from which they were derived. For example, a polypeptide or amino acid sequence derived from a designated protein may be similar, e.g., have a certain percent identity to the starting sequence, e.g., it may be 60%, 70%, 75%, 80%, 85%, 90%, or 95% identical to the starting sequence.

Furthermore, nucleotide or amino acid substitutions, deletions, or insertions leading to conservative substitutions or changes at "non-essential" amino acid regions may be made. For example, a polypeptide or amino acid sequence derived from a designated protein may be identical to the starting sequence except for one or more individual amino acid substitutions, insertions, or deletions, e.g., one, two, three, four, five, six, seven, eight, nine, ten, fifteen, twenty or more individual amino acid substitutions, insertions, or deletions. In certain embodiments, a polypeptide or amino acid sequence derived from a designated protein has one to five, one to ten, one to fifteen, or one to twenty individual amino acid substitutions, insertions, or deletions relative to the starting sequence.

Certain Sp35 antibody polypeptides of the present invention comprise, consist essentially of, or consist of an amino acid sequence derived from a human amino acid sequence. However, certain Sp35 antibody polypeptides comprise one or more contiguous amino acids derived from another mammalian species. For example, an Sp35 antibody of the present invention may include a primate heavy chain portion, hinge portion, or antigen binding region. In another example, one or more murine-derived amino acids may be present in a non-murine antibody polypeptide, e.g., in an antigen binding site of an Sp35 antibody. In certain therapeutic applications, Sp35-specific antibodies, or antigen-binding fragments, variants, or analogs thereof are designed so as to not be immunogenic in the animal to which the antibody is administered.

In certain embodiments, an Sp35 antibody polypeptide comprises an amino acid sequence or one or more moieties not normally associated with an antibody. Exemplary modifications are described in more detail below. For example, a single-chain fv antibody fragment of the invention may comprise a flexible linker sequence, or may be modified to add a functional moiety (e.g., PEG, a drug, a toxin, or a label).

An Sp35 antibody polypeptide of the invention may comprise, consist essentially of, or consist of a fusion protein. Fusion proteins are chimeric molecules which comprise, for example, an immunoglobulin antigen-binding domain with at least one target binding site, and at least one heterologous portion, i.e., a portion with which it is not naturally linked in nature. The amino acid sequences may normally exist in separate proteins that are brought together in the fusion polypeptide or they may normally exist in the same protein but are placed in a new arrangement in the fusion polypeptide. Fusion proteins may be created, for example, by chemical synthesis, or by creating and translating a polynucleotide in which the peptide regions are encoded in the desired relationship.

The term "heterologous" as applied to a polynucleotide or a polypeptide, means that the polynucleotide or polypeptide is derived from a distinct entity from that of the rest of the entity to which it is being compared. For instance, as used herein, a "heterologous polypeptide" to be fused to an Sp35 antibody, or an antigen-binding fragment, variant, or analog thereof is derived from a non-immunoglobulin polypeptide of the same species, or an immunoglobulin or non-immunoglobulin polypeptide of a different species.

A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a non-essential amino acid residue in an immunoglobulin polypeptide is preferably replaced with another amino acid residue from the same side chain family. In another embodiment, a string of amino acids can be replaced with a structurally similar string that differs in order and/or composition of side chain family members.

Alternatively, in another embodiment, mutations may be introduced randomly along all or part of the immunoglobulin coding sequence, such as by saturation mutagenesis, and the resultant mutants can be incorporated into Sp35 antibodies for use in the diagnostic and treatment methods disclosed herein and screened for their ability to bind to the desired antigen, e.g., Sp35.

VI. Fusion Proteins and Antibody Conjugates

As discussed in more detail elsewhere herein, Sp35 antibodies, or antigen-binding fragments, variants, or derivatives thereof of the invention may further be recombinantly fused to a heterologous polypeptide at the N- or C-terminus or chemically conjugated (including covalent and non-covalent conjugations) to polypeptides or other compositions. For example, Sp35-specific Sp35 antibodies may be recombinantly fused or conjugated to molecules useful as labels in detection assays and effector molecules such as heterologous polypeptides, drugs, radionuclides, or toxins. See, e.g., PCT publications WO 92/08495; WO 91/14438; WO 89/12624; U.S. Pat. No. 5,314,995; and EP 396,387, which are incorporated herein by reference in their entireties.

Sp35 antibodies, or antigen-binding fragments, variants, or derivatives thereof of the invention include derivatives that are modified, i.e., by the covalent attachment of any type of molecule to the antibody such that covalent attachment does not prevent the antibody binding Sp35. For example, but not by way of limitation, the antibody derivatives include antibodies that have been modified, e.g., by glycosylation, acetylation, pegylation, phosphylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

Sp35 antibodies, or antigen-binding fragments, variants, or derivatives thereof of the invention can be composed of amino acids joined to each other by peptide bonds or modified peptide bonds, i.e., peptide isosteres, and may contain amino acids other than the 20 gene-encoded amino acids. Sp35-specific antibodies may be modified by natural processes, such as posttranslational processing, or by chemical modification techniques which are well known in the art. Such modifications are well described in basic texts and in more detailed monographs, as well as in a voluminous research literature. Modifications can occur anywhere in the Sp35-specific antibody, including the peptide backbone, the amino acid side-chains and the amino or carboxyl termini, or on moieties such as carbohydrates. It will be appreciated that the same type of modification may be present in the same or varying degrees at several sites in a given Sp35-specific antibody. Also, a given Sp35-specific antibody may contain many types of modifications. Sp35-specific antibodies may be branched, for example, as a result of ubiquitination, and they may be cyclic, with or without branching. Cyclic, branched, and branched cyclic Sp35-specific antibodies may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, *Proteins—Structure And Molecular Properties*, T. E. Creighton, W. H. Freeman and Company, New York 2nd Ed., (1993); *Posttranslational Covalent Modification Of Proteins*, B. C. Johnson, Ed., Academic Press, New York, pgs. 1-12 (1983); Seifter et al., *Meth Enzymol* 182:626-646 (1990); Rattan et al., *Ann NY Acad Sci* 663:48-62 (1992)).

The present invention also provides for fusion proteins comprising an Sp35 antibody, or antigen-binding fragment, variant, or derivative thereof, and a heterologous polypeptide. The heterologous polypeptide to which the antibody is fused may be useful for function or is useful to target the Sp35 polypeptide expressing cells. In one embodiment, a fusion protein of the invention comprises, consists essentially of, or consists of, a polypeptide having the amino acid sequence of any one or more of the $V_H$ regions of an antibody of the invention or the amino acid sequence of any one or more of the $V_L$ regions of an antibody of the invention or fragments or variants thereof, and a heterologous polypeptide sequence. In another embodiment, a fusion protein for use in the diagnostic and treatment methods disclosed herein comprises, consists essentially of, or consists of a polypeptide having the amino acid sequence of any one, two, three of the $V_H$ CDRs of an Sp35-specific antibody, or fragments, variants, or derivatives thereof, or the amino acid sequence of any one, two, three of the $V_L$ CDRs of an Sp35-specific antibody, or fragments, variants, or derivatives thereof, and a heterologous polypeptide sequence. In one embodiment, the fusion protein comprises a polypeptide having the amino acid sequence of a $V_H$ CDR3 of an Sp35-specific antibody of the present invention, or fragment, derivative, or variant thereof, and a heterologous polypeptide sequence, which fusion protein specifically binds to at least one epitope of Sp35. In another embodiment, a fusion protein comprises a polypeptide having the amino acid sequence of at least one $V_H$ region of an Sp35-specific antibody of the invention and the amino acid sequence of at least one $V_L$ region of an Sp35-specific antibody of the invention or fragments, derivatives or variants thereof, and a heterologous polypeptide sequence. Preferably, the $V_H$ and $V_L$ regions of the fusion protein correspond to a single source antibody (or scFv or Fab fragment) which specifically binds at least one epitope of Sp35. In yet another embodiment, a fusion protein for use in the diagnostic and treatment methods disclosed herein comprises a polypeptide having the amino acid sequence of any one, two, three or more of the $V_H$ CDRs of an Sp35-specific antibody and the amino acid sequence of any one, two, three or more of the $V_L$ CDRs of an Sp35-specific antibody, or fragments or variants thereof, and a heterologous polypeptide sequence. Preferably, two, three, four, five, six, or more of the $V_H$CDR(s) or $V_L$CDR(s) correspond to single source antibody (or scFv or Fab fragment) of the invention. Nucleic acid molecules encoding these fusion proteins are also encompassed by the invention.

Exemplary fusion proteins reported in the literature include fusions of the T cell receptor (Gascoigne et al., *Proc. Natl. Acad. Sci. USA* 84:2936-2940 (1987)); *CD4* (Capon et al., *Nature* 337:525-531 (1989); Traunecker et al., *Nature* 339:68-70 (1989); Zettmeissl et al., *DNA Cell Biol. USA* 9:347-353 (1990); and Byrn et al., *Nature* 344:667-670 (1990)); L-selectin (homing receptor) (Watson et al., *J. Cell. Biol.* 110:2221-2229 (1990); and Watson et al., *Nature* 349:164-167 (1991)); *CD44* (Aruffo et al., *Cell* 61:1303-1313 (1990)); *CD28* and B7 (Linsley et al., *J. Exp. Med.* 173:721-730 (1991)); CTLA-4 (Lisley et al., *J. Exp. Med.* 174:561-569 (1991)); *CD22* (Stamenkovic et al., *Cell* 66:1133-1144 (1991)); *TNF receptor* (Ashkenazi et al., *Proc. Natl. Acad. Sci. USA* 88:10535-10539 (1991); Lesslauer et al., *Eur. J. Immunol.* 27:2883-2886 (1991); and Peppel et al., *J. Exp. Med.* 174:1483-1489 (1991)); and IgE receptor a (Ridgway and Gorman, *J. Cell. Biol.* Vol. 115, Abstract No. 1448 (1991)).

In certain embodiments, Sp35 antibodies, antibody fragments, derivatives and variants thereof further comprise a targeting moiety. Targeting moieties include a protein or a peptide which directs localization to a certain part of the body, for example, to the brain or compartments therein. In certain embodiments, Sp35 antibodies, antibody fragments, derivatives and variants thereof are attached or fused to a brain targeting moiety. The brain targeting moieties are attached covalently (e.g., direct, translational fusion, or by chemical linkage either directly or through a spacer molecule, which can be optionally cleavable) or non-covalently attached (e.g., through reversible interactions such as avidin, biotin, protein A, IgG, etc.). In other embodiments, the Sp35 antibodies, antibody fragments, derivatives and variants thereof are attached to one more brain targeting moieties. In additional embodiments, the brain targeting moiety is attached to a plurality of Sp35 antibodies, antibody fragments, derivatives and variants thereof.

A brain targeting moiety associated with an Sp35 antibody, antibody fragment, derivative or variant thereof enhances brain delivery of such an Sp35 antibodies, antibody fragments, derivatives and variants thereof. A number of polypeptides have been described which, when fused to a protein or therapeutic agent, delivers the protein or therapeutic agent through the blood brain barrier (BBB). Non-limiting examples include the single domain antibody FC5 (Abulrob et al. (2005) *J. Neurochem.* 95, 1201-1214); mAB 83-14, a monoclonal antibody to the human insulin receptor (Pardridge et al. (1995) *Pharmacol. Res.* 12, 807-816); the B2, B6 and B8 peptides binding to the human transferrin receptor (hTfR) (Xia et al. (2000) *J. Virol.* 74, 11359-11366); the OX26 monoclonal antibody to the transferrin receptor (Pardridge et al. (1991) *J. Pharmacol. Exp. Ther.* 259, 66-70); and SEQ ID NOs: 1-18 of U.S. Pat. No. 6,306,365. The contents of the above references are incorporated herein by reference in their entirety.

Enhanced brain delivery of an Sp35 antibody, antibody fragment, derivative or variant thereof is determined by a number of means well established in the art. For example, administering to an animal a radioactively, enzymatically or fluorescently labeled Sp35 antibody, antibody fragment, derivative and variant thereof linked to a brain targeting moiety; determining brain localization; and comparing localization with an equivalent radioactively, enzymatically or fluorescently labeled Sp35 antibody, antibody fragment, derivative or variant thereof that is not associated with a brain targeting moiety. Other means of determining enhanced targeting are described in the above references.

As discussed elsewhere herein, Sp35 antibodies, or antigen-binding fragments, variants, or derivatives thereof of the invention may be fused to heterologous polypeptides to increase the in vivo half life of the polypeptides or for use in immunoassays using methods known in the art. For example, in one embodiment, PEG can be conjugated to the Sp35 antibodies of the invention to increase their half-life in vivo. Leong, S. R., et al., *Cytokine* 16:106 (2001); *Adv. in Drug Deliv. Rev.* 54:531 (2002); or Weir et al., *Biochem. Soc. Transactions* 30:512 (2002).

Moreover, Sp35 antibodies, or antigen-binding fragments, variants, or derivatives thereof of the invention can be fused to marker sequences, such as a peptide to facilitate their purification or detection. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., *Proc. Natl. Acad. Sci. USA* 86:821-824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., *Cell* 37:767 (1984)) and the "flag" tag.

Fusion proteins can be prepared using methods that are well known in the art (see for example U.S. Pat. Nos. 5,116,964 and 5,225,538). The precise site at which the fusion is made may be selected empirically to optimize the secretion or binding characteristics of the fusion protein. DNA encoding the fusion protein is then transfected into a host cell for expression.

Sp35 antibodies or antigen-binding fragments, variants, or derivatives thereof of the present invention may be used in non-conjugated form or may be conjugated to at least one of a variety of molecules, e.g., to improve the therapeutic properties of the molecule, to facilitate target detection, or for imaging or therapy of the patient. Sp35 antibodies, or antigen-binding fragments, variants, or derivatives thereof of the invention can be labeled or conjugated either before or after purification, when purification is performed.

In particular, Sp35 antibodies, or antigen-binding fragments, variants, or derivatives thereof of the invention may be conjugated to therapeutic agents, prodrugs, peptides, proteins, enzymes, viruses, lipids, biological response modifiers, pharmaceutical agents, or PEG.

Those skilled in the art will appreciate that conjugates may also be assembled using a variety of techniques depending on the selected agent to be conjugated. For example, conjugates with biotin are prepared e.g. by reacting a binding polypeptide with an activated ester of biotin such as the biotin N-hydroxysuccinimide ester. Similarly, conjugates with a fluorescent marker may be prepared in the presence of a coupling agent, e.g. those listed herein, or by reaction with an isothiocyanate, preferably fluorescein-isothiocyanate. Conjugates of the Sp35 antibodies, or antigen-binding fragments, variants, or derivatives thereof of the invention are prepared in an analogous manner.

The present invention further encompasses Sp35 antibodies, or antigen-binding fragments, variants, or derivatives thereof of the invention conjugated to a diagnostic or therapeutic agent. The Sp35 antibodies can be used diagnostically to, for example, monitor the development or progression of a neurological disease as part of a clinical testing procedure to, e.g., determine the efficacy of a given treatment and/or prevention regimen. Detection can be facilitated by coupling the Sp35 antibody, or antigen-binding fragment, variant, or derivative thereof to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. See, for example, U.S. Pat. No. 4,741,900 for metal ions which can be conjugated to antibodies for use as diagnostics according to the present invention. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}$I, $^{131}$I, $^{111}$In or $^{99}$Tc.

An Sp35 antibody, or antigen-binding fragment, variant, or derivative thereof also can be detectably labeled by coupling it to a chemiluminescent compound. The presence of the chemiluminescent-tagged Sp35 antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

One of the ways in which an Sp35 antibody, or antigen-binding fragment, variant, or derivative thereof can be detectably labeled is by linking the same to an enzyme and using the linked product in an enzyme immunoassay (EIA) (Voller, A., "The Enzyme Linked Immunosorbent Assay (ELISA)" Microbiological Associates Quarterly Publication, Walkersville, Md., *Diagnostic Horizons* 2:1-7 (1978)); Voller et al., *J. Clin. Pathol.* 31:507-520 (1978); Butler, J. E., *Meth. Enzymol.* 73:482-523 (1981); Maggio, E. (ed.), *Enzyme Immunoassay*, CRC Press, Boca Raton, Fla., (1980); Ishikawa, E. et al., (eds.), *Enzyme Immunoassay*, Kgaku Shoin, Tokyo (1981). The enzyme, which is bound to the Sp35 antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. Additionally, the detection can be accomplished by colorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the Sp35 antibody, or antigen-binding fragment, variant, or derivative thereof, it is possible to detect the antibody through the use of a radioimmunoassay (RIA) (see, for example, Weintraub, B., *Principles of Radioimmunoassays, Seventh Training Course on Radioligand Assay Techniques*, The Endocrine Society, (March, 1986)), which is incorporated by reference herein). The radioactive isotope can be detected by means including, but not limited to, a gamma counter, a scintillation counter, or autoradiography.

An Sp35 antibody, or antigen-binding fragment, variant, or derivative thereof can also be detectably labeled using fluorescence emitting metals such as 152Eu, or others of the lanthanide series. These metals can be attached to the antibody using such metal chelating groups as diethylenetriaminepentacetic acid (DTPA) or ethylenediaminetetraacetic acid (EDTA).

Techniques for conjugating various moieties to an Sp35 antibody, or antigen-binding fragment, variant, or derivative thereof are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. (1985); Hellstrom et al., "Antibodies For Drug Delivery", in *Controlled Drug Delivery* (2nd Ed.), Robinson et al. (eds.), Marcel Dekker, Inc., pp. 623-53 (1987); Thorpe, "Antibody Carriers Of Cytotoxic Agents In Cancer Therapy: A Review", in *Monoclonal Antibodies '84: Biological And Clinical Applications*, Pinchera et al. (eds.), pp. 475-506 (1985); "Analysis, Results, And Future Prospective Of The Therapeutic Use Of Radiolabeled Antibody In Cancer Therapy", in *Monoclonal Antibodies For Cancer Detection And Therapy*, Baldwin et al. (eds.), Academic Press pp. 303-16 (1985), and Thorpe et al., "The Preparation And Cytotoxic Properties Of Antibody-Toxin Conjugates", *Immunol. Rev.* 62:119-58 (1982).

VII. Expression of Antibody Polypeptides

As is well known, RNA may be isolated from the original hybridoma cells or from other transformed cells by standard techniques, such as guanidinium isothiocyanate extraction and precipitation followed by centrifugation or chromatography. Where desirable, mRNA may be isolated from total RNA by standard techniques such as chromatography on oligo dT cellulose. Suitable techniques are familiar in the art.

In one embodiment, cDNAs that encode the light and the heavy chains of the antibody may be made, either simultaneously or separately, using reverse transcriptase and DNA polymerase in accordance with well known methods. PCR may be initiated by consensus constant region primers or by more specific primers based on the published heavy and light chain DNA and amino acid sequences. As discussed above, PCR also may be used to isolate DNA clones encoding the antibody light and heavy chains. In this case the libraries may be screened by consensus primers or larger homologous probes, such as mouse constant region probes.

DNA, typically plasmid DNA, may be isolated from the cells using techniques known in the art, restriction mapped and sequenced in accordance with standard, well known techniques set forth in detail, e.g., in the foregoing references relating to recombinant DNA techniques. Of course, the DNA may be synthetic according to the present invention at any point during the isolation process or subsequent analysis.

Following manipulation of the isolated genetic material to provide Sp35 antibodies, or antigen-binding fragments, variants, or derivatives thereof of the invention, the polynucleotides encoding the Sp35 antibodies are typically inserted in an expression vector for introduction into host cells that may be used to produce the desired quantity of Sp35 antibody.

Recombinant expression of an antibody, or fragment, derivative or analog thereof, e.g., a heavy or light chain of an antibody which binds to a target molecule described herein, e.g., Sp35, requires construction of an expression vector containing a polynucleotide that encodes the antibody. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes both heavy and light chain polypeptides. In such situations, the light chain is advantageously placed before the heavy chain to avoid an excess of toxic free heavy chain (Proudfoot, *Nature* 322:52 (1986); Kohler, *Proc. Natl. Acad. Sci. USA* 77:2197 (1980)). The coding sequences for the heavy and light chains may comprise cDNA or genomic DNA.

The term "vector" or "expression vector" is used herein to mean vectors used in accordance with the present invention as a vehicle for introducing into and expressing a desired gene in a host cell. As known to those skilled in the art, such vectors may easily be selected from the group consisting of plasmids, phages, viruses and retroviruses. In general, vectors compatible with the instant invention will comprise a selection marker, appropriate restriction sites to facilitate cloning of the desired gene and the ability to enter and/or replicate in eukaryotic or prokaryotic cells.

For the purposes of this invention, numerous expression vector systems may be employed. For example, one class of vector utilizes DNA elements which are derived from animal viruses such as bovine papilloma virus, polyoma virus, adenovirus, vaccinia virus, baculovirus, retroviruses (RSV, MMTV or MOMLV) or SV40 virus. Others involve the use of polycistronic systems with internal ribosome binding sites. Additionally, cells which have integrated the DNA into their chromosomes may be selected by introducing one or more markers which allow selection of transfected host cells. The marker may provide for prototrophy to an auxotrophic host, biocide resistance (e.g., antibiotics) or resistance to heavy metals such as copper. The selectable marker gene can either be directly linked to the DNA sequences to be expressed, or introduced into the same cell by cotransformation. Additional elements may also be needed for optimal synthesis of mRNA. These elements may include signal sequences, splice signals, as well as transcriptional promoters, enhancers, and termination signals.

In particularly preferred embodiments the cloned variable region genes are inserted into an expression vector along with the heavy and light chain constant region genes (preferably human) synthetic as discussed above. In one embodiment, this is effected using a proprietary expression vector of Biogen IDEC, Inc., referred to as NEOSPLA (U.S. Pat. No. 6,159,730). This vector contains the cytomegalovirus promoter/enhancer, the mouse beta globin major promoter, the SV40 origin of replication, the bovine growth hormone polyadenylation sequence, neomycin phosphotransferase exon 1 and exon 2, the dihydrofolate reductase gene and leader sequence. This vector has been found to result in very high level expression of antibodies upon incorporation of variable and constant region genes, transfection in CHO cells, followed by selection in G418 containing medium and methotrexate amplification. Of course, any expression vector which is capable of eliciting expression in eukaryotic cells may be used in the present invention. Examples of suitable vectors include, but are not limited to plasmids pcDNA3, pHCMV/Zeo, pCR3.1, pEF1/His, pIND/GS, pRc/HCMV2, pSV40/Zeo2, pTRACER-HCMV, pUB6/V5-His, pVAX1, and pZeoSV2 (available from Invitrogen, San Diego, Calif.), and plasmid pCI (available from Promega, Madison, Wis.). In general, screening large numbers of transformed cells for those which express suitably high levels if immunoglobulin heavy and light chains is routine experimentation which can be carried out, for example, by robotic systems. Vector systems are also taught in U.S. Pat. Nos. 5,736,137 and 5,658,570, each of which is incorporated by reference in its entirety herein. This system provides for high expression levels, e.g., >30 pg/cell/day. Other exemplary vector systems are disclosed e.g., in U.S. Pat. No. 6,413,777.

In other preferred embodiments the Sp35 antibodies, or antigen-binding fragments, variants, or derivatives thereof of the invention may be expressed using polycistronic constructs such as those disclosed in United States Patent Application Publication No. 2003-0157641 A1, filed Nov. 18, 2002 and incorporated herein in its entirety. In these novel expression systems, multiple gene products of interest such as heavy and light chains of antibodies may be produced from a single polycistronic construct. These systems advantageously use an internal ribosome entry site (IRES) to provide relatively high levels of Sp35 antibodies, e.g., binding polypeptides, e.g., Sp35-specific antibodies or immunospecific fragments thereof in eukaryotic host cells. Compatible IRES sequences are disclosed in U.S. Pat. No. 6,193,980 which is also incorporated herein. Those skilled in the art will appreciate that such expression systems may be used to effectively produce the full range of Sp35 antibodies disclosed in the instant application.

More generally, once the vector or DNA sequence encoding a monomeric subunit of the Sp35 antibody has been prepared, the expression vector may be introduced into an appropriate host cell. Introduction of the plasmid into the host cell can be accomplished by various techniques well known to those of skill in the art. These include, but are not limited to, transfection (including electrophoresis and electroporation), protoplast fusion, calcium phosphate precipitation, cell fusion with enveloped DNA, microinjection, and infection with intact virus. See, Ridgway, A. A. G. "*Mammalian Expression Vectors*" Vectors, Rodriguez and Denhardt, Eds., Butterworths, Boston, Mass., Chapter 24.2, pp. 470-472 (1988). Typically, plasmid introduction into the host is via electroporation. The host cells harboring the expression construct are grown under conditions appropriate to the production of the light chains and heavy chains, and assayed for heavy and/or light chain protein synthesis. Exemplary assay techniques include enzyme-linked immunosorbent assay (ELISA), radioimmunoassay (RIA), or fluorescence-activated cell sorter analysis (FACS), immunohistochemistry and the like.

The expression vector is transferred to a host cell by conventional techniques and the transfected cells are then cultured by conventional techniques to produce an antibody for use in the methods described herein. Thus, the invention includes host cells containing a polynucleotide encoding an antibody of the invention, or a heavy or light chain thereof, operably linked to a heterologous promoter. In preferred embodiments for the expression of double-chained antibodies, vectors encoding both the heavy and light chains may be co-expressed in the host cell for expression of the entire immunoglobulin molecule, as detailed below.

As used herein, "host cells" refers to cells which harbor vectors constructed using recombinant DNA techniques and encoding at least one heterologous gene. In descriptions of processes for isolation of antibodies from recombinant hosts, the terms "cell" and "cell culture" are used interchangeably to denote the source of antibody unless it is clearly specified otherwise. In other words, recovery of polypeptide from the "cells" may mean either from spun down whole cells, or from the cell culture containing both the medium and the suspended cells.

A variety of host-expression vector systems may be utilized to express antibody molecules for use in the methods described herein. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BLK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., *Gene* 45:101 (1986); Cockett et al., *Bio/Technology* 8:2 (1990)).

The host cell line used for protein expression is often of mammalian origin; those skilled in the art are credited with ability to preferentially determine particular host cell lines which are best suited for the desired gene product to be expressed therein. Exemplary host cell lines include, but are not limited to, CHO (Chinese Hamster Ovary), DG44 and DUXB11 (Chinese Hamster Ovary lines, DHFR minus), HELA (human cervical carcinoma), CVI (monkey kidney line), COS (a derivative of CVI with SV40 T antigen), VERY, BHK (baby hamster kidney), MDCK, 293, WI38, R1610 (Chinese hamster fibroblast) BALBC/3T3 (mouse fibroblast), HAK (hamster kidney line), SP2/O (mouse myeloma), P3x63-Ag3.653 (mouse myeloma), BFA-1c1BPT (bovine endothelial cells), RAJI (human lymphocyte) and 293 (human kidney). CHO cells are particularly preferred. Host cell lines are typically available from commercial services, the American Tissue Culture Collection or from published literature.

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which stably express the antibody molecule.

A number of selection systems may be used, including but not limited to the herpes simplex virus thymidine kinase (Wigler et al., *Cell* 11:223 (1977)), hypoxanthine-guanine phosphoribosyltransferase (Szybalska & Szybalski, *Proc. Natl. Acad. Sci. USA* 48:202 (1992)), and adenine phosphoribosyltransferase (Lowy et al., *Cell* 22:817 1980) genes can be employed in tk-, hgprt- or aprt-cells, respectively. Also, antimetabolite resistance can be used as the basis of selection for the following genes: dhfr, which confers resistance to methotrexate (Wigler et al., *Natl. Acad. Sci. USA* 77:357 (1980); O'Hare et al., *Proc. Natl. Acad. Sci. USA* 78:1527 (1981)); gpt, which confers resistance to mycophenolic acid (Mulligan & Berg, *Proc. Natl. Acad. Sci. USA* 78:2072 (1981)); neo, which confers resistance to the aminoglycoside G-418 Clinical Pharmacy 12:488-505; Wu and Wu, *Biotherapy* 3:87-95 (1991); Tolstoshev, *Ann. Rev. Pharmacol. Toxicol.* 32:573-596 (1993); Mulligan, *Science* 260:926-932 (1993); and Morgan and Anderson, *Ann. Rev. Biochem.* 62:191-217 (1993); *TIB TECH* 11(5):155-215 (May, 1993); and hygro, which confers resistance to hygromycin (Santerre et al., *Gene* 30:147 (1984). Methods commonly known in the art of recombinant DNA technology which can be used are described in Ausubel et al. (eds.), *Current Protocols in Molecular Biology*, John Wiley & Sons, NY (1993); Kriegler, *Gene Transfer and Expression*, A Laboratory Manual, Stockton Press, NY (1990); and in Chapters 12 and 13, Dracopoli et al. (eds), *Current Protocols in Human Genetics*, John Wiley & Sons, NY (1994); Colberre-Garapin et al., *J. Mol. Biol.* 150:1 (1981), which are incorporated by reference herein in their entireties.

The expression levels of an antibody molecule can be increased by vector amplification (for a review, see Bebbington and Hentschel, *The use of vectors based on gene amplification for the expression of cloned genes in mammalian cells in DNA cloning*, Academic Press, New York, Vol. 3. (1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., *Mol. Cell. Biol.* 3:257 (1983)).

In vitro production allows scale-up to give large amounts of the desired polypeptides. Techniques for mammalian cell cultivation under tissue culture conditions are known in the art and include homogeneous suspension culture, e.g. in an airlift reactor or in a continuous stirrer reactor, or immobilized or entrapped cell culture, e.g. in hollow fibers, microcapsules, on agarose microbeads or ceramic cartridges. If necessary and/or desired, the solutions of polypeptides can be purified by the customary chromatography methods, for example gel filtration, ion-exchange chromatography, chromatography over DEAE-cellulose or (immuno-)affinity chromatography, e.g., after preferential biosynthesis of a synthetic hinge region polypeptide or prior to or subsequent to the HIC chromatography step described herein.

Genes encoding Sp35 antibodies, or antigen-binding fragments, variants, or derivatives thereof of the invention can also be expressed non-mammalian cells such as bacteria or yeast or plant cells. Bacteria which readily take up nucleic acids include members of the enterobacteriaceae, such as strains of *Escherichia coli* or *Salmonella*; Bacillaceae, such as *Bacillus subtilis; Pneumococcus; Streptococcus*, and *Haemophilus influenzae*. It will further be appreciated that, when expressed in bacteria, the heterologous polypeptides typically become part of inclusion bodies. The heterologous-polypeptides must be isolated, purified and then assembled into functional molecules. Where tetravalent forms of antibodies are desired, the subunits will then self-assemble into tetravalent antibodies (WO02/096948A2).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the *E. coli* expression vector pUR278 (Ruther et al., *EMBO J.* 2:1791 (1983)), in which the antibody coding sequence may be ligated individually into the vector in frame with the lacZ coding region so that a fusion protein is produced; pIN vectors (Inouye & Inouye, *Nucleic Acids Res.* 13:3101-3109 (1985); Van Heeke & Schuster, *J. Biol. Chem.* 24:5503-5509 (1989)); and the like. pGEX vectors may also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free glutathione. The pGEX vectors are designed to include thrombin or factor Xa protease cleavage sites so that the cloned target gene product can be released from the GST moiety.

In addition to prokaryotes, eukaryotic microbes may also be used. *Saccharomyces cerevisiae*, or common baker's yeast, is the most commonly used among eukaryotic microorganisms although a number of other strains are commonly available, e.g., *Pichia pastoris*.

For expression in *Saccharomyces*, the plasmid YRp7, for example, (Stinchcomb et al., *Nature* 282:39 (1979); Kingsman et al., *Gene* 7:141 (1979); Tschemper et al., *Gene* 10:157 (1980)) is commonly used. This plasmid already contains the TRP1 gene which provides a selection marker for a mutant strain of yeast lacking the ability to grow in tryptophan, for example ATCC No. 44076 or PEP4-1 (Jones, *Genetics* 85:12 (1977)). The presence of the trp1 lesion as a characteristic of the yeast host cell genome then provides an effective environment for detecting transformation by growth in the absence of tryptophan.

In an insect system, *Autographa californica* nuclear polyhedrosis virus (AcNPV) is typically used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

Once an antibody molecule of the invention has been recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Alternatively, a preferred method for increasing the affinity of antibodies of the invention is disclosed in US 2002 0123057 A1.

VIII. Treatment Methods Using Therapeutic Sp35 Antibodies

As described herein, Sp35 antibodies, or antigen-binding fragments, variants, or derivatives thereof of the invention can relieve NgR1-mediated inhibition of axonal extension that normally takes place in CNS neurons. This is beneficial in situations where axonal extension or neurite sprouting is needed in the brain or spinal cord. Spinal cord injury, including partial or complete crush or severance, exemplifies a situation in which axonal extension is needed, but is normally inhibited through operation of the Nogo pathway. Examples of diseases or disorders in which axonal extension and/or neurite sprouting in the brain would be beneficial include stroke, multiple sclerosis, and other neurodegenerative diseases or disorders such as multiple sclerosis (MS), progressive multifocal leukoencephalopathy (PML), encephalomyelitis (EPL), central pontine myelolysis (CPM), adrenoleukodystrophy, Alexander's disease, Pelizaeus Merzbacher disease (PMZ), Globoid cell Leucodystrophy (Krabbe's disease) and Wallerian Degeneration, optic neuritis, transverse myelitis, amylotrophic lateral sclerosis (ALS), Huntington's disease, Alzheimer's disease, Parkinson's disease, spinal cord injury, traumatic brain injury, post radiation injury, neurologic complications of chemotherapy, stroke, acute ischemic optic neuropathy, vitamin E deficiency, isolated vitamin E deficiency syndrome, AR, Bassen-Kornzweig syndrome, Marchiafava-Bignami syndrome, metachromatic leukodystrophy, trigeminal neuralgia, Bell's palsy, spinal cord injury and all neurological diseases related to neuronal cell death.

The inventors have further discovered that Sp35 is expressed in oligodendrocytes, and contributes to oligodendrocyte biology. Soluble derivatives of Sp35, certain polynucleotides (e.g. RNAi), as well as certain antibodies which specifically bind to Sp35, as described herein act as antagonists to Sp35 function in oligodendrocytes, promoting proliferation, differentiation and survival of oligodendrocytes and promoting myelination of neurons in vitro and in vivo. This is beneficial in for diseases, disorders or conditions involving demyelination and dysmyelination. Examples of diseases or disorders in which oligodendrocyte proliferation, differentiation and survival, and/or myelination or remyelination would be beneficial include multiple sclerosis (MS), progressive multifocal leukoencephalopathy (PML), encephalomyelitis (EPL), central pontine myelolysis (CPM), adrenoleukodystrophy, Alexander's disease, Pelizaeus Merzbacher disease (PMZ), Globoid cell Leucodystrophy (Krabbe's disease), Wallerian Degeneration, optic neuritis, transverse myelitis, amylotrophic lateral sclerosis (ALS), Huntington's disease, Alzheimer's disease, Parkinson's disease, spinal cord injury, traumatic brain injury, post radiation injury, neurologic complications of chemotherapy, stroke, acute ischemic optic neuropathy, vitamin E deficiency, isolated vitamin E deficiency syndrome, AR, Bassen-Kornzweig syndrome, Marchiafava-Bignami syndrome, metachromatic leukodystrophy, trigeminal neuralgia, and Bell's palsy.

Accordingly, one embodiment of the present invention provides methods for treating spinal cord injury, diseases or disorders associated with inhibition of neuronal growth in the CNS, diseases or disorders associated with inhibition of oligodendrocyte growth or differentiation, and diseases involving demyelination or dysmyelination of CNS neurons in an animal suffering from such injury or disease or predisposed to contract such disease, the method comprising, consisting essentially of, or consisting of administering to the animal an effective amount of an Sp35 antibody, or antigen-binding fragment, variant, or derivative thereof. Antibodies of the invention are described herein, and include the monoclonal antibodies listed in Table 3A and 3B, antibodies which specifically bind to the same epitope as the monoclonal antibodies listed in Table 3A and 3B, antibodies which competitively inhibit binding of the monoclonal antibodies listed in Table 3A and 3B to Sp35, and antibodies comprising polypeptides derived from the monoclonal antibodies listed in Table 3A and 3B.

A therapeutic Sp35 antibody to be used in treatment methods disclosed herein can be prepared and used as a therapeutic agent which promotes CNS neurite outgrowth, neuronal survival, axon guidance and axon regeneration, which promotes oligodendrocyte survival, growth, and/or differentiation, and which promotes myelination or remyelination of CNS neurons. Characteristics of suitable therapeutic Sp35 antibodies include: binding to Sp35 epitopes which result in blocking of Sp35 activity, binding to Sp35 with sufficient affinity to elicit a therapeutic effect, and binding to Sp35 preferentially to normal binding partners, e.g., Nogo Receptor.

Therapeutic Sp35 antibodies may be monoclonal, chimeric or humanized antibodies, or fragments of antibodies that bind specifically to Sp35. The antibodies may be monovalent, bivalent, polyvalent, or bifunctional antibodies. Antibody fragments include without limitation Fab F(ab')$_2$, and Fv fragments.

Therapeutic Sp35 antibodies, or antigen-binding fragments, variants or derivatives thereof according to the invention can be used in unlabeled or unconjugated form, or can be coupled or linked to drugs, labels or stabilization agents which may or may not exert additional therapeutic effects.

A specific dosage and treatment regimen for any particular patient will depend upon a variety of factors, including the particular Sp35 antibody, or antigen-binding fragment, variant or derivative thereof used, the patient's age, body weight, general health, sex, and diet, and the time of administration, rate of excretion, drug combination, and the severity of the particular disease being treated. Judgment of such factors by medical caregivers is within the ordinary skill in the art. The amount will also depend on the individual patient to be treated, the route of administration, the type of formulation, the characteristics of the compound used, the severity of the disease, and the desired effect. The amount used can be determined by pharmacological and pharmacokinetic principles well known in the art.

In the methods of the invention the Sp35 antibodies, or antigen-binding fragments, variants or derivatives thereof may be administered directly to the nervous system, intracerebroventricularly, or intrathecally, e.g. into a chronic lesion of MS, as discussed in more detail below.

In various embodiments, an Sp35 antibody as described above is an antagonist of Sp35 activity. In certain embodiments, for example, binding of an antagonist Sp35 antibody to Sp35, as expressed on neurons, blocks myelin-associated neurite outgrowth inhibition or neuronal cell death. In other embodiments, binding of the Sp35 antibody to Sp35, as expressed on oligodendrocytes, blocks inhibition of oligodendrocyte growth or differentiation, or blocks demyelination or dysmyelination of CNS neurons.

In methods of the present invention, an Sp35 antibody, or an antigen-binding fragment, variant, or derivative thereof, in particular the Sp35 antibodies described herein, can be administered directly as a preformed polypeptide, or indirectly through a nucleic acid vector, to permit beneficial axonal outgrowth, promote oligodendrocyte proliferation, differentiation, and survival, and/or promote myelination or remyelination.

In certain embodiments, a subject may be treated with a nucleic acid molecule encoding an Sp35 antibody, or antigen-binding fragment, variant, or analog thereof, e.g., in a vector. Doses for nucleic acids encoding polypeptides range from about 10 ng to 1 g, 100 ng to 100 mg, 1 µg to 10 mg, or 30-300 µg DNA per patient. Doses for infectious viral vectors vary from 10-100, or more, virions per dose.

In some embodiments of the present invention an Sp35 antibody, or an antigen-binding fragment, variant, or derivative thereof is administered in a treatment method that includes: (1) transforming or transfecting an implantable host cell with a nucleic acid, e.g., a vector, that expresses an Sp35 antibody, or an antigen-binding fragment, variant, or derivative thereof; and (2) implanting the transformed host cell into a mammal, at the site of a disease, disorder or injury. For example, the transformed host cell can be implanted at the site of a spinal cord injury or at a site of dysmyelination. In some embodiments of the invention, the implantable host cell is removed from a mammal, temporarily cultured, transformed or transfected with an isolated nucleic acid encoding a an Sp35 antibody, and implanted back into the same mammal from which it was removed. The cell can be, but is not required to be, removed from the same site at which it is implanted. Such embodiments, sometimes known as ex vivo gene therapy, can provide a continuous supply of the Sp35 polypeptide, localized at the site of site of action, for a limited period of time.

The methods for treating spinal cord injury, diseases or disorders associated with inhibition of neuronal growth in the CNS, diseases or disorders associated with inhibition of oligodendrocyte growth or differentiation, and diseases involving demyelination or dysmyelination of CNS neurons comprising administration of an Sp35 antibody, or antigen-binding fragment, variant, or derivative thereof of the invention are typically tested in vitro, and then in vivo in an acceptable animal model, for the desired therapeutic or prophylactic activity, prior to use in humans. Suitable animal models, including transgenic animals, are will known to those of ordinary skill in the art. For example, in vitro assays to demonstrate the therapeutic utility of Sp35 antibody described herein include the effect of an Sp35 antibody on a cell line or a patient tissue sample. The effect of the Sp35 antibody on the cell line and/or tissue sample can be determined utilizing techniques known to those of skill in the art, such as the assays disclosed elsewhere herein. In accordance with the invention, in vitro assays which can be used to determine whether administration of a specific Sp35 antibody is indicated, include in vitro cell culture assays in which a patient tissue sample is grown in culture, and exposed to or otherwise administered a compound, and the effect of such compound upon the tissue sample is observed.

Supplementary active compounds also can be incorporated into the compositions of the invention. For example, a Sp35 antibody, or antigen-binding fragment, variant, or derivative thereof of the invention may be coformulated with and/or coadministered with one or more additional therapeutic agents.

The invention encompasses any suitable delivery method for a Sp35 antibody, or antigen-binding fragment, variant, or derivative thereof of the invention to a selected target tissue, including bolus injection of an aqueous solution or implantation of a controlled-release system. Use of a controlled-release implant reduces the need for repeat injections.

IX. Pharmaceutical Compositions and Administration Methods

Methods of preparing and administering Sp35 antibodies, or antigen-binding fragments, variants, or derivatives thereof of the invention to a subject in need thereof are well known to or are readily determined by those skilled in the art. The route of administration of the Sp35 antibody, or antigen-binding fragment, variant, or derivative thereof may be, for example, oral, parenteral, by inhalation or topical. The term parenteral as used herein includes, e.g., intravenous, intraarterial, intraperitoneal, intramuscular, subcutaneous, rectal or vaginal administration. While all these forms of administration are clearly contemplated as being within the scope of the invention, a form for administration would be a solution for injection, in particular for intravenous or intraarterial injection or drip. Usually, a suitable pharmaceutical composition for injection may comprise a buffer (e.g. acetate, phosphate or citrate buffer), a surfactant (e.g. polysorbate), optionally a stabilizer agent (e.g. human albumin), etc. However, in other methods compatible with the teachings herein, Sp35 antibodies, or antigen-binding fragments, variants, or derivatives thereof of the invention can be delivered directly to the site of the adverse cellular population thereby increasing the exposure of the diseased tissue to the therapeutic agent.

As previously discussed, Sp35 antibodies, or antigen-binding fragments, variants, or derivatives thereof of the invention may be administered in a pharmaceutically effective amount for the in vivo treatment of mammalian spinal cord injury, diseases or disorders associated with inhibition of neuronal growth in the CNS, diseases or disorders associated with inhibition of oligodendrocyte growth or differentiation, and diseases involving demyelination or dysmyelination of CNS. In this regard, it will be appreciated that the disclosed antibodies will be formulated so as to facilitate administration and promote stability of the active agent. Preferably, pharmaceutical compositions in accordance with the present invention comprise a pharmaceutically acceptable, non-toxic, sterile carrier such as physiological saline, non-toxic buffers, preservatives and the like. For the purposes of the instant application, a pharmaceutically effective amount of an Sp35 antibody, or antigen-binding fragment, variant, or derivative thereof, conjugated or unconjugated, shall be held to mean an amount sufficient to achieve effective binding to a target and to achieve a benefit, e.g., to ameliorate symptoms of a disease or disorder or to detect a substance or a cell.

The pharmaceutical compositions used in this invention comprise pharmaceutically acceptable carriers, including, e.g., ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Preparations for parenteral administration includes sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. In the subject invention, pharmaceutically acceptable carriers include, but are not limited to, 0.01-0.1M and preferably 0.05M phosphate buffer or 0.8% saline. Other common parenteral vehicles include sodium phosphate solutions, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present such as for example, antimicrobials, antioxidants, chelating agents, and inert gases and the like.

More particularly, pharmaceutical compositions suitable for injectable use include sterile aqueous solutions (where water soluble) or dispersions and sterile powders for the extemporaneous preparation of sterile injectable solutions or dispersions. In such cases, the composition must be sterile and should be fluid to the extent that easy syringability exists. It should be stable under the conditions of manufacture and storage and will preferably be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Suitable formulations for use in the therapeutic methods disclosed herein are described in Remington's Pharmaceutical Sciences, Mack Publishing Co., 16th ed. (1980).

Prevention of the action of microorganisms can be achieved by various antibacterial and antifungal agents, for example, parabens, chlorobutanol, phenol, ascorbic acid, thimerosal and the like. In many cases, it will be preferable to include isotonic agents, for example, sugars, polyalcohols, such as mannitol, sorbitol, or sodium chloride in the composition. Prolonged absorption of the injectable compositions can be brought about by including in the composition an agent which delays absorption, for example, aluminum monostearate and gelatin.

In any case, sterile injectable solutions can be prepared by incorporating an active compound (e.g., an Sp35 antibody, or antigen-binding fragment, variant, or derivative thereof, by itself or in combination with other active agents) in the required amount in an appropriate solvent with one or a combination of ingredients enumerated herein, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yields a powder of an active ingredient plus any additional desired ingredient from a previously sterile-filtered solution thereof. The preparations for injections are processed, filled into containers such as ampoules, bags, bottles, syringes or vials, and sealed under aseptic conditions according to methods known in the art. Further, the preparations may be packaged and sold in the form of a kit such as those described in co-pending U.S. Ser. No. 09/259,337 (US-2002-0102208 A1), which is incorporated herein by reference in its entirety. Such articles of manufacture will preferably have labels or package inserts indicating that the associated compositions are useful for treating a subject suffering from, or predisposed to autoimmune or neoplastic disorders.

Parenteral formulations may be a single bolus dose, an infusion or a loading bolus dose followed with a maintenance dose. These compositions may be administered at specific fixed or variable intervals, e.g., once a day, or on an "as needed" basis.

Certain pharmaceutical compositions used in this invention may be orally administered in an acceptable dosage form including, e.g., capsules, tablets, aqueous suspensions or solutions. Certain pharmaceutical compositions also may be administered by nasal aerosol or inhalation. Such compositions may be prepared as solutions in saline, employing benzyl alcohol or other suitable preservatives, absorption promoters to enhance bioavailability, and/or other conventional solubilizing or dispersing agents.

The amount of an Sp35 antibody, or fragment, variant, or derivative thereof that may be combined with the carrier materials to produce a single dosage form will vary depending upon the host treated and the particular mode of administration. The composition may be administered as a single dose, multiple doses or over an established period of time in an infusion. Dosage regimens also may be adjusted to provide the optimum desired response (e.g., a therapeutic or prophylactic response).

In keeping with the scope of the present disclosure, Sp35 antibodies, or antigen-binding fragments, variants, or derivatives thereof of the invention may be administered to a human or other animal in accordance with the aforementioned methods of treatment in an amount sufficient to produce a therapeutic effect. The Sp35 antibodies, or antigen-binding fragments, variants, or derivatives thereof of the invention can be administered to such human or other animal in a conventional dosage form prepared by combining the antibody of the invention with a conventional pharmaceutically acceptable carrier or diluent according to known techniques. It will be recognized by one of skill in the art that the form and character of the pharmaceutically acceptable carrier or diluent is dictated by the amount of active ingredient with which it is to be combined, the route of administration and other well-known variables. Those skilled in the art will further appreciate that a cocktail comprising one or more species of Sp35 antibodies, or antigen-binding fragments, variants, or derivatives thereof of the invention may prove to be particularly effective.

Effective doses of the compositions of the present invention, for treatment of spinal cord injury, diseases or disorders associated with inhibition of neuronal growth in the CNS, diseases or disorders associated with inhibition of oligodendrocyte growth or differentiation, and diseases involving demyelination or dysmyelination of CNS vary depending upon many different factors, including means of administration, target site, physiological state of the patient, whether the patient is human or an animal, other medications administered, and whether treatment is prophylactic or therapeutic. Usually, the patient is a human but non-human mammals including transgenic mammals can also be treated. Treatment dosages may be titrated using routine methods known to those of skill in the art to optimize safety and efficacy.

For treatment of spinal cord injury, diseases or disorders associated with inhibition of neuronal growth in the CNS, diseases or disorders associated with inhibition of oligodendrocyte growth or differentiation, and diseases involving demyelination or dysmyelination of CNS with an Sp35 antibody, or antigen-binding fragment, variant, or derivative thereof, the dosage can range, e.g., from about 0.0001 to 100 mg/kg, and more usually 0.01 to 5 mg/kg (e.g., 0.02 mg/kg, 0.25 mg/kg, 0.5 mg/kg, 0.75 mg/kg, 1 mg/kg, 2 mg/kg, etc.), of the host body weight. For example dosages can be 1 mg/kg body weight or 10 mg/kg body weight or within the range of 1-10 mg/kg, preferably at least 1 mg/kg. Doses intermediate in the above ranges are also intended to be within the scope of the invention. Subjects can be administered such doses daily, on alternative days, weekly or according to any other schedule determined by empirical analysis. An exemplary treatment entails administration in multiple dosages over a prolonged period, for example, of at least six months. Additional exemplary treatment regimes entail administration once per every two weeks or once a month or once every 3 to 6 months. Exemplary dosage schedules include 1-10 mg/kg or 15 mg/kg on consecutive days, 30 mg/kg on alternate days or 60 mg/kg weekly. In some methods, two or more monoclonal antibodies with different binding specificities are administered simultaneously, in which case the dosage of each antibody administered falls within the ranges indicated.

Sp35 antibodies, or antigen-binding fragments, variants, or derivatives thereof of the invention can be administered on multiple occasions. Intervals between single dosages can be daily, weekly, monthly or yearly. Intervals can also be irregular as indicated by measuring blood levels of target polypeptide or target molecule in the patient. In some methods, dosage is adjusted to achieve a plasma polypeptide concentration of 1-1000 µg/ml and in some methods 25-300 µg/ml. Alternatively, Sp35 antibodies, or antigen-binding fragments, variants, or derivatives thereof of the invention can be administered as a sustained release formulation, in which case less frequent administration is required. Dosage and frequency vary depending on the half-life of the antibody in the patient. The half-life of an Sp35 antibody can also be prolonged via fusion to a stable polypeptide or moeity, e.g., albumin or PEG. In general, humanized antibodies show the longest half-life, followed by chimeric antibodies and nonhuman antibodies.

In one embodiment, the Sp35 antibodies, or antigen-binding fragments, variants, or derivatives thereof of the invention can be administered in unconjugated form, In another embodiment, the Sp35 antibodies, or antigen-binding fragments, variants, or derivatives thereof of the invention can be administered multiple times in conjugated form. In still another embodiment, Sp35 antibodies, or antigen-binding fragments, variants, or derivatives thereof of the invention can be administered in unconjugated form, then in conjugated form, or vice versa.

The compositions of the present invention may be administered by any suitable method, e.g., parenterally, intraventricularly, orally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. As described previously, Sp35 antibodies, or antigen-binding fragments, variants, or derivatives thereof of the invention act in the nervous system to promote survival, proliferation and differentiation of oligodendrocytes and myelination of neurons and neuronal survival, axon regeneration and axon guidance. Accordingly, in the methods of the invention, the Sp35 antibodies, or anti-gen-binding fragments, variants, or derivatives thereof are administered in such a way that they cross the blood-brain barrier. This crossing can result from the physico-chemical properties inherent in the Sp35 antibody molecule itself, from other components in a pharmaceutical formulation, or from the use of a mechanical device such as a needle, cannula or surgical instruments to breach the blood-brain barrier. Where the Sp35 antibody is a molecule that does not inherently cross the blood-brain barrier, e.g., a fusion to a moiety that facilitates the crossing, suitable routes of administration are, e.g., intrathecal or intracranial, e.g., directly into a chronic lesion of MS. Where the Sp35 antibody is a molecule that inherently crosses the blood-brain barrier, the route of administration may be by one or more of the various routes described below. In some methods, antibodies are administered as a sustained release composition or device, such as a Medipad™ device. Delivery across the blood brain barrier can be enhanced by a carrying molecule, such as anti-Fc receptor, transferrin, anti-insulin receptor or a toxin conjugate or penetration enhancer.

The Sp35 antibodies, or antigen-binding fragments, variants, or derivatives thereof used in the methods of the invention may be directly infused into the brain. Various implants for direct brain infusion of compounds are known and are effective in the delivery of therapeutic compounds to human patients suffering from neurological disorders. These include chronic infusion into the brain using a pump, stereotactically implanted, temporary interstitial catheters, permanent intracranial catheter implants, and surgically implanted biodegradable implants. See, e.g., Gill et al., "Direct brain infusion of glial cell line-derived neurotrophic factor in Parkinson disease," Nature Med. 9: 589-95 (2003); Scharfen et al., "High Activity Iodine-125 Interstitial Implant For Gliomas," Int. J. Radiation Oncology Biol. Phys. 24(4):583-91 (1992); Gaspar et al., "Permanent $^{125}$I Implants for Recurrent Malignant Gliomas," Int. J. Radiation Oncology Biol. Phys. 43(5):977-82 (1999); chapter 66, pages 577-580, Bellezza et al., "Stereotactic Interstitial Brachytherapy," in Gildenberg et al., Textbook of Stereotactic and Functional Neurosurgery, McGraw-Hill (1998); and Brem et al., "The Safety of Interstitial Chemotherapy with BCNU-Loaded Polymer Followed by Radiation Therapy in the Treatment of Newly Diagnosed Malignant Gliomas: Phase I Trial," J. Neuro-Oncology 26:111-23 (1995).

The compositions may also comprise an Sp35 antibody dispersed in a biocompatible carrier material that functions as a suitable delivery or support system for the compounds. Suitable examples of sustained release carriers include semipermeable polymer matrices in the form of shaped articles such as suppositories or capsules. Implantable or microcapsular sustained release matrices include polylactides (U.S. Pat. No. 3,773,319; EP 58,481), copolymers of L-glutamic acid and gamma-ethyl-L-glutamate (Sidman et al., Biopolymers 22:547-56 (1985)); poly(2-hydroxyethyl-methacrylate), ethylene vinyl acetate (Langer et al., J. Biomed. Mater. Res. 15:167-277 (1981); Langer, Chem. Tech. 12:98-105 (1982)) or poly-D-(−)-3hydroxybutyric acid (EP 133,988).

In some embodiments of the invention, an Sp35 antibody, or antigen-binding fragment, variant, or derivative thereof of the invention is administered to a patient by direct infusion into an appropriate region of the brain. See, e.g., Gill et al., supra. Alternative techniques are available and may be applied to administer an Sp35 antibody according to the invention. For example, stereotactic placement of a catheter or implant can be accomplished using the Riechert-Mundinger unit and the ZD (Zamorano-Dujovny) multipurpose localizing unit. A contrast-enhanced computerized tomography (CT) scan, injecting 120 ml of omnipaque, 350 mg iodine/ml, with 2 mm slice thickness can allow three-dimensional multiplanar treatment planning (STP, Fischer, Freiburg, Germany). This equipment permits planning on the basis of magnetic resonance imaging studies, merging the CT and MRI target information for clear target confirmation.

The Leksell stereotactic system (Downs Surgical, Inc., Decatur, Ga.) modified for use with a GE CT scanner (General Electric Company, Milwaukee, Wis.) as well as the Brown-Roberts-Wells (BRW) stereotactic system (Radionics, Burlington, Mass.) can be used for this purpose. Thus, on the morning of the implant, the annular base ring of the BRW stereotactic frame can be attached to the patient's skull. Serial CT sections can be obtained at 3 mm intervals though the (target tissue) region with a graphite rod localizer frame clamped to the base plate. A computerized treatment planning program can be run on a VAX 11/780 computer (Digital Equipment Corporation, Maynard, Mass.) using CT coordinates of the graphite rod images to map between CT space and BRW space.

Sp35 antibodies, or antigen-binding fragments, variants, or derivatives thereof of the invention can optionally be administered in combination with other agents that are effective in treating the disorder or condition in need of treatment (e.g., prophylactic or therapeutic).

X. Diagnostics

The invention further provides a diagnostic method useful during diagnosis of neuronal disorders or injuries, which involves measuring the expression level of Sp35 protein or transcript in tissue or other cells or body fluid from an individual and comparing the measured expression level with a standard Sp35 expression levels in normal tissue or body fluid, whereby an increase in the expression level compared to the standard is indicative of a disorder.

Sp35-specific antibodies can be used to assay protein levels in a biological sample using classical immunohistological methods known to those of skill in the art (e.g., see Jalkanen, et al., J. Cell. Biol. 101:976-985 (1985); Jalkanen, et al., J. Cell Biol. 105:3087-3096 (1987)). Other antibody-based methods useful for detecting protein expression include immunoassays, such as the enzyme linked immunosorbent assay (ELISA), immunoprecipitation, or western blotting. Suitable assays are described in more detail elsewhere herein.

By "assaying the expression level of Sp35 polypeptide" is intended qualitatively or quantitatively measuring or estimating the level of Sp35 polypeptide in a first biological sample either directly (e.g., by determining or estimating absolute protein level) or relatively (e.g., by comparing to the cancer associated polypeptide level in a second biological sample). Preferably, Sp35 polypeptide expression level in the first biological sample is measured or estimated and compared to a standard Sp35 polypeptide level, the standard being taken from a second biological sample obtained from an individual not having the disorder or being determined by averaging levels from a population of individuals not having the disorder. As will be appreciated in the art, once the "standard" Sp35 polypeptide level is known, it can be used repeatedly as a standard for comparison.

By "biological sample" is intended any biological sample obtained from an individual, cell line, tissue culture, or other source of cells potentially expressing Sp35. Methods for obtaining tissue biopsies and body fluids from mammals are well known in the art.

Sp35 antibodies for use in the diagnostic methods described above include any Sp35 antibody which specifically binds to an Sp35 gene product, as described elsewhere herein.

XI. Immunoassays

Sp35 antibodies, or antigen-binding fragments, variants, or derivatives thereof of the invention may be assayed for immunospecific binding by any method known in the art. The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al., eds, Current Protocols in Molecular Biology, John Wiley & Sons, Inc., New York, Vol. 1 (1994), which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1-4 hours) at 4.degree. C., adding protein A and/or protein G sepharose beads to the cell lysate, incubating for about an hour or more at 4.degree. C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al., eds, Current Protocols in Molecular Biology, John Wiley & Sons, Inc., New York, Vol. 1 (1994) at 10.16.1.

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., 32p or 125I) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al., eds, Current Protocols in Molecular Biology, John Wiley & Sons, Inc., New York Vol. 1 (1994) at 10.8.1.

ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al., eds, Current Protocols in Molecular Biology, John Wiley & Sons, Inc., New York, Vol. 1 (1994) at 11.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., $^3H$ or $^{125}I$) with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with antibody of interest is conjugated to a labeled compound (e.g., $^3H$ or $^{125}I$) in the presence of increasing amounts of an unlabeled second antibody.

Sp35 antibodies, or antigen-binding fragments, variants, or derivatives thereof of the invention, additionally, be employed histologically, as in immunofluorescence, immunoelectron microscopy or non-immunological assays, for in situ detection of cancer antigen gene products or conserved variants or peptide fragments thereof. In situ detection may be accomplished by removing a histological specimen from a patient, and applying thereto a labeled Sp35 antibody, or antigen-binding fragment, variant, or derivative thereof, preferably applied by overlaying the labeled antibody (or fragment) onto a biological sample. Through the use of such a procedure, it is possible to determine not only the presence of Sp35 protein, or conserved variants or peptide fragments, but also its distribution in the examined tissue. Using the present invention, those of ordinary skill will readily perceive that any of a wide variety of histological methods (such as staining procedures) can be modified in order to achieve such in situ detection.

Immunoassays and non-immunoassays for Sp35 gene products or conserved variants or peptide fragments thereof will typically comprise incubating a sample, such as a biological fluid, a tissue extract, freshly harvested cells, or lysates of cells which have been incubated in cell culture, in the presence of a detectably labeled antibody capable of binding to Sp35 or conserved variants or peptide fragments thereof, and detecting the bound antibody by any of a number of techniques well-known in the art.

The biological sample may be brought in contact with and immobilized onto a solid phase support or carrier such as nitrocellulose, or other solid support which is capable of immobilizing cells, cell particles or soluble proteins. The support may then be washed with suitable buffers followed by treatment with the detectably labeled Sp35 antibody, or antigen-binding fragment, variant, or derivative thereof. The solid phase support may then be washed with the buffer a second time to remove unbound antibody. Optionally the antibody is subsequently labeled. The amount of bound label on solid support may then be detected by conventional means.

By "solid phase support or carrier" is intended any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

The binding activity of a given lot of Sp35 antibody, or antigen-binding fragment, variant, or derivative thereof may be determined according to well known methods. Those skilled in the art will be able to determine operative and optimal assay conditions for each determination by employing routine experimentation.

There are a variety of methods available for measuring the affinity of an antibody-antigen interaction, but relatively few for determining rate constants. Most of the methods rely on either labeling antibody or antigen, which inevitably complicates routine measurements and introduces uncertainties in the measured quantities.

Surface plasmon reasonance (SPR) as performed on BIAcore offers a number of advantages over conventional methods of measuring the affinity of antibody-antigen interactions: (i) no requirement to label either antibody or antigen; (ii) antibodies do not need to be purified in advance, cell culture supernatant can be used directly; (iii) real-time measurements, allowing rapid semi-quantitative comparison of different monoclonal antibody interactions, are enabled and are sufficient for many evaluation purposes; (iv) biospecific surface can be regenerated so that a series of different monoclonal antibodies can easily be compared under identical conditions; (v) analytical procedures are fully automated, and extensive series of measurements can be performed without user intervention. BIAapplications Handbook, version AB (reprinted 1998), BIACORE code No. BR-1001-86; BIAtechnology Handbook, version AB (reprinted 1998), BIACORE code No. BR-1001-84.

SPR based binding studies require that one member of a binding pair be immobilized on a sensor surface. The binding partner immobilized is referred to as the ligand. The binding partner in solution is referred to as the analyte. In some cases, the ligand is attached indirectly to the surface through binding to another immobilized molecule, which is referred as the capturing molecule. SPR response reflects a change in mass concentration at the detector surface as analytes bind or dissociate.

Based on SPR, real-time BIAcore measurements monitor interactions directly as they happen. The technique is well suited to determination of kinetic parameters. Comparative affinity ranking is extremely simple to perform, and both kinetic and affinity constants can be derived from the sensorgram data.

When analyte is injected in a discrete pulse across a ligand surface, the resulting sensorgram can be divided into three essential phases: (i) Association of analyte with ligand during sample injection; (ii) Equilibrium or steady state during sample injection, where the rate of analyte binding is balanced by dissociation from the complex; (iii) Dissociation of analyte from the surface during buffer flow.

The association and dissociation phases provide information on the kinetics of analyte-ligand interaction ($k_a$ and $k_d$, the rates of complex formation and dissociation, $k_d/k_a=K_D$). The equilibrium phase provides information on the affinity of the analyte-ligand interaction ($K_D$).

BIAevaluation software provides comprehensive facilities for curve fitting using both numerical integration and global fitting algorithms. With suitable analysis of the data, separate rate and affinity constants for interaction can be obtained from simple BIAcore investigations. The range of affinities measurable by this technique is very broad ranging from mM to pM.

Epitope specificity is an important characteristic of a monoclonal antibody. Epitope mapping with BIAcore, in contrast to conventional techniques using radioimmunoassay, ELISA or other surface adsorption methods, does not require labeling or purified antibodies, and allows multi-site specificity tests using a sequence of several monoclonal antibodies. Additionally, large numbers of analyses can be processed automatically.

Pair-wise binding experiments test the ability of two MAbs to bind simultaneously to the same antigen. MAbs directed against separate epitopes will bind independently, whereas MAbs directed against identical or closely related epitopes will interfere with each other's binding. These binding experiments with BIAcore are straightforward to carry out.

For example, one can use a capture molecule to bind the first Mab, followed by addition of antigen and second MAb sequentially. The sensorgrams will reveal: 1. how much of the antigen binds to first Mab, 2. to what extent the second MAb binds to the surface-attached antigen, 3. if the second MAb does not bind, whether reversing the order of the pair-wise test alters the results.

Peptide inhibition is another technique used for epitope mapping. This method can complement pair-wise antibody binding studies, and can relate functional epitopes to structural features when the primary sequence of the antigen is known. Peptides or antigen fragments are tested for inhibition of binding of different MAbs to immobilized antigen. Peptides which interfere with binding of a given MAb are assumed to be structurally related to the epitope defined by that MAb.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, *Molecular Cloning A Laboratory Manual*, 2nd Ed., Sambrook et al., ed., Cold Spring Harbor Laboratory Press: (1989); *Molecular Cloning: A Laboratory Manual*, Sambrook et al., ed., Cold Springs Harbor Laboratory, New York (1992), DNA Cloning, D. N. Glover ed., Volumes 1 and 11 (1985); *Oligonucleotide Synthesis*, M. J. Gait ed., (1984); Mullis et al. U.S. Pat. No. 4,683,195; *Nucleic Acid Hybridization*, B. D. Hames & S. J. Higgins eds. (1984); *Transcription And Translation*, B. D. Hames & S. J. Higgins eds. (1984); *Culture Of Animal Cells*, R. I. Freshney, Alan R. Liss, Inc., (1987); *Immobilized Cells And Enzymes*, IRL Press, (1986); B. Perbal, *A Practical Guide To Molecular Cloning* (1984); the treatise, *Methods In Enzymology*, Academic Press, Inc., N.Y.; *Gene Transfer Vectors For Mammalian Cells*, J. H. Miller and M. P. Calos eds., Cold Spring Harbor Laboratory (1987); *Methods In Enzymology*, Vols. 154 and 155 (Wu et al. eds.); *Immunochemical Methods In Cell And Molecular Biology*, Mayer and Walker, eds., Academic Press, London (1987); *Handbook Of Experimental Immunology*, Volumes I-IV, D. M. Weir and C. C. Blackwell, eds., (1986); *Manipulating the Mouse Embryo*, Cold Spring Harbor Laboratory Press, Cold Spring Harbor, N.Y., (1986); and in Ausubel et al., *Current Protocols in Molecular Biology*, John Wiley and Sons, Baltimore, Md. (1989).

General principles of antibody engineering are set forth in *Antibody Engineering*, 2nd edition, C. A. K. Borrebaeck, Ed., Oxford Univ. Press (1995). General principles of protein engineering are set forth in *Protein Engineering, A Practical Approach*, Rickwood, D., et al., Eds., IRL Press at Oxford Univ. Press, Oxford, Eng. (1995). General principles of antibodies and antibody-hapten binding are set forth in: Nisonoff, A., *Molecular Immunology*, 2nd ed., Sinauer Associates, Sunderland, M A (1984); and Steward, M. W., *Antibodies, Their Structure and Function*, Chapman and Hall, New York, N.Y. (1984). Additionally, standard methods in immunology known in the art and not specifically described are generally followed as in *Current Protocols in Immunology*, John Wiley & Sons, New York; Stites et al. (eds), *Basic and Clinical-Immunology* (8th ed.), Appleton & Lange, Norwalk, Conn. (1994) and Mishell and Shiigi (eds), *Selected Methods in Cellular Immunology*, W.H. Freeman and Co., New York (1980).

Standard reference works setting forth general principles of immunology include *Current Protocols in Immunology*, John Wiley & Sons, New York; Klein, J., Immunology. *The Science of Self-Nonself Discrimination*, John Wiley & Sons, New York (1982); Kennett, R., et al., eds., *Monoclonal Antibodies, Hybridoma: A New Dimension in Biological Analyses*, Plenum Press, New York (1980); Campbell, A., "Monoclonal Antibody Technology" in Burden, R., et al., eds., *Laboratory Techniques in Biochemistry and Molecular Biology*, Vol. 13, Elsevere, Amsterdam (1984), *Kuby Immunnology* $4^{th}$ ed. Ed. Richard A. Goldsby, Thomas J. Kindt and Barbara A. Osborne, H. Freemand & Co. (2000); Roitt, I., Brostoff, J. and Male D., *Immunology* $6^{th}$ ed. London: Mosby (2001); Abbas A., Abul, A. and Lichtman, A., *Cellular and Molecular Immunology* Ed. 5, Elsevier Health Sciences Division (2005); Kontermann and Dubel, *Antibody Engineering*, Springer Verlan (2001); Sambrook and Russell, *Molecular Cloning: A Laboratory Manual*. Cold Spring Harbor Press (2001); Lewin, *Genes VIII*, Prentice Hall (2003); Harlow and Lane, *Antibodies: A Laboratory Manual*, Cold Spring Harbor Press (1988); Dieffenbach and Dveksler, *PCR Primer* Cold Spring Harbor Press (2003).

All of the references cited above, as well as all references cited herein, are incorporated herein by reference in their entireties.

EXAMPLES

Example 1

Sp35 is Involved in Oligodendrocyte Biology

Oligodendrocytes mature through several developmental stages from A2B5 progenitor cells (which express A2B5), differentiating into pre-myelinating oligodendrocytes (which express O1 and O4) and finally into mature myelinating oligodendrocytes (which express O1, O4 and MBP). Thus, by monitoring the presence and absence of the A2B5, O1, O4 and MBP markers it is possible to determine a given cell's developmental stage and to evaluate the role of Sp35-Fc in oligodendrocyte biology. For a general review of oligodendrocyte biology, see, e.g., Baumann and Pham-Dinh, *Physiol. Rev.* 81: 871-927 (2001).

Monoclonal antibodies against O4, MBP and CNPase were from Sternberger Monoclonals; antibody to APC (clone CC-1; ref. 29) was from Calbiochem. Other antibodies were to βIII tubulin (Covance), Sp35 (Biogen Idec), Fyn (Santa Cruz Biotechnology) and phospho-Fyn (Biosource). Monoclonal antibodies against A2B5 are available from Chemicon.
Sp35 is Expressed in Oligodendrocytes The expression of Sp35 in purified rat P13 CG neuron, P2 oligodendrocyte, and P4 astrocyte cultures was analyzed by polymerase chain reaction after reverse transcription (RT-PCR). A kit from Ambion, Inc. was used to extract mRNA from the rat brain cells according to the manufacturer's instructions. Semi-quantitative RT-PCR was carried out using forward primer 5' AGAGACATGCGATTGGTGA 3' (SEQ ID NO:344), and reverse primer 5' AGAGATGTAGACGAG-GTCATT 3' (SEQ ID NO:345) showed high expression in neurons, lower expression in oligodendrocytes, and no expression in astrocytes.

The expression of Sp35 in oligodendrocytes was confirmed by in situ hybridization in sections derived from adult rat optic nerve. Rat optic nerve sections were prepared and processed as described in Mi et al., "Sp35 is a component of the Nogo-66 receptor/p75 signaling complex," *Nat. Neurosci.* 7: 221-28 (2004) and probed with digoxigenin-labeled Sp35 antisense or sense RNAs using the first 500 nucleotides of the Sp35 coding sequence. The sections were stained according to the manufacturers' instructions using a Tyramide Signal Amplification kit (Amersham Biosciences) and a fluorescent anti-digoxigenin conjugated antibody kit (Perkin Elmer). For combined in situ and immunofluorescence analyses, the sections were first probed with digoxigenin-labeled RNAs and then with antibodies, e.g. CC1 antibody (Calbiochem; a marker of mature oligodendrocytes) or anti-Sp35 antibody. We observed that oligodendrocytes that hybridized to an antisense Sp35 probe also co-stained with an antibody to CC1 (data not shown). No specific labeling was observed using a sense Sp35 probe. Sp35 expression in oligodendrocytes also was confirmed by immunohistochemistry studies of tissue sections from the lateral ventricle region of P7 rat cortex. A majority of cortical cells that labeled with CC1 antibody also labeled with anti-Sp35 antibody. Data not shown. The specificity of the interaction was confirmed by preadsorption of the anti-Sp35 antibody with Sp35-Fc (see Example 2), which eliminated the signal.
Sp35-specific RNAi Knockdown of Sp35 Expression Promotes Oligodendrocyte Growth and Differentiation Sp35-specific RNAi was used to ablate Sp35 expression in oligodendrocyte precursor cells to examine how Sp35 contributes to oligodendrocyte growth and differentiation. 50,000 A2B5 oligodendrocyte precursor cells were infected with lentivirus carrying Sp35-specific RNAi sequence or control RNAi prepared as follows.

Murine and rat Sp35 DNA sequences were compared to find homologous regions to use for candidate small-hairpin RNAs (shRNA). CH324, for lentivirus expression of Sp35 RNAi, was constructed by annealing oligonucleotides LV1-035 and LV1-036 and ligating to HpaI and XhoI digested pLL3.7. The pLL3.7 vector, additional methodology and virus production were as described in Rubinson et al., *Nat. Genet.* 33, 401-06 (2003). The Sp35 RNAi oligonucleotides were purchased from MWG and have the following sequences: LV1-035 (sense oligo) 5'-TGA TCG TCA TCC TGC TAG ACT TCA AGA GAG TCT AGC AGG ATG ACG ATC TTT TTT C-3' (SEQ ID NO:346) and LV1-036 (antisense oligo) 5'-TCG AGA AAA AAG ATC GTC ATC CTG CTA GAC TCT CTT GAA GTC TAG CAG GAT GAC GAT CA-3' (SEQ ID NO:347).

Control RNAi was designed with the same oligonucleotide sequences except for the nucleotide changes indicated in lower-case letters: 5'-TGA TCc TCA TcC ttC Tat ACT TCA AGA GAG TgT AGC AGG ATG AcG ATC TTT TTT CTC GA-3' (SEQ ID NO:348) and 5'-TCG AGA AAA AAG ATC GTC ATC CTG CTA GAC TCT CTT GAA GTa TAG aAG GAT GAC GAT CA-3'. (SEQ ID NO:349).

Prior to producing the lentivirus, DNA from pLL3.7 or candidate shRNA in pLL3.7 were cotransfected with murine Sp35-HA tagged plasmid at a ratio of 5 to 1 into CHO cells in a 6-well format. Knockdown was analyzed by western blot detection of Sp35-HA tag from transfected CHO cell lysates as well as by northern blot of total RNA prepared from duplicate wells. The blot was probed with a fragment of Sp35 cDNA. Assays were performed 48 hours post-transfection. As expected, there was a 10-fold reduction of Sp35 mRNA in CH324 RNAi-treated CHO cells relative to control-treated cells. Data not shown. RNAi lentiviruses carrying green fluorescent protein (GFP) were generated as described in Rubinson et al. In cultures treated with either control or Sp35 RNAi, approximately 80% of the oligodendrocytes were GFP positive. Total cell number was not altered by the RNAi treatments. To quantify the effects of RNAi on differentiation, only GFP-expressing oligodendrocytes were counted.

Enriched populations of oligodendrocytes were grown from female Long Evans P2 rats as described by Conn, *Meth. Neurosci.* 2:1-4 (Academic Press; 1990) with modifications as follows. Briefly, the forebrain was dissected and placed in Hank's buffered salt solution (HBSS; Invitrogen). The tissue was cut into 1-mm fragments and was incubated at 37° C. for 15 min in 0.01% trypsin and 10 µg/ml DNase. Dissociated cells were plated on poly-L-lysine-coated T75 tissue culture flasks and were grown at 37° C. for 10 d in DMEM medium with 20% fetal calf serum (Invitrogen). Oligodendrocyte precursors (A2B5$^+$) were collected by shaking the flask overnight at 200 rpm at 37° C., resulting in a 95% pure population. Cultures were maintained in high-glucose Dulbecco's modified Eagle's medium (DMEM) with FGF/PDGF (10 ng/ml; Peprotech) for 1 week. Removal of FGF/PDGF allowed A2B5+ cells to differentiate into O4+ premyelinating oligodendrocytes after 3-7 d, and to differentiate into O4+ and MBP+ mature oligodendrocytes after 7-10 d. These differentiation states are readily apparent from changes in morphology: A2B5+ cells are bipolar in shape, O4+ premyelinating oligodendrocytes have longer and more branched processes and MBP+ mature oligodendrocytes contain myelin sheet structures between processes.

A2B5 oligodendrocyte precursor cells were infected with the lentivirus containing the CH324 RNAi. The resulting cells were cultured for 3 days and the number of O4-positive (a marker for oligodendrocyte differentiation) oligodendrocytes was counted. Endogenous Sp35 expression was reduced by infection with Sp35 RNAi lentivirus and was confirmed by RT-PCR. Reduction of Sp35 resulted in more highly differentiated, mature oligodendrocytes as compared with control infected cells, as was evident by increases in the length of cell processes and by the presence of abundant myelin sheet structures (data not shown). In cells that expressed Sp35 RNAi, there were three times as many mature (O4-positive) oligodendrocytes as in control cultures. These data indicate that Sp35 may negatively regulate oligodendrocyte differentiation.

Dominant-Negative Sp35 Promotes Oligodendrocyte Growth and Differentiation

Lentiviral vectors that express wild-type and a dominant-negative form of Sp35 were constructed. DNA sequence encoding mouse full length Sp35 (FL-Sp35, amino acid residues 34-614 of SEQ ID NO:2) was amplified by PCR using primers 5'-GAG GAT CTC GAC GCG GCC GCA TGG AGA CAG ACA CAC TCC TG-3' (SEQ ID NO:350) and 5'-GGG GCG GAA TTG GAT CCT CAC AGA TCC TCT TCT GAG ATG AG-3' (SEQ ID NO:351) and inserted into the HRST-IRESeGFP lentiviral vector at the NotI and BamHI sites. Similarly, DNA sequence encoding dominant negative Sp35 (DN-Sp35, amino acid residues 34-581 of SEQ ID NO:2) was amplified by PCT using primers 5'-GAG GAT CTC GAC GCG GCC GCA TGG AGA CAG ACA CAC TCC TG-3' (SEQ ID NO:352) and 5'-GAT ACG GAT CCT CAG CCT TTG CCC CGG CTC CAT AGA AAC AGC-3' (SEQ ID NO:353). The FL-Sp35 and DN-Sp35 plasmids were transfected into 293 cells to produce lentivirus as described by Rubinson et al., "A lentivirus-based system to functionally silence genes in primary mammalian cells, stem cells and transgenic mice by RNA interference," Nat. Genet. 33: 401-06 (2003). Oligodendrocytes were infected with lentivirus at 2 MOI per cell and confirmed expression of FL-Sp35 and DN-Sp35 by western blot.

DN-Sp35 promoted oligodendrocyte differentiation, producing an increase in the number of mature oligodendrocytes. In contrast, overexpression of full-length Sp35 (FL-Sp35) had the opposite effect and inhibited differentiation, as was evident by a reduction in the number of mature oligodendrocytes as compared with the control (data not shown).

Example 2

Construction and Purification of Sp35-Fc Fusion Protein

A construct was made fusing the extra-cellular portion of human Sp35 (residues 1-532) to the hinge and Fc region of human IgG1 to study the biological function of Sp35. A partial coding sequence for human Sp35 was obtained by PCR from clone 227.2 using the forward primer 5'-CAG CAG GTC GAC GCG GCC GCA TGC TGG CGG GGG GCG T-3' (SEQ ID NO:354) and reverse primer 5'-CAG CAG GTC GAC CTC GCC CGG CTG GTT GGC CAA CCA GCC GGG CGA GGT CGA CCT CGA GG-3' (SEQ ID NO:355).

The blunt-end PCR product was subcloned into the SrfI site of the PCR SCRIPT AMP vector (Stratagene) to create PCR SCRIPT AMP-Sp35. A SalI fragment was isolated from PCR SCRIPT AMP-Sp35 and subcloned into the PCRCAMP Ig vector (derivative of Stratagene vector PCR SCRIPT AMP). In the PCRCAMP Ig vector, the hinge and Fc gamma sequence is subcloned as a SalI(5') to NotI(3') fragment. The SalI Sp35 fragment was subcloned into the SalI site of the PCRCAMP Ig vector thereby fusing the Sp35 signal sequence and extracellular domain (codons 1-532) in-frame with sequences encoding the hinge and Fc region of human Ig1. Correct isolates were identified, and a NotI fragment encompassing the Sp35 Fc fragment was subcloned into the single NotI cloning site of the CHO expression vector, PV90 (Biogen Idec). The resulting plasmid was confirmed by DNA sequencing and designated GT123.

Stable cell lines expressing the Sp35-Fc fusion protein were generated by electroporation of CHO host cells DG44 with plasmid GT123. Transfected CHO cells were cultured in alpha minus MEM in the presence of 10% dialyzed serum and 4 mM glutamine to select for nucleoside-independent growth. Fourteen days post-transfection, cells were fed fresh media. To screen for cells expressing Sp35-Fc, CHO cells were labeled with phycoerythrin (PE)-labeled goat anti-human IgG (Jackson Labs) and subjected to high speed flow cytometry sorting in a FACS Mo-Flo (Cytomation). The cells that expressed the highest levels of Sp35-Fc were selected. These cells were expanded in culture for 7 days, then re-labeled and re-sorted. Cells expressing the highest levels of Sp35-Fc were isolated as individual clones in 96-well plates. These clones were grown for two weeks and then fed fresh media one day prior to FACS analysis to check for expression levels. Clones that expressed the highest levels of Sp35-Fc were expanded, and frozen cell banks were established. The cell lines were adapted to grow in suspension culture in the serum-free media BCM16. The titer of Sp35-Fc produced by these clones was determined by growing cell lines at 37° C. for 4-5 passages, then growing the cells to 50% maximal cell density and culturing them for 10-15 days at 28° C. until the viable cell density dropped to 75%. At this time, the culture media were harvested, cleared of cells and debris by centrifugation, and the culture supernatants titered for Sp35-Fc levels by Western blot analysis using an anti-human Ig antibody (Jackson Lab) as the probe.

Sp35-Fc fusion protein was purified from the clarified culture medium as follows: 9 ml of 1M HEPES pH 7.5 was added to 900 ml of conditioned medium. The medium was batch loaded for 3 hr at 4° C. onto 3 ml of Protein A Sepharose (Amersham Bioscience). The resin was collected in a 1.5 cm (I.D.) column, and washed four times with 3 ml PBS, two times with 4 ml of PBS containing 800 mM NaCl, and then again with 3 ml of PBS. The Sp35-Fc was eluted from the column with 25 mM $NaH_2PO_4$, pH 2.8 and 100 mM NaCl in 1.5 ml fractions and neutralized by adding 75 µl of 0.5 M $NaH_2PO_4$, pH 8.6. Peak protein-containing fractions were identified by absorbance at 280 nm, pooled, and subjected to further purification on a 1 mL Protein A column. Prior to loading, NaCl was added to 600 mM and HEPES, pH 7.5 to 50 mM. The column was washed twice with 600 µl of 10 mM HEPES pH 7.5 and 1 M NaCl, and then with 1 ml PBS. Sp35-Fc was eluted from the column with 25 mM $NaH_2PO_4$, pH 2.8 and 100 mM NaCl, collecting 0.5 mL fractions, and neutralized by adding 25 µl of 0.5 M $NaH_2PO_4$, pH 8.6. Peak protein-containing fractions were identified by absorbance at 280 nm and pooled. By reducing SDS-PAGE, the Sp35-Fc protein migrated as a single band (>95% pure) with an apparent mass of 90 kDa. Under non-reducing conditions, the protein ran as a dimer with an approximate mass of 180 kDa. The purified Sp35-Fc protein was aliquoted and stored at −70° C.

Example 3

Production of Sp35-Specific Monoclonal Antibodies

Anti-Sp35 Antibodies that specifically bind an Sp35 polypeptide of the invention were made using the following methods and procedures.
A. Antibody Screening Assays
1. ELISA Assay
Sp35-Fc (0.5 µg in 50 µl of 0.1 M sodium bicarbonate buffer, pH 9.0) was added to each well of 96-well MaxiSorp™ plates (Nunc™). The plates were then incubated at 37° C. for 1 hour or 4° C. for 16 hours. Non-specific binding sites on the plates were blocked using 25 mM HEPES, pH 7.4 containing 0.1% BSA, 0.1% ovalbumin, 0.1% (5% (w/v) nonfat dry milk in 150 mM NACE) and 0.001% azide. Dilutions of serum or hybridoma supernatants (for example, serial three-fold dilutions) were added across each row of the plate, and incubated at 25° C. for 1 hour. After washing three times with PBS, 50 µl of a 1:10,000 dilution of horseradish peroxidase-conjugated goat anti-mouse secondary antibody (Jackson ImmunoResearch Inc.) was added to each well and incubated further for 1 hour. After three washings, color was developed by TMB (Pierce) and stopped with 2 M sulfuric acid. Color intensity was monitored in a spectrophotometer at 450 nm.
2. FACS Assay
COS-7 cells were labeled with 0.1 µM CellTracker™ Green CMFDA (Molecular Probes, Eugene, Oreg.) as described by the vendor. Equal volumes of CellTracker™ labeled control cells were mixed with washed Sp35-COS-7 cells (produced by transient transfection of Sp35 expression vector) before incubation with anti-Sp35 test sera or hybridoma supernatants. Fifty microliters of the cell mixture was dispensed into each well of a 96-well V-bottom polystyrene plates (Costar® 3877, Corning, N.Y.) and 100 µl of mouse serum, hybridoma supernatant, or a control anti-Sp35 antibody was added. After incubation at 4° C. for 30 minutes, the cells were washed and incubated with 50 µl of phycoerythrin-conjugated affinity pure F(ab')$_2$ fragment goat anti-mouse IgG Fc gamma specific second antibody (1:200, Jackson ImmunoResearch Laboratory, West Grove, Pa.) in PBS. At the end of the incubation, the cells were washed twice with PBS and suspended in 200 µl of PBS containing 1% fetal bovine serum (FBS), and subjected to FACS analyses. Alternately, Sp35-COS-7 cells were mixed with mouse serum or hybridoma supernatant and then treated with R-phycoerythrin-conjugated goat anti-mouse secondary antibody and directly subjected to standard FACS analyses.
B. Hybridoma Production of Murine Monoclonal Anti-Sp35 Antibodies
Eight-week-old female RBF mice (Jackson Labs, Bar Harbor, Me.) were immunized intraperitoneally with emulsion containing 50 µg Sp35-Fc (amino acids 34 to 532 of SEQ ID NO:2 fused to the hinge and Fc region of human IgG1), produced as described in Example 2 or were immunized intraperitoneally with an emulsion containing 50 µg of human Sp35-Fc, and 50 µl complete Freund's adjuvant (Sigma® Chemical Co., St. Louis, Mo.) once every two weeks. Sera from the immunized mice were collected before the first immunization and 1 week after the second and third immunizations, and anti-Sp35 antibody titers were measured by FACS assay on Sp35-expressing COS-7 cells as described above. A booster final dose was given after the third immunization and three days prior to when hybridoma fusions were initiated.

Sera from mice immunized with the various Sp35 peptides were screened by ELISA as described above. Mice that were positive for antibodies that specifically bound Sp35 expressing COS-7 cells were identified by flow cytometry (FACS) as described above, and were sacrificed. Splenocytes were isolated from the mice and fused to the FL653 myeloma (an APRT-derivative of a Ig-/HGPRT-Balb/c mouse myeloma, maintained in DMEM containing 10% FBS, 4500 mg/L glucose, 4 mM L-glutamine, and 20 mg/ml 8-azaguanine) as described in *Monoclonal Antibodies. Hybridomas: A New Dimension in Biological Analyses*, ed. Kennett, R. H., McKearn, T. J. and Bechtol, K. B. New York: Plenum Press (1982). Fused cells were plated into 24- or 48-well plates (Corning Glass Works, Corning, N.Y.), and fed with adenine, aminopterin and thymidine (AAT, available from Sigma® Chemical Co., St. Louis, Mo.) containing culture medium. AAT resistant cultures were screened by ELISA or flow cytometry as described above for binding to either Sp35-COS-7 cells or to Sp35-Fc. Positive hybridomas were further subcloned by limiting dilution.

Seventeen hybridoma cell lines producing monoclonal antibodies produced from mice immunized with Sp35-Fc were isolated. Properties of the hybridoma-derived monoclonal antibodies are shown in Tables 3A and 3B.

Polynucleotides encoding the variable domains ($V_H$ and $V_L$) of monoclonal antibodies 1A7, 2F3, 3P1D10.2C3 and 3P1E11.3B7 were isolated by PCR, cloned and were subjected to sequence analysis by the following method. Total RNA was extracted from hybridoma cells using Qiagen® RNeasy® mini kit and cDNA was generated from the isolated RNA by RT PCR, using standard conditions. A cocktail of primers were used for the RT-PCR. A preferred set of primers included a primer with the 5' of the primer hybridizing to the signal sequence and the 3' end of the primer hybridizing to the constant domain 3' of the FR4/constant domain junction. This allows for the amplification of an intact variable domain with no ambiguities about the monoclonal antibody N-terminus and the V/C junction. One of skill in the art will recognize that primer sets need to be modified for amplifying different templates and for different PCR conditions. Occasionally, the presence of highly abundant nonproductive messages (e.g. the CDR3-FR4 frameshifted nonproductive light chain from the fusion partner) or nonspecific productive messages can be produced and complicate the cloning of variable chains. One solution is to use N-terminal sequence data from the authentic purified antibody to design a degenerate primer to enable cloning. Alternatively, one can use "universal framework" primers, such as those described in Orlandi et al, PNAS 86:3833 (1989), which "fix" the N- and C-termini of the variable domains (i.e. the N-terminus of FR1 and the C-terminus of FR4 are primer-determined).

Additionally, sequence data, for designing more effective primers, can be obtained from the bulk RT-PCR products which have been gel purified and then sequenced. The PCR product can also be subcloned using, for example, the TOPO Cloning Kit (Invitrogen) then sequence. Sequence data is then obtained from multiple independent subclones or gel purified fragments to firmly establish the consensus sequence.

The sequence of the light chain of the P1E11.3B7 was determined by using a cocktail of 5' murine kappa light chain signal sequence primers: (i) 5' GGG GAT ATC CAC CAT GGA TTT TCA GGT GCA GAT TTT CAG 3' (SEQ ID NO:356), (ii) 5' GGG GAT ATC CAC CAT GRA GTC ACA KAC YCA GGT CTT YRT A 3' (SEQ ID NO:357), (iii) 5' GGG GAT ATC CAC CAT GAA GTT GCC TGT TAG GCT GTT G 3' (SEQ ID NO:358), and (iv) 5' GGG GAT ATC CAC CAT GAG GKC CCC WGC TCA GYT YCT KGG A 3' (SEQ ID NO:359), with a single 3' murine kappa constant domain primer: 5' GCG TCT AGA ACT GGA TGG TGG GAG ATG GA 3' (SEQ ID NO:4), where K=G/T, R=A/G, W=A/T and Y=C/T. The resulting PCR product was subcloned and multiple independent subclones were sequenced. The deduced consensus sequence was consistent with the Edman degradation sequencing data. Sequencing indicated that the degenerate signal sequence 5' primer 5' GGG GAT ATC CAC CAT GRA GTC ACA KAC YCA GGT CTT YRT A 3' (SEQ ID NO:357) was the one that had yielded the 3P1E11.3B7 light chain variable domain during the amplification.

The 3P1E11.3B7 heavy chain sequence was determined using a cocktail of murine heavy chain signal sequence 5' PCR primers: (i) 5' GGG GAT ATC CAC CAT GGR ATG SAG CTG KGT MAT SCT CTT 3', (SEQ ID NO:360) (ii) 5' GGG GAT ATC CAC CAT GRA CTT CGG GYT GAG CTK GGT TTT 3' (SEQ ID NO:361), and (iii) 5' GGG GAT ATC CAC CAT GGC TGT CTT GGG GCT GCT CTT CT 3' (SEQ ID NO:362), with a degenerate murine IgG CH1 constant domain 3' primer 5' AGG TCT AGA AYC TCC ACA CAC AGG RRC CAG TGG ATA GAC 3' (SEQ ID NO:363), where K=G/T, M=A/C, R=A/G, and Y=C/T. PCR using this cocktail of primers, with a variety of different cycling conditions, failed to yield a heavy chain variable domain sequence in which the deduced N-terminus was consistent with that determined by Edman degradation sequence of the purified 3P1E11.3B7 antibody. We therefore used heavy chain universal primers: FR15' AGG TSM ARC TGC AGS AGT CWG G 3' (SEQ ID NO:364) and FR45' TGA GGA GAC GGT GAC CGT GGT CCC TTG GCC CCA G 3' (SEQ ID NO:365), where M=A/C, R=A/G, S=C/G, and W=A/T. This set yielded a murine heavy chain variable domain whose deduced sequence was consistent with the empirical 3P1E11.3B7 data.

In order to verify that the heavy chain variable domain N- and C-termini were authentic and not primer-determined, another PCR reaction was performed with a degenerate signal sequence primer 5' ATG GAR TGY AAY TGG ATH CTN CCN TTY A 3' (SEQ ID NO:366) and the aforementioned constant domain 3' primer 5' AGG TCT AGA AYC TCC ACA CAC AGG RRC CAG TGG ATA GAC 3' (SEQ ID NO:367), where H=A/C/T, N=A/C/G/T, R=A/G, and Y=C/T. The design of the degenerate signal sequence primer was based upon signal sequences of the best hits derived from a TFASTA search of the Genbank rodent sequence database queried with the 3P1E11.3B7 consensus deduced FR1 sequence from the PCR reaction with the "universal primer" described above. This PCR yielded a product with a complete murine heavy chain variable domain.

The complete 3P1E11.3B7 murine variable domains were used (with silent mutagenesis as necessary to introduce restriction sites) in conjunction with human IgG1 and kappa constant domain cDNAs to construct chimeric heavy and light chain cDNAs, respectively. The full-length immunoglobulin cDNAs were subcloned into an expression vector called pNE001, a derivative of the commercial EBV mammalian cell episomal expression vector pCEP4. The heavy and light chain expression vectors (called pXW372 and pXW363, respectively) were co-transfected into 293-EBNA cells. Western blot analysis (probed with human IgG-specific reagents) of conditioned medium from transiently transfected cells confirmed the expression of chimeric 3P1E11.3B7-huIgG1, kappa mAb. The resulting 3P1E11.3B7 VH and VL polypeptide sequences are shown in Tables 6 and 8 and are SEQ ID NOs: 173 and 209, respectively. The heavy and light chain sequences for the 1A7, 2F3, and 3P1D10.2C3 monoclonal antibodies were determined by similar methods.

C. Identification of Anti-Sp35 Monoclonal Antibodies by Phage Display

Anti-Sp35 monoclonal antibody Fab fragments were identified and isolated from phage display libraries as described in Hoet et al., *Nat. Biotech.* 23:344-348 (2005); Rauchenberger, et al., *J. Biol. Chem.* 278:194-205 (2003); and Knappik, et al., *J. Mol. Biol.* 296:57-86 (2000), all of which are incorporated herein by reference in their entireties.

The MorphoSys Fab-phage display library HuCAL® GOLD ("Phage Display Library-2" in Table 3B), which comprises humanized synthetic antibody variable regions was screened against recombinant human soluble Sp35-Fc protein by standard ELISA AND IHC screening methods. See, e.g., Ostendorp, R., Frisch, C. and Urban M, "Generation, engineering and production of human antibodies using HuCAL®." *Antibodies, Volume 2 Novel Technologies and Therapeutic Use.* New York: Kluwer Academic/Plenum 13-52 (2004). Fab-phages that specifically bound to Sp35 were purified and characterized. Properties of these phage display-derived monoclonal antibody Fab fragments are shown in Table 3B as "phage display library-2-derived monoclonal Fab fragments." Isolated Fab-phage 1968 was selected for further analysis.

Example 4

Immunoprecipitation of Sp35 by Anti-Sp35 Monoclonal Antibodies

To perform the immunoprecipitation, COS-1 cells expressing Sp35, fused to a hemaglutinin (HA) tag on the N-terminus, were produced by transiently transfecting COS-1 cells with a DNA construct which expresses the full-length Sp35 protein with an HA tag. Cells were harvested 48 hr after transfection and were lysed in 1 ml lysis buffer (50 mM HEPES, pH 7.5, 150 mM NaCl, 1.5 mM $MgCl_2$, 1 mM EGTA, 1% Triton X-100 and 10% glycerol) for 30 min at 4° C. After centrifugation at 14,000×g for 15 min, the supernatants were incubated with Protein A/G-Sepharose beads (Santa Cruz) at 4° C. for 1 hr, and then incubated at 4° C. for 1 hr with either the 1A7 or the 2F3 anti-Sp35 murine monoclonal antibodies. The beads were washed 3 times with lysis buffer, boiled in Laemmli sample buffer, subjected to 4-20% SDS-PAGE, and analyzed by Western blotting using an antibody which recognizes the HA tag. As shown on the SDS-PAGE gel, monoclonal antibodies 1A7 and 2F3, immunoprecipitated human and murine Sp35 (FIG. 1). As shown in FIG. 1, monoclonal antibody 2F3 strongly immunoprecipitated both human and murine Sp35, while monoclonal antibody 1A7, which strongly immunoprecipitated human Sp35, only recognized murine Sp35 protein weakly. Similarly, monoclonal antibodies 1G7, 2B10, 2F3, 3P4C2.2D2, 3P4C8.2G9, L100, Li03, Li05, Li06, Li07, Li08, Li11 and Li12 immunoprecipitate human or mouse or human and mouse Sp35 (See Table 3B). Additionally, Li08 immunoprecipitates AP-Sp35 and monoclonal antibodies 1B6.4 and 3E3.1 immunoprecipitate endogenous Sp35 (See Table 3B).

Example 5

Anti-Sp35 Antibody Binding Specifically to Sp35 Determined by ELISA

In order to determine which regions of the Sp35 polypeptide were bound by the various hybridoma- and phage display-derived monoclonal antibodies produced in Example 2, an ELISA assay was performed using a panel of truncated Sp35 polypeptides, each fused to the hinge and Fc regions of IgG1 by the methods described in Example 1. The panel consisted of the following Sp35 fragments: amino acids 34-425 of SEQ ID NO:2, amino acids 417-532 of SEQ ID NO:2, amino acids 417-493 of SEQ ID NO:2, and amino acids 34-532 of SEQ ID NO:2. Ovalbumin and BSA were used as controls. As shown in Table 3B, hybridoma-derived mAbs 2F3, 2B10, 3A3, 3P4c2.2d2, and 3P4c8.2 g9, and Fab-phage derived mAbs 3383, 3563, 3564, 3565, 3568, 3569, 3570, and 3582 all specifically bound to the 1-417 and 1-534 Sp35 fragments, suggesting that these antibodies bind to epitopes in the LRR region of Sp35. Hybridoma-derived Mabs 1A7, 3P1B11F9, 3P1D10.2C3, 3P1E11.3B7, 3P2C63G10.2H7, 2P2C9.2G4, 3P4A61D9, and 394C51D8, and Fab-phage-derived Mabs 3495, 3566, 3567, and 1968 specifically bound to the 34-532 Sp35 fragment and weakly bound to the 417-532 Sp35, suggesting that these antibodies likely bind to epitopes which at least include a portion of Sp35 C-terminal to the LRR region. In similar experiments, these latter antibodies also specifically bound an Sp35 polypeptide consisting of amino acids 34-534 of human Sp35 and low affinity to mouse and rat Sp35. The affinity of these latter antibodies for mouse and rat Sp35 was restored to the level seen using human Sp35 when amino acid 419 of the mouse or rat Sp35 is changed from histidine (H) to arginine (R). Arginine is the amino acid at position 419 in human Sp35. The $K_D$ for monoclonal antibody 1A7 was determined to be 10 nM ($1\times10^{-9}$M) for binding human Sp35 and 20 µM ($2\times10^{-5}$ M) for binding murine Sp35. For Ap-Sp35 ELISA to detect the antibodies bound to the 417 to 532 region, the ELISA was performed as follows: The Mabs were coated onto ELISA plates, then incubated either with an Sp35-AP fusion protein at 4° C. overnight followed by AP-linked anti-human (H+L) (1:5,000, Jackson ImmunoResearch) at RT for 1 hr, or with AP-fusion proteins at 4° C. overnight. AP substrate was then developed by 10 mg/ml 4NPP in 0.1 M Glycin, 1 mM $MgCl_2$, 1 mM $ZnCl_2$, pH 10.5, and read at O.D. 405.

Example 6

Anti-Sp35 Antibody Binding Specifically to Sp35 Determined by FACS

To further characterize the binding properties of hybridoma-derived anti-Sp35 mAbs 1A7 and 2F3 produced as described in Example 3, binding to both fixed and live COS-7 or 293 cells expressing mouse or human Sp35 was compared. Sp35 transfected and non-transfected cells were fixed and subject to FACS analysis (FACS: Cells transfected with human or mouse Sp35 or vector control were dissociated from culture plates, washed with 2% FBS/PBS, and incubated with primary antibody at 1 µg/ml on ice for 1 hr. The cells were washed 3 times with 2% FBS/PBS, then incubated with PE labeled secondary antibody (1:100, JacksonImmunoResearch) on ice for 30 min. After 2 washes with 2% FBS/PBS, cells were fixed in 2% PFA and subjected to FACS analysis by PE.) FACS result showed that MAbs 1A7 and 2F3 bound to COS-7 or 293 cells expressing Sp35, but not bind to control cells with no Sp35 expression (FIG. 2).

Example 7

Neurite Outgrowth Assay

To test the ability of the hybridoma-derived and Fab-phage-derived monoclonal antibodies produced above to reverse the inhibitory effect of CNS myelin inhibitors, e.g., OMgp, on neurons, Lab-Tek® culture slides (4 wells) were coated with 0.1 mg/ml poly-D-lysine (Sigma®). Ap-OMgp (1 µg/spot) or PBS was spotted as 3 µl drops. Lab-Tek® slides were then rinsed and coated with 10 µg/ml laminin (Gibco™). Dorsal root ganglions (DRG's) from P6-7 Sprague Dawley rat pups were dissociated with 1 mg/ml collagenase type 1 (Worthington), triturated with fire-polished Pasteur pipettes pre-plated to enrich in neuronal cells and finally plated at 10,000 cells/well on the pre-coated Lab-Tek® culture slides. Ten µg/ml of mAb 1A7 or 2F3 were added immediately after plating of the DRGs. The culture medium was F12 (available from Gibco/Invitrogen) containing 5% heat inactivated donor horse serum, 5% heat inactivated fetal bovine serum and 50 ng/ml mouse nerve growth factor (mNGF) and incubated at 37° C. and 5% $CO_2$ for 6 hours. Following incubation, the slides were fixed in 4% paraformaldehyde/20% sucrose and stained with anti-βIII-tubulin TUJ1 antibody (Covance) after 16 hours.

As secondary antibody anti-mouse Alexa-Fluor® 594 (Molecular Probes) diluted 1:300 was added to the slides and incubated for 2 hours at room temperature. The slides were coverslipped with Gel/Mount™ (Biømeda™). 5× digital images were acquired with OpenLab™ software (Improvision, Inc., Lexington, Mass.), and the images were analyzed for quantification of neurite outgrowth using the OPEN-LAB™ software, all according to manufacturer's specified parameters.

Both MAbs 1A7 and 2F3 protected DRG neurons from OMgp-mediated inhibition of neurite outgrowth. (FIG. 3).

Example 8

Monoclonal Antibody 1A7 Promotes Functional Recovery in the Rat Spinal Cord Injury Model Spinal cord injury ("SCI") was induced by dorsal over-hemi-section as follows, modified from methods described previously (Li, S. et al. *J. Neurosci.* 24, 10511-10520 (2004)). Anesthetized female Long Evans rats (7 weeks old, Charles River) were given pre-operative analgesia (Buprenorphine/Buprenex, 0.05 mg/kg s.c.) and tranquillized (Midazolam, 2.5 mg/kg i.p.) and a dorsal hemi-section was performed at thoracic vertebra 6/7 completely interrupting the main dorsomedial and the dorsolateral corticospinal tract (CST). The dorsal and dorso-lateral components of the corticospinal tract (CST) were completely interrupted and the ventral portion of the CST left intact. The ventral tissue bridge remaining after hemi-section constituted approximately 20% of the cord in both treatment groups (data not shown).

Hindlimb function was quantified using the Basso-Beattie-Bresnahan (BBB) open field scoring method (Eby, M. T. et al., *J. Biol. Chem.* 275, 15336-15342 (2000), incorporated herein by reference) and all animals sustained marked functional deficits after SCI, with almost complete hindlimb paralysis the day after surgery. Immediately after CST transection, an intrathecal catheter was inserted into the subarachnoid space at T7 and connected to a primed mini-osmotic pump (Alzet model 2004, Alza Corp) inserted into the subcutaneous space. Mini-osmotic pumps delivered Human IgG isotype control protein (5 mg/ml) or monoclonal antibody 1A7 (4.8 mg/ml) continuously at a rate of 0.25 μl/h over 5 weeks. Control (Human IgG-treated) animals recovered substantial function over the 5 week duration of the experiment, but plateaued at 3-4 weeks, ultimately attaining a mean BBB score of 9±0.45 (FIG. 7). In contrast, continuous intrathecal infusion of 1A7 for 5 weeks after spinal cord transection resulted in significantly improved BBB scores over the control animals by 5 weeks with a continued improvement in function in the 2-5 week timeframe, reaching a mean BBB score of 11.1±0.7 (FIG. 4). These results demonstrate that treatment with anti-Sp35 monoclonal antibody 1A7 promoted recovery of function after spinal cord injury as demonstrated by an increase in BBB score, axon regeneration and less axon retraction observed by immunohistochemical staining of the axons.

Example 9

Anti-Sp35 Antibodies 1A7, 2F3, 3P1D10.2C3, 3P1E11.3B7, 6P4F4.1D3, 6P4F4.1F9, 7P1D5.1G9, Li05, Li06, Li08, Li13, Li28, Li33, D05 and D08 Promote Myelination In Vitro The role of anti-Sp35 antibodies 1A7 and 2F3 in myelination was investigated in vitro by treating co-cultures of dorsal root ganglion (DRG) neurons and oligodendrocytes with anti-Sp35 antibodies 1A7 and 2F3 and testing for myelination by immunohistochemistry and Western blotting. For these studies, it was necessary to first generate primary cultures of DRG neurons and of oligodendrocytes.

Female Long Evans rat E14-E17 embryonic dorsal root ganglia were cultured as described by Plant et al., *J. Neurosci.* 22:6083-91 (2002). Dissected DRGs were plated on poly-L-lysine-coated cover slips (100 μg/ml) for 2 weeks. The cells were incubated in the presence of fluorodeoxyuridine for days 2-6 and in NLA medium containing 1×B27, 100 ng/ml NGF (Gibco) for days 8-11.

Female Long Evans post-natal day 2 (P2) rat oligodendrocytes were cultured as described by Conn, *Meth. Neurosci.* 2:1-4 (Academic Press; 1990) with modifications as follows. Briefly, the forebrain was extirpated from P2 rats and placed in cold HBSS medium (Gibco). The tissue fragments were cut into 1 mm pieces and incubated at 37° C. for 15 min in 0.01% trypsin and 10 μg/ml DNase. Dissociated cells were plated on a poly-L-lysine coated T75 tissue culture flasks and grown in DMEM with 20% fetal bovine serum at 37° C. for 10 days. A2B5-positive oligodendrocytes were collected by shaking the flasks overnight at 200 rpm at 37° C. The A2B5 oligodendrocytes were cultured for 7 days in DMEM (Gibco) containing 25 mM D-glucose, 4 mM L-glutamine, 1 mM sodium pyruvate, 50 μg/ml human apo-transferrin, 5 μg/ml bovine pancreatic insulin, 30 nM sodium selenate, 10 nM hydrocortisone, 10 nM D-biotin, 1 mg/ml BSA, 10 ng/ml FGF and PDGF (Peprotech). The cells were then harvested by trypsinization. The cells then co-cultured with the DRG neurons in the presence or absence of 1, 3, 10, or 30 μg/ml of anti Sp35 monoclonal antibodies 1A7 or 2F3, or a negative control antibody in NLA medium containing 2% fetal bovine serum, 50 μg/ml ascorbic acid, 100 ng/ml NGF (Gibco). An effective antibody dose to administer in such an assay has been determined to be in the range of 0.1 μg/ml to 10 μg/ml, depending upon the antibody. One of skill in the art would be able to determine an effective dose using assays described herein.

The culture medium was changed and the various monoclonal antibodies were replenished every three days. After 30 days at 37° C., the co-cultured cells were stained by immunohistochemical staining ("IHC") for neurofilaments with anti-βIII-tubulin antibody to identify axons, or anti-MBP antibody to identify oligodendrocytes (FIG. 4A-E). Co-cultured cells were also lysed and subjected to Western blot analysis to quantify the MBP (FIG. 4G). Based on IHC and Western blot analyses, co-cultured cells treated with anti-Sp35 antibodies 1A7 and 2F3 showed increased survival of oligodendrocyte and neurons, increased numbers of bundled axons and increased numbers of MBP positive cells (FIG. 4F, 10-fold more MBP-positive cells when compared to control-antibody treated co-cultures.

In a similar experiment, oligodendrocyte and DRG co-cultures were incubated in the presence or absence of anti-Sp35 antibodies Li05 and Li06, or a negative control antibody. Co-cultured cells were lysed and subjected to Western blot analysis to quantify the MBP (FIG. 8). Based on Western blot analyses, co-cultured cells treated with anti-Sp35 antibodies Li05 and Li06 showed increased numbers of MBP positive cells, similar to co-cultured cells treated with 3, 10 and 30 μg of Sp35-Fc (LINGO-1-Fc).

In similar experiments oligodendrocyte and DRG co-cultures were incubated in the presence or absence of anti-Sp35 antibodies 3P1D10.2C3, 3P1E11.3B7, 6P4F4.1D3, 6P4F4.1F9, 7P1D5.1G9, Li08, Li13, Li28, and Li33 and also promoted myelination. Similarly, full-length antibodies D05 and D08 also promoted myelination.

These results indicated that treatment of DRG-oligodendrocyte cocultures with anti-Sp35 antibodies 1A7, 2F3, 3P1D10.2C3, 3P1E11.3B7, 6P4F4.1D3, 6P4F4.1F9, 7P1D5.1G9, Li05, Li06, Li08, Li13, Li28, Li33, D05 and D08 promoted mature oligodendrocyte axon interactions and myelination compared to control-antibody treated co-cultures.

Example 10

Anti-Sp35 Antibody 1A7 Promotes Oligodendrocyte Survival and Myelination In Vivo Adult wild-type C57Bl/6 male mice were fed cuprizone (0.2% milled with ground mouse chow by weight) for 6 weeks to induce demyelination within the corpus callosum according to the method described by Morell P et al., *Mol Cell Neurosci.* 12:220-7 (1998). Briefly, anti-Sp35 monoclonal antibody 1A7 was stereotactically injected into the demyelinating corpus callosum at weeks 2, 2.5, and 3 weeks of cuprizone feeding, by the method described below. Control mice were stereotactically injected at the same intervals with sterilized media containing control antibody. After the 6 weeks of cuprizone feeding was completed, the mice were returned to a normal diet for 2, 4 and 6 weeks (ground mouse chow only) to allow remyelination.

The 1A7 and control monoclonal antibodies were delivered as follows. The cuprizone-treated mice were anesthetized with ketamine (80 mg/kg body weight) and xylazine (10 mg/kg body weight) and positioned in an immobilization apparatus designed for stereotactic surgery (David Kopf Instruments). The scalp was opened and the sterile compounds injected (1 μM in 1 ml of HBSS) unilaterally into the acutely demyelinated corpus callosum of the wild-type recipient mice with a 10 μl Hamilton syringe using stereotactic coordinates of 0.7 mm posterior and 0.3 mm lateral to bregma at a depth of 1.7 mm (Messier et al., *Pharmacol. Biochem. Behav.* 63: 313-18 (1999)). Additional control recipient mice were stereotactically injected with HBSS containing no compounds. The opening in the skull was filled with Gelfoam, and the area was swabbed with penicillin and streptomycin (Gibco) and the wound was sutured. Mice were sacrificed every week of the experiment after injection and their brains removed and processed for molecular, biochemical and histological analysis.

The animals receiving anti-Sp35 antibody 1A7 treatment showed increased mature oligodendrocyte survival (based on CC1 antibody staining, FIG. 5A) and axon myelination by IHC using anti-MBP protein antibody or luxol fast blue (FIG. 5B). CC1 antibody-positive oligodendrocytes were quantitated at four weeks and 6 weeks (FIG. 5C). These results indicated that anti-Sp35 antibody 1A7 treatment promoted mature oligodendrocyte survival and axon myelination compared to control-antibody treated mice. Similarly, animals receiving the 1A7 antibody in a lysolecithin model of demyelination also promoted axon myelination compared to control animals (data not shown).

Example 11

Anti-Sp35 Antibody 1A7 Promotes Retinal Ganglion Cell (RGC) Survival in the Optic Nerve Transection Model Anti-Sp35 antibody 1A7 was tested in an optic nerve transection model, which investigates factors that affect neuronal function. Young adult female Sprague Dawley (SD) rats were used in this study. The right optic nerve of each animal was transected intraorbitally 1.5 mm from the optic disc. A piece of gelfoam soaked with 6% Fluoro-Gold (FG) was applied to the newly transected site right behind the optic disc to label the surviving retinal ganglion cells (RGCs). The animals were divided into three groups (n=6 in each group) which received either anti-Sp35 antibody 1A7, control antibody, or just PBS, by intravitreal injection. The volume of each intravitreal injection was 4 µl while the dosage of each injection was 2 µg. The intravitreal injections were performed immediately after the optic nerve transection.

All animals were allowed to survive for 1 week. Two days before sacrificing the animals, the left optic nerve of each animal was transected and 6% FG was administered as described above to label the surviving RGCs, to serve as the internal control. Animals were sacrificed with an overdose of Nembutal and the retinas dissected in 4% paraformaldehyde. Four radial cuts were made to divide the retinas into four quadrants (superior, inferior, nasal and temporal). The retinas were then post-fixed in the same fixative for 1 hour before they were flat-mounted with the mounting medium (Dako). The slides were examined under a fluorescence microscope using an ultra-violet filter (excitation wavelength=330-380 nm). Labeled RGCs were counted along the median line of each quadrants starting from the optic disc to the peripheral border of the retina at 500 µm intervals, under an eyepiece grid of 200×200 µm². The percentage of surviving RGCs resulting from each treatment was expressed by comparing the number of surviving RGCs in the injured eyes with their contra-lateral eyes. All data were expressed as mean±SEM. Statistical significance was evaluated by one way ANOVA, followed by a Tukey-Kramer post hoc test. Differences were considered significant for p<0.05. Anti-Sp35 antibody 1A7 treated animals showed more neuronal survival (80%) when compared to control-antibody or PBS treated animals, which each only showed approximately 50% neuronal survival (FIG. 6).

Example 12

Testing Anti-Sp35 Antibodies for Remyelination in the Optic Nerve Crush Model

The right optic nerve receives complete crush by #5 forceps for 10 seconds around 1.5 mm behind the eyeball intraorbitally just before administration of 2 µl of monoclonal antibody 1A7, 2F3, Li05 and Li06 in 2 ml by intravitreal injection.

The animals receive a second intravitreal injection of the same treatment one week after the surgery. Two weeks after the surgery, the animals are perfused with EM fixatives, postfixed and processed for semithin and ultrathin sections. The longitudinal optic nerve sections are stained and prepared for myelin observation. The myelination of the proximal and the distal parts of the crushed optic nerve are compared among different treatment groups. Sp35-Fc and 1A7, 2F3, Li05 and Li06 treated animals, as well as appropriate controls, will be analyzed for remyelination in the distal part of the optic nerve compared to the controls.

Example 13

Testing Anti-Sp35 Antibodies for Axon Regeneration in the Optic Nerve Crush Model The right optic nerve was crushed by #5 forceps for 10 seconds around 1.5-2 mm behind the eyeball intraorbitally just before administration of 2 µg of monoclonal antibody 1A7 in PBS via intravitreal injection. 4 rats were tested with the 1A7 antibody and 8 rats were used as control animals. The animals received a second intravitreal injection of the same treatment one week after the surgery. Three days prior to sacrifice of the test animals (day 11 of the experiment), 2 ml of CTB-FITC was injected intravitreally to label, anterograde, the regenerative optic nerve axons. On the 14th day post surgery, the animals were perfused and postfixed. The crushed optic nerve was processed for frozen longitudinal sections. The CTB-FITC labeled axons, which cross the lesion site were counted as regenerative fibers at various distances beyond the crush site. When 1A7 was injected into the eye, regeneration of axons was observed up to 250 µm beyond the crush site. See FIG. 10.

Example 14

Anti-Sp35 Antibodies Promote Remyelination and Repair in the Optic Nerve Using the MOG Induced EAE Rat Model For theses experiments, the Myelin Oligodendrocyte Glycoprotein (MOG) induced Experimental Autoimmune Encephalomyelitis (EAE) rat model was used. This is the animal model for human multiple sclerosis. 50 µl of 200 ng complete Freund's adjuvant (Chondrex Inc.) plus 50 µl of 50 µg MOG in saline was emulsified (1:1) and kept on ice before being injected intradermally at the base of the tail for each animal. Female brown Norway rats, 8-10 weeks old, were used for all experiments. General observation in the art indicates that the EAE model is induced around 15 days after MOG injection. Rats are scored for clinical signs of EAE. The signs are scored as follows: grade 0.5, distal paresis of the tail;

grade 1, complete tail paralysis; grade 1.5, paresis of the tail and mild hind leg paresis; grade 2.0, unilateral severe hind leg paresis; grade 2.5, bilateral severe hind limb paresis; grade 3.0, complete bilateral hind limb paralysis; grade 3.5, complete bilateral hind limb paralysis and paresis of one front limb; grade complete paralysis (tetraplegia), moribund state, or death. The animals receive treatment once the EAE model is induced.

2 µg/µl of an anti-Sp35 antibody (1A7) was injected intravitreally at day 15 upon MOG-EAE induction. 2 µg/µl of the anti-Sp35 antibody, 1A7, was injected two additional times at day 22 and day 28. Upon termination of the experiment, the animals were perfused with 4% PFA. The optic nerves were post fixed in 1% $OsO_4$, dehydrated and embedded in Epon. Semithin sections (1 µM) were cut and stained with Toluidine blue for evaluation of myelination. The optic nerves of treated animals were compared to untreated animals for axon regeneration and remyelination in the optic nerve. All procedures were performed following a protocol approved by institutional animal care and use committee (IACUC).

Animals receiving treatment with the anti-Sp35 antibody 1A7 showed remyelination and repair of the optic nerve as compared to normal optic nerves or animals which were subjected to MOG-induced EAE, but received no treatment (FIG. 9). In FIG. 9C, the arrows point to myelinated axons. Animals receiving an antibody which recognizes domain III of Protein G from Streptococcus (MOPC21), not specific for Sp35, showed no signs of remyelination or repair of the optic nerve as compared to normal optic nerves or the optic nerves of untreated animals (data not shown). The Sp35 antagonist antibody 1A7 promoted remyelination and repair of optic nerves in a rat MOG-induced EAE optic neuritis model (FIG. 9).

Example 15

Testing Anti-Sp35 Antibodies for Promotion of CNS Remyelination Using MOG Induced EAE Mouse Model EAE is induced in the 129B6 mixed strain of mice by intradermal immunization (day 0) with 100 µg MOG1-125 protein emulsified with complete Freund's adjuvant (CFA). The injected volume is 100 µl per mouse and is distributed over 3 sites (pinnae, back and skin). The emulsion is prepared on the basis of a 1:1 volume ratio and contains 1 mg/ml MOG1-125 and 2 mg/ml M. tuberculosis (strain H37Ra, Chondrex). Pertussis toxin (200 ng/mouse) is administered intra-peritoneally at the time of immunization and 2 days thereafter. Body weight and clinical EAE scores (0=no clinical signs; 1=limp tail; 2=hind limb weakness, impaired righting reflex or waddled gait; 3=complete hind limb paralysis or absent righting reflex; 4=complete hind limb paralysis with some degree of fore limb involvement; 5=animal fully paralyzed; 6=moribund or dead) are recorded daily. All procedures are performed following a protocol, approved by our institutional animal care and use committee (IACUC). The animals receive the treatment with 1A7, 2F3, Li05 and Li06 monoclonal antibodies or control antibody at day 0 of the study. Blood samples are taken at various times throughout the experiments by retro-orbital bleeding technique. Plasma is separated from PBMC by centrifugation and cell phenotyping performed by FACS staining. Profiling of the humoral anti-MOG antibody response is performed by ELISA using subclass-/isotype-specific mAbs (Pharmingen). At the end of each experiment, brain, spinal cord, optic nerves and sciatic nerves are harvested following perfusion.

This same protocol is used to induce the EAE in Sp35 knockout mice and litter mates. Sp35 knockout mice typically show lower EAE score (1.5), and no relapse compared to control (over a 45 day period), then wild type litter mates (EAE score 3.5).

Sp35-Fc and 1A7, 2F3 treated animals will be analyzed for remyelination comparing to the control.

The His-tagged $MOG_{1-125}$ protein was expressed in Pichia pastoris using a Doxycycline inducible TetO-AOX1 promoter (M. Levesque, D. Krushinskie and K. Strauch, manuscript in preparation). The extracellular coding sequence (Gly1 through Gly125 of the mature protein after removal of signal sequence) of rat MOG was PCR amplified using the following primers: 5' GGGGTATCTCTCGAGAAAA-GAGAGCATCATCATCATCATCATATGG-GACAGTTCAGAGT GATAGGG 3' (SEQ ID NO:368), and 5' TTCGCGGCCGCTATTAGCCAGGGTTG ATCCAGTA-GAAGGG3' (SEQ ID NO:369).

The present invention is not to be limited in scope by the specific embodiments described which are intended as single illustrations of individual aspects of the invention, and any compositions or methods which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

All publications and patent applications mentioned in this specification are herein incorporated by reference to the same extent as if each individual publication or patent application was specifically and individually indicated to be incorporated by reference.

---

What is claimed is:

1. An isolated monoclonal antibody or antigen-binding fragment thereof that can specifically bind to the same Sp35 epitope as a reference antibody comprising
   a VH region comprising the amino acids of SEQ ID NO:168, and
   a VL region comprising the amino acids of SEQ ID NO:282.

2. The isolated monoclonal antibody or antigen-binding fragment thereof of claim 1, wherein the antibody or fragment thereof can competitively inhibit the reference monoclonal antibody from specifically binding to Sp35.

3. The antibody or fragment thereof of claim 1, which is an antagonist of Sp35-mediated myelination inhibition.

4. The antibody or fragment thereof of claim 1, which is an antagonist of Sp35 mediated oligodendrocyte cell death.

5. The antibody or fragment thereof of claim 1, which is an antagonist of Sp35 mediated oligodendrocyte differentiation inhibition.

6. The antibody or fragment thereof of claim 1, further comprising a heterologous polypeptide fused thereto.

7. The antibody or fragment thereof of claim 1, wherein said antibody is conjugated to an agent selected from the group consisting of a therapeutic agent, a prodrug, a peptide, a protein, an enzyme, a virus, a lipid, a biological response modifier, a pharmaceutical agent, or PEG.

8. A composition comprising the antibody or fragment thereof of claim 1, and a carrier.

9. The antibody or antigen-binding fragment thereof of claim 1, wherein the antibody or antigen-binding fragment comprises a VH region and a VL region, and wherein the VH region comprises the amino acids of SEQ ID NO: 168.

10. The antibody or antigen-binding fragment thereof of claim 1, wherein the antibody or antigen-binding fragment comprises a VH region and a VL region, and wherein the VL region comprises the amino acids of SEQ ID NO: 282.

11. The antibody or antigen-binding fragment thereof of claim 1, wherein the VH region comprises the amino acids of SEQ ID NO: 168, and wherein the VL region comprises the amino acids of SEQ ID NO: 282.

12. The antibody or antigen-binding fragment thereof of claim 1, wherein the antibody or antigen-binding fragment comprises a VH region and a VL region, wherein the VH region comprises CDR1, CDR2, and CDR3 regions, and wherein the CDR1, CDR2, and CDR3 regions comprise the amino acids of SEQ ID NOs: 54, 56, and 58, respectively.

13. The antibody or antigen-binding fragment thereof of claim 1, wherein the antibody or antigen-binding fragment comprises a VH region and a VL region, wherein the VL region comprises CDR1, CDR2, and CDR3 regions, and wherein the CDR1, CDR2, and CDR3 regions comprise the amino acids of SEQ ID NOs: 129, 131, and 133, respectively.

14. The antibody or antigen-binding fragment of claim 1, wherein the antibody or antigen-binding fragment comprises a VH region and a VL region,
wherein the VH region comprises CDR1, CDR2, and CDR3 regions, and wherein the CDR1, CDR2, and CDR3 regions comprise the amino acids of SEQ ID NOs: 54, 56, and 58, respectively, and
wherein the VL region comprises CDR1, CDR2, and CDR3 regions, and wherein the CDR1, CDR2, and CDR3 regions comprise the amino acids of SEQ ID NOs: 129, 131, and 133, respectively.

15. The antibody or antigen-binding fragment of claim 1, wherein the antibody or antigen-binding fragment comprises a brain targeting moiety.

16. The antibody or antigen-binding fragment of claim 15, wherein the brain targeting moiety is selected from the group consisting of FC5, mAB 83-14, OX26, B2, B6, and B8 polypeptides, an anti-Fc receptor antibody, transferrin, an anti-transferrin receptor antibody, and an anti-insulin receptor antibody.

* * * * *